US011541009B2

(12) United States Patent
Fallon et al.

(10) Patent No.: US 11,541,009 B2
(45) Date of Patent: Jan. 3, 2023

(54) METHODS OF PROPHYLAXIS OF CORONAVIRUS INFECTION AND TREATMENT OF CORONAVIRUSES

(71) Applicant: Curemark, LLC, Rye Brook, NY (US)

(72) Inventors: Joan M. Fallon, White Plains, NY (US); Matthew Heil, Sherman, CT (US); James J. Fallon, Armonk, NY (US); Janice Hughes, Boulder, CO (US)

(73) Assignee: CUREMARK, LLC, Rye Brook, NY (US)

( * ) Notice: Subject to any disclaimer, the term of this patent is extended or adjusted under 35 U.S.C. 154(b) by 0 days.

(21) Appl. No.: 17/410,743

(22) Filed: Aug. 24, 2021

(65) Prior Publication Data

US 2022/0071904 A1     Mar. 10, 2022

Related U.S. Application Data

(60) Provisional application No. 63/076,500, filed on Sep. 10, 2020.

(51) Int. Cl.
| | | |
|---|---|---|
| *A61K 9/127* | (2006.01) | |
| *A61K 38/48* | (2006.01) | |
| *A61K 9/02* | (2006.01) | |
| *A61K 38/47* | (2006.01) | |
| *A61K 9/00* | (2006.01) | |
| *A61K 38/46* | (2006.01) | |

(52) U.S. Cl.
CPC .......... *A61K 9/1271* (2013.01); *A61K 9/0029* (2013.01); *A61K 9/025* (2013.01); *A61K 38/465* (2013.01); *A61K 38/47* (2013.01); *A61K 38/48* (2013.01)

(58) Field of Classification Search
None
See application file for complete search history.

(56) References Cited

U.S. PATENT DOCUMENTS

| | | |
|---|---|---|
| 3,002,883 A | 10/1961 | Butt et al. |
| 3,223,594 A | 12/1965 | Hoek |
| 3,322,626 A | 5/1967 | D'Argento |
| 3,357,894 A | 12/1967 | Uriel et al. |
| 3,515,642 A | 6/1970 | Hiroyuki et al. |
| 3,536,809 A | 10/1970 | Applezweig et al. |
| 3,574,819 A | 4/1971 | Franz et al. |
| 3,598,123 A | 8/1971 | Zaffaroni |
| 3,710,795 A | 1/1973 | Higuchi et al. |
| 3,786,615 A | 1/1974 | Bauer |
| 3,845,770 A | 11/1974 | Theeuwes et al. |
| 3,860,708 A | 1/1975 | Prout |
| 3,916,899 A | 11/1975 | Theeuwes et al. |
| 3,940,478 A | 2/1976 | Kurtz |
| RE28,819 E | 5/1976 | Thompson |
| 4,008,719 A | 2/1977 | Theeuwes et al. |
| 4,044,126 A | 8/1977 | Cook et al. |
| 4,079,125 A | 3/1978 | Sipos |
| 4,145,410 A | 3/1979 | Sears |
| 4,199,322 A | 4/1980 | Danna et al. |
| 4,241,046 A | 12/1980 | Papahadjopoulos et al. |
| 4,280,971 A | 7/1981 | Wischniewski et al. |
| 4,328,245 A | 5/1982 | Yu et al. |
| 4,358,603 A | 11/1982 | Yu |
| 4,364,923 A | 12/1982 | Cook et al. |
| 4,395,454 A | 7/1983 | Baldwin |
| 4,409,239 A | 10/1983 | Yu |
| 4,410,545 A | 10/1983 | Yu et al. |
| 4,414,209 A | 11/1983 | Cook et al. |
| 4,447,412 A | 5/1984 | Bilton |
| 4,456,544 A | 6/1984 | Lupova et al. |
| 4,623,624 A | 11/1986 | Schultze |
| 4,710,384 A | 12/1987 | Rotman |
| 4,826,679 A | 5/1989 | Roy |
| 4,965,012 A | 10/1990 | Olson |
| 5,023,108 A | 6/1991 | Bagaria et al. |
| 5,059,595 A | 10/1991 | Le Grazie |
| 5,073,543 A | 12/1991 | Marshall et al. |
| 5,120,548 A | 6/1992 | Mcclelland et al. |
| 5,190,775 A | 3/1993 | Klose |
| 5,227,166 A | 7/1993 | Ueda et al. |
| 5,250,418 A | 10/1993 | Moeller et al. |

(Continued)

FOREIGN PATENT DOCUMENTS

| | | |
|---|---|---|
| CA | 2198317 A1 | 8/1998 |
| CA | 2263703 A1 | 8/1999 |

(Continued)

OTHER PUBLICATIONS https://www.dictionary.com/browse/prophylaxis accessed Jan. 11, 2022.*
https://medical-dictionary.thefreedictionary.com/mitigate> accessed Jan. 11, 2022.*
NIH COVID-19 treatment guidelines (https://www.covid19treatmentguidelines.nih.gov/about-the-guidelines/whats-new/ updated Jan. 5, 2022).*
Cui et al. (Origin and evolution of pathogenic coronaviruses Nature Reviews, vol. Mar. 17, 2019).*
Johns Hopkins medicine (https://www.hopkinsmedicine.org/health/conditions-and-diseases/coronavirus/covid-19-vaccine-what-you-need-to-know updated Nov. 23, 2021).*

(Continued)

*Primary Examiner* — Julie Ha
*Assistant Examiner* — Tara L Martinez
(74) *Attorney, Agent, or Firm* — Wilson Sonsini Goodrich & Rosati

(57) ABSTRACT

Methods for prophylaxis, treatment, and reduction of infection, re-infection, and transmission rates of Coronaviruses and more particularly Coronavirus Disease 2019 (COVID-19) resulting from a SARS-CoV-2 viral infection with the use of a pharmaceutical preparation comprising one or more coated or uncoated digestive enzymes, such as pancreatic enzymes and porcine pancreatic enzymes are described herein.

17 Claims, 31 Drawing Sheets

(56) References Cited

U.S. PATENT DOCUMENTS

| | | |
|---|---|---|
| 5,324,514 A | 6/1994 | Sipos |
| 5,354,556 A | 10/1994 | Sparks et al. |
| 5,378,462 A | 1/1995 | Boedecker et al. |
| 5,436,319 A | 7/1995 | Kung et al. |
| 5,437,319 A | 8/1995 | Garuglieri |
| 5,439,935 A | 8/1995 | Rawlings et al. |
| 5,460,812 A | 10/1995 | Sipos |
| 5,476,661 A | 12/1995 | Pillai et al. |
| 5,527,678 A | 6/1996 | Blaser et al. |
| 5,585,115 A | 12/1996 | Sherwood et al. |
| 5,591,767 A | 1/1997 | Mohr et al. |
| 5,607,863 A | 3/1997 | Chandler |
| 5,639,476 A | 6/1997 | Oshlack et al. |
| 5,648,335 A | 7/1997 | Lewis et al. |
| 5,674,532 A | 10/1997 | Atzl et al. |
| 5,674,533 A | 10/1997 | Santus et al. |
| 5,686,255 A | 11/1997 | Deth |
| 5,686,311 A | 11/1997 | Shaw |
| 5,750,104 A | 5/1998 | Sipos |
| 5,753,223 A | 5/1998 | Shibahara et al. |
| 5,776,917 A | 7/1998 | Blank et al. |
| 5,858,758 A | 1/1999 | Hillman et al. |
| 5,860,957 A | 1/1999 | Jacobsen et al. |
| 5,948,433 A | 9/1999 | Burton et al. |
| 5,952,178 A | 9/1999 | Lapidus et al. |
| 5,958,875 A | 9/1999 | Longo et al. |
| 5,977,175 A | 11/1999 | Lin |
| 5,983,134 A | 11/1999 | Ostrow |
| 5,985,317 A | 11/1999 | Venkateshwaran et al. |
| 5,985,891 A | 11/1999 | Rowe |
| 6,010,715 A | 1/2000 | Wick et al. |
| 6,011,001 A | 1/2000 | Navia et al. |
| 6,013,286 A | 1/2000 | Klose |
| 6,020,310 A | 2/2000 | Beck et al. |
| 6,020,314 A | 2/2000 | Mcmichael |
| 6,024,975 A | 2/2000 | D'Angelo et al. |
| 6,096,338 A | 8/2000 | Lacy et al. |
| 6,100,080 A | 8/2000 | Johansen |
| 6,149,585 A | 11/2000 | Gray |
| 6,153,236 A | 11/2000 | Wu et al. |
| 6,167,301 A | 12/2000 | Flower et al. |
| 6,168,569 B1 | 1/2001 | McEwen et al. |
| 6,187,309 B1 | 2/2001 | McMichael et al. |
| 6,197,746 B1 | 3/2001 | Beck et al. |
| 6,210,950 B1 | 4/2001 | Johnson et al. |
| 6,238,727 B1 | 5/2001 | Takemoto et al. |
| 6,251,478 B1 | 6/2001 | Pacifico et al. |
| 6,256,533 B1 | 7/2001 | Yuzhakov et al. |
| 6,261,595 B1 | 7/2001 | Stanley et al. |
| 6,261,602 B1 | 7/2001 | Calanchi et al. |
| 6,261,613 B1 | 7/2001 | Narayanaswamy et al. |
| 6,267,983 B1 | 7/2001 | Fujii et al. |
| 6,280,726 B1 | 8/2001 | Weinrauch et al. |
| 6,287,585 B1 | 9/2001 | Johansen |
| 6,309,669 B1 | 10/2001 | Setterstrom et al. |
| 6,312,741 B1 | 11/2001 | Navarro |
| 6,399,101 B1 | 6/2002 | Frontanes et al. |
| 6,482,839 B1 | 11/2002 | Thornfeldt |
| 6,498,143 B1 | 12/2002 | Beck et al. |
| 6,534,063 B1 | 3/2003 | Fallon |
| 6,534,259 B1 | 3/2003 | Wakefield |
| 6,558,708 B1 | 5/2003 | Lin |
| 6,562,629 B1 | 5/2003 | Lin et al. |
| 6,569,463 B2 | 5/2003 | Patel et al. |
| 6,616,954 B1 | 9/2003 | Dally et al. |
| 6,632,429 B1 | 10/2003 | Fallon |
| 6,660,831 B2 | 12/2003 | Fallon |
| 6,699,885 B2 | 3/2004 | Phillips |
| 6,727,073 B1 | 4/2004 | Moore et al. |
| 6,743,447 B2 | 6/2004 | Labergerie et al. |
| 6,764,447 B2 | 7/2004 | Iliff |
| 6,783,757 B2 | 8/2004 | Brudnak |
| 6,790,825 B2 | 9/2004 | Beck et al. |
| 6,797,291 B2 | 9/2004 | Richardson |
| 6,808,708 B2 | 10/2004 | Houston |
| 6,821,514 B2 | 11/2004 | Houston |
| 6,827,688 B2 | 12/2004 | Goto et al. |
| 6,835,397 B2 | 12/2004 | Lee et al. |
| 6,852,487 B1 | 2/2005 | Barany et al. |
| 6,861,053 B1 | 3/2005 | Lin et al. |
| 6,890,561 B1 | 5/2005 | Blatt et al. |
| 6,899,876 B2 | 5/2005 | Houston |
| 6,923,988 B2 | 8/2005 | Patel et al. |
| 6,980,958 B1 | 12/2005 | Surwit et al. |
| 7,048,906 B2 | 5/2006 | Lin et al. |
| 7,081,239 B2 | 7/2006 | Lin |
| 7,091,182 B2 | 8/2006 | Beck et al. |
| 7,101,573 B2 | 9/2006 | Szymczak et al. |
| 7,122,357 B2 | 10/2006 | Sander-Struckmeier et al. |
| 7,129,053 B1 | 10/2006 | Reiter et al. |
| 7,138,123 B2 | 11/2006 | Fallon |
| 7,232,670 B2 | 6/2007 | D'Azzo et al. |
| 7,244,412 B2 | 7/2007 | Lin |
| 7,285,633 B2 | 10/2007 | Wu et al. |
| RE40,059 E | 2/2008 | Pacifico et al. |
| 7,381,698 B2 | 6/2008 | Fein et al. |
| 7,395,216 B2 | 7/2008 | Rosenfeld et al. |
| 7,479,378 B2 | 1/2009 | Potthoff et al. |
| 7,483,747 B2 | 1/2009 | Gliner et al. |
| 7,588,757 B2 | 9/2009 | Ozawa et al. |
| 7,608,245 B2 | 10/2009 | Lin |
| 7,630,913 B2 | 12/2009 | Kay |
| 7,658,918 B1 | 2/2010 | Ortenzi et al. |
| 7,718,169 B2 | 5/2010 | Margolin et al. |
| 7,736,622 B2 | 6/2010 | Lin et al. |
| 7,935,799 B2 | 5/2011 | Lin et al. |
| 7,945,451 B2 | 5/2011 | Cosentino et al. |
| 8,008,036 B2 | 8/2011 | Fallon |
| 8,012,710 B2 | 9/2011 | Fallon |
| 8,012,930 B2 | 9/2011 | Fallon |
| 8,030,002 B2 | 10/2011 | Fallon |
| 8,055,516 B2 | 11/2011 | Iliff |
| 8,066,636 B2 | 11/2011 | Iliff |
| 8,084,025 B2 | 12/2011 | Fallon |
| 8,105,584 B2 | 1/2012 | Fallon |
| 8,163,278 B2 | 4/2012 | Fallon |
| 8,211,661 B2 | 7/2012 | Fallon |
| 8,221,747 B2 | 7/2012 | Ortenzi et al. |
| 8,318,158 B2 | 11/2012 | Fallon |
| 8,437,689 B2 | 5/2013 | Mazar |
| 8,486,390 B2 | 7/2013 | Fallon |
| 8,580,522 B2 | 11/2013 | Fallon |
| 8,613,918 B2 | 12/2013 | Fallon |
| 8,658,163 B2 | 2/2014 | Fallon |
| 8,673,877 B2 | 3/2014 | Fallon et al. |
| 8,778,335 B2 | 7/2014 | Fallon |
| 8,815,233 B2 | 8/2014 | Fallon |
| 8,921,054 B2 | 12/2014 | Fallon |
| 8,980,252 B2 | 3/2015 | Fallon et al. |
| 9,017,665 B2 | 4/2015 | Fallon |
| 9,023,344 B2 | 5/2015 | Fallon |
| 9,056,050 B2 | 6/2015 | Fallon et al. |
| 9,061,033 B2 | 6/2015 | Fallon |
| 9,084,784 B2 | 7/2015 | Fallon et al. |
| 9,107,419 B2 | 8/2015 | Fallon et al. |
| 9,233,146 B2 | 1/2016 | Fallon |
| 9,320,780 B2 | 4/2016 | Fallon |
| 9,345,721 B2 | 5/2016 | Fallon et al. |
| 9,377,459 B2 | 6/2016 | Fallon |
| 9,408,895 B2 | 8/2016 | Fallon |
| 9,415,014 B2 | 8/2016 | Fallon et al. |
| 9,492,515 B2 | 11/2016 | Fallon et al. |
| 9,511,125 B2 | 12/2016 | Fallon et al. |
| 9,624,525 B2 | 4/2017 | Fallon |
| 9,624,526 B2 | 4/2017 | Fallon |
| 9,687,452 B2 | 6/2017 | Fallon et al. |
| 9,687,534 B2 | 6/2017 | Fallon |
| 9,687,535 B2 | 6/2017 | Fallon |
| 9,895,427 B2 | 2/2018 | Fallon et al. |
| 9,925,250 B2 | 3/2018 | Fallon |
| 9,931,302 B2 | 4/2018 | Fallon et al. |
| 10,098,844 B2 | 10/2018 | Fallon et al. |
| 10,209,253 B2 | 2/2019 | Fallon |
| 10,272,141 B2 | 4/2019 | Fallon |

(56) References Cited

U.S. PATENT DOCUMENTS

| | | |
|---|---|---|
| 10,279,016 B2 | 5/2019 | Fallon |
| 10,350,229 B2 | 7/2019 | Fallon et al. |
| 10,350,278 B2 | 7/2019 | Fallon et al. |
| 10,413,601 B2 | 9/2019 | Fallon |
| 10,588,948 B2 | 3/2020 | Fallon et al. |
| 10,716,835 B2 | 7/2020 | Fallon et al. |
| 10,776,453 B2 | 9/2020 | Fallon et al. |
| 10,940,187 B2 | 3/2021 | Fallon et al. |
| 11,016,104 B2 | 5/2021 | Fallon |
| 11,033,563 B2 | 6/2021 | Fallon et al. |
| 11,045,527 B2 | 6/2021 | Fallon |
| 2001/0006644 A1 | 7/2001 | Bova et al. |
| 2001/0023360 A1 | 9/2001 | Nelson et al. |
| 2001/0024660 A1 | 9/2001 | Ullah et al. |
| 2002/0001575 A1 | 1/2002 | Foreman |
| 2002/0037284 A1 | 3/2002 | Fallon |
| 2002/0061302 A1 | 5/2002 | Sander-Struckmeier et al. |
| 2002/0081628 A1 | 6/2002 | Fallon |
| 2002/0090653 A1 | 7/2002 | Fallon |
| 2002/0094367 A1 | 7/2002 | Fuglsang et al. |
| 2002/0103675 A1 | 8/2002 | Vanelli |
| 2002/0119914 A1 | 8/2002 | Zhu et al. |
| 2002/0141987 A1 | 10/2002 | Bjarnason |
| 2002/0183229 A1 | 12/2002 | Simpson |
| 2003/0097122 A1 | 5/2003 | Ganz et al. |
| 2004/0005304 A1 | 1/2004 | Brudnak |
| 2004/0028689 A1 | 2/2004 | Borody |
| 2004/0029752 A1 | 2/2004 | Sava et al. |
| 2004/0057944 A1 | 3/2004 | Galle et al. |
| 2004/0057962 A1 | 3/2004 | Timmerman |
| 2004/0071683 A1 | 4/2004 | Fallon |
| 2004/0076590 A1 | 4/2004 | Wilkins |
| 2004/0101562 A1 | 5/2004 | Maio |
| 2004/0121002 A1 | 6/2004 | Lee et al. |
| 2004/0209790 A1 | 10/2004 | Sava et al. |
| 2005/0026892 A1 | 2/2005 | Bodor |
| 2005/0036950 A1 | 2/2005 | Jones et al. |
| 2005/0079594 A1 | 4/2005 | Marion |
| 2005/0137134 A1 | 6/2005 | Gill et al. |
| 2005/0170479 A1 | 8/2005 | Weaver et al. |
| 2005/0187130 A1 | 8/2005 | Brooker et al. |
| 2005/0232894 A1 | 10/2005 | Weiner et al. |
| 2006/0105379 A1 | 5/2006 | Wu et al. |
| 2006/0115467 A1 | 6/2006 | Pangborn et al. |
| 2006/0121017 A1 | 6/2006 | Margolin et al. |
| 2006/0182728 A1 | 8/2006 | Fallon |
| 2006/0183180 A1 | 8/2006 | Fallon |
| 2006/0198838 A1 | 9/2006 | Fallon |
| 2006/0253045 A1 | 11/2006 | Coifman |
| 2006/0258599 A1 | 11/2006 | Childers |
| 2006/0258708 A1 | 11/2006 | Andrulis |
| 2006/0259995 A1 | 11/2006 | Cayouette et al. |
| 2006/0294108 A1 | 12/2006 | Adelson et al. |
| 2007/0031399 A1 | 2/2007 | Edens et al. |
| 2007/0053895 A1 | 3/2007 | Fallon |
| 2007/0092501 A1 | 4/2007 | Houston |
| 2007/0116695 A1 | 5/2007 | Fallon |
| 2007/0148151 A1 | 6/2007 | Frink et al. |
| 2007/0148152 A1 | 6/2007 | Shlieout et al. |
| 2007/0148153 A1 | 6/2007 | Shlieout et al. |
| 2007/0203426 A1 | 8/2007 | Kover et al. |
| 2008/0019959 A1 | 1/2008 | Becher et al. |
| 2008/0020036 A1 | 1/2008 | Jolly |
| 2008/0057086 A1 | 3/2008 | Etter |
| 2008/0058282 A1 | 3/2008 | Fallon et al. |
| 2008/0112900 A1 | 5/2008 | Du-Thumm et al. |
| 2008/0112944 A1 | 5/2008 | Pangborn et al. |
| 2008/0152637 A1 | 6/2008 | Fallon |
| 2008/0161265 A1 | 7/2008 | Fallon et al. |
| 2008/0166334 A1 | 7/2008 | Fallon |
| 2008/0177578 A1 | 7/2008 | Zakim |
| 2008/0187525 A1 | 8/2008 | Porubcan |
| 2008/0193436 A1 | 8/2008 | Shan et al. |
| 2008/0199448 A1 | 8/2008 | Ross et al. |
| 2008/0219966 A1 | 9/2008 | Fallon |
| 2008/0248558 A1 | 10/2008 | Deinhammer et al. |
| 2008/0254009 A1 | 10/2008 | Finegold |
| 2008/0274174 A1 | 11/2008 | Ortenzi et al. |
| 2008/0279839 A1 | 11/2008 | Schuler et al. |
| 2008/0279953 A1 | 11/2008 | Ortenzi et al. |
| 2008/0311554 A1 | 12/2008 | Slotman |
| 2008/0317731 A1 | 12/2008 | Gramatikova et al. |
| 2009/0004285 A1 | 1/2009 | Yu et al. |
| 2009/0063402 A1 | 3/2009 | Hayter |
| 2009/0110674 A1 | 4/2009 | Loizou |
| 2009/0117180 A1 | 5/2009 | Ortenzi et al. |
| 2009/0130081 A1 | 5/2009 | Fallon |
| 2009/0171696 A1 | 7/2009 | Allard et al. |
| 2009/0197289 A1 | 8/2009 | Fallon |
| 2009/0226414 A1 | 9/2009 | Tijssen et al. |
| 2009/0232789 A1 | 9/2009 | Fallon |
| 2009/0233344 A1 | 9/2009 | Kurfurst et al. |
| 2009/0263372 A1 | 10/2009 | Fallon |
| 2009/0285790 A1 | 11/2009 | Fallon |
| 2009/0286270 A1 | 11/2009 | Fallon |
| 2009/0304670 A1 | 12/2009 | Edens et al. |
| 2009/0324572 A1 | 12/2009 | Fallon |
| 2009/0324730 A1 | 12/2009 | Fallon |
| 2010/0092447 A1 | 4/2010 | Fallon |
| 2010/0196344 A1 | 8/2010 | Margolin et al. |
| 2010/0209507 A1 | 8/2010 | Lin et al. |
| 2010/0233218 A1 | 9/2010 | Fallon |
| 2010/0239559 A1 | 9/2010 | Freedman et al. |
| 2010/0260857 A1 | 10/2010 | Fallon et al. |
| 2010/0270183 A1 | 10/2010 | Ortenzi et al. |
| 2010/0285116 A1 | 11/2010 | Joshi |
| 2011/0029922 A1 | 2/2011 | Hoffberg et al. |
| 2011/0052706 A1 | 3/2011 | Moest et al. |
| 2011/0081320 A1 | 4/2011 | Westall et al. |
| 2011/0112005 A1 | 5/2011 | Brooker et al. |
| 2011/0200574 A1 | 8/2011 | Jolly et al. |
| 2011/0280853 A1 | 11/2011 | Fallon et al. |
| 2011/0280854 A1 | 11/2011 | Fallon et al. |
| 2012/0003628 A1 | 1/2012 | Fallon |
| 2012/0004192 A1 | 1/2012 | Fallon et al. |
| 2012/0070504 A1 | 3/2012 | Fallon |
| 2012/0128764 A1 | 5/2012 | Venkatesh et al. |
| 2012/0189703 A1 | 7/2012 | Fallon et al. |
| 2012/0201875 A1 | 8/2012 | Ortenzi et al. |
| 2012/0207740 A1 | 8/2012 | Fallon |
| 2012/0230970 A1 | 9/2012 | Fallon |
| 2013/0059001 A1 | 3/2013 | Fallon |
| 2013/0095152 A1 | 4/2013 | Fallon |
| 2013/0113129 A1 | 5/2013 | Fallon et al. |
| 2013/0171121 A1 | 7/2013 | Pierzynowski et al. |
| 2013/0195833 A1 | 8/2013 | Fallon |
| 2013/0202581 A1 | 8/2013 | Fallon et al. |
| 2013/0224172 A1 | 8/2013 | Fallon et al. |
| 2014/0030333 A1 | 1/2014 | Fallon |
| 2014/0127184 A1 | 5/2014 | Fallon et al. |
| 2014/0147500 A1 | 5/2014 | Fallon et al. |
| 2014/0161787 A1 | 6/2014 | Fallon |
| 2014/0170637 A1 | 6/2014 | Fallon |
| 2014/0348881 A1 | 11/2014 | Fallon |
| 2015/0023944 A1 | 1/2015 | Fallon |
| 2015/0147308 A1 | 5/2015 | Fallon et al. |
| 2015/0151198 A1 | 6/2015 | Dugan et al. |
| 2015/0182607 A1 | 7/2015 | Jolly et al. |
| 2015/0246105 A1 | 9/2015 | Fallon et al. |
| 2016/0045576 A1 | 2/2016 | Fallon et al. |
| 2017/0157221 A1 | 6/2017 | Fallon |
| 2017/0246265 A1 | 8/2017 | Fallon |
| 2018/0071375 A1 | 3/2018 | Fallon |
| 2018/0243282 A1 | 8/2018 | Fallon |
| 2019/0175704 A1 | 6/2019 | Fallon |
| 2019/0201507 A1 | 7/2019 | Fallon |
| 2019/0209667 A1 | 7/2019 | Fallon |
| 2019/0275123 A1 | 9/2019 | Fallon et al. |
| 2019/0275128 A1 | 9/2019 | Gleiberman et al. |
| 2020/0101145 A1 | 4/2020 | Fallon et al. |
| 2020/0282030 A1 | 9/2020 | Fallon et al. |

(56) References Cited

U.S. PATENT DOCUMENTS

| | | |
|---|---|---|
| 2020/0286620 A1 | 9/2020 | Fallon et al. |
| 2021/0162024 A1 | 6/2021 | Fallon et al. |

FOREIGN PATENT DOCUMENTS

| | | |
|---|---|---|
| CA | 2667976 A1 | 5/2008 |
| CA | 2719102 A1 | 9/2009 |
| CN | 1031562 A | 3/1989 |
| CN | 1275897 A | 12/2000 |
| CN | 1329923 A | 1/2002 |
| CN | 1552836 A | 12/2004 |
| CN | 1791430 A | 6/2006 |
| CN | 101039667 A | 9/2007 |
| CN | 101208092 A | 6/2008 |
| CN | 102300989 A | 12/2011 |
| DE | 3738599 A1 | 5/1989 |
| DE | 4332985 A1 | 3/1995 |
| DE | 202010004926 U1 | 7/2010 |
| EP | 0425214 A2 | 5/1991 |
| EP | 0436110 A1 | 7/1991 |
| EP | 0451484 A1 | 10/1991 |
| EP | 0564739 A2 | 10/1993 |
| EP | 0564739 A3 | 4/1995 |
| EP | 1162995 B1 | 6/2003 |
| EP | 1413202 A1 | 4/2004 |
| EP | 1335706 B1 | 4/2005 |
| EP | 1019072 B1 | 5/2005 |
| EP | 1604677 A1 | 12/2005 |
| EP | 1931317 B1 | 12/2008 |
| EP | 2258837 A1 | 12/2010 |
| EP | 2318035 A1 | 5/2011 |
| GB | 669782 A | 4/1952 |
| GB | 2347742 A | 9/2000 |
| GB | 2506537 A | 4/2014 |
| JP | S523819 A | 1/1977 |
| JP | S62230714 A | 10/1987 |
| JP | H04364119 A | 12/1992 |
| JP | 2003517831 A | 6/2003 |
| JP | 2004500591 A | 1/2004 |
| JP | 2005515223 A | 5/2005 |
| JP | 2006512091 A | 4/2006 |
| JP | 2007523664 A | 8/2007 |
| JP | 2007530503 A | 11/2007 |
| JP | 2008512468 A | 4/2008 |
| JP | 2008521906 A | 6/2008 |
| JP | 2008283895 A | 11/2008 |
| JP | 2013517251 A | 5/2013 |
| KR | 20050084485 A | 8/2005 |
| RU | 2356244 C1 | 5/2009 |
| TW | 310277 B | 7/1997 |
| WO | WO-8402846 A1 | 8/1984 |
| WO | WO-8908694 A1 | 9/1989 |
| WO | WO-9002562 A1 | 3/1990 |
| WO | WO-9219708 A1 | 11/1992 |
| WO | WO-9219709 A1 | 11/1992 |
| WO | WO-9419005 A1 | 9/1994 |
| WO | WO-9522344 A1 | 8/1995 |
| WO | WO-9732480 A1 | 9/1997 |
| WO | WO-9822499 A2 | 5/1998 |
| WO | WO-9826807 A1 | 6/1998 |
| WO | WO-9822499 A3 | 7/1998 |
| WO | WO-9832336 A2 | 7/1998 |
| WO | WO-9852593 A1 | 11/1998 |
| WO | WO-9964059 A2 | 12/1999 |
| WO | WO-0009142 A1 | 2/2000 |
| WO | WO-9964059 A3 | 3/2000 |
| WO | WO-0021504 A1 | 4/2000 |
| WO | WO-0127612 A2 | 4/2001 |
| WO | WO-0143764 A2 | 6/2001 |
| WO | WO-0145835 A1 | 6/2001 |
| WO | WO-0127612 A3 | 10/2001 |
| WO | WO-0143764 A3 | 11/2001 |
| WO | WO-0214537 A2 | 2/2002 |
| WO | WO-0219828 A1 | 3/2002 |
| WO | WO-0214537 A3 | 5/2002 |
| WO | WO-02051352 A2 | 7/2002 |
| WO | WO-02051436 A2 | 7/2002 |
| WO | WO-03051345 A2 | 6/2003 |
| WO | WO-03059088 A1 | 7/2003 |
| WO | WO-2004060074 A1 | 7/2004 |
| WO | WO-2004093883 A2 | 11/2004 |
| WO | WO-2005115445 A1 | 12/2005 |
| WO | WO-2006031554 A2 | 3/2006 |
| WO | WO-2006044529 A1 | 4/2006 |
| WO | WO-2006031554 A3 | 9/2006 |
| WO | WO-2007002572 A2 | 1/2007 |
| WO | WO-2007074454 A2 | 7/2007 |
| WO | WO-2007147714 A1 | 12/2007 |
| WO | WO-2008021987 A2 | 2/2008 |
| WO | WO-2008102264 A2 | 8/2008 |
| WO | WO-2009114757 A2 | 9/2009 |
| WO | WO-2009155689 A1 | 12/2009 |
| WO | WO-2010002972 A1 | 1/2010 |
| WO | WO-2010025126 A1 | 3/2010 |
| WO | WO-2010053492 A1 | 5/2010 |
| WO | WO-2010080830 A1 | 7/2010 |
| WO | WO-2010080835 A1 | 7/2010 |
| WO | WO-2010120781 A1 | 10/2010 |
| WO | WO-2011000924 A1 | 1/2011 |
| WO | WO-2011050135 A1 | 4/2011 |
| WO | WO-2011114225 A1 | 9/2011 |
| WO | WO-2012067621 A1 | 5/2012 |
| WO | WO-2012145651 A2 | 10/2012 |
| WO | WO-2013103746 A1 | 7/2013 |
| WO | WO-2013116732 A1 | 8/2013 |
| WO | WO-2013181447 A1 | 12/2013 |
| WO | WO-2022056103 A1 | 3/2022 |

OTHER PUBLICATIONS

Funnell et al. ("A cautionary perspective regarding the isolation and serial propagation of SARS-CoV-2 in Vero cells" NPJ vaccines, (20216:83).*

Kumar et al. ("Moxidectin and Ivermectin inhibit SARS-CoV-2 replication in Vero E6 cells but not in human primary epithelium cells" Antimicrob Agents Chemother. Oct. 2021).*

Lopez-Otin et al. ("Proteases: Multifunctional Enzymes in Life and Disease" J Biol Chem Nov. 7, 2008;283(45):30433-30437).*

ABCNEWS. Changing Face of Autism: Numbers Rise as More Behaviors Included. ABCnews. Nov. 1, 2007.

Adams. "Summary of Defeat Autism Now! (DNN!) Oct. 2001 Conference," retrieved from the internet Dec. 18, 2008. http://puterakembara.org/rm/DAN2001.htm.

Advisory Action dated Jun. 3, 2008 for U.S. Appl. No. 10/681,018.

Aman, et al. Outcome measures for clinical drug trials in autism. CNS Spectr. Jan. 2004;9(1):36-47.

American Family Physician. Cuts, Scrapes, and Stitches. Am Fam Physician 69(11):2647-2648 (Jun. 1, 2004).

Amsterdam, D. Susceptibility testing of antimicrobials in liquid media. Antibiotics in Laboratory Medicine. 52-111 (1996).

Ang, et al. Biological role and regulation of the universally conserved heat shock proteins. J Biol Chem. Dec. 25, 1991;266(36):24233-6.

Anonymous: Emulsifiers for the preparation of active dry yeast, Research Disclosure, Mason Publications, Hampshire, GB, 236(6), Dec. 1983 (attached).

APDA. Basic Information About Parkinson's Disease. Jul. 14, 2008.

Arribas, et al. A comparative study of the chymotrypsin-like activity of the rat liver multicatalytic proteinase and the ClpP from *Escherichia coli*. J Biol Chem. Oct. 5, 1993;268(28):21165-71.

Arrigo, et al. Expression of heat shock proteins during development in *Drosophila*. Results Probl Cell Differ. 1991;17:106-19.

ASH. Patient Information Guide—Understanding Hypertension. American Society of Hypertension. 2004. 1-7.

Ashwood, et al. Immune activation of peripheral blood and mucosal CD3+ lymphocyte cytokine profiles in children with autism and gastrointestinal symptoms. J Neuroimmunol. Dec. 19, 2005; 1-9.

Ashwood, et al. Intestinal lymphocyte populations in children with regressive autism: evidence for extensive mucosal immunopathology. J Clin Immunol. Nov. 2003;23(6):504-17.

(56) References Cited

OTHER PUBLICATIONS

Ashwood, et al. Spontaneous mucosal lymphocyte cytokine profiles in children with autism and gastrointestinal symptoms: mucosal immune activation and reduced counter regulatory interleukin-10. J Clin Immunol. Nov. 2004;24(6):664-73.
AUSTIC. Development and adaptation of protein digestion. J Nutr. May 1985;115(5):686-97.
Autism Diagnosis. Autism Statistics. Www.autism-diagnosis.com/autism_statistics/autism_statistics.html. 2007.
AUTISM Society of America. Incidence Numbers from Other Countries, www.autism-society.org. Accessed: Jul. 14, 2008.
Awazuhara, et al. Antigenicity of the proteins in soy lecithin and soy oil in soybean allergy. Clin Exp Allergy. Dec. 1998;28(12):1559-64.
Axcan Pharma Inc. Cdn Prescribing Information on VIOKASE Pancrelipase, USP tablets, powder. 2000: 1-3.
Axelrod. Secretin Treatment for Gastrointestinal Dysmobility in Patients with Familial Dysautonomia. New York University School of Medicine, Grant Recipient awards, Mar.-May 2000. www.med.nyu.edu/ogars/awards/awards2000/page2.html.
Azilect et al. "Correlation between protein intake and daily levodopa dosage," Obtained from the internet May 2, 2007, http://www.azilect.eu/media/cnsnews/showitem.aspx?i=d1c603e4-3c61-4aa1-a376-6e519a5a0f80.
Bailey, et al. Co-occurring conditions associated with FMR1 gene variations: findings from a national parent survey. Am J Med Genet A. Aug. 15, 2008;146A(16):2060-9.
Bakkaloglu, et al. Atopic features in early childhood autism. Eur J Paediatr Neurol. Nov. 2008;12(6):476-9.
Barboza et al., Measurement of intestinal permeability using mannitol and lactulose in children with diarrheal diseases. Brazilian Journal of Medical and Biological Research 32: 1499-1504 (1999).
Barlow. A comparison of the blood pressure, kidney volume and the pancreatic secretory response following the vein administration of various secretin preparations. Am J Phys. 1927;81:182-188.
Barry, J. Mode of action of penetration enhancers in human skin. Controlled Release 6: 85-97 (1987).
Beilmann, et al. Neoexpression of the c-met/hepatocyte growth factor-scatter factor receptor gene in activated monocytes. Blood. Dec. 1, 1997;90(11):4450-8.
Beliaev, O.A. The therapeutic efficacy of the triase preparation in experimental pancreatic exocrine insufficiency. Eksp Lin Farmakiol. 57:38-40 (1994) (Abstract Only—English Translation).
Bellanti, et al. Abnormalities of Th1 function in non-lgE food allergy, celiac disease, and ileal lymphonodular hyperplasia: a new relationship? Ann Allergy Asthma Immunol. Jun. 2003;90(6 Suppl 3):84-9.
Belmonte et al. Fragile X syndrome and autism at the intersection of genetic and neural networks. Nat Neurosci. Oct. 2006; 9(10):1221-5 (abstract only).
Berg, et al. Section 10.5 Many Enzymes Are Activated by Specific Proteolytic Cleavage. 2002.
Berg, et al. Section 9.1 Proteases: Facilitating a Difficult Reaction. 2002.
Berg, et al. Table of Contents. Biochemistry, 5th edition. 2002.
Bhattacharjee et al., Treatment of Pancreatic Exocrine Insufficiency with Enteric Coated Pancreatin Formulations: An Overview. International Journal of Pharmaceutical Sciences and Nanotechnology. 6(3):2125-2130 (2013). .
Birnbaum, et al. Heat shock or stress proteins and their role as autoantigens in multiple sclerosis. Ann N Y Acad Sci. Dec. 19, 1997;835:157-67. Abstract only.
BLACKMER. Parkinson disease: treatment and medication. Mar. 10, 2009., retrieved from the internet on Sep. 15, 2009, http://emedicine.medscape.com/article/312519-treatment.
Block, et al. A rapid food screener to assess fat and fruit and vegetable intake. Am J Prev Med. May 2000;18(4):284-8.
BLOG. Acid Phosphatase Research (blog). Acid-phosphatase.blogspot.com. 2008.
Bode et al. Usefulness of a simple photometric determination of chymotrypsin activity in stools-results of a multicentre study. Clin Biochem. 1986; 19:333-37.
Boorom. Is this recently characterized gastrointestinal pathogen responsible for rising rates of inflammatory bowel disease (IBD) and IBD associated autism in Europe and the United States in the 1990s? Med Hypotheses. 2007;69(3):652-9.
Borlongan. Recent preclinical evidence advancing cell therapy for Alzheimer's disease. Exp Neurol. Sep. 2012;237(1):142-6. doi: 10.1016/j.expneurol.2012.06.024. Epub Jun. 27, 2012.
Borowitz et al., Study of a novel pancreatic enzyme replacement therapy in pancreatic insufficient subjects with cystic fibrosis J.Pediatr., 149:658-662 (2006).
Borowitz, et al. Use of pancreatic enzyme supplements for patients with cystic fibrosis in the context of fibrosing colonopathy. Consensus Committee. J Pediatr. Nov. 1995;127(5):681-4.
Bowen. Exocrine secretions of the pancreas. Jul. 5, 2006. Accessed online at www.vivo.colostate.edu/hbooks/pathphys/digestion/pancreas/exocrine.html.
Boyd, et al. Positively charged amino acid residues can act as topogenic determinants in membrane proteins. Proc Natl Acad Sci U S A. Dec. 1989;86(23):9446-50.
Bradstreet, et al. Detection of Measles Virus Genomic RNA in Cerebrospinal Fluid of Children with Regressive Autism: a Report of Three Cases. J. Am Phys Surg. 2004; 9(2):38-45.
Bray, et al. Effect of dietary protein content on weight gain, energy expenditure, and body composition during overeating. A randomized controlled trial. JAMA. Jan. 4, 2012; 307(1):47-55.
Brinkley, et al. Factor analysis of the aberrant behavior checklist in individuals with autism spectrum disorders. J Autism Dev Disord. Nov. 2007;37(10):1949-59. Epub Dec. 21, 2006.
Brown. Background to Parkinson's Disease, biomed.brown.edu. Jul. 14, 2008.
Brudnak et al. Enzyme-based therapy for autism spectrum disorders—is it worth another look? Med Hypoth. 2002; 58:422-428.
Brudnak, Mark et al., Guide to intestinal health in autism spectrum disorder, Kirkman Laboratories, (Oct. 2001).
Bruhat, et al. Amino acid limitation induces expression of CHOP, a CCAAT/enhancer binding protein-related gene, at both transcriptional and post-transcriptional levels. J Biol Chem. Jul. 11, 1997;272(28):17588-93.
Buie, et al. Evaluation, diagnosis, and treatment of gastrointestinal disorders in individuals with ASDs: a consensus report. Pediatrics. Jan. 2010;125 Suppl 1:S1-18.
Button, KS et al. Power failure: why small sample size undermines the reliability of neuroscience. Nat. Rev. Neurosci. 14:365376 (2013).
Calderon-Garciduenas, et al. Immunotoxicity and environment: immunodysregulation and systemic inflammation in children. Toxicol Pathol. 2009;37(2):161-9.
Caldwell, et al. Crystalline Pancreatic Amylase. II. Improved Method for its Preparation from Hog Pancreas Glands and Additional Studies of its Properties. J. Am. Chem. Soc. 1952; 74(16):4033-4035.
Campbell et al. A genetic variant that disrupts MET transcription is associated with autism. Proc Natl Acad Sci USA. 2006; 103(45):16834-16839.
Campbell, et al. Distinct genetic risk based on association of MET in families with co-occurring autism and gastrointestinal conditions. Pediatrics. Mar. 2009;123(3):1018-24.
Capua et al., Influenza A viruses grow in human pancreatic cells and cause pancreatitis and diabetes in an animal model. Journal of Virology 87(1): 597-610 (2013).
Carlton. Autism and malnutrition: the milk connection. Retrieved from the internet on Feb. 18, 2008, http://www.mercola.com/2004/autism_malnutrition.htm.
Caronna, et al. Autism spectrum disorders: clinical and research frontiers. Arch Dis Child. Jun. 2008;93(6):518-23.
Carroccio et al. Effectiveness of Enteric-coated Preparations on Nutritional Parameters in Cystic Fibrosis. Digestion 41:201-206 (1988).

(56) References Cited

OTHER PUBLICATIONS

Carroccio, et al. Pancreatic enzyme therapy in childhood celiac disease. A double-blind prospective randomized study. Dig Dis Sci. Dec. 1995;40(12):2555-60.
Carroccio et al. Role of pancreatic impairment in growth recovery during gluten-free diet in childhood celiac disease. Gastroenterology 112:1839-1844 (1997).
Carroccio, et al. Secondary impairment of pancreatic function as a cause of severe malabsorption in intestinal giardiasis: a case report. Am J Trop Med Hyg. Jun. 1997;56(6):599-602.
Carroccio, et al. Secretin-cerulein test and fecal chymotrypsin concentration in children with intestinal giardiasis. Int J Pancreatol. Oct. 1993;14(2):175-80.
Cassidy, et al. A new concept for the mechanism of action of chymotrypsin: the role of the low-barrier hydrogen bond. Biochemistry. Apr. 15, 1997;36(15):4576-84.
CDC. Attention-Deficit/Hyperactivity Disorder (ADHD). Www.cdc. org. 2005.
CDC. Autism Information Center/FAQs. Dept of Health and Human Services/CDC. Jan. 30, 2008.
CDC, Escherichia coli, Travelers Health, Chapter 3: Infectious Diseases Related to Travel, Jul. 10, 2015, Available Online at: wwwnc.cdc.gov/travel/yellowbook/2016/infectious-diseases-related-to-travel/escherichia-coli.
CDC. High Blood Pressure. Division for Heart Disease Stroke Prevention. Jul. 15, 2003.
Chaignon et al. Susceptibility of staphylococcal biofilms to enzymatic treatments depends on their chemical compositions. Appl. Microbiol. Appl. Microbiol. 75:125-132 (2007).
Chazalette, J.P. et al., A double-bind placebo-controlled trial of a pancreatic enzyme formulation (Panzytrat 25000) in the treatment of impaired lipid digestion in patients with cystic fibrosis. Drug Invest., 5(5):274-280 (1993).
Chen, et al. Identification of two lysosomal membrane glycoproteins. J Cell Biol. Jul. 1985;101(1):85-95.
Chen, et al. Lysine 43 is trimethylated in subunit C from bovine mitochondrial ATP synthase and in storage bodies associated with batten disease. J Biol Chem. May 21, 2004;279(21):21883-7.
Chen, et al. Medicinal Functions of Bromelain and Its Application Prospect in Animal Husbandry, China Animal Husbandry & Veterinary Medicine. 2005; vol. 32, No. 1, p. 14-16. (in Chinese with English translation).
Childhood Autism Rating Scale (CARS), Wikipedia, downloaded May 5, 2014.
Chung, et al. Effects of a central cholinesterase inhibitor on reducing falls in Parkinson disease. Neurology. Oct. 5, 2010;75(14):1263-9. Epub Sep. 1, 2010.
Cichoke, AJ The Complete Book of Enzyme Therapy, Penguin (1999) pp. 206-208 and 38.
Cichoke. Celiac disease. The complete book of enzyme therapy. Penguin. New York, NY. 1999; 174-177.
Cichoke, et al. The complete book of enzyme therapy. Penguin. 1998: 39, 42, 47, 50, and 53.
Cichoke. Influenza. In: The Complete Book of Enzyme Therapy. Anthony J. Cichoke. Avery, a member of Penguin Putnam, Inc., publisher. Ed.: Dara Stewart, pp. 37, 40-45 (1999).
Cichoke. Influenza. In: The Complete Book of Enzyme Therapy. D. Stewart, ed. Copyright 1999. Anthony J. Cichoke. Penguin Putnam, Inc., New York, New York. pp. "Contents", 50, 273-275 and 455.
Claud, et a. Hypothesis: inappropriate colonization of the premature intestine can cause neonatal necrotizing enterocolitis. FASEB J. Jun. 2001;15(8):1398-403.
Commentary on the Japanese Pharmacopoeia, 14th ed., D929-D931, 2001.
Concerta. Adhd Myths and Facts. ADHD Myths and Facts about medication, girls, and symptoms and causes. Concerta.net. Jul. 15, 2008.
Cornish. A balanced approach towards healthy eating in autism, Journal of Human Nutrition and Dietetics 11:501-509 (1998).

Corring, et al. Development of digestive enzymes in the piglet from birth to 8 weeks. I. Pancreas and pancreatic enzymes. Nutr Metab. 1978;22(4):231-43.
Couet, et al. Identification of peptide and protein ligands for the caveolin-scaffolding domain. Implications for the interaction of caveolin with caveolae-associated proteins. J Biol Chem. Mar. 7, 1997;272(10):6525-33.
Cox, Rj et al. Influenza Virus: Immunity and Vaccination Strategies. Comparison of the Immune Response to Inactivated and Live, Attenuated Influenza Vaccines. Scandinavian Journal of Immunology 59, 1-15 (2004).
Coyle. Treating the Negative Symptoms of Schizophrenia: An Expert Interview with Joseph Coyle, MD. www.narsad.org/?q=node/438/latest-research. 2006.
Craig, et al. Heat shock proteins: molecular chaperones of protein biogenesis. Microbiol Rev. Jun. 1993;57(2):402-14.
Creon—FDA Prescribing information side effects and uses. Revised Apr. 2015.
Creon digestive enzymes. Celic.com/ Jun. 2009. http://www.celiac.com/gluten-free/topic/59195-creon-digestive-enzymes.
Creon. Full prescribing information. Last edited Mar. 2013. Abbvie Inc 2012. www.rxabbvie.com/pdf/creon_PI.pdf.
Croonenberghs, et al. Peripheral markers of serotonergic and noradrenergic function in post-pubertal, Caucasian males with autistic disorder. Neuropsychopharmacology. Mar. 2000;22(3):275-83.
Cruse et al. Illustrated dictionary of immunology. CRC Press, New York. 1995.
Cuervo, et al. Cathepsin A regulates chaperone-mediated autophagy through cleavage of the lysosomal receptor. Embo J. Jan. 2, 2003;22(1):47-59.
Curemark press release. Curemark Receives Investigational New Drug Clearance for CM-AT for Autism. Mar. 26, 2009. http://www.medicalnewstoday.com/releases/143723.php.
Curemark Trademark/Service mark application, Principal Register. Serial No. 77527223. Filing date: Jul. 21, 2008.
Dajcs, et al. Lysostaphin is effective in treating methicillin-resistant Staphylococcus aureus Endophthalmitis in the rabbit. Curr Eye Res. Jun. 2001;22(6):451-7.
Darman. An introduction to alternative medicine for psychiatric conditions. Oct. 22, 2007, retrieved on Sep. 18, 2009, http://web.archive.org/web/20071022104238/http://altp[therapies4bipolar.info/ortho/html.
Dawe, et al. Antipsychotic drugs dose-dependently suppress the spontaneous hyperactivity of the chakragati mouse. Neuroscience. Nov. 24, 2010;171(1):162-72. Epub Sep. 17, 2010.
Dawe, et al. The chakragati mouse: a mouse model for rapid in vivo screening of antipsychotic drug candidates. Biotechnol J. Nov. 2007;2(11):1344-52.
Dawn. Autism: the Latest Prevalence Rates in USA—Now 1 in 175. Disabled Women's Network Ontario. Dawn.thot.net/autism2.html. 2006.
Dawson lab. Research Projects in Synthetic Protein Chemistry. 2005; 1-2.
DeFelice, Viruses Part 2-results of two informal studies, Chapter 14. In: Enzymes: Go with your Gut-more practical guidelines for digestive enzymes. Published by ThunderSnow. pp. 195-218 (2006).
Delong. News on Parkinson's. The Dana Foundation. Jul. 14, 2008.
Derwent. English abstract for RU 2286785 Nov. 10, 2006. Downloaded from the Derwent file Jul. 13, 2011.
D'Eufemia et al., Abnormal intestinal permeability in children with autism. Acta Paediatr 85: 1076-1079(1996).
Diagnostic and Statistical Manual of Mental Disorders, Fourth Edition, Primary Care Version, Chapter 6, American Psychiatric Association (2000).
Diagnostic and Statistical Manual of Mental Disorders, Fourth Edition, Text Revision, DSM-IV-TR, American Psychiatric Association (2000).
Diaz-Hernandez, et al. Neuronal induction of the immunoproteasome in Huntington's disease. J Neurosci. Dec. 17, 2003;23(37):11653-61.
Digestive Enzyme Preparation: Pancreatin listed in Japanese Pharmacopoeia, Aug. 2008, < URL:http: > (in Japanese with English translation) < /URL:http: > .

(56) References Cited

OTHER PUBLICATIONS

Digestive Enzyme Wikipedia. Retrieved from the internet Sep. 10, 2009, http://en.wikipedia.org/wiki/Digestive_enzyme.
Ding, et al. Proteasome inhibition in oxidative stress neurotoxicity: implications for heat shock proteins. J Neurochem. May 2001;77(4):1010-7.
Dobbs et al. Link between helicobacter pylori infection and idiopathic parkinsonism. Medical Hypothesis. 2000; 55(2):93-98.
Dockter et al. Determination of chymotrypsin in the feces by a new photometric method. Padiatr Padol. 1985; 20(3):257-265.
Dominquez-Munoz, et al. Optimising the therapy of exocrine pancreatic insufficiency by the association of a proton pump inhibitor to enteric coated pancreatic extracts. Gut. Jul. 2006;55(7):1056-7.
Dudzinska. Dissertation. Development of lipid-based enteric coatings. Oct. 18, 1988. Martin Luther University, Halle-Wittenberg, pp. 1-125.
Dupiereux, et al. Creutzfeldt-Jakob, Parkinson, lewy body dementia and Alzheimer diseases: from diagnosis to therapy. Cent Nerv Syst Agents Med Chem. Mar. 2009;9(1):2-11.
Durie et al. Uses and abuses of enzyme therapy in cystic fibrosis. Journal of the Royal Society of Medicine. 91:(Suppl. 34):2-13 (1998).
Durkin, et al. Socioeconomic inequality in the prevalence of autism spectrum disorder: evidence from a U.S. cross-sectional study. PLoS One. Jul. 12, 2010;5(7):e11551.
Eaves, et al. The criterion-related validity of the Childhood Autism Rating Scale and the Autism Behavior Checklist. J Abnorm Child Psychol. Oct. 1993;21(5):481-91. abstract only.
Edelson, et al. 3-Cyclohexene-1-glycine, an Isoleucine Antagonist. J. Am. Chern. Soc. 1958; 80(11):2698-2700.
Elkashef, et al. Biological markers of cocaine addiction: implications for medications development. Addict Biol. Jun. 2003;8(2):123-39.
Elphick, et al. Impaired luminal processing of human defensin-5 in Crohn's disease: persistence in a complex with chymotrypsinogen and trypsin. Am J Pathol. Mar. 2008;172(3):702-13.
Emc, Creon 10000 Capsules, May 18, 2015, Available Online at: www.medicines.org.uk/emc/medicine/2068.
EMed Expert, Antibiotics: Cephalosporins, Available online at: http://www.emedexpert.com/compare/ cephalosporins.shtml, available as early as Jun. 2, 2007 per Internet Archive Wayback Machine.
Ethridge, et al. Acute pancreatitis results in induction of heat shock proteins 70 and 27 and heat shock factor-1. Pancreas. Oct. 2000;21(3):248-56.
Evans, et al. Pancreatic insufficiency in adult celiac disease: do patients require long-term enzyme supplementation? Dig Dis Sci. Oct. 2010;55(10):2999-3004. doi: 10.1007/s10620-010-1261-y. Epub May 11, 2010.
Exocrine Pancreatic Insufficiency (Enzymes) Document downloaded online on Jan. 8, 2016 at: http://www.epi4dogs.com/enzyme.htm < http: > < /http: >.
Fafournoux, et al. Amino acid regulation of gene expression. Biochem J. Oct. 1, 2000;351(Pt 1):1-12.
Fallingborg, et al. Measurement of gastrointestinal pH and regional transit times in normal children. J Pediatr Gastroenterol Nutr. Aug. 1990;11(2):211-4.
Fallon. Could one of the most widely prescribed antibiotics amoxicillin/clavulanate "augmentin" be a risk factor for autism? Med Hypotheses. 2005;64(2):312-5.
FAMILY Caregiver Alliance. Fact Sheet: Parkinson's Disease. Caregiver.org. Jul. 14, 2008.
Fan et al., Guidelines for Standard Operation of Toxicological Safety Assessment (vol. 1). University of Electronic Science and Technology Press (2009).
Fernell, et al. No evidence for a clear link between active intestinal inflammation and autism based on analyses of faecal calprotectin and rectal nitric oxide. Acta Paediatr. Jul. 2007;96(7):1076-9.
Ferrone, et al. Pancreatic enzyme pharmacotherapy. Pharmacotherapy. 2007; 27:910-920.
Fido, et al. Olanzapine in the treatment of behavioral problems associated with autism: an open-label trial in Kuwait. Med Prine Pract. 2008;17(5):415-8. doi: 10.1159/000141508. Epub Aug. 6, 2008.
Filipek et al. The screening and diagnosis of autistic spectrum disorders. J. of Autism and Dev Disorders. 1999; 29(6).
Final Office Action dated Jan. 3, 2012 for U.S. Appl. No. 10/681,018.
Final Office Action dated Jan. 26, 2012 for U.S. Appl. No. 12/487,864.
Final Office Action dated Nov. 8, 2011 for U.S. Appl. No. 12/054,343.
Final Office Action dated Nov. 8, 2011 for U.S. Appl. No. 12/786,739.
Final Office Action dated Nov. 9, 2010 for U.S. Appl. No. 09/990,909.
Final Office Action dated Feb. 14, 2011 for U.S. Appl. No. 12/049,613.
Final Office Action dated Feb. 27, 2009 for U.S. Appl. No. 11/555,697.
Final Office Action dated Mar. 13, 2009 for U.S. Appl. No. 11/232,180.
Final Office Action dated Mar. 17, 2008 for U.S. Appl. No. 10/681,018.
Final Office Action dated Apr. 28, 2009 for U.S. Appl. No. 10/681,018.
Final Office Action dated May 11, 2010 for U.S. Appl. No. 11/555,697.
Final Office Action dated Jun. 25, 2008 for U.S. Appl. No. 11/213,255.
Final Office Action dated Jul. 2, 2010 for U.S. Appl. No. 12/046,252.
Final Office Action dated Jul. 27, 2004 for U.S. Appl. No. 09/990,909.
Finegold et al. Gastrointestinal microflora studies in late-onset autism. Clinical Infectious Diseases. 2002; 35(1):S6-S15.
Fitzsimmons, et al. High-dose pancreatic-enzyme supplements and fibrosing colonopathy in children with cystic fibrosis. N Engl J Med. May 1, 1997;336(18):1283-9.
Flament, M.P. et al. Development of 400 pm Pellets by Extrusion-Spheronization Application with Gelucire 50/02 to Produce a "Sprinkle" Form, Drug Development and industrial Pharmacy, 30:1, 43-51, DOI: 10.1081/DDC-120027510 (2004).
Fliri, et al. Drug effects viewed from a signal transduction network perspective. J Med Chem. Dec. 24, 2009;52(24):8038-46. doi: 10.1021/jm901001p.
Frossard, et al. Both thermal and non-thermal stress protect against caerulein induced pancreatitis and prevent trypsinogen activation in the pancreas. Gut. Jan. 2002;50(1):78-83.
Frossard. Trypsin activation peptide (TAP) in acute pancreatitis: from pathophysiology to clinical usefulness. JOP. Mar. 2001;2(2):69-77.
Furlano, et al. Colonic CD8 and gamma delta T-cell infiltration with epithelial damage in children with autism. J Pediatr. Mar. 2001;138(3):366-72.
Garcia et al. Detection of Giardia lamblia, Entamoeba histolytica/Entamoeba dispar, and Cryptosporidium parvum antigens in human fecal specimens using the triage parasite panel enzyme immunoassay. Am Soc for Microbiology. 2000; 38(9):3337-3340.
Gardner. Absorption of intact peptides: studies on transport of protein digests and dipeptides across rat small intestine in vitro. Q J Exp Physiol. Oct. 1982;67(4):629-37.
Garner Jr, et al. Porcine Pancreatic Lipase—A Glycoprotein. J Biol Chem. Jan. 25, 1972;247(2):561-5.
Gass, et al. Enhancement of dietary protein digestion by conjugated bile acids. Gastroenterology. Jul. 2007;133(1):16-23.
Generation Rescue. Autism and Vaccines Around the World: Vaccine Schedules, Autism Rates, and Under 5 Mortality. Apr. 1, 2009.
Giglio, et al. Failure to thrive: the earliest feature of cystic fibrosis in infants diagnosed by neonatal screening. Acta Paediatr. Nov. 1997;86(11):1162-5.
GM Chemie 2010 "Products: Hypromellose Phthalate" accessed from www.gmchemie.com on Sep. 22, 2014.
Goff, et al. Production of abnormal proteins in *E. coli* stimulates transcription of Ion and other heat shock genes. Cell. Jun. 1985;41(2):587-95.
Gonzalez, et al. Endoscopical, histological and immunological characteristics of the digestive mucosa in autistic children with gastrointestinal symptoms. 2005; 1-7.
Green, et al. Amino-terminal polymorphisms of the human beta 2-adrenergic receptor impart distinct agonist-promoted regulatory properties. Biochemistry. Aug. 16, 1994;33(32):9414-9.
Gupta, et al. Analysis of data gaps pertaining to enterotoxigenic *Escherichia coli* in low and medium human development index countries, 1984-2005. Epidemiol Infect. 2008; 136:721-738.

(56) References Cited

OTHER PUBLICATIONS

Gupta, et al. Th1- and Th2-like cytokines in CD4+ and CD8+ T cells in autism. J Neuroimmunol. May 1, 1998;85(1):106-9.
Hadjivassiliou, et al. Does cryptic gluten sensitivity play a part in neurological illness? Lancet. Feb. 10, 1996;347(8998):369-71.
Happe et al. The neuropsychology of autism. Brain. 1996; 119:1377-1400.
Happe et al. Time to give up on a simple explanation for autism. Nat Neurosci. Oct. 2006; 9(10):1218-20.
Harrison, Bipolar Disorder. Healing Depression Naturally, Twin Streams. Kensington Publishing Corp: 31-32. (2004).
HEALTH.com. Who is affected by Parkinson's disease, www.health.com. Jul. 14, 2008.
Heijerman, et al. Omeprazole enhances the efficacy of pancreatin (pancrease) in cystic fibrosis. Ann Intern Med. Feb. 1, 1991;114(3):200-1.
Hendren et al. Mechanistic biomarkers for autism treatment. Medical Hypotheses. 2009; 73:950-954.
HITTI. Allergy, celiac disease, and ileal lymphonodular. WebMD. 2005. 1-2.
Holquist et al. FDA safety page: Delayed-release vs. extended release Rxs. Drug Topics [online] Jul. 23, 2007 [Retrieved on Jul. 30, 2012] Retrieved from the internet: http://drugtopics.modernmedicine.com/drugtopics/Top+News/FDA-safety-page-Delayed-release-vs-extended-release/ArticleStandard/Article/detail/442606.
Holten, et al. Appropriate prescribing of oral beta-lactam antibiotics. Am Fam Physician. Aug. 1, 2000;62(3):611-20.
Horsmans et al., Lactulose improves psychometric testing in cirrhotic patients with subclinical encephalopathy. Aliment Pharmocol Ther 11:165-170 (1997).
Horvath, et al. Autism and gastrointestinal symptoms. Curr Gastroenterol Rep. Jun. 2002;4(3):251-8.
Horvath, et al. Autistic disorder and gastrointestinal disease. Curr Opin Pediatr. Oct. 2002;14(5):583-7.
Horvath, et al. Gastrointestinal abnormalities in children with autistic disorder. J Pediatr. Nov. 1999;135(5):559-63.
Horvath et al. Improved social and language skills after secretin administration in patients with autistic spectrum disorders. Journal of the Association for Academic Minority Physicians. Jan. 1998; 9(1):9-15.
Hoshiko et al. The effect of the gastrointestinal hormones on colonic muscosal blood flow. Acta Medica Nagasakiensia. 1994; 39(4):125-130.
Houston. Autism—One Conference. May 2006. 1-83.
Hsiao, et al. The microbes of the intestine: an introduction to their metabolic and signaling capabilities. Endocrinol Metab Clin North Am. Dec. 2008;37(4):857-71.
Huang, et al. Apoptotic cell death in mouse models of GM2 gangliosidosis and observations on human Tay-Sachs and Sandhoff diseases. Hum Mol Genet. Oct. 1997;6(11):1879-85.
Huang, et al. Mapping of the human APOB gene to chromosome 2p and demonstration of a two-allele restriction fragment length polymorphism. Proc Natl Acad Sci U S A. Feb. 1986;83(3):644-8.
Ijuin, H. Evaluation of pancreatic exocrine function and zinc absorption in alcoholism. The Kurume Medical Journal 45.1 (1998): 1-5.
Information of Papain from Worthington Enzymes webpage http://www.worthington-biochem.com/pap/default.html Downloaded Jan. 17, 2013.
International preliminary report on patentability dated Jul. 17, 2014 for PCT/US2013/020183.
International Preliminary Reporton Patentability dated Oct. 15, 2019 for PCT/US2018/026841.
International search report and written opinion dated Feb. 21, 2013 for PCT/US2013/020183.
International search report and written opinion dated May 9, 2013 for PCT/US2013/024453.
International search report and written opinion dated Aug. 27, 2013 for PCT/US2013/043444.
International search report and written opinion dated Nov. 12, 2012 for PCT/US2012/034489.
International search report and written opinion dated Jan. 18, 2011 for PCT/US2010/057341.
International search report and written opinion dated Feb. 15, 2011 for PCT/US2010/053484.
International search report and written opinion dated Mar. 2, 2010 for PCT/US2010/020253.
International search report and written opinion dated Mar. 5, 2010 for PCT/US2010/020259.
International search report and written opinion dated Jun. 9, 2010 for PCT/US2010/030895.
International search report and written opinion dated Sep. 25, 2009 for PCT/US2009/049374.
International search report dated Mar. 11, 2002 for PCT/US2001/25343.
International search report dated Jun. 29, 2001 for PCT/US2000/34000.
Isaksson, et al. Pain reduction by an oral pancreatic enzyme preparation in chronic pancreatitis. Digestive Dis. Sci. 1983; 28(2):97-102.
James, et al. Thimerosal neurotoxicity is associated with glutathione depletion: protection with glutathione precursors. Neurotoxicology. 2004; 26(1):1-8.
Jeffrey. Global burden of hypertension may reach 1.5 billion by 2025. Medscape Medical News. Jul. 14, 2008.
Jenkins, et al. Management of gastroenteritis. Archives of Disease in Childhood. 1990; 65:939-941.
Johnson et al. Eating Habits and Dietary Status in Young Children with Autism. J Dev Phys Disabil 20:437-448 (2008).
Juhl. Fibromyalgia and the serotonin pathway. Altern Med Rev. 1998; 3(5):367-375.
Jyonouchi, et al. Dysregulated innate immune responses in young children with autism spectrum disorders: their relationship to gastrointestinal symptoms and dietary intervention. Neuropsychobiology. 2005;51 (2):77-85.
Jyonouchi, et al. Evaluation of an association between gastrointestinal symptoms and cytokine production against common dietary proteins in children with autism spectrum disorders. J Pediatr. May 2005;146(5):605-10.
Jyonouchi, et al. Proinflammatory and regulatory cytokine production associated with innate and adaptive immune responses in children with autism spectrum disorders and developmental regression. J Neuroimmunol. Nov. 1, 2001;120(1-2):170-9.
Kachrimanis, et al. Tensile strength and disintegration of tableted silicified microcrystalline cellulose: influences of interparticle bonding. J Pharm Sci. Jul. 2003;92(7):1489-501.
Kaemmerer, et al. Effects of lipid peroxidation-related protein modifications on RPE lysosomal functions and POS phagocytosis. Invest Ophthalmol Vis Sci. Mar. 2007;48(3):1342-7.
Kaminski, et al. Polymorphism of bovine beta-casein and its potential effect on human health. J Appl Genet. 2007;48(3):189-98.
Kaspar et al. New photometric assay for chymotrypsin in stool. Clinical Chemistry. 1984; 30(11):1753-1757.
Katritos. New finding may have implications for schizophrenia, autism. Autism/Schizophrenia findings relating to protein, etc. Feb. 10, 2011. e-mail.
Kearney, et al. Global burden of hypertension: analysis of worldwide data. Lancet. Jan. 15-21, 2005;365(9455):217-23. Abstract only.
Keeley et al., Gradual vs. abrupt withdrawal of methylphenidate in two older dependent males. Journal of Substance Abuse Treatment. 2(2):123-125 (1985).
Keller, et al. Pancreatic enzyme supplementation therapy. Current Treatment Options in Gastroenterology 6.5 (2003): 369-374.
Kidd, P.M., Autism, an extreme challenge to integrative medicine. Part 2: medical management. Altern. Med. Rev., 7(6):472-499 (Dec. 2002).
King, et al. Effects of bacterial microflora of the lower digestive tract of free-range waterfowl on influenza virus activation. Appl Environ Microbiol. Jun. 2011;77(12):4119-25. doi: 10.1128/AEM.02578-10. Epub Apr. 29, 2011.

(56) References Cited

OTHER PUBLICATIONS

Klopfleisch et al. Encephalitis in a stone marten (Martes foina) after natural infection with highly pathogenic avian influenza virus subtype H5N1. Journal of Comparative Pathology 137:155-159 (2007).
Knivsberg, et al. A randomised, controlled study of dietary intervention in autistic syndromes. Nutr Neurosci. Sep. 2002;5(4):251-61.
Koh et al. Inflammation and wound healing: The role of the macrophage. Expert Rev Mol Med. 13:e23 (2011) (Author manuscript).
Koivu et al. Determination of Phylloquinone in Vegetables, Fruits, and Berries by High-Performance Liquid Chromatography with Electrochemical Detection. J. Agric. Food Chem. 45(12):4644-4649 (1997).
Kokai-Kun, et al. Lysostaphin as a treatment for systemic *Staphylococcus aureus* infection in a mouse model. J Antimicrob Chemother. Nov. 2007;60(5):1051-9. Epub Sep. 10, 2007.
Koller, et al. Falls and Parkinson's Disease (Abstract). Clin Neuropharmacol. 1989; 12(2):98-105.
Koplin, et al. Soy consumption is not a risk factor for peanut sensitization. J Allergy Clin Immunol. Jun. 2008;121(6):1455-9.
Koster et al. Evidence based medicine and extradigestive manifestations of helicobacter pylori. Acta Gastro-Enterologica Belgica. 2000; 63(4):388-392.
Krishnaswami, et al. A systematic review of secretin for children with autism spectrum disorders. Pediatrics. May 2011;127(5):e1322-5. doi: 10.1542/peds.2011-0428. Epub Apr. 4, 2011.
Kronenberg, et al. Folate deficiency induces neurodegeneration and brain dysfunction in mice lacking uracil DNA glycosylase. J Neurosci. Jul. 9, 2008;28(28):7219-30.
Kujoth, et al. Mitochondrial DNA mutations, oxidative stress, and apoptosis in mammalian aging. Science. Jul. 15, 2005;309(5733):481-4.
Kumar. Neurologic presentations of nutritional deficiencies. Neurol Clin. Feb. 2010;28(1):107-70.
Larimore. How Common Is ADHD? Facts About ADHD. Jul. 15, 2008.
Lashkari, et al. Williams-Beuren Syndrome: An update and review for the primary physician. Clinical Pediatrics. 1999; 38(4):189-208.
Layer et al. Pancreatic enzyme replacement therapy. Current Gastroenterology Reports. 2001;3:101-108.
Lebenthal, et al. Enzyme therapy for pancreatic insufficiency: present status and future needs. Pancreas. Jan. 1994;9(1):1-12.
Leeds, et al. Is exocrine pancreatic insufficiency in adult coeliac disease a cause of persisting symptoms? Aliment Pharmacol Ther. Feb. 1, 2007;25(3):265-71.
Levy, et al. Relationship of dietary intake to gastrointestinal symptoms in children with autistic spectrum disorders. Biol Psychiatry. Feb. 15, 2007;61(4):492-7.
Leyfer, et al. Comorbid psychiatric disorders in children with autism: interview development and rates of disorders. J Autism Dev Disord. Oct. 2006;36(7):849-61.
Lieberman. Pharmaceutical Dosage Forms. vol. 2: Disperse Systems. New York Marcel Dekker, Inc. 1996; 243-258.
Life Plus Somazyne accessed Jun. 10, 2016, Online at www.lifeplus.com/media/pdf/piSheets/US/ 6141-PI_EN.pdf.
LIPASE 30, Technical Data sheet, 1 page, Scientific Protein Laboratories LLC Jun. 13, 2005.
Liyanage, et al. Bioavailability of iron from micro-encapsulated iron sprinkle supplement. Food and Nutrition bulletin. 2002; 23(3):133-137.
Lloyd. Lysosome membrane permeability: implications for drug delivery. Adv Drug Deliv Rev. Mar. 30, 2000;41(2):189-200.
Lockner et al. Dietary intake and parents' perception of mealtime behaviors in preschool-age children with autism spectrum disorder and in typically developing children. J Am Diet Assoc 108(8):1360-1363 (2008).
Loh, et al. Highly tolerated amino acid substitutions increase the fidelity of *Escherichia coli* DNA polymerase I. J Biol Chem. Apr. 20, 2007;282(16):12201-9.
Lord, et al. Diagnostic Instruments in Autistic Spectrum Disorders, info.med.yale.edu. 2005; 11:730-771.
Luedtke, et al. Cathepsin A is expressed in a cell- and region-specific manner in the testis and epididymis and is not regulated by testicular or pituitary factors. J Histochem Cytochem. Aug. 2000;48(8):1131-46.
MacDonald. Thyrotoxicosis treated with pancreatic extract and iodine. Lancet. 1943; 244(6251):788.
MacFabe, et al. Neurobiological effects of intraventricular propionic acid in rats: possible role of short chain fatty acids on the pathogenesis and characteristics of autism spectrum disorders. Behav Brain Res. 2006; 176(1):149-69.
MacReady. Parkinson's Disease Treatment: what you should know. Retrieved from the internet on Sep. 15, 2009, http://www.everydayhealth.com/parkinsons-disease-treatment-overview.aspx.
Mannino, et al. Surveillance for asthma—United States, 1960-1995. MMWR CDC Surveill Summ. Apr. 24, 1998;47(1):1-27.
Marcus, et al. A placebo-controlled, fixed-dose study of aripiprazole in children and adolescents with irritability associated with autistic disorder. J Am Acad Child Adolesc Psychiatry. Nov. 2009;48(11):1110-19.
Marczewska et al. Protein intake in parkinsonian using the EPIC food frequency questionnaire. Mov Diord. Aug. 2006; 21(8):1229-1231.
Marion et al., A New Procedure Allowing the Complete Removal and Prevention of Hemodialysis. Blood Purification, 23:339-348 (2005).
Marlicz et al. Determination of chymotrypsin in the stool in the diagnosis of chronic pancreatitis. Wiadomosci lekarskie. 1988; 41(11):704-707. (in Polish with English abstract/summary).
Marsh. Neuropsychiatric aspects of Parkinson's disease. Psychosomatics. 2000; 41(1):15-23.
Martin, et al. A rapid and sensitive spectrophotometric method for the assay of chymotrypsin. Biol Chem. Feb. 1959;234(2):294-8.
Matikainen, et al. Autonomic dysfunction in long-standing alcoholism. Alcohol. 1986;21(1):69-73. Abstract only.
Maurin, et al. Cellular adaptation to amino acid availability: mechanisms involved in the regulation of gene expression. 2006; 319-326.
Mayo Clinic Staff. Autism. Retrieved from internet Mar. 10, 2008, http://www.mayoclinic.com/health/autism/DS00348DSECTION=2.
Mayo Clinic Staff. Bipolar disorder. Jan. 4, 2008, http://www.mayoclinic.com/health/bipolardisorder/DS00356/DSECTION=symptoms.
Mayo Clinic Staff. Obsessive-compulsive disorder. Dec. 21, 2006. http://www.preferredalternatives.org/lat/WellnessLibrary/anxiety&PanicDisorders/Obsessive-CompulsiveDisorder/Obsessive-CompulsiveDisorder-Mayoclinic.pdf.
Mayo Clinic Staff. Oppositional defiant disorder. Dec. 19, 2007, http://www.mayoclinic.com/health/oppositional-defiant-disorder/DS00630/DSECTION=symptoms.
McAlonan, et al. Brain anatomy and sensorimotor gating in Asperger's syndrome, ain. Jul. 2002;125(Pt 7):1594-606.
McCormack, et al. Localization of the disulfide bond involved in post-translational processing of glycosylasparaginase and disrupted by a mutation in the Finnish-type aspartylglycosaminuria. J Biol Chem. Feb. 17, 1995;270(7):3212-5.
McCracken, et al. Risperidone in children with autism and serious behavioral problems. N Engl J Med. Aug. 1, 2002;347(5):314-21.
Medori et al. Fatal Familial Insomnia, A Prion Disease With a Mutation at Condon 178 of the Prion Protein Case. N Engl J Med 326:444-449 (1992).
MedSafe. Data sheet for alpha-lactose, Jul. 21, 2008, http://www.medsafe.govt.nz/Profs/Datasheet/a/Alphalactulosesyrup.htm.
MedScape. Burden of Hypertension in the United States Greater Than Ever. www.medscape.com. Jul. 14, 2004.
Melmed, et al. Metabolic markers and gastrointestinal symptoms in children with autism and related disorders. J Pediatr Gast Nutr. 2000; 31:S31-S32. Abstract only.

(56) References Cited

OTHER PUBLICATIONS

Merck. Autism, Merck manual online medical library home addition, retrieved from the internet Mar. 10, 2008, http://www.mercl.com/mmhge/sec23/ch286/ch286b.html.
Merriam Webster Dictionary: definition of prevent.
Merriam-Webster 2014 "Definition: Precipitate" accessed from www.mirriam-webster.com on Sep. 22, 2014.
MeSH browser. "Child Development Disorders, Pervasive," and "Attention Deficit and Disruptive Behavior Disorders," National Library of medicine. 2001, http://www.nlm.nih.gov/mesh/2002/Mbrowser.html.
Meyer-Lindenberg, et al. Neural mechanisms in Williams syndrome: a unique window to genetic influences on cognition and behavior. Nat. Rev. Neurosci. 2006; 7(5):380-93.
Michael's Naturopathic Programs, Digestive Enzymes, Product #011161, Accessed on Jun. 10, 2016, online at: www.michaelshealth.com/retail/digestive-enzymes-659.html.
Michell et al. Biomarkers and Parkinson's disease. Brain. 2004; 127(8):1693-1705.
Millipore EMD catalog (online). Papain, unit definition, EMD Millipore Corp, 2013. Downloaded May 13, 2013.
Minamino, et al. Vascular cell senescence: contribution to atherosclerosis. Circ Res. Jan. 5, 2007;100(1):15-26.
Ming, et al. Autism spectrum disorders: concurrent clinical disorders. J Child Neurol. Jan. 2008;23(1):6-13.
Mitchell, et al. Comparative trial of viokase, pancreatin and Pancrease pancrelipase (enteric coated beads) in the treatment of malabsorption in cystic fibrosis. Aust Paediatr J. Jun. 1982;18(2):114-7.
Mitsui, et al. Role of aminopeptidases in the blood pressure regulation. Biological and Pharmaceutical Bulletin of Japan, Pharmaceutical Society of Japan. 2004; 27(6):768-771.
Mizutani, et al. Effects of placental proteases on maternal and fetal blood pressure in normal pregnancy and preeclampsia. Am J Hypertens. Jun. 1996;9(6):591-7.
Molinari et al., Fecal chymotrypsin and alastase-1 determination on one single stool collected at random: diagnostic value for exocrine pancreatic status. Clinical Biochemistry 37: 758-763 (2004).
Mononen, et al. Aspartylglycosaminuria in the Finnish population: identification of two point mutations in the heavy chain of glycoasparaginase. Proc Natl Acad Sci U S A. Apr. 1, 1991;88(7):2941-5.
Moretti, et al. Acute pancreatitis: hypertonic saline increases heat shock proteins 70 and 90 and reduces neutrophil infiltration in lung injury. Pancreas. Jul. 2009;38(5):507-14. Abstract only.
Mosqueira, et al. Chronic hypoxia impairs muscle function in the *Drosophila* model of Duchenne's muscular dystrophy (DMD). PLoS One. Oct. 20, 2010;5(10):e13450.
Munasinghe et al. Digestive enzyme supplementation for autism spectrum disorders: a double-blind randomized controlled trial. J Autism Dev Disord. Sep. 2010;40(9):1131-8.
Munesue, et al. High prevalence of bipolar disorder comorbidity in adolescents and young adults with high-functioning autism spectrum disorder: a preliminary study of 44 outpatients. Journal of Affective Disorders 111.2-3 (2008): 170-175.
Nachaegari et al. Coprocessed excipients for solid dosage forms. Pharmaceutical Technology. 2004; p. 52, 54, 56 ,58, 60, 64.
Nagamoto. Jacobson: Psychiatric Secrets, 2nd ed. 2001. Ch 28 Antipsychotic meds.
Nater et al., Determinants of the diurnal course of salivary alpha-amylase. Psychoneuroendocrinology 32: 392-401 (2007).
National Institutes of Health. Thin Bones Seen in Boys with Autism and Autism Spectrum Disorder. 3 pages (2008).
Naver.com entry for Rare Disease Information: Osteopenia—Osteopsathyrosis, Fragilitasossium, Fragilitasossium (accessed Sep. 25, 2019).
Neuer, et al. The role of heat shock proteins in reproduction. Hum Reprod Update. Mar.-Apr. 2000;6(2):149-59.
Nevo et al. Acute immune polyneuropathies: correlations of serum antibodies to Campylobacter jejuni and helicobacter pylori with anti-gm antibodies and clinical patterns of disease. J of Inf Diseases . 1997; 175(S2):S154-6.
Newhorizons. ADD/ADHD: New Perspectives on Attentional Priority Disorders. New Horizons for Learning. Jul. 15, 2008.
NIH, "Celiac Disease", National Digestive Diseases Information Clearinghouse: Bethesda, MD, 2008; 12 pages.
NIH. National Institutes of Health. National Diabetes Statistics 2007. diabetes.niddk.nih.gov. Jun. 1, 2008.
NINDS Guillain-Barre Syndrome Information Page, retrieved from the internet Sep. 15, 2009, http://www.ninds.nih.gov/disorders/gbs/gbs.htm.
NINDS Dysautonomia Information Page, retrieved from the internet Sep. 10, 2009, http://www.ninds.nih.gov/disorders/dysautonomia/dysautonomia.htm.
No Author. RSDSA, 2015: Telltale signs and symptoms of CRPS/RSD on the web at rsds.org/telltale-signs-and-symptoms-of-crpsrsd. [Accessed: Sep. 5, 2018].
Notice of allowance dated Jan. 2, 2014 for U.S. Appl. No. 13/204,881.
Notice of allowance dated Feb. 2, 2015 for U.S. Appl. No. 13/926,822.
Notice of Allowance dated Feb. 17, 2012 for U.S. Appl. No. 10/681,018.
Notice of allowance dated Feb. 20, 2015 for U.S. Appl. No. 12/386,051.
Notice of allowance dated Feb. 27, 2015 for U.S. Appl. No. 14/037,696.
Notice of allowance dated Mar. 1, 2016 for U.S. Appl. No. 14/087,930.
Notice of Allowance dated Mar. 21, 2012 for U.S. Appl. No. 12/487,864.
Notice of allowance dated Apr. 3, 2015 for U.S. Appl. No. 13/737,225.
Notice of allowance dated Apr. 10, 2015 for U.S. Appl. No. 13/144,290.
Notice of allowance dated Apr. 14, 2015 for U.S. Appl. No. 13/144,286.
Notice of Allowance dated Apr. 15, 2011 for U.S. Appl. No. 12/487,868.
Notice of allowance dated Apr. 22, 2016 for U.S. Appl. No. 14/528,715.
Notice of Allowance dated Apr. 29, 2011 for U.S. Appl. No. 12/046,402.
Notice of Allowance dated May 23, 2011 for U.S. Appl. No. 09/990,909.
Notice of Allowance dated May 29, 2013 for U.S. Appl. No. 13/481,087.
Notice of allowance dated Jun. 12, 2014 for U.S. Appl. No. 13/448,061.
Notice of Allowance dated Jun. 27, 2011 for U.S. Appl. No. 12/238,415.
Notice of Allowance dated Jun. 28, 2011 for U.S. Appl. No. 12/487,868.
Notice of Allowance dated Jun. 30, 2011 for U.S. Appl. No. 09/990,909.
Notice of Allowance dated Jul. 3, 2012 for U.S. Appl. No. 13/271,783.
Notice of Allowance dated Jul. 8, 2011 for U.S. Appl. No. 12/046,402.
Notice of Allowance dated Aug. 8, 2011 for U.S. Appl. No. 12/426,794.
Notice of allowance dated Aug. 11, 2014 for U.S. Appl. No. 13/193,346.
Notice of allowance dated Aug. 19, 2013 for U.S. Appl. No. 13/208,963.
Notice of allowance dated Aug. 30, 2013 for U.S. Appl. No. 12/047,818.
Notice of allowance dated Sep. 9, 2015 for U.S. Appl. No. 13/193,346.
Notice of allowance dated Sep. 15, 2014 for U.S. Appl. No. 14/037,652.
Notice of Allowance dated Sep. 20, 2011 for U.S. Appl. No. 12/283,090.
Notice of allowance dated Oct. 29, 2013 for U.S. Appl. No. 13/204,881.
Notice of allowance dated Nov. 16, 2015 for U.S. Appl. No. 14/493,734.
Notice of allowance dated Dec. 23, 2014 for U.S. Appl. No. 14/007,793.

(56) References Cited

OTHER PUBLICATIONS

Notice of allowance dated Dec. 23, 2015 for U.S. Appl. No. 12/493,122.
O'Connell. Hypertension Guide, cmbi.bjmu.edu. Jul. 14, 2008.
Office action dated Jan. 12, 2012 for U.S. Appl. No. 12/047,818.
Office action dated Jan. 15, 2014 for U.S. Appl. No. 13/836,135.
Office action dated Jan. 15, 2016 for U.S. Appl. No. 13/502,989.
Office action dated Jan. 16, 2014 for U.S. Appl. No. 12/046,252.
Office action dated Jan. 16, 2015 for U.S. Appl. No. 12/535,676.
Office action dated Jan. 22, 2013 for U.S. Appl. No. 13/562,999.
Office action dated Jan. 24, 2014 for U.S. Appl. No. 12/054,343.
Office action dated Jan. 24, 2014 for U.S. Appl. No. 12/786,739.
Office action dated Jan. 25, 2013 for U.S. Appl. No. 13/208,963.
Office action dated Jan. 26, 2016 for U.S. Appl. No. 12/054,343.
Office action dated Jan. 29, 2016 for U.S. Appl. No. 12/786,739.
Office Action dated Feb. 1, 2012 for U.S. Appl. No. 12/493,122.
Office action dated Feb. 1, 2016 for U.S. Appl. No. 13/503,844.
Office action dated Feb. 14, 2013 for U.S. Appl. No. 13/193,346.
Office action dated Feb. 14, 2013 for U.S. Appl. No. 13/407,408.
Office action dated Feb. 17, 2016 for U.S. Appl. No. 14/713,178.
Office action dated Feb. 21, 2013 for U.S. Appl. No. 12/047,818.
Office action dated Feb. 26, 2016 for U.S. Appl. No. 12/535,676.
Office action dated Mar. 2, 2016 for U.S. Appl. No. 14/693,711.
Office Action dated Mar. 5, 2012 for U.S. Appl. No. 12/535,676.
Office action dated Mar. 5, 2013 for U.S. Appl. No. 12/493,122.
Office action dated Mar. 6, 2015 for U.S. Appl. No. 13/757,412.
Office action dated Mar. 11, 2014 for U.S. Appl. No. 11/533,818.
Office Action dated Mar. 19, 2012 for U.S. Appl. No. 13/204,881.
Office action dated Mar. 22, 2016 for U.S. Appl. No. 13/733,873.
Office Action dated Mar. 23, 2012 for U.S. Appl. No. 13/271,783.
Office Action dated Mar. 29, 2011 for U.S. Appl. No. 12/054,343.
Office Action dated Mar. 30, 2011 for U.S. Appl. No. 12/786,739.
Office action dated Mar. 30, 2016 for U.S. Appl. No. 14/296,091.
Office action dated Apr. 4, 2016 for U.S. Appl. No. 13/313,629.
Office Action dated Apr. 5, 2012 for U.S. Appl. No. 11/555,697.
Office action dated Apr. 5, 2016 for U.S. Appl. No. 14/713,242.
Office action dated Apr. 6, 2015 for U.S. Appl. No. 14/493,734.
Office action dated Apr. 6, 2016 for U.S. Appl. No. 13/313,708.
Office Action dated Apr. 9, 2012 for U.S. Appl. No. 13/208,963.
Office action dated Apr. 10, 2014 for U.S. Appl. No. 13/502,989.
Office action dated Apr. 13, 2016 for U.S. Appl. No. 14/612,604.
Office action dated Apr. 16, 2014 for U.S. Appl. No. 13/705,763.
Office action dated Apr. 21, 2015 for U.S. Appl. No. 13/660,642.
Office action dated Apr. 21, 2015 for U.S. Appl. No. 14/087,930.
Office action dated Apr. 22, 2015 for U.S. Appl. No. 13/836,135.
Office action dated Apr. 24, 2015 for U.S. Appl. No. 12/786,739.
Office Action dated Apr. 27, 2011 for U.S. Appl. No. 10/681,018.
Office action dated Apr. 27, 2015 for U.S. Appl. No. 12/054,343.
Office Action dated Apr. 28, 2011 for U.S. Appl. No. 12/283,090.
Office action dated May 6, 2015 for U.S. Appl. No. 12/493,122.
Office action dated May 7, 2015 for U.S. Appl. No. 13/705,763.
Office action dated May 9, 2013 for U.S. Appl. No. 13/204,881.
Office action dated May 12, 2014 for U.S. Appl. No. 13/733,873.
Office action dated May 13, 2014 for U.S. Appl. No. 13/313,629.
Office action dated May 15, 2013 for U.S. Appl. No. 13/502,989.
Office action dated May 15, 2014 for U.S. Appl. No. 13/448,061.
Office action dated May 16, 2014 for U.S. Appl. No. 13/313,708.
Office Action dated May 24, 2011 for U.S. Appl. No. 12/487,864.
Office action dated May 27, 2015 for U.S. Appl. No. 13/502,989.
Office action dated Jun. 3, 2015 for U.S. Appl. No. 13/002,136.
Office action dated Jun. 13, 2012 for U.S. Appl. No. 12/493,122.
Office action dated Jun. 17, 2014 for U.S. Appl. No. 13/737,225.
Office action dated Jun. 17, 2014 for U.S. Appl. No. 13/757,412.
Office action dated Jun. 19, 2014 for U.S. Appl. No. 12/386,051.
Office action dated Jun. 25, 2013 for U.S. Appl. No. 13/144,286.
Office action dated Jun. 25, 2013 for U.S. Appl. No. 13/144,290.
Office action dated Jun. 27, 2012 for U.S. Appl. No. 12/493,147.
Office action dated Jun. 27, 2014 for U.S. Appl. No. 14/007,793.
Office action dated Jun. 29, 2011 for U.S. Appl. No. 11/555,697.
Office action dated Jul. 7, 2014 for U.S. Appl. No. 12/535,676.
Office action dated Jul. 11, 2012 for U.S. Appl. No. 12/573,353.
Office action dated Jul. 15, 2013 for U.S. Appl. No. 13/002,136.
Office action dated Jul. 17, 2015 for U.S. Appl. No. 13/733,873.
Office action dated Jul. 18, 2012 for U.S. Appl. No. 12/047,818.
Office action dated Jul. 31, 2013 for U.S. Appl. No. 13/757,412.
Office action dated Aug. 2, 2013 for U.S. Appl. No. 12/535,676.
Office action dated Aug. 7, 2014 for U.S. Appl. No. 13/836,135.
Office action dated Aug. 13, 2012 for U.S. Appl. No. 13/208,963.
Office action dated Aug. 14, 2013 for U.S. Appl. No. 13/448,061.
Office action dated Aug. 28, 2013 for U.S. Appl. No. 13/313,629.
Office action dated Aug. 29, 2014 for U.S. Appl. No. 13/144,286.
Office action dated Aug. 31, 2015 for U.S. Appl. No. 12/535,676.
Office action dated Sep. 8, 2015 for U.S. Appl. No. 11/533,818.
Office action dated Sep. 9, 2013 for U.S. Appl. No. 13/502,989.
Office action dated Sep. 10, 2015 for U.S. Appl. No. 13/313,629.
Office action dated Sep. 11, 2015 for U.S. Appl. No. 13/313,708.
Office action dated Sep. 13, 2012 for U.S. Appl. No. 13/481,087.
Office action dated Sep. 18, 2014 for U.S. Appl. No. 13/502,989.
Office action dated Sep. 19, 2014 for U.S. Appl. No. 11/533,818.
Office action dated Sep. 19, 2014 for U.S. Appl. No. 13/737,225.
Office action dated Sep. 30, 2014 for U.S. Appl. No. 13/144,290.
Office action dated Sep. 30, 2014 for U.S. Appl. No. 13/660,642.
Office action dated Oct. 2, 2014 for U.S. Appl. No. 12/054,343.
Office action dated Oct. 6, 2014 for U.S. Appl. No. 12/493,122.
Office action dated Oct. 9, 2014 for U.S. Appl. No. 12/786,739.
Office Action dated Oct. 1, 2001 for U.S. Appl. No. 09/466,559.
Office action dated Oct. 10, 2012 for U.S. Appl. No. 13/204,881.
Office action dated Oct. 19, 2011 for U.S. Appl. No. 12/386,051.
Office action dated Oct. 24, 2013 for U.S. Appl. No. 13/313,708.
Office action dated Oct. 25, 2012 for U.S. Appl. No. 13/144,286.
Office action dated Oct. 25, 2012 for U.S. Appl. No. 13/144,290.
Office action dated Oct. 30, 2015 for U.S. Appl. No. 14/528,715.
Office Action dated Oct. 5, 2010 for U.S. Appl. No. 12/046,402.
Office action dated Nov. 7, 2014 for U.S. Appl. No. 13/705,763.
Office Action dated Nov. 14, 2007 for U.S. Appl. No. 11/213,255.
Office Action dated Nov. 15, 2010 for U.S. Appl. No. 12/238,415.
Office action dated Nov. 16, 2015 for U.S. Appl. No. 13/705,763.
Office action dated Nov. 19, 2015 for U.S. Appl. No. 14/713,242.
Office action dated Nov. 20, 2015 for U.S. Appl. No. 14/296,091.
Office action dated Nov. 20, 2015 for U.S. Appl. No. 14/612,604.
Office action dated Nov. 21, 2014 for U.S. Appl. No. 13/926,822.
Office Action dated Nov. 25, 2009 for U.S. Appl. No. 11/232,180.
Office Action dated Nov. 26, 2001 for U.S. Appl. No. 09/466,559.
Office action dated Nov. 29, 2013 for U.S. Appl. No. 13/193,346.
Office action dated Dec. 6, 2012 for U.S. Appl. No. 13/002,136.
Office action dated Dec. 10, 2013 for U.S. Appl. No. 13/407,408.
Office action dated Dec. 10, 2015 for U.S. Appl. No. 13/836,135.
Office Action dated Jan. 21, 2011 for U.S. Appl. No. 12/386,051.
Office action dated Dec. 12, 2013 for U.S. Appl. No. 13/144,286.
Office action dated Dec. 13, 2013 for U.S. Appl. No. 12/493,122.
Office action dated Dec. 13, 2013 for U.S. Appl. No. 13/144,290.
Office action dated Dec. 15, 2011 for U.S. Appl. No. 12/493,147.
Office action dated Dec. 15, 2015 for U.S. Appl. No. 14/087,930.
Office action dated Dec. 16, 2013 for U.S. Appl. No. 12/535,676.
Office action dated Dec. 18, 2014 for U.S. Appl. No. 14/037,696.
Office action dated Dec. 18, 2015 for U.S. Appl. No. 14/640,385.
Office Action dated Dec. 19, 2005 for U.S. Appl. No. 10/730,567.
Office action dated Dec. 19, 2014 for U.S. Appl. No. 13/733,873.
Office Action dated Dec. 22, 2006 for U.S. Appl. No. 10/681,018.
Office action dated Dec. 24, 2015 for U.S. Appl. No. 13/757,412.
Office Action dated Jan. 29, 2002 for U.S. Appl. No. 09/707,395.
Office Action dated Jan. 8, 2010 for U.S. Appl. No. 10/681,018.
Office Action dated Mar. 18, 2008 for U.S. Appl. No. 11/468,379.
Office Action dated Mar. 25, 2008 for U.S. Appl. No. 11/213,382.
Office Action dated Mar. 28, 2008 for U.S. Appl. No. 11/555,697.
Office Action dated Apr. 12, 2010 for U.S. Appl. No. 09/990,909.
Office Action dated Apr. 21, 2008 for U.S. Appl. No. 11/232,180.
Office Action dated Apr. 22, 2003 for U.S. Appl. No. 09/929,592.
Office Action dated May 22, 2002 for U.S. Appl. No. 09/466,559.
Office Action dated Jun. 30, 2004 for U.S. Appl. No. 10/730,567.
Office Action dated Jul. 22, 2010 for U.S. Appl. No. 12/049,613.
Office Action dated Jul. 29, 2003 for U.S. Appl. No. 09/990,909.
Office Action dated Jul. 30, 2002 for U.S. Appl. No. 09/707,395.

(56) References Cited

OTHER PUBLICATIONS

Office Action dated Jul. 30, 2002 for U.S. Appl. No. 09/990,909.
Office Action dated Jul. 6, 2010 for U.S. Appl. No. 11/533,818.
Office Action dated Aug. 13, 2002 for U.S. Appl. No. 09/929,592.
Office Action dated Aug. 18, 2008 for U.S. Appl. No. 10/681,018.
Office Action dated Aug. 18, 2010 for U.S. Appl. No. 10/681,018.
Office Action dated Aug. 20, 2010 for U.S. Appl. No. 12/283,090.
Office Action dated Aug. 25, 2010 for U.S. Appl. No. 12/487,868.
Office Action dated Aug. 26, 2003 for U.S. Appl. No. 10/041,073.
Office Action dated Aug. 3, 2009 for U.S. Appl. No. 11/555,697.
Office Action dated Aug. 7, 2007 for U.S. Appl. No. 10/681,018.
Office Action dated Aug. 8, 2007 for U.S. Appl. No. 11/213,382.
Office Action dated Sep. 22, 2004 for U.S. Appl. No. 10/730,567.
Office Action dated Sep. 24, 2009 for U.S. Appl. No. 12/046,252.
Office Action Mailed May 11, 2016 U.S. Appl. No. 14/713,242.
Okahata, et al. Lipid-coated enzymes as efficient catalysts in organic media. Trends in Biotechnology. 1997; 15(2):50-54.
O'Keefe, Stephen J.D. et al. The Exacerbation of Pancreatic Endocrine Dysfunction by Potent Pancreatic Exocrine Supplements in Patients with Chronic Pancreatitis. J. Clin. Gastroenterol. 32(4):319-323 (2001).
Olivar-Parra, et al. Training referential communicative skills to individuals with autism spectrum disorder: a pilot study. Psychological Reports. 2011; 109:921-939.
Owley, et al. Multisite, double-blind, placebo-controlled trial of porcine secretin in autism. J Am Acad Child Adolesc Psychiatry. Nov. 2001;40(11):1293-9.
Pancrease. Patient information leaflet. Pancrease HL Capsules. Last updated Apr. 30, 2013. Janssen-cilag LTD. www.medicines.org.uk/EMC/medicine/7326.
Pancreatic Enzyme Concentrate (PEC) Undiluted, Technical Data Sheet. 1 page, Scientific Protein Laboratories LLC Jun. 13, 2005.
Pancreatin 4X USP, Technical Data Sheet, 1 page, Scientific Protein laboratories LLC Jun. 13, 2005.
Pancreatin 8X USP Powder. Product Specification. Jul. 2000. In: Product Manual. American Laboratories Incorporated. Omaha, NE. p. 1.
Parisi et al. Evaluation of new rapid commercial enzyme immunoassay for detection of Crytosporidium oocysts in untreated stool specimens. J Clin Microbiol. 1995; 33(7):1963-1965.
Park, et al. Increased apoptosis in cystinotic fibroblasts and renal proximal tubule epithelial cells results from cysteinylation of protein kinase Cdelta. J Am Soc Nephrol. Nov. 2006;17(11):3167-75.
Parkinsons Disease Foundation. Parkinson's Disease Q&A. 2007. 1-44.
Parkinsons Disease Foundation. Ten Frequently-Asked Questions about Parkinson's Disease. 2006.
Parracho, et al. Differences between the gut microflora of children with autistic spectrum disorders and that of healthy children. J Med Microbiol. Oct. 2005;54(Pt 10):987-91.
Patel, et al. Formulation and evaluation of mucoadhesive glipizide microspheres. AAPS PharmSciTech. 2005; 6(1):E49-E55.
PDTALKS. Motivational & Inspirational Speaking From a Parkinson's Patient Perspective. pdtalks.com/Parkinson_s_Disease.html. Jul. 14, 2008.
Perman et al. Role of pH in production of hydrogen from carbohydrates by colonic bacterial flora. J Clin Invest. 1981; 24(4):684-685.
Persico, et al. Searching for ways out of the autism maze: genetic, epigenetic and environmental clues. Trends Neurosci. Jul. 2006;29(7):349-58.
Peters et al. Prevalence of enteric parasites in homosexual patients attending an outpatient clinic. J of Clin Micro. 1986; 24(4):684-685.
Peters, et al. Treatment of alcoholic polyneuropathy with vitamin B complex: a randomised controlled trial. Alcohol. Nov.-Dec. 2006;41(6):636-42. Epub Aug. 21, 2006.
Petrolatum: Pharmaceutical Excipients. London: Pharmaceutical Press. 2006. 1-6.
Pisani, et al. Levodopa-induced dyskinesia and striatal signaling pathways. Proc Natl Acad Sci U S A. Mar. 3, 2009;106(9):2973-4. Epub Feb. 26, 2009.
Polanczyk, et al. The worldwide prevalence of ADHD: a systematic review and metaregression analysis. Am J Psychiatry. Jun. 2007;164(6):942-8.
Ponsky, et al. Alterations in gastrointestinal physiology after Roux-en-Y gastric bypass. J Am Coll Surg. Jul. 2005;201(1):125-31.
Proesmans, Marijke et al. Omeprazole, a proton pump inhibitor, improves residual steatorrhoea in cystic fibrosis patients treated with high dose pancreatic enzymes. European Journal of Pediatrics 162(11): 760-763 (Nov. 2003).
Puri, et al. Isolated segmental duodenal ganglionosis. Indian Journal of Radiology and Imaging. 2000; 153-154.
Qi, et al. Solubility and emulsifying properties of soy protein isolates modified by pancreatin. Journal of Food Science 62.6 (1997): 1110-1115.
Raimondo, et al. Rapid endoscopic secretin simulation test and discrimination of chronic pancreatitis and pancreatic cancer from disease controls. Clin Gastroenterol Hepatol. Sep. 2003;1(5):397-403.
Rajakumar, et al. Proteasomal activity in placentas from women with preeclampsia and intrauterine growth restriction: implications for expression of HIF-alpha proteins. Placenta. Mar. 2008;29(3):290-9. Epub Jan. 28, 2008.
Rakonczay, et al. A new severe acute necrotizing pancreatitis model induced by L-ornithine in rats. Grit Care Med. Jul. 2008;36(7):2117-27.
Ray, et al. Growth factor regulation of enterocyte nutrient transport during intestinal adaptation. Am J Surg. Apr. 2002;183(4):361-71.
Reeves, G et al. Pharmacological Management of Attention-deficit hyperactivity disorder, Expert Opinion on Pharmacotherapy, 5:6; 1313-1320. (Feb. 25, 2005)DOI: 10.1517/14656566.5.6.1313 http://dx.doi.org/10.1517/14656566.5.6.1313.
Regan, et al. Comparative effects of antacids, cimetidine and enteric coating on the therapeutic response to oral enzymes in severe pancreatic insufficiency. N Engl J Med. Oct. 20, 1977;297(16):854-8.
Remtulla et al. Stool chymotrypsin activity measured by a spectrophotometric procedure to identify pancreatic disease in infants. Clinical Biochemistry. Dec. 1986; 19:341-342.
REVOLUTION health. Enzyme therapy, revolutionhealth.com/drugs-treatments/enzyme-therapy. Sep. 2, 2008.
Richards, et al. Diagnosis, management, and treatment of Alzheimer disease: a guide for the internist. Arch Intern Med. Apr. 26, 1999;159(8):789-98.
Rider, et al. Perspective of biochemical research in the neuronal ceroid-lipofuscinosis. Am J Med Genet. Feb. 15, 1992;42(4):519-24.
Riedel, L et al. Limitations of faecal chymotrypsin as a screening test for chronic pancreatitis. Gut, 32:321-324(1991).
Rogers. No more heartburn: Stop the pain in 30 days—naturally. 2000; 172.
Rottier, et al. Lack of PPCA expression only partially coincides with lysosomal storage in galactosialidosis mice: indirect evidence for spatial requirement of the catalytic rather than the protective function of PPCA. Hum Mol Genet. Oct. 1998;7(11):1787-94.
Roxas, et al. Colds and influenza: a review of diagnosis and conventional, botanical, and nutritional considerations. Alternative Medicine Review. 2007; 12(1):25-48.
Rubenstein, et al. Model of autism: increased ratio of excitation/inhibition in key neural systems. Genes Brain Behav. Oct. 2003;2(5):255-67.
Rudell, et al. The anterior piriform cortex is sufficient for detecting depletion of an indispensable amino acid, showing independent cortical sensory function. J Neurosci. Feb. 2, 2011;31(5):1583-90. Abstract only.
Sabra, et al. Linkage of ileal-lymphoid-nodular hyperplasia (ILNH), food allergy and CNS developmental: evidence for a non-IgE association. Ann Aller Asth Immunol. 1999; 82(1):81. Abstract only.
Sahelian. Enzymes, raysahelian.com/enzymes.html. Sep. 2, 2008.
Salpekar, et al. Bipolar Spectrum Disorder Comorbid With Autism Spectrum Disorder; NADD Bulletin, vol. X, 2007. No. 6, Article 1,

(56) References Cited

OTHER PUBLICATIONS pp. 1-5, downloaded from http://www.thenadd.org/nadd-bulletin/archive/volunne-x/ on Dec. 11, 2018.
Sandler, et al. Lack of benefit of a single dose of synthetic human secretin in the treatment of autism and pervasive developmental disorder. N Engl J Med. Dec. 9, 1999;341(24):1801-6.
Sandler et al. Short term benefit from oral vancomycin treatment of regressive-onset autism. J of Child Neuro. 2000; 15(7):42-435.
Schafer, et al. Stress kinases and heat shock proteins in the pancreas: possible roles in normal function and disease. J Gastroenterol. 2000;35(1):1-9.
Schiller. Review article: the therapy of constipation. Aliment Pharmacol Ther. 2001; 15:749-763.
Schizophreniform disorder. Merck Manuals Online Medical Library. Nov. 2005. (in Japanese with English translation).
Schlessingerman, Mass of an Adult. The Physics Factbook (2003).
Schneider, et al. Oral human immunoglobulin for children with autism and gastrointestinal dysfunction: a prospective, open-label study. J Autism Dev Disord. Nov. 2006;36(8):1053-64.
Schreck et al. Food preferences and factors influencing food selectivity for children with autism spectrum disorders. Res Develop Disabil. 2006; 27:353-363.
Schumann. Medical, nutritional and technological properties of lactulose. An update. Eur J Nutr. Nov. 2002;41 Suppl 1:117-25.
Seltzer, et al. The Symptoms of Autism Spectrum Disorders in Adolescence and Adulthood. Journal of Autism and Developmental Disorders. 2003; 33(6):565-581.
Seneca et al. Enhancement of brain l-dopa concentration with a-chymotrypsin. J American Geriatrics Society. 1973; 256-258. Abstract only.
Serna, et al. Pathogenesis and treatment of Shiga toxin-producing Escherichia coli infections. Curr Opin Gastroenterol. Jan. 2008;24(1):38-47.
Settembre, et al. A block of autophagy in lysosomal storage disorders. Hum Mol Genet. Jan. 1, 2008;17(1):119-29.
Shadel. Expression and maintenance of mitochondrial DNA: new insights into human disease pathology. Am J Pathol. Jun. 2008;172(6):1445-56.
Shaul. Report to the Chairman and Ranking Minority Member, Subcommittee on Human Rights and Wellness, Committee on Government Reform, House of Representatives. GEO. Jan. 2005. 1-40.
Shelby, et al. Enzymatic debridement with activated whole pancreas. American Journal of Surgery. Oct. 1958; 96(4):545-549.
Sherwood et al. A new class of high-functionality excipients: silicified microcrystalline cellulose. Pharm Tech. 1998; 22(10):78-88.
Sherwood, et al. Activation of trypsinogen in large endocytic vacuoles of pancreatic acinar cells. Proc Natl Acad Sci U S A. Mar. 27, 2007;104(13):5674-9.
Shimabukuro, et al. Medical expenditures for children with an autism spectrum disorder in a privately insured population. J Autism Dev Disord. 2007;38(3):546-52.
Shpacovitch, et al. Protease-activated receptors: novel PARtners in innate immunity. Trends Immunol. Dec. 2007;28(12):541-50.
Shpacovitch, et al. Role of protease-activated receptors in inflammatory responses, innate and adaptive immunity. J Leukoc Biol. Jun. 2008;83(6):1309-22.
Sienaert, et al. Evidence-based treatment strategies for treatment-resistant bipolar depression: a systematic review. Bipolar Disord. Feb. 2013;15(1):61-9. doi: 10.1111/bdi.12026. Epub Nov. 27, 2012.
Sillanaukee, et al. Improved diagnostic classification of alcohol abusers by combining carbohydrate-deficient transferrin and gamma-glutamyltransferase. Clin Chem. Apr. 2001;47(4):681-5.
Simonoff, et al. Psychiatric disorders in children with autism spectrum disorders: prevalence, comorbidity, and associated factors in a population-derived sample. J Am Acad Child Adolesc Psychiatry. Aug. 2008;47(8):921-9.
Singh et al. Past, Present, and Future Technologies for Oral Delivery of Therapeutic Proteins. J Pham Sci 97(7):2497-2523 (2008).
Singh, et al. Plasma increase of interleukin-12 and interferon-gamma. Pathological significance in autism. J Neuroimmunol. May 1996;66(1-2):143-5.
Skeels et al. Crytosporidium infection in Oregon public health clinic patients 1985-88: the value of statewide laboratory surveillance. AJPH. 1990; 80(3):305-308.
Skinner, et al. Treatment of Prion Disease with Heterologous Prion Proteins. PLoS One. Jul. 2, 2015;10(7):e0131993. doi: 10.1371/journal.pone.0131993. eCollection 2015.
Smith, et al. Fecal chymotrypsin and trypsin determinations. Canadian Medical Association Journal. 1971; 104(8):691-4 and 697.
Sousa, et al. Polymorphisms in leucine-rich repeat genes are associated with autism spectrum disorder susceptibility in populations of European ancestry. Mol Autism. Mar. 25, 2010;1(1):7.
Statemaster. Number of Children with Autism (most recent) by state. Statemaster.com Jul. 14, 2008.
Statemaster. Number of Children with Autism (most recent w/graph) by state. Statemaster.com Jul. 14, 2003.
Statemaster. Number of Children with Autism (per capita)(most recent) by state. Statemaster.com Jul. 14, 2003.
Stein, et al. Nitrogen metabolism in normal and hyperkinetic boys. Am J Clin Nutr. Apr. 1984;39(4):520-4.
Steinherz, et al. Patterns of amino acid efflux from isolated normal and cystinotic human leucocyte lysosomes. J Biol Chem. Jun. 10, 1982;257(11):6041-9.
Sternby, et al. Carboxyl Ester Lipase (Bile Salt-Stimulated Lipase), Colipase, Lipase, and Phospholipase A2 Levels in Pancreatic Enzyme Supplements, 1997, Scandinavian Journal of Gastroenterology 32(3): 261-267.
Stoll, et al. Enteral nutrient intake level determines intestinal protein synthesis and accretion rates in neonatal pigs. Am J Physiol Gastrointest Liver Physiol. Aug. 2000;279(2):G288-94.
Stott, et al. MMR and Autism in Perspective: the Denmark Story. J. Am Phys Surg. 2004; 9(3):89-91.
Strader, et al. Structural basis of ß-adrenergic receptor function. FASEB J. May 1989;3(7):1825-32.
Sturmey. Secretin is an ineffective treatment for pervasive developmental disabilities: a review of 15 double-blind randomized controlled trials. Res Dev Disabil. Jan.-Feb. 2005;26(1):87-97.
Sundstrom, et al. A deadly prion disease: fatal familial insomnia. J Neurosci Nurs. Dec. 2003;35(6):300-5. Abstract only.
Swayne, et al. Pathobiology of H5N2 Mexican avian influenza virus infections of chickens. Vet Pathol. Nov. 1997;34(6):557-67.
Tager-Flusberg, et al. Language disorders: autism and other pervasive developmental disorders. Pediatr Clin North Am. Jun. 2007;54(3):469-81, vi.
TAMARO. Vitamin K deficiency as a cause of autistic symptoms. Http://web.archive.org/web/20090612022246/http://www.gutresearch.com/VitaminK.pdf. Published Jun. 12, 2009 as per Wayback Engine.
Terrie, et al. Understanding Pancreatic Enzyme Products. Dec. 15, 2008.
The Alzheimer's Association. Basics of Alzheimer's Disease. 2005, 32 pages. http://www.alz.org/national/documents/brochure_Basicsofalz_low/pdf.
TheFreeDictionary. Term Sprinkles. Www.thefreedictionary.com. Accessed Nov. 2, 2011. 1 page.
Therapeutic research center. Approved Pancreatic Enzyme Products. Pharmacist's Letter/Prescriber's Letter 2010. Oct. 2010. 1-3.
Thomas, Bipolar Disorder-Balancing Moods by Balancing Nutrients; What Doctors Don't Tell You. 14)7): 1-13 (2003).
Thomas, et al. Defective protein folding as a basis of human disease. Trends Biochem Sci. Nov. 1995;20(11):456-9.
Tiedermann, et al. Identification of a potent natural triterpenoid inhibitor of proteosome chymotrypsin-like activity and NF-kappaB with antimyeloma activity in vitro and in vivo. Blood. Apr. 23, 2009;113(17):4027-37.
Torrente, et al. Focal-enhanced gastritis in regressive autism with features distinct from Crohn's and Helicobacter pylori gastritis. Am J Gastroenterol. Apr. 2004;99(4):598-605.
Torrente, et al. Small intestinal enteropathy with epithelial IgG and complement deposition in children with regressive autism. Mol Psychiatry. 2002;7(4):375-82, 334.

(56) References Cited

OTHER PUBLICATIONS

Tran, et al. Treatment of complex regional pain syndrome: a review of the evidence. Can J Anaesth. Feb. 2010;57(2):149-66.
Trauner, et al. Specific cognitive deficits in young children with cystinosis: evidence for an early effect of the cystinosin gene on neural function. J Pediatr. Aug. 2007;151(2):192-6.
Troy. Pancreatic Enzymes. Remington: The Science and Practice of Pharmacy, 21st edition. Lippincot Williams & Wilkins, 2006. p. 1304.
Tsan, et al. Heat shock proteins and immune system. J Leukoc Biol. Jun. 2009;85(6):905-10.
Tsang et al. Extragastroduodenal conditions associated with Helicobacter pylori infection. Hong Kong Medical Journal. 1999; 5(2):169-174.
Types of Fats, Healthwise-Mich Med, pp. 1-2, downloaded from https://www/uofmhealth.org/health-library/aa160619 on Feb. 3, 2021.
Uhlmann, et al. Potential viral pathogenic mechanism for new variant inflammatory bowel disease. Mol Pathol. Apr. 2002;55(2):84-90.
Ultresa—FDA Prescribing Information Side Effects and Uses. Revised Sep. 2014.
Ultresa. Highlights of prescribing information. Aptalis Pharma US Inc. Revised Mar. 2012.
Unis, et al. A randomized, double-blind, placebo-controlled trial of porcine versus synthetic secretin for reducing symptoms of autism. J Am Acad Child Adolesc Psychiatry. Nov. 2002;41(11):1315-21.
UPI. Number of autistic Calif, students triples. United Press International. Jul. 12, 2008.
U.S. Appl. No. 11/533,818 Final Office Action dated Jun. 7, 2016.
U.S. Appl. No. 12/054,343 Final Office Action dated May 10, 2017.
U.S. Appl. No. 12/054,343 Non-Final Office Action dated Dec. 26, 2017.
U.S. Appl. No. 12/054,343 Office Action dated Aug. 19, 2016.
U.S. Appl. No. 12/535,676 Non-Final Office Action dated Apr. 21, 2017.
U.S. Appl. No. 12/535,676 Non-Final Office Action dated Sep. 6, 2018.
U.S. Appl. No. 12/535,676 Office Action dated Sep. 13, 2016.
U.S. Appl. No. 12/786,739 Final Office Action dated Jun. 23, 2017.
U.S. Appl. No. 12/786,739 Final Office Action dated Sep. 25, 2018.
U.S. Appl. No. 12/786,739 Non-Final Office Action dated Jan. 4, 2018.
U.S. Appl. No. 12/786,739 Office Action dated Sep. 20, 2016.
U.S. Appl. No. 13/002,136 Advisory Office Action dated Jul. 9, 2018.
U.S. Appl. No. 13/002,136 Final Office Action dated Sep. 11, 2020.
U.S. Appl. No. 13/002,136 Final Office Action dated Jan. 8, 2018.
U.S. Appl. No. 13/002,136 Final Office Action dated Jun. 24, 2016.
U.S. Appl. No. 13/002,136 Non-Final Office Action dated Dec. 18, 2018.
U.S. Appl. No. 13/002,136 Non-Final Office Action dated Feb. 27, 2017.
U.S. Appl. No. 13/002,136 Notice of Allowance dated Feb. 24, 2021.
U.S. Appl. No. 13/193,346 Notice of Allowability dated Jul. 14, 2016.
U.S. Appl. No. 13/193,346 Notice of Allowability dated Jun. 2, 2016.
U.S. Appl. No. 13/313,629 Notice of Allowance dated Dec. 22, 2016.
U.S. Appl. No. 13/313,708 Notice of Allowance dated Dec. 15, 2016.
U.S. Appl. No. 13/502,989 Notice of Allowance dated Aug. 10, 2016.
U.S. Appl. No. 13/503,844 Final Office Action dated Nov. 30, 2017.
U.S. Appl. No. 13/503,844 Office Action dated Aug. 25, 2016.
U.S. Appl. No. 13/503,844 Office Action dated Mar. 27, 2017.
U.S. Appl. No. 13/705,763 Final Office Action dated May 24, 2016.
U.S. Appl. No. 13/733,873 Final Office Action dated Feb. 6, 2020.
U.S. Appl. No. 13/733,873 Final Office Action dated Feb. 21, 2018.
U.S. Appl. No. 13/733,873 Non-Final Office Action dated May 25, 2017.
U.S. Appl. No. 13/757,412 Final Office Action dated Dec. 22, 2020.
U.S. Appl. No. 13/757,412 Final Office Action dated Jun. 30, 2016.
U.S. Appl. No. 13/757,412 Final Office Action dated Sep. 12, 2017.
U.S. Appl. No. 13/757,412 Office Action dated Apr. 16, 2019.
U.S. Appl. No. 13/757,412 Office Action dated Feb. 10, 2017.
U.S. Appl. No. 13/836,135 Final Office Action dated Dec. 14, 2018.
U.S. Appl. No. 13/836,135 Final Office Action dated May 15, 2017.
U.S. Appl. No. 13/836,135 Non-Final Office Action dated Mar. 15, 2018.
U.S. Appl. No. 13/836,135 Notice of Allowance dated Apr. 25, 2019.
U.S. Appl. No. 13/836,135 Office Action dated Jul. 22, 2016.
U.S. Appl. No. 14/296,091 Final Office Action dated Aug. 23, 2017.
U.S. Appl. No. 14/296,091 Final Office Action dated Jan. 3, 2017.
U.S. Appl. No. 14/296,091 Final Office Action dated Oct. 1, 2018.
U.S. Appl. No. 14/296,091 Non-Final Office Action dated Mar. 22, 2018.
U.S. Appl. No. 14/612,580 Final Office Action dated Aug. 10, 2017.
U.S. Appl. No. 14/612,580 Notice of Allowability dated Mar. 1, 2018.
U.S. Appl. No. 14/612,580 Notice of Allowance dated Jan. 12, 2018.
U.S. Appl. No. 14/612,580 Office Action dated Sep. 21, 2016.
U.S. Appl. No. 14/612,604 Notice of Allowance dated Jul. 20, 2016.
U.S. Appl. No. 14/639,425 Notice of Allowance dated Mar. 10, 2017.
U.S. Appl. No. 14/639,425 Office Action dated Jul. 14, 2016.
U.S. Appl. No. 14/640,385 Supplemental Notice of Allowability dated May 26, 2016.
U.S. Appl. No. 14/693,711 Final Office Action dated Dec. 15, 2016.
U.S. Appl. No. 14/693,711 Notice of Allowability dated May 26, 2017.
U.S. Appl. No. 14/693,711 Notice of Allowance dated Apr. 21, 2017.
U.S. Appl. No. 14/713,178 Advisory Office Action dated Jan. 19, 2017.
U.S. Appl. No. 14/713,178 Final Office Action dated Oct. 14, 2016.
U.S. Appl. No. 14/713,178 Notice of Allowance dated Apr. 12, 2017.
U.S. Appl. No. 14/713,221 Final Office Action dated Jun. 16, 2016.
U.S. Appl. No. 14/713,221 Non-Final Office Action dated Dec. 30, 2016.
U.S. Appl. No. 14/713,221 Notice of Allowance dated Oct. 19, 2017.
U.S. Appl. No. 14/713,242 Final Office Action dated Jan. 9, 2019.
U.S. Appl. No. 14/713,242 Final Office Action dated Jul. 21, 2017.
U.S. Appl. No. 14/713,242 Non-Final Office Action dated Mar. 29, 2018.
U.S. Appl. No. 14/713,242 Office Action dated Dec. 7, 2016.
U.S. Appl. No. 14/921,896 Final Office Action dated Jan. 25, 2018.
U.S. Appl. No. 14/921,896 Notice of Allowability dated Sep. 12, 2018.
U.S. Appl. No. 14/921,896 Notice of Allowance dated Jul. 18, 2018.
U.S. Appl. No. 14/921,896 Office Action dated Apr. 26, 2017.
U.S. Appl. No. 15/089,842 Final Office Action dated Dec. 4, 2018.
U.S. Appl. No. 15/089,842 Non-Final Office Action dated Jun. 26, 2018.
U.S. Appl. No. 15/089,842 Office Action dated Dec. 8, 2017.
U.S. Appl. No. 15/164,493 Non-Final Office Action dated Feb. 27, 2018.
U.S. Appl. No. 15/164,493 Notice of Allowance dated Nov. 15, 2018.
U.S. Appl. No. 15/185,511 Notice of Allowance dated Nov. 16, 2017.
U.S. Appl. No. 15/265,415 Non-Final Office Action dated Apr. 11, 2018.
U.S. Appl. No. 15/265,620 Non-Final Office Action dated Jan. 22, 2019.
U.S. Appl. No. 15/265,620 Non-Final Office Action dated Jun. 20, 2018.

(56) References Cited

OTHER PUBLICATIONS

U.S. Appl. No. 15/354,940 Non-Final Office Action dated Nov. 2, 2018.
U.S. Appl. No. 15/593,121 Non-Final Office Action dated Mar. 8, 2018.
U.S. Appl. No. 15/593,129 Office Action dated Jan. 3, 2019.
U.S. Appl. No. 15/840,883 Non-Final Office Action dated Apr. 30, 2021.
U.S. Appl. No. 15/889,917 Final Office Action dated Feb. 13, 2020.
U.S. Appl. No. 15/889,917 Non-Final Office Action dated Sep. 3, 2020.
U.S. Appl. No. 15/889,917 Notice of Allowance dated Mar. 29, 2021.
U.S. Appl. No. 16/103,192 Non-Final Office Action dated Feb. 10, 2021.
U.S. Appl. No. 16/103,192 Office Action dated Nov. 4, 2019.
U.S. Appl. No. 16/281,908 Notice of Allowance dated Nov. 3, 2020.
U.S. Appl. No. 16/281,937 Non-Final Office Action dated Mar. 17, 2021.
U.S. Appl. No. 16/422,079 Final Office Action dated Sep. 16, 2020.
U.S. Appl. No. 16/422,079 Notice of Allowance dated Mar. 3, 2021.
U.S. Appl. No. 16/422,462 Non-Final Office Action dated Jul. 22, 2021.
U.S. Appl. No. 16/884,701 Non-Final Office Action dated Jun. 10, 2021.
U.S. Appl. No. 12/786,739 Office Action dated May 8, 2019.
U.S. Appl. No. 13/733,873 Office Action dated May 16, 2019.
U.S. Appl. No. 15/074,115 Office Action dated Mar. 6, 2019.
U.S. Appl. No. 15/265,415 Notice of Allowance dated Dec. 26, 2018.
U.S. Appl. No. 15/354,940 Final Office Action dated Aug. 21, 2019.
U.S. Appl. No. 15/593,121 Notice of Allowance dated Dec. 26, 2018.
U.S. Appl. No. 15/840,883 Office Action dated Aug. 8, 2019.
U.S. Appl. No. 12/535,676 Office Action dated Jun. 26, 2019.
U.S. Appl. No. 12/535,676 Notice of Allowance dated Apr. 1, 2020.
U.S. Appl. No. 13/002,136 Non-Final Office Action dated May 26, 2020.
U.S. Appl. No. 13/002,136 Office Action dated Jun. 21, 2019.
U.S. Appl. No. 13/757,412 Non-Final Office Action dated Mar. 18, 2020.
U.S. Appl. No. 14/612,580 Office Action dated Dec. 24, 2015.
U.S. Appl. No. 14/713,242 Notice of Allowance dated Apr. 2, 2020.
U.S. Appl. No. 15/074,115 Notice of Allowance dated Dec. 11, 2019.
U.S. Appl. No. 15/074,115 Notice of Allowance dated Feb. 11, 2020.
U.S. Appl. No. 15/265,620 Non-Final Office Action dated Jan. 30, 2020.
U.S. Appl. No. 15/265,620 Notice of Allowance dated Apr. 29, 2020.
U.S. Appl. No. 15/354,940 Final Office Action dated Jul. 2, 2020.
U.S. Appl. No. 15/840,883 Final Office Action dated Jun. 9, 2020.
U.S. Appl. No. 15/889,917 Office Action dated May 24, 2019.
U.S. Appl. No. 16/281,908 Non-Final Office Action dated May 1, 2020.
U.S. Appl. No. 16/296,546 Non-Final Office Action dated Feb. 14, 2020.
U.S. Appl. No. 16/422,079 Non-Final Office Action dated Apr. 20, 2020.
U.S. Appl. No. 15/089,842 Notice of Allowance dated Mar. 29, 2019.
USDA. FDA Drug Safety Communication: Clostridium difficile-associated diarrhea can be associated with stomach acid drugs known as proton pump inhibitors (PPIs). Safety announcement. Feb. 8, 2012. Accessed Apr. 1, 2013. http://www.fda.gov/drugs/drugsafety/ucm290510.htm.
USP (32)-NF(27) 2009, Pancreatin, V.3, pp. 3194-3195.

Valicenti-McDermott, et al. Frequency of gastrointestinal symptoms in children with autistic spectrum disorders and association with family history of autoimmune disease. J Dev Behav Pediatr. Apr. 2006;27(2 Suppl):S128-36.
Vargas, et al. Neuroglial activation and neuroinflammation in the brain of patients with autism. Ann Neurol. Jan. 2005;57(1):67-81.
Vellard. The enzyme as drug: application of enzymes as pharmaceuticals. Curr Opin Biotechnol. Aug. 2003;14(4):444-50.
Vilanova, et al. Preparative isolation of the two forms of pig pancreatic pro-(carboxypeptidase A) and their monomeric carboxypeptidases A. Biochem J. Aug. 1, 1985;229(3):605-9.
Viokace—FDA Prescribing Information, Side Effects and Uses. Revised Mar. 2012.
Viokace. Highlights of prescribing information. Aptalis Pharma US Inc. Revised Mar. 2012.
Vojdani, et al. Antibodies against CNS antigens in autism: Possible cross-reaction with dietary proteins and infectious agent antigens. Neuropsychiatric Disorders and Infection. 2004; 19:171-186.
Vojdani, et al. Heat shock protein and gliadin peptide promote development of peptidase antibodies in children with autism and patients with autoimmune disease. Clin Diagn Lab Immunol. May 2004;11(3):515-24.
Vojdani, et al. Immune response to dietary proteins, gliadin and cerebellar peptides in children with autism. Nutr Neurosci. Jun. 2004;7(3):151-61.
Volkmar, et al. Practice Parameters for the Assessment and Treatment of Children, Adolescents, and Adults with Autism and other Pervasive Developmental Disorders. American Academy of Child and Adolescent Psychiatry. J Am Acad Child Adolesc Psychiatry. (Part 2) Dec. 1999;38(12):1611-6.
Volkmar, et al. Practice parameters for the assessment and treatment of children, adolescents, and adults with autism and other pervasive developmental disorders. American Academy of Child and Adolescent Psychiatry Working Group on Quality Issues. J Am Acad Child Adolesc Psychiatry. (Part 1) Dec. 1999;38(12 Suppl):32S-54S.
Wakefield. Autistic enterocolitis: is it a histopathological entity? Histopathology. 2006; 1-5.
Wakefield. Enterocolitis, Autism, and Measles Virus. Consensus in Child Neurology: Biological Bases and Clinical Perspectives in Autism. 2002; 74-81.
Wakefield, et al. Enterocolitis in children with developmental disorders. Am J Gastroenterol. Sep. 2000;95(9):2285-95.
Wakefield, et al. Ileal-lymphoid-nodular hyperplasia, non-specific colitis, and pervasive developmental disorder in children. Lancet. Feb. 2,8 1998;351(9103):637-41.
Wakefield, et al. Review article: the concept of entero-colonic encephalopathy, autism and opioid receptor ligands. Aliment Pharmacol Ther. Apr. 2002;16(4):663-74.
Wakefield, et al. The significance of ileo-colonic lymphoid nodular hyperplasia in children with autistic spectrum disorder. Eur J Gastroenterol Hepatol. Aug. 2005;17(8):827-36.
Wakefield. The gut-brain axis in childhood developmental disorders. J Pediatr Gastroenterol Nutr. May-Jun. 2002;34 Suppl 1:S14-7.
Walsh, et al. Heat shock and the role of the HSPs during neural plate induction in early mammalian CNS and brain development. Cell Mol Life Sci. Feb. 1997;53(2):198-211.
Walsh, et al. Reduced violent behavior following chemical therapy. Physiology and behavior. 2004; 82:835-839.
Wang, et al. Activation of Ras/Erk pathway by a novel MET-interacting protein RanBPM. J Biol Chem. Sep. 27, 2002;277(39):36216-22.
Wang, et al. Effect of chymotrypsin 0 and related proteins on pancreatic cancer cell migration. Acta Biochim Biophys Sin (Shanghai). May 2011;43(5):362-71. Epub Apr. 2, 2011. Jan. 7, 2011. Abstract only.
Wang et al., Extraction of Pancreatin from Pig Pancreas and Isolation and Purification of Kallikrein. Academic Journal of Kunming Medical College 1: 107-108 (2002).
We Move, PD Workbook, The WEMOVE Clinician's Guide to Parkinson's Disease, 2006.

(56) References Cited

OTHER PUBLICATIONS

Weintraub, et al. Morphometric studies of pancreatic acinar granule formation in NCTR-Balb/c mice. J Cell Sci. May 1992;102 (Pt 1):141-7.
Welch, et al. Brain effects of chronic IBD in areas abnormal in autism and treatment by single neuropeptides secretin and oxytocin. J Mol Neurosci. 2004;25(3):259-74.
Wender et al. Prevalence of attention deficit disorder, residual type, and other psychiatric disorders in patients with irritable colon syndrome. Am J Psychiatry. 1983; 140(12):1579-82 Abstract only.
WhiteHouse. Fact Sheet: Combating Autism Act of 2006. www.whitehouse.gov. Dec. 19, 2006.
Williams, et al. Eating habits of children with autism. Pediatr Nurs. May-Jun. 2000;26(3):259-64.
Williams, et al. Intravenous secretin for autism spectrum disorders (ASD). Cochrane Database Syst Rev. Apr. 18, 2012;4:CD003495. doi: 10.1002/14651858.CD003495.pub3.
Wisniewski, et al. Therapeutic approaches for prion and Alzheimer's diseases. FEBS J. Aug. 2007;274(15):3784-98. Epub Jul. 6, 2007.
Witmer. ADD and ADHD Statistics—CDC Report Looks at Attention-Deficit/Hyperactivity Disorder. About.com—Parenting of Adolescents. Jul. 15, 2008.
Wohlman et al. Enhancement of drug activity by chymotrypsin, penicillin penetration into granulomatous lesions and inflammatory fluids. Cellular and Molecular Life Sciences. 1969; 25(9):953-954.
Wolfson, D., Making sense of digestive enzymes, Klaire Labs, Mar. 13, 2006.
Woodward et al. Ischaemic enterocolitis complicating aidiopathic dysautonomia. Gut. 1998; 43:285-287.
Xie, Development and Application of New Traditional Chinese Medicine 2nd Edition. People's Medical Publishing House (2000).
Xu. Pancreatin therapy in chronic pancreatitis. Clin J Dig, May 2005; 25(5):313-315. (in Chinese with English translation).
YAHOO!.com. Who is affected by Parkinson's disease. Yahoo! Health. Jul. 14, 2008.
Yang, et al. Polymeric Porous Framework of a Bismuth Citrate-Based Complex: A Potential Vehicle for Drug Delivery. Medical News Today. Dec. 17, 2010. 1-4.
Yang, Xinyi et al. Advances in anti-staphylococcal agent lysostaphin. Chinese Journal of New Drugs 14(9):1113-1117 (2005).
YAZBAK. Autism in the United States: a perspective. Journal of American Physicians and Surgeons. 2003;8:103-107.
Youngberg, et al. Comparison of gastrointestinal pH in cystic fibrosis and healthy subjects. Dig Dis Sci. May 1987;32(5):472-80.
Yuan, et al. Freeze-Thaw Stability of Three Waxy Maize Starch Pastes Measured by Centrifugation and Calorimetry. Cereal Chem. 1998; 75(4):571-573.
Zeiner, et al. Mammalian protein RAP46: an interaction partner and modulator of 70 kDa heat shock proteins. EMBO J. Sep. 15, 1997;16(18):5483-90.
Zenpep—FDA Prescribing Information, Side Effects and Uses. Revised Sep. 2014.
Zenpep. Highlights of prescribing information. Eurand Pharmaceuticals Inc. Revised Jul. 2011.
Zhang et al. Lactulose-mannitol intestinal permeability test in children with diarrhea caused by rotavirus and cryptosporidium. J of Pediatric Gastro & Nutrition. 2000; 31(1):16-21.
Aerts et al.: Modulation of protease activated receptor 1 influences human metapneumovirus disease severity in a mouse model. PLoS One. 8(8):e72529 doi:10.1371/journal.pone.0072529 [1-13] (2013).
Aguila et al.: COVID-19 and its effects on the digestive system and endoscopy practice. JGH Open 4(3):324-331 (2020).
Allen et al.. Enteric Coating: An Overview Pharmapproach. Retrieved from Pharmaceutical Technology: https://www.pharmapproach.com/tablet-coating-process-film-coating-2/.
Aman et al.: Challenges for Child and Adolescent Psychiatric Research in the Era of COVID-19. J Child Adolesc Psychopharmacol. 30(5):280-284 (2020).
Amirian: Potential fecal transmission of SARS-CoV-2: Current evidence and implications for public health. Int J Infect Dis. 95:363-370 (2020).
Arey: The role of glycosylation in receptor signaling. IntechOpen 12:273-286 DOI:10.5772/50262 (2012).
Arnaud: Adding the missing sugars to coronavirus protein structures. C&EN News 98(16)[pp. 1-7](2020)URL: cen.acs.org/biological-chemistry/proteomics/Adding-missing-sugars-coronavirus-protein/98/i16.
Aronson et al.: When will it be over?: An introduction to viral reproduction numbers, R0 and Re, https://www.cebm.net/covid19/when-will-it-be-over-an-introduction-to-viral-reproduction-numbers-r0-and-re/, On behalf of the Oxford COVID-19 Evidence Service Team, Centre for Evidence-Based Medicine (CEBM), Nuffield Department of Primary Care Health Sciences, University of Oxford. 10 pages (Apr. 14, 2020).
Atkeson: What will be the economic impact of COVID-19 in the US? Rough estimates of disease scenarios. National Bureau of Economic Research, NBER Working Paper No. 26867, pp. 1-27. (2020)http://www.nber.org/system/files/working_papers/w26867/w26867.pdf.
Baez-Santos et al.: The SARS-coronavirus papain-like protease: structure, function and inhibition by designed antiviral compounds. Antiviral Res. 115:21-38 (2015).
Baraniuk, C. (2020). Scientists scan for weaknesses in the SARS-CoV-2 spike protein. Retrieved from The Scientist: https://www.the-scientist.com/news-opinion/scientists-scan-for-weaknesses-in-the-sars-cov-2-spike-protein-67404.
Belouzard et al.: Mechanisms of coronavirus cell entry mediated by the viral spike protein. Viruses. 4(6): 1011-1033 (2012).
Bence: Examination of the regulatory role and n-glycolylation of chymotrypsin C. PhD Thesis, Semmelweis University, pp. 1-13 (2011) URL: repo.lib.semmelweis.hu/bitstream/handle/123456789/1375/bencemelinda.e_t%C3%A9zis.pdf?s equence=5.
Berg et al.: Structural Biochemistry/Proteases. Wikibooks, pp. 1-4 (2012) URL: en.wikibooks.org/wiki/Structural_Biochemistry/Proteases.
Biggerstaff et al.: Systematic assessment of multiple routine and near-real time indicators to classify the severity of influenza seasons and pandemics in the United States, 2003-04 through 2015-2016. Am J Epidemiol 187(5): 1040-1050 (2018).
Biwas et al.: Emergence of Novel Coronavirus and COVID-19: whether to stay or die out? Crit Rev Microbiol. 46(2):182-193 (2020).
Bouchard, Mathew Brain Chat CDC_Common Conditions in Adults with Coronavirus.
Bouwman et al.: Three amino acid changes in avian coronavirus spike protein allow binding to kidney tissue.J Virol. 94(2):e01363-19 doi:10.1128/JVI.01363-19 [1-14] (2020).
Braun et al.: Furin-mediated protein processing in infectious diseases and cancer. Clin Transl Immunology. 8(8):e1073 doi:10.1002/cti2.1073 [1-19] (2019).
Caldwell, P.: Projecting Coronavirus' Long-Run Economic Impact. https://www.morningstar.com/articles/984843/projecting-coronavirus-long-run-economic-impact, May 14, 2020. 21 pages (Accessed on Jul. 7, 2020).
Campbell, P.: Understanding the receivers and the reception of science's uncertain messages. Philos Trans A Math Phys Eng Sci. 369(1956): 4891-4912 (2011).
Canadian Cancer Society. Anatomy and physiology of the stomach. (2020)www.cancer.ca/en/cancer-information/cancer-type/stomach/stomach-cancer/the-stomach/?region=qc.
Cao et al.: A trial of Lopinavir-ritonavir in adults hospitalized with severe Covid-19. N Engl J Med. 382(19): 1787-1799 (2020).
Cascella et al.: Features, Evaluation and Treatment Coronavirus (COVID-19) [Updated Apr. 6, 2020]. In: StatPearls [Internet]. Treasure Island (FL): StatPearls Publishing; Jan. 2020-. Available from: https://www.ncbi.nlm.nih.gov/books/NBK554776/. 20 pages (Accessed on Jul. 7, 2020).
Centers for Disease Control and Prevention. 2017-2018 Estimated Influenza Illnesses, Medical visits, Hospitalizations, and Deaths and Estimated Influenza Illnesses, Medical visits, Hospitalizations, and Deaths Averted by Vaccination in the United States. Retrieved from

(56) References Cited

OTHER PUBLICATIONS

Centers for Disease Control and Prevention (CDC) (2019) URL: www.cdc.gov/flu/about/burden-averted/2017-2018.htm.
Centers for Disease Control and Prevention. Estimates of influenza vaccination coverage and adults—United States, 2017-18 flu season. Available at: https://www.cdc.gov/flu/fluvaxview/coverage-1718estimates.htm. 6 pages (Accessed on Jul. 8, 2020).
Centers for Disease Control and Prevention. Influenza (Flu). Retrieved from The Flu Season. (2018) URL: www.cdc.gov/flu/about/season/flu-season.htm.
Chan et al.: Detection of SARS coronavirus in patients with suspected SARS. Emerg Infect Dis. 10(2):294-299 (2004).
Chandel et al.: In Silico Identification of Potent COVID-19 Main Protease Inhibitors from FDA Approved Antiviral Compounds and Active Phytochemicals through Molecular Docking: A Drug Repurposing Approach. PrePrints doi:10.20944/preprints202003.0349.v1 [1-28] (2020).
Chang et al.: Epidemiologic and Clinical Characteristics of Novel Coronavirus Infections Involving 13 Patients Outside Wuhan, China. JAMA. 323(11):1092-1093 (2020).
Cheng et al.: Severe acute respiratory syndrome coronavirus as an agent of emerging and reemerging infection. Clin Microbiol Rev. 20(4):660-694 (2007).
Cheung et al.: The spectrum of pathological changes in severe acute respiratory syndrome (SARS). Histopathology 45(2):119-124 (2004).
Choi et al: Human microbiome studies in Korea. Allergy Asthma Respir Dis. 4(5):311-320 https://doi.org/10.4168/aard.2016.4.5.311 (2016).
Choi et al.: The maternal interleukin-17a pathway in mice promotes autism-like phenotypes in offspring. Science 351(6276):933-939 (2016).
Chung et al.: Effects of influenza vaccination in the United States during the 2018-2019 influenza season. Clin Infect Dis. 71(8):e368-e376 doi:10.1093/cid/ciz1244 (2020).
Ciotti et al.: COVID-19 Outbreak: An Overview. Chemotherapy 64(5-6):215-223 doi:10.1159/000507423 (2019).
Cohen: The coronavirus may shut down the immune system's vital classrooms. Science, 1. (Aug. 25, 2020).
Cooper et al.: Protecting public trust in immunization. Pediatrics 122(1): 149-153 (2008).
Corum et al.: Bad news wrapped in protein: inside the coronavirus genome. The New York times, 1-2. (Apr. 3, 2020).
Cosgriff et al.: A multinational report to characterise SARS-CoV-2 infection in people with cystic fibrosis. J Cyst Fibros. 19(3):355-358 (2020).
Coutard, et al. The spike glycoprotein of the new coronavirus 2019-nCoV contains a furin-like cleavage site absent in CoV of the same clade. Antiviral research 176 (2020): 104742.
COVID-19: Developing Drugs and Biological Products for Treatment or Prevention Guidance for Industry, U.S. Department of Health and Human Services Food and Drug Administration Center for Drug Evaluation and Research (CDER),Center for Biologies Evaluation and Research (CBER), May 2020 Clinical/Medical, 18 pages.
COVID-19 Treatment Guidelines Panel. Coronavirus Disease 2019 (COVID-19) Treatment Guidelines. National Institutes of Health. Available at https://covid19treatmentguidelines.nih.gov/. 146 pages (Accessed on Jul. 8, 2020).
Da Silva Filho et al.: The differential clinical impact of human coronavirus species in children with cystic fibrosis. J Infect Dis. 206(3):384-388 (2012).
D'Amico et al.: Inflammatory bowel diseases and COVID-19: The invisible enemy. Gastroenterology, 158(8):2302-2304 (2020).
Ding et al.: Organ distribution of severe acute respiratory syndrome (SARS) associated coronavirus (SARS-CoV) in SARS patients: implications for pathogenesis and virus transmission pathways. J Pathol. 203(2):622-630 (2004).
Du et al.: The spike protein of SARS-CoV—a target for vaccine and therapeutic development. Nat Rev Microbiol. 7(3):226-236 (2009).

Eisenberg: Ro: How scientists quantify the intensity of an outbreak like coronavirus and its pandemic potential. University of Michigan School of Public Health, 1. (Feb. 12, 2020).
Emery et al., Real-time reverse transcription-polymerase chain reaction assay for SARS-associated coronavirus. Emerging Infectious Diseases, 10(2): 311-316 (2004).
Estes et al., Maternal immune activation: implications for neuropsychiatric disorders. Science, 353: 772-777 (2016).
Farkas et al., Wastewater and public health: the potential of wastewater surveillance for monitoring COVID-19. Science Direct, 17, 14-20 (2020).
Fauci et al., Covid-19—navigating the unchartered. New England Journal of Medicine (2020).
FDA Guidance for Industry (May 2020) COVID-19 Public Health Emergency: General Considerations for Pre-IND Meeting Requests for COVID-19 Related Drugs and Biological Products, U.S. FDA. Retrieved from FDA.gov: https://www.fda.gov/media/137927/download.
Fehr et al., (2015). Chapter 1—Coronaviruses:an overview of their replication and pathogenesis. In H. J. Maier, E. Bickerton, & P. Britton, Coronaviruses—Methods and Protocols. Springer Link.
Filone et al., Identification of a broad-spectrum inhibitor of viral RNA synthesis: validation of a prototype virus-based approach. Chemistry and Biology, 20, 424-433 (2013).
Flannery et al.: Interim estimates of 2017-18 seasonal influenza vaccine effectiveness—United States, Feb. 2018. MMWR Morb Mortal Wkly Rep 67(6): 180-185 (2018).
Garg, et al., Letter: gastrointestinal ACE2, COVID-19, and IBD-opportunity in the face of tragedy? Gastroenterology, 1-6 (2020).
Garg, M, Letter: intestinal inflammation, COVID-19 and gastrointestinal ACE2—exploring RAS inhibitors, doi: 10.1111/apt.15814. (2020).
Garten et al.: Update: influenza activity in the United states during the 2017-18 season and composition of the 2018-19 influenza Vaccine. MMWR Morb Mortal Wkly Rep 67(22): 634-642 (2018).
Gerlach, H. Agents to reduce cytokine storm. F1000 Research, (2016).
Gheblawi et al., Angiotensin-converting enzyme 2: SARS-CoV-2 receptor and regulator of the renin-angiotensin system. Circulation Research, 126, 1456-1474 (2020).
Ghosh et al.. Microbial lipases: production and applications. Science Progress, 79(2), 119-157 (1996).
Giaimo et al., Severe acute respiratory syndrome coronavirus-2. (2021).
Goh et al., Rigidity of the outer shell predicted by a protein intrinsic disorder model sheds light on the COVID-19 (Wuhan-2019-nCoV) infectivity. Biomolecules, 10: 331 (2020).
Gordon et al., A SARS-CoV-2 protein interaction map reveals targets for drug repurposing. Nature (Accelerated Article Preview), 1-32 (2020).
Grant et al., 3D models of glycosylated SARS-CoV-2 spike protein suggest challenges and opportunities for vaccine development. bioRxiv, 1-17 (2020).
Gu et al., COVID-19: gastrointestinal manifestations and potential fecal-oral transmission. Gastroenterology, 158(6) (2020).
Gu et al., Multiple organ infection and the pathogenesis of SARS. Journal of Experimental Medicine, 2020(3), 415-424 (2005).
Guan et al.: Clinical Characteristics of Coronavirus Disease 2019 in China. The New England Journal of Medicine 382(18): 1708-1720 https://doi.org/10.1056/ NEJMoa2002032 (2020).
Guo et al., Coronavirus disease 2019 (COVID-19) and cardiovascular disease: a viewpoint on the potential influence of angiotensin-converting enzyme inhibitors/angiotensin receptor blockers on onset and severity of severe acute respiratory syndrome coronavirus infection. Journal of the American Heart Association, 1-5 (2020).
Hammer et al., Importance of the major histocompatibility complex (swine leukocyte antigen) in swine health and biomedical research. Annual Review of Animal Bioscience, 8, 171-198 (2020).
Hamming et al., Tissue distribution of ACE2 protein, the functional receptor for SARS coronavirus. a first step in understanding SARS pathogenesis. Journal of Pathology, 203, 631-637 (2004).

(56) References Cited

OTHER PUBLICATIONS

Han et al., Digestive symptoms in COVID-19 patients with mild disease severity: clinical presentation, stool viral RNA testing, and outcomes. The American Journal of Gastroenterology (2020) 23 pages.
Han et al., Sequential analysis of viral load in a neonate and her mother infected with severe acute respiratory syndrome coronavirus 2 (SARS-2). Clinical Infectious Diseases, 1-4 (2020).
Heald-Sargent et a., Ready, set fuse! the coronavirus spike protein and acquisition of fusion competence. Viruses, 4, 557-580 (2012).
Heller et al., COVID-19 faecal-oral transmission: are we asking the right questions? Science of the Total Environment, 729, 1-4 (2020).
Herrewegh et al., Detection of feline coronavirus RNA in feces, tissues, and body fluids of naturally infected cats by reverse transcriptase PCR. Journal of Clinical Microbiology, 33(3), 684-689 (1995).
Hikmet et al., The protein expression profile of ACE2 in human tissues. Molecular Systems Biology, 16, 1-16(2020).
Hoffman et al., SARS-CoV-2 cell entry depends on ACE2 and TMPRSS2 and is blocked by a clinically proven protease inhibitor. Cell Press, 181, 271-280 (2020).
Hoffman et al., The novel coronavirus 2019 (2019-nCoV) uses the SARS-1 coronavirus receptor ACE2 and the cellular protease TMPRSS2 for entry into target cells. bioRxiv Preprint. 23 pages (2020).
Houston et al., Potentiated virucidal activity of pomegranate rind extract (PRE) and punicalagin against herpes simplex virus (HSV) when coadministered with zinc (II) ions, and antiviral activity of PRE against HSV and aciclovirresistant HSV. PLoS ONE, 12(6) (2017).
Hu et al., The m protein of SARS-CoV: basic structural and immunological properties. Genomics, Proteomics & Bioinformatics, 1:2 (2003).
Huang et al., Clinical features of patients infected with 2019 novel coronavirus in Wuhan, China. The Lancet, 395, 497-506 (2020).
Huang et al., Fast assessment of human receptor-binding capability of 2019 novel coronavirus (2019-nCoV). bioRxiv (2020).
Hulkower et al., Inactivation of surrogate coronaviruses on hard surfaces by health care germicides. American Journal of Infection Control, 39, 401-407 (2011).
Ianiro et al., Digestive enzyme supplementation in gastrointestinal diseases. Current Drug Metabolism, 17, 187-193 (2016).
Ibrahim et al., COVID-19 spike-host cell receptor GRP78 binding site prediction. Journal of Infection, 80, 554-562 (2020).
Ijaz, Virucidal Effectiveness Test—Coronavirus. Microbiotest, Inc. (2003).
Jevšnik et al., Detection of human coronaviruses in simultaneously collected stool samples and nasopharyngeal swabs from hospitalized children with acute gastroenteritis. Virology Journal, 10(46):1-7 (2013).
Jin et al., Epidemiological, clinical and virological characteristics of 74 cases of coronavirus-infected disease 2019 (COVID-19) with gastrointestinal symptoms. Gut, 6, 1002-1009 (2020).
Kadkhoda, COVID-19 serologic testing: FAQs and caveats. Cleveland Clinic Journal of Medicine, 87(6) (2020).
Kampf, Efficacy of ethanol against viruses in hand disinfection. Journal of Hospital Infection, 98, 331-338 (2018).
Kampf et al., Persistence of coronaviruses on inanimate surfaces and their inactivation with biocidal agents. Journal of Hospital Infection, 104, 246-251 (2020).
Kapadia et al., Hepatitis C virus RNA replication is regulated by host geranylgeranylation and fatty acids. PNAS, 102(7), 2561-2566 (2005).
Kawase et al., Simultaneous treatment of human bronchial epithelial cells with serine and cysteine protease inhibitors prevents severe acute respiratory syndrome coronavirus entry. Journal of Virology, 86(12), 6537-6545 (2012).
Kim et al., Development of a reverse transcription-nested polymerase chain reaction assay for differential diagnosis of transmissible gastroenteritis virus and porcine respiratory coronavirus from feces and nasal swabs of infected pigs. Journal of Veterinary Diagnostic Investigation, 12, 385-388 (2000).
Kim et al., Identification of Coronavirus Isolated from a Patient in Korea with COVID-19. Osong public health and research perspectives, 11(1): 3-7 (2020).
Kim et al., Rates of co-infection between SARS CoV-2 and other respiratory pathogens. American Medical Association—Research Letter, 323(20), 2085-2086 (2020).
Kim et al., Therapy for Early COVID-19, A Critical Need, JAMA Published online Nov. 11, 2020.
Kindermann et al., Virus disinfection for biotechnology applications: Different effectiveness on surface versus in suspension. Biologicals, 64, 1-9 (2020).
Kuba et al., Trilogy of ACE2: a peptidase in the renin-angiotensin system, a SARS receptor, and a partner for amino acid transporters. Pharmacology & Therapeutics, 128: 119-128 (2010).
Kuster et al., SARS-CoV2: should inhibitors of the renin-angiotensin system be withdrawn in patients with COVID-19? European Heart Journal, 1-3 (2020).
Kwok et al., Face touching: A frequent habit that has implications for hand hygiene. American Journal of Infection Control, 43: 112-114 (2015).
Larners et al., SARS-CoV-2 productively infects human gut enterocytes. Science , 369: 50-54 (2020).
Lane, Profile—Sarah Gilbert: carving a path towards a COVID-19 vaccine. The Lancet, 395: 1247 (2020).
Larson et al.: New Decade of Vaccines 5, Addressing the vaccine confidence gap. Lancet 378: 526-535 Published Online, Jun. 9, 2011, DOI:10.1016/S0140-6736(11)60678-8 (2011).
Larson, Negotiating vaccine acceptance in an era of reluctance. Human Vaccines & Immunotherapy, 9, 1779-1781 (2013).
Le et al.: The COVID-19 vaccine development landscape, http://www.nature.com/nrd, Nature Reviews 19: 305-306 (May 2020).
Lee et al., Current concepts in the diagnosis and management of cytokine release syndrome. Blood, 124: 188-195 (2014).
Leung et al., The epidemiology of severe acute respiratory syndrome in the 2003 Hong Kong epidemic: an analysis of All 1755 patients. Annals of Internal Medicine, 141, 662-673; W-125 to 128 (2004).
Li et al., Physiological and pathological regulation of ACE2, the SARS-CoV-2 receptor. Pharmacological Research, 157: 104833 (2020).
Li et al., The human coronavirus HCoV-229E S-protein structure and receptor binding. Life 8: e51230 (2019).
Li et al., Therapeutic options for the 2019 novel coronavirus (2019-nCoV). Nature Reviews, 19 149-150 (2020).
Li, F, Receptor recognition mechanisms of coronaviruses: a decade of structural studies. Journal of Virology, 89, 1954-1964 (2015).
Lippi et al., Coronavirus disease 2019 (COVID-19): the portrait of a perfect storm. Annals of Translational Medicine, 1-7 (2020).
Lippi et al., Laboratory abnormalities in patients with COVID-2019 infection. Clinical Chemistry and Laboratory Medicine 58(7): 1131-1134 (2020).
Liu et al., Potential inhibitors for 2019-nCoV coronavirus m protease from clinically approved medicines. bioRxiv. 12 pages (2020).
Liu et al., Using heparin molecules to manage COVID-2019. Research and Practice in Thrombosis and Haemostasis, 4: 518-523 (2020).
Lombardi, COVID-19: first case of reinfection confirmed, researchers say. Armonk Daily Voice, 1 page (2020).
Lorizate et al., Role of lipids in virus replication. Cold Spring Harbor Perspectives in Biology, 3(10): a004820 (2011).
Lurie et al., Research as Part of Public Health Emergency Response N Engl J Med 368 (13): 1251-1255 (2013).
Lurie, N et al. (May 2020) Developing Vaccines at Pandemic Speed N Engl J Med 382(21): 1969-1973 (2020).
Magro , Chapter 12: Angiotensin-converting enzyme (ACE) in gut inflammation. In U. Lendeckel, & N. M. Hooper, Proteases in Gastrointestinal Tissue, 301-314. Netherlands: Springer (2006).
Mahase, COVID-19: WHO declares pandemic because of "alarming levels" of spread, severity, and inaction. The British Medical Journal, 368 (2020).

(56) References Cited

OTHER PUBLICATIONS

Maillard et al., Lipoprotein lipase inhibits hepatitis c virus (HCV) infection by blocking virus cell entry. Plos One, 6(10): e26637 (2011).

Masters et al., The molecular biology of coronaviruses. Advances in Virus Research. 66, 193-292 (2006).

Medema et al., Presence of SARS-coronavirus-1 in sewage. MedRxxiv, 1-9 (2020).

Millet et al., Host cell proteases: Critical determinants of coronavirus tropism and Pathogenesis, Virus Research 202: 120-134 (2015).

Moheb et al.: Gastrointestinal Complications in Critically Ill Patients With and Without COVID-19. JAMA 324(18):E1-E3 (2020).

Mora-Diaz et al., Porcine hemagglutinating encephalomyelitis virus: a review. Frontiers in Veterinary Science, 6(53) (2019).

Mori et al., Prevention of RNA Virus Replication,, Okayama University (2016).

Mortensen et al., Coronavirus like particles in human gastrointestinal disease. The American Journal of Diseases of Children 139: 928-934 (1985).

Muus et al., Integrated analyses of single-cell atlases reveal age, gender, and smoking status associations with cell type-specific expression of mediators of SARS-CoV-2 viral entry and highlights inflammatory programs in putative target cells. BioRxiv, 1-87 (2020).

Nao, What is a polybasic cleavage site? News-Medical.Net, 1-5 (2017).

Neuman et al., A structural analysis of M protein in coronavirus assembly and morphology. Journal of Structural Biology 174: 11-22 (2011).

Nikiforuk, A.: Even a Vaccine Won't Erase this Pandemic. Jun. 3, 2020. The Tyee.ca, https://thetyee.ca/Analysis/2020/06/03/Vaccine-Will-Not-Erase-Pandemic/?fbclid=lwAR0XWnrZe38uESRFuJZDK6onjwG32ApyyyJfhiF8JvKdzZu0RIOrPuBg1H o 6 pages (Accessed on Jul. 7, 2020).

Nouri-Vaskeh et al., Fecal transmission in COVID-19: a potential shedding route. Journal of Medical Virology 1-2 (2020).

Onu, A. (2010). Viruses and lipids. Viruses 2: 1236-1238 (2010).

Orenstein, D. (Apr. 28, 2020). How could COVID-19 and the body's immune response affect the brain? MIT News, 1.

Otter et al., Transmission of SARS and MERS coronaviruses and influenza virus in healthcare settings: the possible role of dry surface contamination. Journal of Hospital Infection, 92, 235-250 (2016).

Ou et al., Characterization of spike glycoprotein of SARS-CoV-2 on virus entry and its immune cross-reactivity with SARS-CoV. Nature Communications 11: 1620 (2020).

Pan et al., Clinical characteristics of COVID-19 patients with digestive symptoms in hubei, china: a descriptive, cross-sectional, multicenter study. Journal of American Gastroenterology, 115, 766-773 (2020).

Pan et al., Viral load of SARS-CoV-2 in clinical samples. The Lancet, 20 (2020).

Parasa et al., Prevalence of gastrointestinal symptoms and fecal viral shedding in patients with coronavirus disease 2019—a systematic review and meta-analysis. Journal of the American Medical Association, 1-14 (2020).

Patel et al., COVID-19 and Angiotensin-Converting Enzyme Inhibitors and Angiotensin Receptor Blockers: What Is the Evidence? JAMA 323(18):1769-1770 (2020).

Peckham, COVID-19 and the anti-lessons of history. The Lancet, 395, 850-852 (2020).

Pei et al., Renal involvement and early prognosis in patients with COVID-19 pneumonia. Journal of the American Society of Nephrology, 31, 1157-1165 (2020).

Petkova et al., Pooling data from individual clinical trials in the COVID-19 era. Journal of the American Medical Association, E1-E3 (2020).

Phan, T., Genetic diversity and evolution of SARS-CoV-2. Infection, Genetics and Evolution 81: 104260 (2020).

Pharmapproach et al., Tablet Coating Process Film Coating, Pharmaceutical Technology, Pharmapproach.com.pdf.

Poland et al.: The age-old struggle against the anti-vaccinationists. NEJM 364(2): 97-99 (2011).

Post et al., Multiple enzyme approach for the characterization of glycan modifications on the c-terminus of the intestinal MUC2Mucin. Journal of Proteome Research 13: 6013-6023 (2014).

Pringproa et al., In vitro virucidal and virustatic properties of the crude extract of cynodon dactylon against porcine reproductive and respiratory syndrome virus. Veterinary Medicine International 2014: 947589 (2014).

Rabaan et al., SARS-CoV-2, SARS-CoV, and MERS-CoV: a comparative overview. Le Infezioni in Medicina, 2, 174-184 (2020).

Rabenau et al., Efficacy of various disinfectants against SARS coronavirus. Journal of Hospital Infection, 61: 107-111 (2005).

Rabenau et al., Stability and inactivation of SARS coronavirus. Medical Microbiology and Immunology, 194, 1-6 (2005).

Rettner, DNA: definition, structure and discovery. Live Science, 1-3 (2017).

Rettner, R. (2020). Diarrhea is first sign of illness for some COVID-19 patients. Retrieved from Live Science: https://www.livescience.com/coronavirus-diarrhea-symptoms.html.

Reynolds et al., Microbial transmission in an outpatient clinic and impact of an intervention with an ethanol-based disinfectant. American Journal of Infection Control, 47: 128-132 (2019).

Richardson et al., Presenting characteristics, comorbidities, and outcomes among 5700 patients hospitalized with COVID-19 in the new york city area. Journal of the American Medical Association, 323(20), 2052-2059 (2020).

Ricklin et al., Complement in immune and inflammatory disorders: pathophysiological mechanisms. The Journal of Immunology, 190: 3831-3838 (2013).

Rolfes et al.: Effect of Flu Vaccination in 2017-2018 Influenza Season. Clinical Infectious Diseases 69(11): 1845-1853 (2019).

Rothe et al.: Transmission of 2019-nCoV Infection from an Asymptomatic Contact in Germany. The New England Journal of Medicine 2020, 382(10):970-971. https://doi.org/10.1056/NEJMc2001468. (Accessed Jul. 7, 2020).

Rousseaux et al., Sigma receptors [pRs]: biology in normal and diseased states. The Journal of Receptors and Signal Translation, 36: 327-388 (2016).

Sah et al., Complete genome sequence of a 2019 novel coronavirus (SARS-CoV-2) strain isolated in Nepal. American Society for Microbiology, 9(11), 1-3 (2019).

Saiy, T (Mar. 2020) Repurposed drugs may help scientists fight the new coronavirus, Science News, https://www.sciencenews.org/article/coronavirus-covid19-repurposed-treatments-drugs.

Sakai et al., Two-amino acids change in the nsp4 of SARS coronavirus abolishes viral replication. Virology, 510: 165-174 (2017).

Sanchis-Gomar et al., Angiotensin-converting enzyme 2 and antihypertensives (angiotensin receptor blockers and angiotensin-converting enzyme inhibitors) in coronavirus disease 2019. Mayo Clinic Proceedings, 1-9.

Sanchis-Gomar et al., PrePrint Angiotensin-converting enzyme 2 and antihypertensives (angiotensin receptor blockers and angiotensin-converting enzyme inhibitors) in coronavirus disease 2019. Mayo Clinic Proceedings, 1-9 (2020).

Sattar et al., Chemical disinfection of non-porous inanimate surfaces experimentally contaminated with four human pathogenic viruses. Epidemics, 102: 493-505 (1989).

Schoeman et al., Coronavirus envelope protein: current knowledge. Virology Journal. 16: 69 (2019).

School of Social Work, University of Virginia (Feb. 2020) Covid-19 coronavirus spike hold infectivity Details.

Sette et al., Pre-existing immunity to SARS-CoV-2: the knowns and unknowns. Nature Reviews2 pages (2020).

Shafiee et al., A mini-review on the current COVID-19 therapeutic strategies, Chemical Review and Letters 3: 19-22 (2020).

Shah et al., Guide to understanding the 2019 novel coronavirus (commentary). Mayo Clinic Proceedings, 95(4): 646-652 (2020).

Shajahan et al., Deducing the N- and O-glycosylation profile of the spike protein of novel coronavirus SARS-CoV-2. bioRxiv 30(12): 981-988 (2020).

(56) References Cited

OTHER PUBLICATIONS

Shen et al., Genomic diversity of severe acute respiratory syndrome-coronavirus 2 in Patients With coronavirus disease 2019. Clinical Infectious Disease, 1-8 (2020).
Shetty, P.: Experts concerned about vaccination backlash. Lancet 375: 970-971 (2010).
Shi et al.: COVID-19 infection: the perspectives on immune responses, Cell Death & Differentiation 27: 1451-1454 https://doi.org/10.1038/s41418-020-0530-3 (2020).
Shulla et al., Transmembrane serine protease link to the severe acute respiratory syndrome (SARS) coronavirus receptor. Journal of Virology, 85(2): 873-882 (2011).
Simmons et al., Characterization of severe acute respiratory syndrome-associated coronavirus (SARS-CoV) spike glycoprotein-mediated viral entry. Proceedings of the National Academy of Sciences of the USA (PNAS), 101(12): 4240-4245 (2004).
Simmons et al., Proteolytic activation of the SARS-coronavirus spike protein: cutting enzymes at the cutting edge of antiviral research. Antiviral Research 100: 605-614 (2013).
Sizun et al., Survival of human coronaviruses 229E and OC43 in suspension and after drying on surfaces: a possible source of hospital-acquired infections. Journal of Hospital Infections, 46: 55-60 (2000).
Skoreński et al., Viral proteases as targets for drug design. Current Pharmaceutical Design, 19(6), 1126-1153 (2013).
Smillie et al., Intra- and inter-cellular rewiring of the human colon during ulcerative colitis. Cell, 178(3): 714-730 (2019).
Snoeck et al., The role of enterocytes in the intestinal barrier function and antigen uptake. Microbes and Infection, 7: 997-1004 (2005).
Song et al., SARS-CoV-2 induced diarrhea as onset symptom in patient with COVID-19. Gut, 69(6): 1143-1144 (2020).
South et al., COVID-19, ACE2, and the cardiovascular consequences. American Journal of Physiology, Heat and Circulation Physiology, 318: H1084-H1090 (2020).
Sparks et al. (2020). ACE2 and hypertension. NephJC, 1-3.
Sungnak et al., SARS-CoV-2 entry factors are highly expressed in nasal epithelial cells together with innate immune genes. Nature Medicine 26(5): 681-687 (2020).
Swigon, The mathematics of DNA structure, mechanics, and dynamics. Pittsburgh, PA: ResearchGate 293-320 (2009).
Tang et al., Detection of novel coronavirus by RT-PCR in stool specimen from asymptomatic child, china. Emerging Infectious Diseases, 26(6): 1337-1339 (2020).
Tang et al., On the origin and continuing evolution of SARS-CoV-2. National Science Review, 7: 1012-1023 (2020).
The Flu Season, Centers for Disease Control and Prevention, National Center for Immunization and Respiratory Diseases (NCIRD).
The Human Protein Atlas—ACE2 Summary. (2020) Retrieved from Protein Atlas: https://www.proteinatlas.org/ENSG00000130234-ACE2.
The Human Protein Atlas—RNA Expression Overview (Sorted). (2020) (n.d.). Retrieved from Protein Atlas: https://www.proteinatlas.org/ENSG00000130234-ACE2/celltype.
The Human Protein Atlas—Tissue Expression of Ace2 (2020) Retrieved from Protein Atlas: https://www.proteinatlas.org/ENSG00000130234-ACE2/tissue.
Tikellis et al., Angiotensin-converting enzyme 2 (ACE2) is a key modulator of the renin angiotensin systemin health and disease. International Journal of Peptides 2012: 256291 (2011). pp. 1-8.
Timmer, J. (Mar. 20, 2020). COVID-19: the biology of an effective therapy. Viral Weak Spots—ArsTechnica, 1-2.
Tortorici et al., Structural insights into coronavirus entry. Advances in Virus Research, 105: 93-116 (2019).
Trafton, A (2020) An experimental peptide could block Covid-19, MIT News Office, https://news.mit.edu/2020/peptide-drug-block-covid-19-cells-0327.
U.S. Food and Drug Administration. (Dec. 2019). Demonstrating Substantial Evidence of Effectiveness for Human Drug and Biological Products Guidance for Industry U.S. FDA. Retrieved from FDA.gov: https://www.fda.gov/regulatory-information/search-fda-guidance-documents/demonstrating-substantial-evidence-effectiveness-human-drug-and-biological-products.
van der Post, S et al., Multiple Enzyme Approach for the Characterization of Glean Modifications on the C-Terminus of the Intestinal MUC2Mucin, Journal of proteome research 13: 6013-6023 (2014).
Velthuis et al., Zn2+ Inhibits Coronavirus and Arterivirus RNA Polymerase Activity In Vitro and Zinc Ionophores Block the Replication of These Viruses in Cell Culture. PLoS Pathog 6(11): e1001176 (2010).
Walls, A et al., COVID-19 coronavirus spike holds infectivity details. (2020). Retrieved from UW Medicine Newsroom: https://newsroom.uw.edu/news/covid-19-coronavirus-spike-holds-infectivity-details.
Walls et al., Cryo-electron microscopy structure of a coronavirus spike glycoprotein trimer Nature 531:115(2016).
Walls et al., Structure, function, and antigenicity of the SARSCoV A., McGuire, A—2 spike glycoprotein. Cell, 180: 281-292 (2020).
Wang et al., A human monoclonal antibody blocking SARS-CoV-2 infection. Nature Communications 11:6 pages (2020).
Wang et al., Case Report—Persistence of intestinal SARS-CoV-2 infection in patients with COVID-19 leads to re-admission after pneumonia resolved. International Journal of Infectious Disease, 25: 433-435 (2020).
Wang et al.: Clinical Characteristics of 138 Hospitalized Patients With 2019 Novel Coronavirus-Infected Pneumonia in Wuhan, China. JAMA 323(11): 1061-1069. https://doi.org/10.1001/jama.2020.1585. (2020).
Wang et al., Detection of SARS-CoV-2 in different types of clinical specimens. Journal of the American Medical Association 323(18): 1843-1844 (2020).
Wang et al., Study on the resistance of severe acute respiratory syndrome-associated coronavirus. Journal of Virological Methods, 126:171-177 (2005).
Wang et al., Susceptibility analysis of COVID-19 in smokers based on ACE2. Europe PMC, Preprints, 1-8 (2020).
Wang et al., The genetic sequence, origin, and diagnosis of SARS-CoV-2. European Journal of Clinical Microbiology & Infectious Disease, 1-7 (2020).
Warren et al., HLA redictions from the bronchoalveolar lavage fluid samples of five patients at the early stage of the Wuhan seafood market COVID-19 outbreak. Preprint, 1-4 (2020).
Watanabe et al., Review Article—Exploitation of glycosylation in enveloped virus pathobiology. BBA—General Subjects 1863(10): 1480-1407 (2019).
Watanabe, Y., Allen, J. D., Wrapp, D., McLellan, J. S., & Crispin, M. (2020). Site-specific analysis of the SARS-CoV-2 glycan shield. bioRxiv 369(6501) 1-20 (2020).
Weber et al., New and emerging infectious diseases (ebola, middle eastern respiratory syndrome coronavirus, carbapenem-resistant enterobacteriaceae, candida auris): Focus on environmental survival and germicide susceptibility. Journal of Infection Control, 47: A29-A38 (2019).
Weingartl et al., Susceptibility of pigs and chickens to SARS coronavirus. Emerging Infectious Diseases, 10(2): 179-184 (2004).
Whitcomb et al., Human Pancreatic Digestive Enzymes, Springer Dig Dis Sci 52:1-17 (2007).
Wicht et al., Proteolytic activation of the porcine epidemic diarrhea coronavirus spike fusion protein by trypsin in cell culture. Journal of Virology 88(14): 7952-7961 (2014).
Wigginton et al., Virus disinfection mechanisms: the role of virus composition, structure, and function. Current Opinion in Virology, 2: 84-89 (2012).
WikiBooks (2012) Structural Biochemistry Proteases https://en.wikibooks.org/wiki/Structural_Biochemistry/Proteases.
Wikipedia (2020) Enterocyte.
Wikipedia (2020) Pancreatic Enzymes (Medication).
Wikipedia (2020) Protease.
Wikipedia (2020) Severe acute respiratory syndrome coronavirus 2.
Wikipedia, (May 21, 2020), Alpha-1 antitrypsin deficiency.
Wong et al., Covid-19 and the digestive system. Journal of Gastroenterology and Hepatology 35: 744-748 (2020).

(56) References Cited

OTHER PUBLICATIONS

World Health Organization, W. (May 10, 2020). World Health Organization—Situation Report 111. Retrieved from WHO Coronavirus Disease Dashboard: https://www.who.int/emergencies/diseases/novel-coronavirus-2019/situation-reports/.
World Health Organization, W. (May 25, 2020). World Health Organization—Situation Report 126. Retrieved from WHO Coronavirus Disease Dashboard: https://www.who.int/emergencies/diseases/novel-coronavirus-2019/situation-reports/.
World Health Organization, W. (May 5, 2020). World Health Organization—Situation Report 106. Retrieved from WHO Coronavirus Disease Dashboard: https://www.who.int/emergencies/diseases/novel-coronavirus-2019/situation-reports/.
World Health Organization (WHO) Coronavirus disease (COVID-19) Situation Report—114, https://www.who.int/docs/default-source/coronaviruse/situation-reports/20200513-covid-19-sitrep-114.pdf?sfvrsn=17ebbbe_4. 16 pages (May 13, 2020).
World Health Organization (WHO) Health topics Communicable diseases Influenza Pandemic influenza Past pandemics, http://www.euro.who.int/en/health-topics/communicable-diseases/influenza/pandemic-influenza/past-pandemics. 1 page (2020).
World Health Organization (WHO) Home / Newsroom/ Detail /WHO: People living longer and healthier lives but COVID-19 threatens to throw progress off track, May 13, 2020 News Release, Geneva, https://www.who.int/news-room/detail/13-05-2020-people-living-longer-and-healthier-lives-but-covid-19-threatens-to-throw-progress-off-track. 3 pages (Accessed on Jul. 7, 2020).
Wu et al., Prolonged presence of SARS-CoV-2 viral RNA in faecal samples. The Lancet, 5: 434-435 (2020).
Wu et al., The outbreak of COVID-19: An overview. Journal of Chinese Medical Association 217-220 (2020).
Wu et al., Viewpoint: Characteristics of and Important lessons From the Coronavirus disease 2019 (COVID-19) outbreak in China summary of a report from the Chinese center for disease control and prevention. JAMA Network, 323(13): 1239-1242 (2020).
Xiao et al., Evidence for gastrointestinal infection of SARS-CoV-2. Gastroenterology, 158(6): 1-7 (2020).
Xu et al., Characteristics of pediatric SARS-CoV-2 infection and potential evidence for persistent fecal viral shedding. Nature Medicine, 26: 502-510 (2020).
Xu et al., Crystal structure of severe acute respiratory syndrome coronavirus spike protein fusion core. The Journal of Biological Chemistry, 279: 4914-4919 (2004).
Xu et al., Evolution of the novel coronavirus from the ongoing Wuhan outbreak and modeling of its spike protein for risk of human transmission. Science China Life Sciences, 63(3): 457-460 (2020).
Xu et al.: Pathological findings of COVID-19 associated with acute respiratory distress syndrome. The Lancet Respiratory Medicine 8: 420-422. https://doi.org/10.1016/S2213-2600(20)30076-X. (2020).
Yan et al., Structural basis for the recognition of SARS-CoV-2 by full-length human ACE2. Science, 367: 1444-1448 (2020).
Yanuck et al., Evidence supporting a phased immuno-physiological approach to COVID-19 from prevention through recovery. Integrative Medicine, 19(S1): 8-35 (2020).
Yao et al., In vitro antiviral activity and projection of optimized dosing design of hydroxychloroquine for the treatment of severe acute respiratory syndrome coronavirus 2 (SARS-CoV-2). Clinical Infectious Diseases, 71: 732-739 (2020).
Yeo et al., Enteric involvement of coronaviruses: is faecal-oral transmission of SARS-CoV-2 possible? The Lancet: Gastro and Hepatology, 5: 335-337 (2020).
Yeoh et al., Gut Microbia composition reflects disease severity and dysfunctional immune response in patients with COVID19. Gut 70: 698-706 (2021).
Zhang et al., Clinical characteristics of 140 patients infected with SARS-CoV-2 in Wuhan, China. European Journal of Allergy and Clinical Immunology, 75(7): 1730-1741 (2020).
Zhang et al., Crystal structure of SARS-CoV-2 main protease provides a basis for design of improved a-ketoamide inhibitors. Science, 368: 409-412 (2020).
Zhang et al., Cytokine release syndrome in severe COVID-19: interleukin-6 receptor antagonist tocilizumab may be the key to reduce mortality. International Journal of Antimicrobial Agents, 55: 2-7 (2020).
Zhang et al., Isolation of 2019-nCoV from a stool specimen of a laboratory-confirmed case of the coronavirus disease 2019 (COVID-19). China CDC Weekly 2(8): 123-124 (2020).
Zhang et al.. Molecular and serological investigation of 2019- nCoV infected patients: implication of multiple shedding routes. Emerging Microbes and Infections 9: 386-389 (2020).
Zhang et al., Ninety days in: a comprehensive review of the ongoing COVID-19 outbreak. Health Science Journal, 14(2): 706 (2020).
Zhang et al., Probable pangolin origin of SARS-CoV-2 associated with the COVID-19 outbreak. Current Biology, 30: 1346-1351 (2020).
Zhang et al.. The first-in-class peptide binder to the SARS-CoV-2 spike protein. bioRxiv. (2020).
Zhang et al. The digestive system is a potential route of 2019-nCov infection: a bioinformatics analysis based on single-cell transcriptomes. bioRxiv, 1-26 (2020).
Zhang et al.. Potential interventions for novel coronavirus in China: a systematic review. Journal of Medical Virology 92: 479-490 (2020).
Zheng et al., Novel antibody epitopes dominate the antigenicity of spike glycoprotein in SARS-CoV-2 compared to SARS-CoV. Nature Cellular & Molecular Immunology 17: 536-538 (2020).
Zhou et al., The human epigenome browser at Washington University. Nature methods, 8(12): 989-990 (2011).
Ziegler et al., SARS-CoV-2 receptor ACE2 is an interferon-stimulated gene in human airway epithelial cells and is enriched in specific cell subsets across tissues. Cell, 181(5), 1016-1035 (2020).
Zou et al., Single-cell RNA-seq data analysis on the receptor ACE2 expression reveals the potential risk of different human organs vulnerable to 2019-nCoV infection. Frontiers in Medicine. 14(2): 185-192 (2020).
Barnhart, et al. Symptomatic granular cell tumor involving the pituitary gland in a dog: a case report and review of the literature. Vet Pathol. May 2001;38(3):332-6.
Beers et al., The Merck Manual of Diagnosis and Therapy. Eighteenth Edition. Section 15: 1713-1717 (2006).
Beers et al., The Merck Manual of Diagnosis and Therapy. Eighteenth Edition. Section 19: 2308-2313 (2006).
Beers et al., The Merck Manual of Diagnosis and Therapy. Eighteenth Edition. Section 19: 2486-2489 (2006).
Creon 10000 (Kreon 10000). Reg. P N015581/01 14.05.09. Instructions for use, pp. 1-7 English Machine Translation, included with original pp. 1-5 in Russian [retrieved online Jan. 14, 2022] Retrieved from URL: https://www.vidal.ru/drugs/kreon_10000_2221 (2020).
Gubergrits et al.: Differentiated approach to replacement therapy in exocrine pancreatic insufficiency. Herald of Pancreatic Club, Lectures for Doctors 47(2):37-49 doi:10.33149/vkp.2020.02.04 [English Abstract] (2020).
HAYK: Coronavirus Infection and Chymotrypsin. Tokyo Medical University Hospital [online] [retrieved on Jan. 14, 2022], pp. 1-2 Retrieved from URL: https://www.researchgate.net/publication/341867070_Coronavirus_Infection_and_Chymotrypsin (Jun. 2020).
Muruato et al.: A high-throughput neutralizing antibody assay for COVID-19 diagnosis and vaccine evaluation. Nat Commun. 11(1):4059:1-6 doi:10.1038/s41467-020-17892-0 (2020).
PCT/US2021/049628 International Search Report and Written Opinion dated Dec. 16, 2021.
U.S. Appl. No. 16/103,192 Non-Final Office Action dated Nov. 26, 2021.
U.S. Appl. No. 16/103,192 Notice of Allowance dated Jun. 6, 2022.

* cited by examiner

FIG. 5

PLATE MAP

| PE LOT 2226-0001 | 1 | 2 | 3 | 4 | 5 | 6 | 7 | 8 | 9 | 10 | 11 | 12 |
|---|---|---|---|---|---|---|---|---|---|---|---|---|
| A | | NO CELLS | NO CELLS | NO CELLS | NO CELLS | NO CELLS | NO CELLS | NO CELLS | NO CELLS | NO CELLS | NO CELLS | NO CELLS |
| B | | 60µg/ml(0.001) | 15µg/ml(0.001) | 7.5µg/ml(0.001) | 3µg/ml(0.001) | VIRUS ONLY(0.001) | CELLS ONLY | 60µg/ml | 7.5µg/ml | CELLS ONLY | CELLS ONLY | CELLS ONLY |
| C | | 60µg/ml(0.001) | 15µg/ml(0.001) | 7.5µg/ml(0.001) | 3µg/ml(0.001) | VIRUS ONLY(0.001) | CELLS ONLY | 60µg/ml | 7.5µg/ml | CELLS ONLY | CELLS ONLY | CELLS ONLY |
| D | | 60µg/ml(0.001) | 15µg/ml(0.001) | 7.5µg/ml(0.001) | 3µg/ml(0.001) | VIRUS ONLY(0.001) | CELLS ONLY | 60µg/ml | 7.5µg/ml | CELLS ONLY | CELLS ONLY | CELLS ONLY |
| E | | 60µg/ml(0.0001) | 15µg/ml(0.0001) | 7.5µg/ml(0.0001) | 3µg/ml(0.0001) | VIRUS ONLY(0.0001) | CELLS ONLY | 15µg/ml | 3µg/ml | CELLS ONLY | CELLS ONLY | CELLS ONLY |
| F | | 60µg/ml(0.0001) | 15µg/ml(0.0001) | 7.5µg/ml(0.0001) | 3µg/ml(0.0001) | VIRUS ONLY(0.0001) | CELLS ONLY | 15µg/ml | 3µg/ml | CELLS ONLY | CELLS ONLY | CELLS ONLY |
| G | | 60µg/ml(0.0001) | 15µg/ml(0.0001) | 7.5µg/ml(0.0001) | 3µg/ml(0.0001) | VIRUS ONLY(0.0001) | CELLS ONLY | 15µg/ml | 3µg/ml | CELLS ONLY | CELLS ONLY | CELLS ONLY |
| H | | | | INFECTED | | | | | UNINFECTED | | | |

| PE LOT 2226-0003 | 1 | 2 | 3 | 4 | 5 | 6 | 7 | 8 | 9 | 10 | 11 | 12 |
|---|---|---|---|---|---|---|---|---|---|---|---|---|
| A | | NO CELLS | NO CELLS | NO CELLS | NO CELLS | NO CELLS | NO CELLS | NO CELLS | NO CELLS | NO CELLS | NO CELLS | NO CELLS |
| B | | 60µg/ml(0.001) | 15µg/ml(0.001) | 7.5µg/ml(0.001) | 3µg/ml(0.001) | VIRUS ONLY(0.001) | CELLS ONLY | 60µg/ml | 7.5µg/ml | CELLS ONLY | CELLS ONLY | CELLS ONLY |
| C | | 60µg/ml(0.001) | 15µg/ml(0.001) | 7.5µg/ml(0.001) | 3µg/ml(0.001) | VIRUS ONLY(0.001) | CELLS ONLY | 60µg/ml | 7.5µg/ml | CELLS ONLY | CELLS ONLY | CELLS ONLY |
| D | | 60µg/ml(0.001) | 15µg/ml(0.001) | 7.5µg/ml(0.001) | 3µg/ml(0.001) | VIRUS ONLY(0.001) | CELLS ONLY | 60µg/ml | 7.5µg/ml | CELLS ONLY | CELLS ONLY | CELLS ONLY |
| E | | 60µg/ml(0.0001) | 15µg/ml(0.0001) | 7.5µg/ml(0.0001) | 3µg/ml(0.0001) | VIRUS ONLY(0.0001) | CELLS ONLY | 15µg/ml | 3µg/ml | CELLS ONLY | CELLS ONLY | CELLS ONLY |
| F | | 60µg/ml(0.0001) | 15µg/ml(0.0001) | 7.5µg/ml(0.0001) | 3µg/ml(0.0001) | VIRUS ONLY(0.0001) | CELLS ONLY | 15µg/ml | 3µg/ml | CELLS ONLY | CELLS ONLY | CELLS ONLY |
| G | | 60µg/ml(0.0001) | 15µg/ml(0.0001) | 7.5µg/ml(0.0001) | 3µg/ml(0.0001) | VIRUS ONLY(0.0001) | CELLS ONLY | 15µg/ml | 3µg/ml | CELLS ONLY | CELLS ONLY | CELLS ONLY |
| H | | | | INFECTED | | | | | UNINFECTED | | | |

| PE LOT 2226-0004 | 1 | 2 | 3 | 4 | 5 | 6 | 7 | 8 | 9 | 10 | 11 | 12 |
|---|---|---|---|---|---|---|---|---|---|---|---|---|
| A | | NO CELLS | NO CELLS | NO CELLS | NO CELLS | NO CELLS | NO CELLS | NO CELLS | NO CELLS | NO CELLS | NO CELLS | NO CELLS |
| B | | 60µg/ml(0.001) | 15µg/ml(0.001) | 7.5µg/ml(0.001) | 3µg/ml(0.001) | VIRUS ONLY(0.001) | CELLS ONLY | 60µg/ml | 7.5µg/ml | CELLS ONLY | CELLS ONLY | CELLS ONLY |
| C | | 60µg/ml(0.001) | 15µg/ml(0.001) | 7.5µg/ml(0.001) | 3µg/ml(0.001) | VIRUS ONLY(0.001) | CELLS ONLY | 60µg/ml | 7.5µg/ml | CELLS ONLY | CELLS ONLY | CELLS ONLY |
| D | | 60µg/ml(0.001) | 15µg/ml(0.001) | 7.5µg/ml(0.001) | 3µg/ml(0.001) | VIRUS ONLY(0.001) | CELLS ONLY | 60µg/ml | 7.5µg/ml | CELLS ONLY | CELLS ONLY | CELLS ONLY |
| E | | 60µg/ml(0.0001) | 15µg/ml(0.0001) | 7.5µg/ml(0.0001) | 3µg/ml(0.0001) | VIRUS ONLY(0.0001) | CELLS ONLY | 15µg/ml | 3µg/ml | CELLS ONLY | CELLS ONLY | CELLS ONLY |
| F | | 60µg/ml(0.0001) | 15µg/ml(0.0001) | 7.5µg/ml(0.0001) | 3µg/ml(0.0001) | VIRUS ONLY(0.0001) | CELLS ONLY | 15µg/ml | 3µg/ml | CELLS ONLY | CELLS ONLY | CELLS ONLY |
| G | | 60µg/ml(0.0001) | 15µg/ml(0.0001) | 7.5µg/ml(0.0001) | 3µg/ml(0.0001) | VIRUS ONLY(0.0001) | CELLS ONLY | 15µg/ml | 3µg/ml | CELLS ONLY | CELLS ONLY | CELLS ONLY |
| H | | | | INFECTED | | | | | UNINFECTED | | | |

| CMAT | 1 | 2 | 3 | 4 | 5 | 6 | 7 | 8 | 9 | 10 | 11 | 12 |
|---|---|---|---|---|---|---|---|---|---|---|---|---|
| A | | NO CELLS | NO CELLS | NO CELLS | NO CELLS | NO CELLS | NO CELLS | NO CELLS | NO CELLS | NO CELLS | NO CELLS | NO CELLS |
| B | | 60µg/ml(0.001) | 15µg/ml(0.001) | 7.5µg/ml(0.001) | 3µg/ml(0.001) | VIRUS ONLY(0.001) | CELLS ONLY | 60µg/ml | 7.5µg/ml | CELLS ONLY | CELLS ONLY | CELLS ONLY |
| C | | 60µg/ml(0.001) | 15µg/ml(0.001) | 7.5µg/ml(0.001) | 3µg/ml(0.001) | VIRUS ONLY(0.001) | CELLS ONLY | 60µg/ml | 7.5µg/ml | CELLS ONLY | CELLS ONLY | CELLS ONLY |
| D | | 60µg/ml(0.001) | 15µg/ml(0.001) | 7.5µg/ml(0.001) | 3µg/ml(0.001) | VIRUS ONLY(0.001) | CELLS ONLY | 60µg/ml | 7.5µg/ml | CELLS ONLY | CELLS ONLY | CELLS ONLY |
| E | | 60µg/ml(0.0001) | 15µg/ml(0.0001) | 7.5µg/ml(0.0001) | 3µg/ml(0.0001) | VIRUS ONLY(0.0001) | CELLS ONLY | 15µg/ml | 3µg/ml | CELLS ONLY | CELLS ONLY | CELLS ONLY |
| F | | 60µg/ml(0.0001) | 15µg/ml(0.0001) | 7.5µg/ml(0.0001) | 3µg/ml(0.0001) | VIRUS ONLY(0.0001) | CELLS ONLY | 15µg/ml | 3µg/ml | CELLS ONLY | CELLS ONLY | CELLS ONLY |
| G | | 60µg/ml(0.0001) | 15µg/ml(0.0001) | 7.5µg/ml(0.0001) | 3µg/ml(0.0001) | VIRUS ONLY(0.0001) | CELLS ONLY | 15µg/ml | 3µg/ml | CELLS ONLY | CELLS ONLY | CELLS ONLY |
| H | | | | INFECTED | | | | | UNINFECTED | | | |

SIEVED PANCREATIC ENZYME CONCENTRATE, LOT#2226-0004
INHIBITION OF SARS-COV-2(MOI=0.001)
(VERO E6 CELLS)

FIG. 30

CMAT INHIBITION OF SARS-COV-2(MOI=0.001)
(VERO E6 CELLS)

FIG. 31

PANCREATIC ENZYME, LOT#2226-0004 INHIBITION OF SARS-COV-2
(VERO E6 CELLS)

○ 0.001
△ 0.0001

CYTOPROTECTION ABSORBANCE (540 nm)

TREATMENT [$LOG_{10}$ (μg/ml)]

FIG. 38

CMAT INHIBITION OF SARS-COV-2
(VERO E6 CELLS)

○ 0.001
△ 0.0001

CYTOPROTECTION ABSORBANCE (540 nm)

TREATMENT [$LOG_{10}$ (μg/ml)]

FIG. 39

METHODS OF PROPHYLAXIS OF CORONAVIRUS INFECTION AND TREATMENT OF CORONAVIRUSES

CROSS-REFERENCE

This application claims the benefit of U.S. Provisional Application No. 63/076,500, filed Sep. 10, 2020, which application is incorporated herein by reference in its entirety.

SUMMARY OF THE INVENTION

Urgent Unmet Need

All over the world, the COVID-19 pandemic is causing significant loss of life, disrupting livelihoods, and threatening the recent advances in health and progress towards global development goals highlighted in the 2020 World Health Statistics published by the World Health Organization (WHO).

From the start of reporting on Dec. 30, 2019, through 4:00 pm CEST Jun. 23, 2021 there have been 178,837,204 confirmed cases of COVID-19 resulting in 3,880,450 deaths.

Initially, the new virus was called 2019-nCoV. Subsequently, experts of the International Committee on Taxonomy of Viruses (ICTV) termed it the Severe Acute Respiratory Syndrome (SARS-CoV-2) virus as it is very similar to the one that caused the SARS outbreak (SARS-CoVs). The virus has been named SARS-CoV-2 and the disease it causes has been named Coronavirus Disease 2019 (COVID-19). On Jan. 31, 2020, the Department of Health and Human Services (HHS) issued a declaration of a public health emergency related to COVID-19, effective Jan. 27, 2020, and mobilized the Operating Divisions of HHS. In addition, on Mar. 13, 2020, the President declared a national emergency in response to COVID-19.

Communicable diseases are currently the leading cause of preventable deaths worldwide, disproportionately affecting resource-poor settings. Pandemic influenzas add to already unacceptable levels of morbidity and mortality from diarrhea, malaria, pneumonia, malnutrition, HIV/AIDS and tuberculosis, in addition to causing high maternal and neonatal death rates. A few key conditions cause 90% of deaths from communicable diseases: pneumonia (3.9 million deaths per year); diarrheal diseases (1.8 million); and malaria (1.2 million). Malnutrition is a significant contributing factor to this mortality. During a pandemic, these illnesses are likely to increase in resource-poor settings where chronically strained health systems would face even higher patient volumes, severe resource constraints, and absenteeism of critical staff.

Influenza pandemics have occurred in both the 21st and 20th Century. According to the world Health Organization the first influenza pandemic of the 21st century occurred in 2009-2010 and was caused by an influenza A(H1N1) virus. It was the first pandemic for which many WHO Member States had developed comprehensive pandemic plans describing the public health measures to be taken, aimed at reducing illness and fatalities. For the first time, pandemic vaccine was developed, produced and deployed in multiple countries during the first year of the pandemic.

While most cases of pandemic H1N1 were mild, globally it is estimated that the 2009 pandemic caused between 100,000-400,000 deaths in the first year alone. Children and young adults were disproportionately affected in comparison to seasonal influenza, which causes severe disease mainly in the elderly, persons with chronic conditions and pregnant women.

Three influenza pandemics occurred at intervals of several decades during the 20th century, the most severe of which was the so-called "Spanish Flu" (caused by an A(H1N1) virus), estimated to have caused 20 to 50 million deaths in 1918-1919. Milder pandemics occurred subsequently in 1957-1958 (the "Asian Flu" caused by an A(H2N2) virus) and in 1968 (the "Hong Kong Flu" caused by an A(H3N2) virus), which were estimated to have caused 1 to 4 million deaths each.

There is an urgent unmet need for Prophylaxis of SARS-CoV-2 Infection and Treatment of COVID-19. The current COVID-19 prevention and treatment guidelines are unsustainable in terms of human loss, economic impact, and the burden on the healthcare system. The economic impact on the world's economy is unprecedented. The coronavirus pandemic is already delivering significant economic data, with the U.S. unemployment rate reaching the worst number since the Great Depression. Further, with the resumption of normal business activities, if ever, coupled possibility of future recurrences of COVID-19 pandemic including possible future mutations of SARS-CoV-2, there exists significant uncertainty in the timing and magnitude of any economic recovery.

long-term symptoms are known to exist with SARS-CoV-2 infection well after the virus has left the respiratory tract. According to the Mayo Clinic, COVID-19 symptoms may persist for months and there are multiple long-term health risks. The virus can damage the lungs, heart and brain, which increases the risk of long-term health problems. Individuals with long-term health issues are sometimes describe as "long haulers" and the conditions have been called post-COVID-19 syndrome or "long COVID-I9." These health issues are sometimes called post-COVID-I9 conditions. They're generally considered to be effects of COVID-19 that persist for more than four weeks after you've been diagnosed with the COVID-19 virus. Older people and people with many serious medical conditions are the most likely to experience lingering COVID-19 symptoms, but even young, otherwise healthy people can feel unwell for weeks to months after infection. Common signs and symptoms that linger over time include: fatigue, shortness of breath or difficulty breathing, cough, joint pain, chest pain, memory, concentration or sleep problems, muscle pain or headache, fast or pounding heartbeat, loss of smell or taste, depression or anxiety, fever, dizziness when you stand, worsened symptoms after physical or mental activities.

Although COVID-19 is seen as a disease that primarily affects the lungs, it can damage many other organs as well. This organ damage may increase the risk of long-term health problems. Organs that may be affected by COVID-19 include the heart, lungs, brain, kidneys, and multi-symptom inflammatory syndrome.

Lasting damage to the heart muscle from COVID-19 has been shown by imaging tests taken months after recovery from COVID-19, even in people who experienced only mild COVID-19 symptoms. This may increase the risk of heart failure or other heart complications in the future.

Long-term damage to the lungs may be induced by the type of pneumonia often associated with COVID-19. Long-standing damage to the tiny air sacs (alveoli) in the lungs, resulting scar tissue, can lead to long-term breathing problems.

COVD-19 is known to cause long-term brain damage. Even in young people, COVID-19 can cause strokes, seizures and Guillain-Barre syndrome, a condition that causes temporary paralysis. COVID-19 may also increase the risk of developing Parkinson's disease and Alzheimer's disease.

In addition, some adults and children experience multisystem inflammatory syndrome after they have had COVID-19. In this condition, some organs and tissues become severely inflamed.

COVID-19 is also known to cause blood clots and blood vessel problems. COVID-19 can make blood cells more likely to clump up and form clots. While large clots can cause heart attacks and strokes, much of the heart damage caused by COVID-19 is believed to stem from very small clots that block tiny blood vessels (capillaries) in the heart muscle. Other parts of the body affected by blood clots include the lungs, legs, liver and kidneys. COVID-19 can also weaken blood vessels and cause them to leak, which contributes to potentially long-lasting problems with the liver and kidneys.

People who have severe symptoms of COVID-19 often have to be treated in a hospital's intensive care unit with mechanical assistance, such as ventilators, to breathe. Simply surviving this experience can make a person more likely to later develop posttraumatic stress syndrome, depression and anxiety.

Since much of the long-term effects of SARS-CoV-2 infection are still unknown, we can look to long-term effects seen in related viruses, such as the virus that causes severe acute respiratory syndrome (SARS) develop chronic fatigue syndrome, a complex disorder characterized by extreme fatigue that worsens with physical or mental activity, but doesn't improve with rest. The same may be true for people who have had COVID-19.

There is a clear and urgent unmet need for treatments to accelerate the recovery from COVID-19 and mitigate and damage due to long-term effects. In addition, long haulers need a treatment to accelerate their recovery from COVID-19.

The present COVID-19 pandemic has necessitated the rapid innovation and deployment of strategies for the prophylaxis of infection and emergent treatments for patients. At present, there is no pre-exposure or post exposure prophylaxis agents for SARS-CoV-2 other than vaccines. In addition, there are limited recommended options for the treatment of COVID-19; currently approved medications include the antiviral Remdesivir and Dexamethasone. Treatments are symptomatic, and in addition to Remdesivir and Dexamethasone, oxygen therapy represents the major treatment intervention for patients with severe infection. Mechanical ventilation may be necessary in cases of respiratory failure refractory to oxygen therapy, whereas hemodynamic support is essential for managing septic shock.

The genetic sequence of SARS-CoV-2, the coronavirus that causes COVID-19, was published on 11 Jan. 2020, triggering an intense global R&D activity to develop a vaccine against the disease. The scale of the humanitarian and economic impact of the COVID-19 pandemic is driving evaluation of next-generation vaccine technology platforms through novel paradigms to accelerate development, and the first COVID-19 vaccine candidate entered human clinical testing with unprecedented rapidity on 16 Mar. 2020.

A striking feature of the vaccine development land-scape for COVID-19 is the range of technology platforms being evaluated, including nucleic acid (DNA and RNA), virus-like particle, peptide, viral vector (replicating and non-replicating), recombinant protein, live attenuated virus and inactivated virus approaches. Public information on the specific SARS-CoV-2 antigen(s) used in vaccine development is limited. Most candidates for which information is available aim to induce neutralizing antibodies against the viral spike (S) protein, preventing uptake via the human ACE2 receptor. However, it is unclear how different forms and/or variants of the S protein used in different candidates relate to each other, or to the genomic epidemiology of the disease.

The global vaccine R&D effort in response to the COVID-19 pandemic is unprecedented in terms of scale and speed. Given the imperative for speed, in early 2021 emergency use has been granted by the FDA for several vaccines. This represents a fundamental change from the traditional vaccine development pathway, which takes on average over 10 years, even compared with the accelerated 5-year timescale for development of the first Ebola vaccine. There are currently no COVID-19 vaccines authorized for children. In addition, the long-term effects of the emergency use authorized COVID-19 vaccines are unknown and, ultimately, they may not be suitable for children, those who wish to have children, pregnant women, or even adults or adolescents.

Even It is not clear that a vaccines alone will avoid another pandemic. Much will depend on the actual COVID-19 viral reproduction rates. Current estimates put SARS-CoV-2 Viral Basic Reproduction Number ($R_0$) near 2.7 where $R_0$ is utilized in predicting the extent of immunization that a population requires (P) if herd immunity is to be achieved, the spread of the infection limited, and the population protected against future infection. FIG. 1 illustrates the Basic Reproduction Number $R_0$ for a variety of infectious diseases including: Influenza H1N1 in 2009, Influenza in Spring 1918, Influenza H2N2 in 1957, Ebola Virus, Zika, SARS-CoV-2, HIV, SARS-CoV-1, Influenza in Autumn of 1918, MERS-CoV, Smallpox, Rhinovirus, Poliomyelitis, and Measles. Note that SARS-CoV-2 $R_0$ is only slightly less infectious that HIV, for which, despite an enormous effort, does not currently have a vaccine.

To prevent sustained spread of the infection the proportion of the population that has to be immunized (P) has to be greater than $1-1/R_0$. The relation between P and Ro is shown in FIG. 2. The fundamental relationship is given by the equation $P=1-1/R_0$. Thus, with a COVID-19 $R_0$ of approximately 2.7, a population will require an immunization P of approximately 62.96%. Given that the best-case immunization numbers for a mature H1N1 vaccine are 41% and that any COVID-19 vaccine will likely have less than 100% effectiveness, it is unlikely that a vaccine alone will suffice to prevent a future COVID-19 pandemic.

By way of recent example, the 2017 to 2018 influenza season in the United States was a high severity season. Circulation of influenza viruses was widespread for an extended period throughout the country. Influenza A(H3N2) viruses predominated but influenza A(H1N1)pdm09 and B viruses also circulated. The Centers for Disease Control and Prevention (CDC) has estimated that there were 48.8 million influenza illnesses, 959,000 hospitalizations, and 79,400 influenza-associated deaths during 2017-2018, the highest morbidity and mortality since the 2009 pandemic. Influenza vaccination is the primary strategy to prevent influenza illness and its complications. Recent reports estimate that 42% of the US population was vaccinated against influenza during the 2017 to 2018 season, the mid-season estimates of the effectiveness of influenza vaccine were 36% against all influenza A and B virus infections and 25% against A(H3N2) virus infection.

Overall, the vaccine effectiveness against outpatient, medically attended, laboratory-confirmed influenza was 38% (95% confidence interval [CI], 31% to 43%), including 22% (95% CI, 12% to 31%) against influenza A(H3N2), 62% (95% CI, 50% to 71%) against influenza A(H1N1) pdm09, and 50% (95% CI, 41% to 57%) against influenza B.

It is estimated that influenza vaccination prevented 7.1 million (95% Credible Interval [CrI], 5.4 million to 9.3 million) illnesses, 3.7 million (95% CrI, 2.8 million to 4.9 million) medical visits, 109 000 (95% CrI, 39 000 to 231,000) hospitalizations, and 8000 (95% CrI, 1,100 to 21,000) deaths. Vaccination prevented 10% of expected hospitalizations overall and 41% among young children (6 months to 4 years). As of Jun. 10, 2021, approximately 43% of the US Population has been fully vaccinated. A remarkable achievement. However worldwide only 5.9% of the population is fully vaccinated.

In the US it is likely that several factors have substantially contributed to help mitigate infections and deaths from COVID-19. COVID-19 occurred late in the influenza (flu) season. While seasonal influenza viruses are detected year-round in the United States, influenza viruses are most common during the fall and winter. The exact timing and duration of flu seasons can vary, but influenza activity often begins to increase in October. Most of the time flu activity peaks between December and February, although activity can last as late as May. In addition, the unprecedented shelter in place federal, state, and local mandates, the closure of all non-essential businesses, schools, and public gatherings, coupled the use of preventive measures such as social distancing and appropriate protective equipment and procedures significantly reduced the rate of spread of the disease.

Further compounding a reduced effectiveness of COVID-19 vaccines is the growing reluctance for otherwise healthy individuals to take vaccines. Tremendous progress has been made in the development of new vaccines, along with increasing access to new and underused vaccines in the lowest income countries. But vaccines, often lauded as one of the greatest public health interventions, are losing public confidence. Some vaccine experts describe the problem as a "crisis of public confidence" and a "vaccination backlash". Public concerns about vaccine safety and vaccine legislation are as old as vaccines themselves, dating back to the anti-compulsory vaccination league against mandated smallpox vaccination in the mid-1800s. Some common concerns shared by the antivaccination groups of the 1800s and those of today are related primarily to arguments against mandated vaccination, or imposed vaccine schedules. But current antivaccination groups have new levels of global reach and influence, empowered by the internet and social networking capacities allowing like minds to rapidly self-organize transnationally, whether for or against vaccines. Many of these groups reach people who are not necessarily against vaccines, but who are seeking answers to questions about vaccine safety, vaccine schedules, changing policies, and the relevance of some new, and old, vaccines.

Traditional vaccines evoke concerns different from other health interventions because many healthy people need to be vaccinated to achieve a protective public health benefit. Several factors drive public questions and concerns: perceptions of business and financial motives of the vaccine industry and their perceived pressures on public institutions, such as during the H1N1 influenza response; coincidental rather than causal adverse events that are perceived as vaccine-related; challenges in management and communication of uncertainty about risks including serious, (albeit rare, ones); less risk tolerance for vaccines given to those who are healthy than for drugs given to treat an illness; skepticism of scientific truths, which later become untruths, or amended truths as new research becomes available; elitism of a group of people that believe they should not risk vaccination of their child if enough other children are being vaccinated; and/or outright nonacceptance of scientific evidence such as in the case of antivaccine movements that persist in the belief that autism can be caused by thiomersal or the measles.

For COVID-19 and many other diseases, the most affected population are individuals over the age of 60, who also represent the most difficult population to develop effective vaccines for. It is as-yet unclear what the long-term effectiveness of the present vaccines are for the elderly. As the immune system ages, the effectiveness and duration of vaccines wanes with it.

Coronaviruses make for difficult vaccine candidates because they produce many proteins that allow them to trick and evade the immune system. Coronaviruses (e.g., SARS-CoV-2) can play tricks with the immune system in a way other viruses cannot. The human immune system offers a two-pronged response to a viral invasion. One response produces antibodies which bind to the virus and eliminate the intruder. The other response more directly attacks infected cells. But coronaviruses (e.g., SARS-CoV-2) can mute the first response and make the other response hyperactive. Coronaviruses (e.g., SARS-CoV-2) effectively is amplifies what happens to humans naturally as our immune systems age. As a result, experiments with vaccines for Severe Acute Respiratory Syndrome (SARS) and Middle East Respiratory Syndrome (MERS) have not ended well. Some groups generated neutralizing antibodies, but they didn't provide adequate protection.

Globalization and human population growth have created pretty good ecosystems for new colonizing viruses. Every day the viral world makes trillions of random mutations and some of these mutations produce viruses that can adapt to human environments better than others While the current emergency use authorization for COVID-19 vaccines includes individuals with many types of underlying medical conditions, currently there is no long-term safety data for persons with underlying medical conditions. Those individuals with underlying medical conditions are the most at risk from SARS-CoV-2. Underlying medicals conditions include, but are not limited to, asthma; reactive airways disease, or other chronic disorders of the pulmonary or cardiovascular systems; metabolic diseases such as diabetes, renal dysfunction, and hemoglobinopathies; or known or suspected immunodeficiency diseases or immunosuppressed states, such as HIV, The long-term effects on children or adolescents receiving aspirin or other salicylates of their association of Reye syndrome and salicylates with wild-type virus infections are also unknown. long-term effects on individuals with acute febrile illness are similarly unknown.

Transplant Recipients immunogenicity for persons with solid organ transplants varies according to transplant type. Among persons with kidney or heart transplants, the proportion that developed seroprotective antibody concentrations was similar or slightly reduced compared with healthy persons. However, a study among persons with liver transplants indicated reduced immunologic responses to the influenza vaccination, especially if vaccination occurred within the 4 months after the transplant procedure. There is also no known long-term safety data for transplant recipients who receive a COVID-19 vaccination.

In summary, it is clear that the current COVID-19 prevention and treatment guidelines are unsustainable in terms of human loss, economic impact, and burden on our healthcare system: the lack of pre-exposure or post exposure prophylaxis agents other than vaccines; the limited number of antiviral treatments recommended for COVID-19; the lack of any treatment for COVID-19 long haulers, and the uncertainties surrounding the safety, efficacy, and acceptance of the vaccines, clearly demonstrates an urgent ever pressing unmet need for new prophylaxis and accelerated treatment modalities.

INCORPORATION BY REFERENCE

All publications, patents, and patent applications mentioned in this specification are herein incorporated by reference to the same extent as if each individual publication, patent, or patent application was specifically and individually indicated to be incorporated by reference.

No discussion of any information within this application shall be construed as an admission of prior art.

BRIEF DESCRIPTION OF THE DRAWINGS

The novel features of the are set forth with particularity in the appended claims. A better understanding of the features and advantages of the present will be obtained by reference to the following detailed description that sets forth illustrative embodiments, in which the principles of the are utilized, and the accompanying drawings of which:

FIG. 5 is a summary of ACE2 expression in human tissues based on publicly available transcriptomics and proteomics datasets

FIG. 19 depicts an Assay Plate Map for an experiment demonstrating the efficacy of CoGEN2 against SARS-CoV-2.

FIG. 30 demonstrate inhibition of SASRS-CoV-2 in Vero E6 Cells with Multiple of Infection (MOI)=0.001 after treatment with Pancreatic Enzyme Concentrate lot number 2226-0004.

FIG. 31 demonstrate inhibition of SASRS-CoV-2 in Vero E6 Cells with Multiple of Infection (MOI)=0.001 after treatment with Microencapsulated Pancreatic Enzyme Concentrate.

FIG. 38 demonstrate inhibition of SASRS-CoV-2 in Vero E6 Cells with Multiples of Infection (MOI)=0.0001 and MOI=0.001 after treatment with Sieved Pancreatic Enzyme Concentrate lot number 2226-0004.

FIG. 39 demonstrate inhibition of SASRS-CoV-2 in Vero E6 Cells with Multiples of Infection (MOI)=0.0001 and MOI=0.001 after treatment with Microencapsulated Pancreatic Enzyme Concentrate.

DETAILED DESCRIPTION OF THE INVENTION

Figure 1:
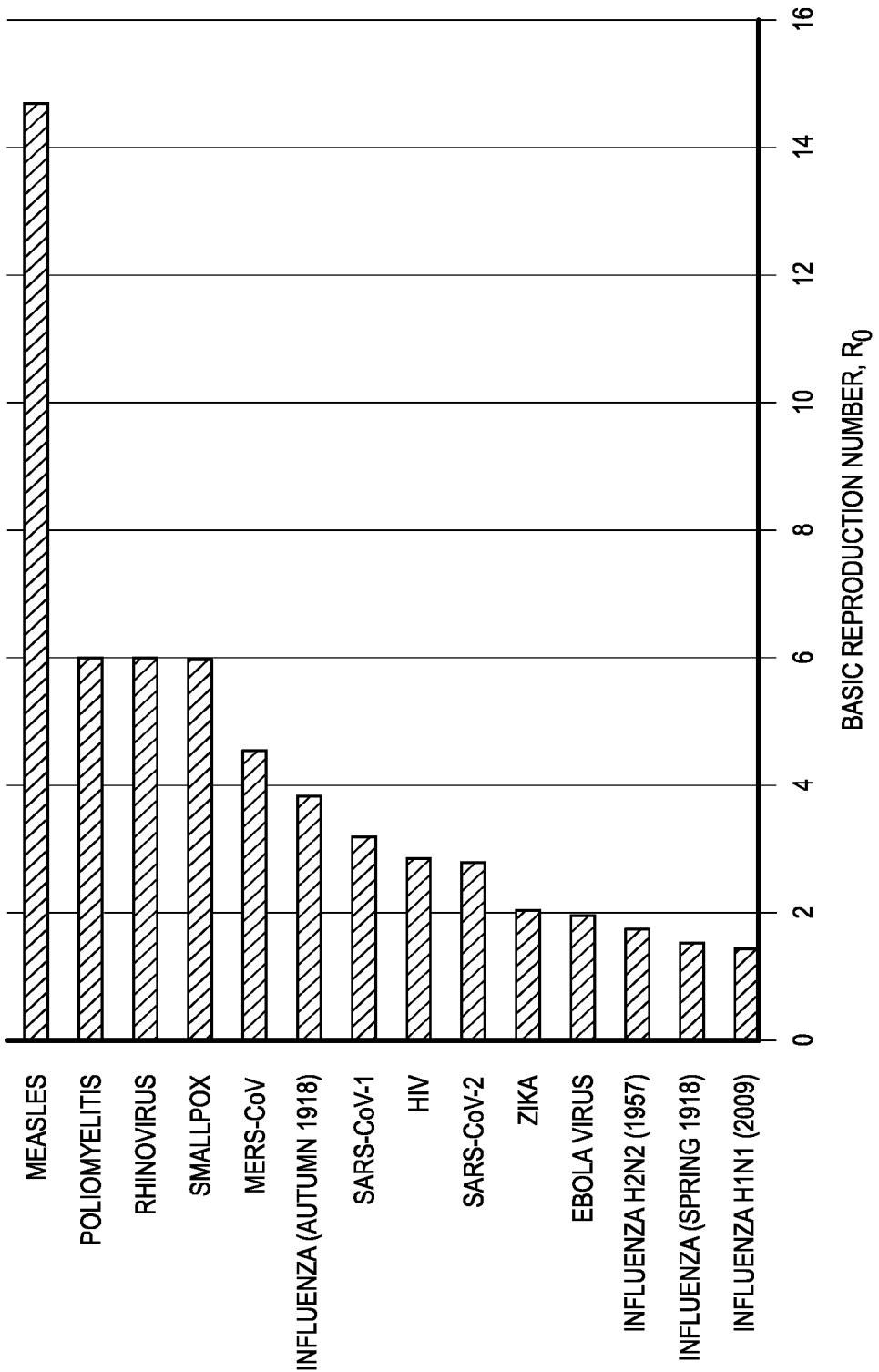
FIG. 1 is a chart presenting COVID-19 viral reproduction versus various diseases.
Figure 2:
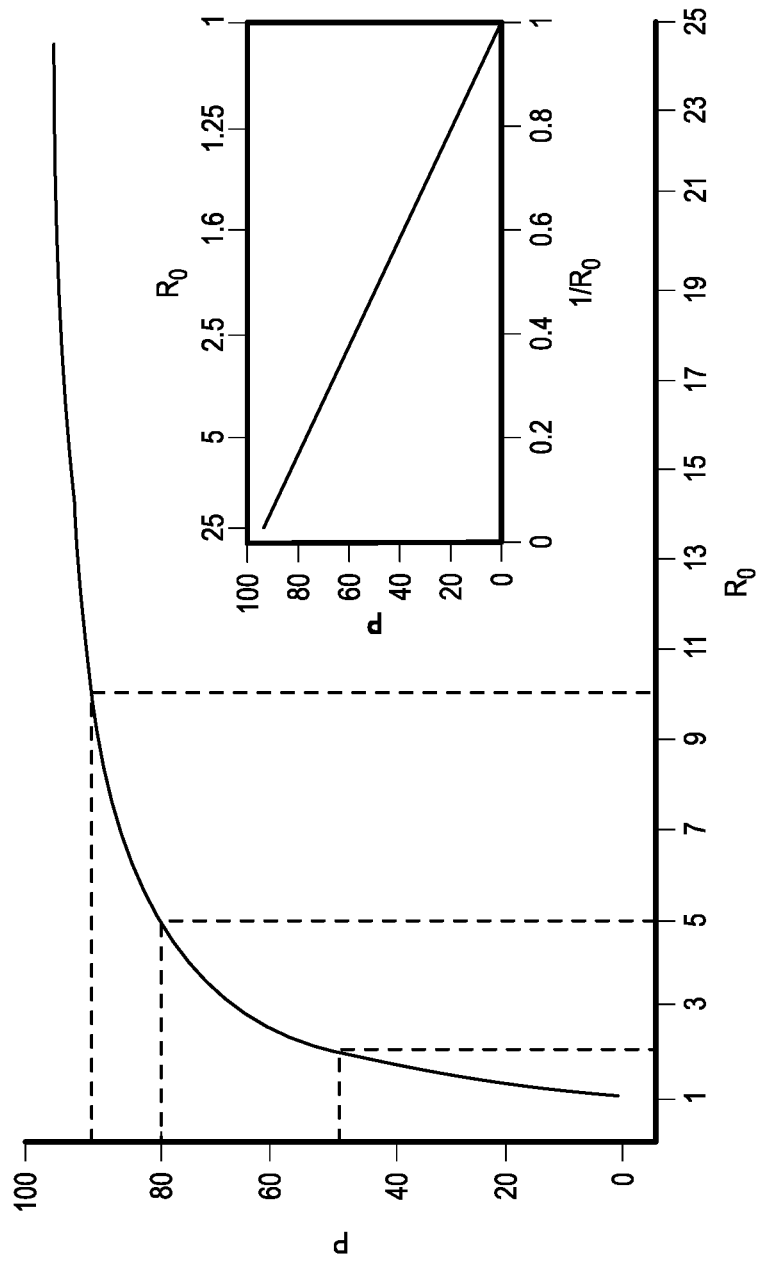
FIG. 2 is a graph depicting viral reproduction versus percent of population required to be immune to disease to avoid a pandemic.

The present provides a method utilizing a pharmaceutical composition comprised of coated or uncoated digestive enzymes and their derivatives as a prophylaxis against, and treatment of a coronavirus infection (e.g., SARS-CoV-2 infection) resulting in disease (e.g., COVID-19).

Coronaviruses Pre-SARS-CoV-2

Historically, coronaviruses (CoVs), enveloped positive-sense RNA viruses, are characterized by club-like spikes that project from their surface, an unusually large RNA genome, and a unique replication strategy. Coronaviruses cause a variety of diseases in mammals and birds ranging from enteritis in cows and pigs and upper respiratory disease in chickens to potentially lethal human respiratory infections. Coronaviruses (CoVs) are the largest group of viruses belonging to the Nidovirales order, which includes Coronaviridae, Arteriviridae, Mesoniviridae, and Roniviridae families. The Coronavirinae comprise one of two subfamilies in the Coronaviridae family, with the other being the Torovirinae. The Coronavirinae are further subdivided into four genera: the alpha ($\alpha$), beta ($\beta$), gamma ($\gamma$), and delta ($\delta$) coronaviruses. The viruses were initially sorted into these genera based on serology but are now divided by phylogenetic clustering.

All viruses in the Nidovirales order are enveloped, non-segmented positive-sense RNA viruses. They all contain very large genomes for RNA viruses, with some viruses having the largest identified RNA genomes, containing up to 33.5 kilobase (kb) genomes. Other common features within the Nidovirales order include: (1) a highly conserved genomic organization, with a large replicase gene preceding structural and accessory genes; (2) expression of many non-structural genes by ribosomal frameshifting; (3) several unique or unusual enzymatic activities encoded within the large replicase-transcriptase polyprotein; and (4) expression of downstream genes by synthesis of 3' nested subgenomic mRNAs. In fact, the Nidovirales order name is derived from these nested 3' mRNAs as nido is Latin for "nest." The major differences within the Nidovirus families are in the number, type, and sizes of the structural proteins. These differences cause significant alterations in the structure and morphology of the nucleocapsids and virions.

Genomic Organization

Coronaviruses contain a non-segmented, positive-sense RNA genome of ~30 kb. The genome contains a 5' cap structure along with a 3' poly (A) tail, allowing it to act as an mRNA for translation of the replicase polyproteins. The replicase gene encoding the nonstructural proteins (nsps) occupies two-thirds of the genome, about 20 kb, as opposed to the structural and accessory proteins, which make up only about 10 kb of the viral genome. The 5' end of the genome contains a leader sequence and untranslated region (UTR) that contains multiple stem loop structures required for RNA replication and transcription. Additionally, at the beginning of each structural or accessory gene are transcriptional regulatory sequences (TRSs) that are required for expression of each of these genes. The 3' UTR also contains RNA structures required for replication and synthesis of viral RNA. The organization of the coronavirus genome is 5'-leader-UTR-replicase-S (Spike)-E (Envelope)-M (Membrane)-N (Nucleocapsid)-3' UTR-poly (A) tail with accessory genes interspersed within the structural genes at the 3' end of the genome. The accessory proteins are almost exclusively nonessential for replication in tissue culture; however, some have been shown to have important roles in viral pathogenesis.

Virion Structure

Coronavirus virions are spherical with diameters of approximately 125 nm as depicted in recent studies by cryo-electron tomography and cryo-electron microscopy. The most prominent feature of coronaviruses is the club-shaped spike projections emanating from the surface of the virion. These spikes are a defining feature of the virion and give them the appearance of a solar corona, prompting the name, coronaviruses. Within the envelope of the virion is the nucleocapsid. Coronaviruses have helically symmetrical nucleocapsids, which is uncommon among positive-sense RNA viruses, but far more common for negative-sense RNA viruses.

Figure 3:
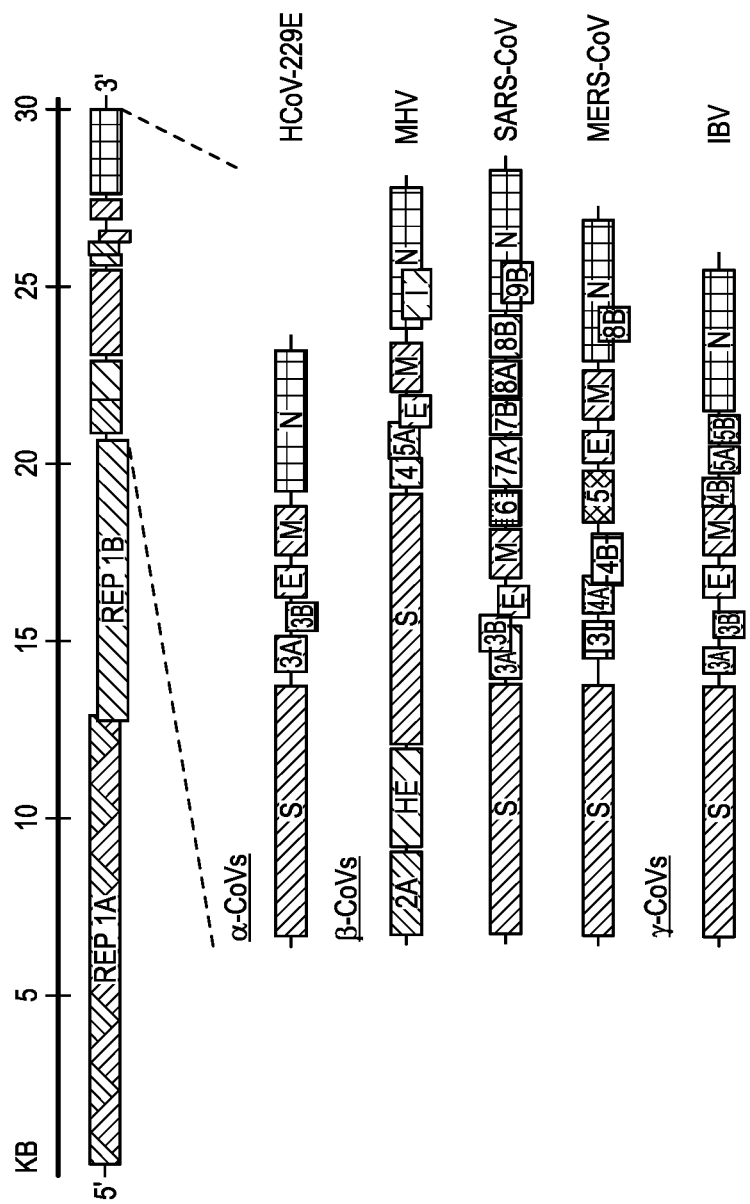
FIG. 3 provides a genomic organization of representative α, β, and γ coronaviruses illustrating the MHV genome along with the structural and accessory proteins in the 3' regions of the HCoV-229E, Murine Hepatitis Virus (MHV), SARS-CoV, MERS, and Infectious Bronchitis Virus (IBV).

FIG. 3 provides a genomic organization of representative $\alpha$, $\beta$, and $\gamma$ coronaviruses illustrating the MHV genome along with the structural and accessory proteins in the 3' regions of the HCoV-229E, MHV, SARS-CoV, MERS-CoV and IBV.

Coronavirus particles contain four main structural proteins. These are the spike (S), membrane (M), envelope (E), and nucleocapsid (N) proteins, all of which are encoded within the 3' end of the viral genome. The S protein (~150 kDa), utilizes an N-terminal signal sequence to gain access to the endoplasmic reticulum (ER), and is heavily N-linked glycosylated. Homotrimers of the virus encoded S protein make up the distinctive spike structure on the surface of the virus. The trimeric S glycoprotein is a class I fusion protein and mediates attachment to the host receptor. In most coronaviruses, the S protein is cleaved by a host cell furin-like protease into two separate polypeptides noted S1 and S2. S1 makes up the large receptor binding domain (RBD) of the S protein, while S2 forms the stalk of the spike molecule.

The M protein is the most abundant structural protein in the virion. It is a small (~25-30 kDa) protein with three transmembrane domains and is thought to give the virion its shape. It has a small N-terminal glycosylated ectodomain and a much larger C-terminal end domain that extends 6-8 nm into the viral particle. Despite being co-translationally inserted in the ER membrane, most M proteins do not contain a signal sequence. Recent studies suggest the M protein exists as a dimer in the virion, and may adopt two different conformations, allowing it to promote membrane curvature as well as to bind to the nucleocapsid.

The E protein (~8-12 kDa) is found in small quantities within the virion. The coronavirus E proteins are highly divergent but have a common architecture. The membrane topology of E protein is not completely resolved but most data suggest that it is a transmembrane protein. The E protein has an N-terminal ectodomain and a C-terminal endodomain and has ion channel activity. As opposed to other structural proteins, recombinant viruses lacking the E protein are not always lethal, although this is virus type dependent. The E protein facilitates assembly and release of the virus, but also has other functions. For instance, the ion channel activity in SARS-CoV E protein is not required for viral replication but is required for pathogenesis.

The N protein constitutes the only protein present in the nucleocapsid. It is composed of two separate domains, an N-terminal domain (NTD) and a C-terminal domain (CTD), both capable of binding RNA in vitro, but each domain uses different mechanisms to bind RNA. It has been suggested that optimal RNA binding requires contributions from both domains. N protein is also heavily phosphorylated, and phosphorylation has been suggested to trigger a structural change enhancing the affinity for viral versus non-viral RNA. The N protein binds the viral genome in a beads-on-a-string type conformation. Two specific RNA substrates have been identified for N protein: the TRSs and the genomic packaging signal. The genomic packaging signal has been found to bind specifically to the second, or C-terminal RNA binding domain. The N protein also binds nsp3, a key component of the replicase complex, and the M protein. These protein interactions likely help tether the viral genome to the replicase-transcriptase complex (RTC) and subsequently package the encapsidated genome into viral particles.

A fifth structural protein, the hemagglutinin-esterase (HE), is present in a subset of β-coronaviruses. The protein acts as a hemagglutinin, binds sialic acids on surface glycoproteins, and contains acetyl-esterase activity. These activities are thought to enhance S protein-mediated cell entry and virus spread through the mucosa. Interestingly, HE enhances murine hepatitis virus (MHV) neurovirulence; however, it is selected against in tissue culture for unknown reasons.

Viral Receptors

The initial attachment of the virion to the host cell is initiated by interactions between the S protein and its receptor. The sites of receptor binding domains (RBD) within the S1 region of a coronavirus S protein vary depending on the virus, with some having the RBD at the N-terminus of S1 (e.g., MHV), while others (e.g., SARS-CoV), have the RBD at the C-terminus of S1. The S protein-receptor interaction is the primary determinant for a coronavirus to infect a host species and also governs the tissue tropism of the virus. Many coronaviruses utilize peptidases as their cellular receptor. It is unclear why peptidases are used, as entry occurs even in the absence of the enzymatic domain of these proteins. Many α-coronaviruses utilize aminopeptidase N (APN) as their receptor, SARS-CoV and HCoV-NL63 use angiotensin converting enzyme 2 (ACE2) as their receptor, MHV enters through CEACAM1, and the recently identified MERS-CoV binds to dipeptidyl-peptidase 4 (DPP4) to gain entry into human cells. Table 1 below presents a listing of known CoV receptors pre-SARS-CoV-19.

TABLE 1

Virus Receptor References

| | Receptor |
| --- | --- |
| Alphacoronaviruses | |
| HCoV-229E | Aminopeptidase N (APN) |
| HCoV-NL63 | Angiotensin Converting Enzyme 2 (ACE2) |
| TGEV | APN |
| PEDV | APN |
| FIPV | APN |
| CCoV | APN |
| Betacoronaviruses | |
| MHV | Murine Carcinoembryonic Antigen-Related Adhesion Molecule I (mCEACAM) |
| BCoV | N-acetyl-9-O-acetylneuraminic acid |
| SARS-CoV | ACE2 |
| MERS-CoV | Dipeptidyl Peptidase 4 (DPP4) |

SARS-CoV-2 Phylogenetics and Taxonomy

SARS-CoV-2 also belongs to the broad family of viruses known as coronaviruses. It is a positive-sense single-stranded RNA (+ssRNA) virus, with a single linear RNA segment. Other coronaviruses are capable of causing illnesses ranging from the common cold to more severe diseases such as MERS (fatality rate ~34%). It is the seventh known coronavirus to infect people, after 229E, NL63, OC43, HKU1, MERS-CoV, and the original SARS-CoV. The SARS-CoV-2 virus belongs to the Realm: Riboviria, Kingdom: Orthornavirae, Phylum: Pisuviricota, Class: Pisoniviricetes, Order: Nidovirales, Family: Coronaviridae, Genus: Betacoronavirus, Subgenus: Sarbecovirus, Species Severe acute Respiratory syndrome-related coronavirus, Strain: Severe acute respiratory syndrome coronavirus 2 (SARS-Cov-2).

Like the SARS-related coronavirus strain implicated in the 2003 SARS outbreak, SARS-CoV-2 is a member of the subgenus Sarbecovirus (beta-CoV lineage B). Its RNA sequence is approximately 30,000 bases in length. SARS-CoV-2 is unique among known betacoronaviruses in its incorporation of a polybasic cleavage site, a characteristic known to increase pathogenicity and transmissibility in other viruses.

Proteolytic excision at polybasic cleavage sites is a post-translational modification phenomenon required for the maturation and activation of several precursor proteins, including neuropeptides, peptide hormones, growth factors, membrane receptors, coagulation factors, and adhesion proteins.

Various cellular proteases such as furin, trypsin, cathepsin, and trans-membrane protease/serine that catalyze the proteolytic activation process cleave various viral cell surface proteins, which is required for the viral entry to host cells. A wide range of evidence indicates that the proteolytic cleavage of viral surface proteins at the polybasic cleavage site is essential for viral pathogenicity, virulence, and interspecies transmission.

The pathogenicity and interspecies transmission of novel coronavirus (SARS-Cov-2) strictly depends on the S protein present on the viral cell surface. The S protein plays a vital role in attaching the virus with the host cell receptor (e.g., ACE2) and subsequently mediating viral entry through membrane fusion. Proteolytic cleavage of the S protein is an indispensable step for the viral entry to host cells. Many host cellular proteases, including furin, trypsin, and cathepsin, are present to catalyze the proteolytic activation of the S protein. Of these proteases, furin recognizes a polybasic cleavage site and cleaves the S protein during its synthesis in the trans-Golgi network or during entry of the virus in endosomes. In contrast, trypsin cleaves the S protein at monobasic cleavage sites in the extracellular area and the cell surface. Most interestingly, the acquisition of a polybasic cleavage site at the junction of two domains of the spike protein (S1 and S2) is a newly evolved feature of a novel coronavirus, which may be a potential reason for the deadly outbreak of this highly pathogenic virus. The polybasic cleavage site is generated as a result of the insertion of 12 nucleotides, which subsequently results in the predicted acquisition of 3 glycans around the site. This particular feature is not present in the spike proteins of other coronaviruses, including bat coronavirus and SARS-CoV.

Each SARS-CoV-2 virion is 50-200 nanometers in diameter. Protein modeling experiments on the S protein of the virus soon suggested that SARS-CoV-2 has sufficient affinity to the receptor angiotensin converting enzyme 2 (ACE2) on human cells to use them as a mechanism of cell entry. SARS-CoV-2 has a higher affinity to human ACE2 than the original SARS virus strain. SARS-CoV-2 may also assist in cell entry. Initial S protein priming by transmembrane protease, serine 2 (TMPRSS2) is essential for entry of SARS-CoV-2. After a SARS-CoV-2 virion attaches to a target cell, the cell's protease TMPRSS2 cuts open the S protein of the virus, exposing a fusion peptide in the S2 subunit, and the host receptor ACE2. After fusion, an endosome forms around the virion, separating it from the rest of the host cell. The virion escapes when the pH of the endosome drops or when cathepsin, a host cysteine protease, cleaves it. The virion then releases RNA into the cell and forces the cell to produce and disseminate copies of the virus, which infect more cells. SARS-CoV-2 produces at least three virulence factors that promote shedding of new virions from host cells and inhibit immune response. Whether they include downregulation of ACE2, as seen in similar coronaviruses remains under investigation.

COVID-19 Pathogenesis

The pathogenesis of COVID-19 has a number of significant attributes. For example, not all people exposed to SARS-CoV-2 are infected and not all infected patients develop severe respiratory illness. SARS-CoV-2 infection can be roughly divided into three stages: stage I, an asymptomatic incubation period with or without detectable virus; stage II, non-severe symptomatic period with the presence of virus; and stage III, severe respiratory symptomatic stage with high viral load. From the point of view of prevention, individuals at stage I (the stealth carriers) are the least manageable because, at least on some occasions, they unknowingly spread the virus.

Clinically, the immune responses induced by SARS-CoV-2 infection are two-phased. During the incubation and non-severe stages, a specific adaptive immune response is required to eliminate the virus and to preclude disease progression to severe stages. Genetic differences are well-known to contribute to individual variations in the immune response to pathogens. However, when a protective immune response is impaired, virus will propagate and massive destruction of the affected tissues will occur, especially in organs that have high ACE2 expression, such as intestine and kidney. The damaged cells induce innate inflammation in the lungs that is largely mediated by pro-inflammatory macrophages and granulocytes. Lung inflammation is the main cause of life-threatening respiratory disorders at the severe stage.

Alarmingly, after discharge from hospital, some patients remain/return viral positive and others even relapse. This indicates that a virus-eliminating immune response to SARS-CoV-2 may be difficult to induce, at least in some patients, and vaccines may not work in these individuals.

It has become increasingly clear that the mechanism for SARS-CoV-2 infection is the requisite binding of the virus to the membrane-bound form of angiotensin-converting enzyme 2 (ACE2) and subsequent internalization of the complex by the host cell. As ACE2 may be a coreceptor for the coronavirus, new therapeutic approaches are being researched to block the enzyme or reduce its expression to prevent the cellular entry and subsequent SARS-CoV-2 infection in tissues that express ACE2 including lung, heart, kidney, brain, and gut. The blocking on the host side or on the viral side are both being given consideration as part of the novel paradigms being considered both for anti-virial medications and vaccine development.

Figure 4:
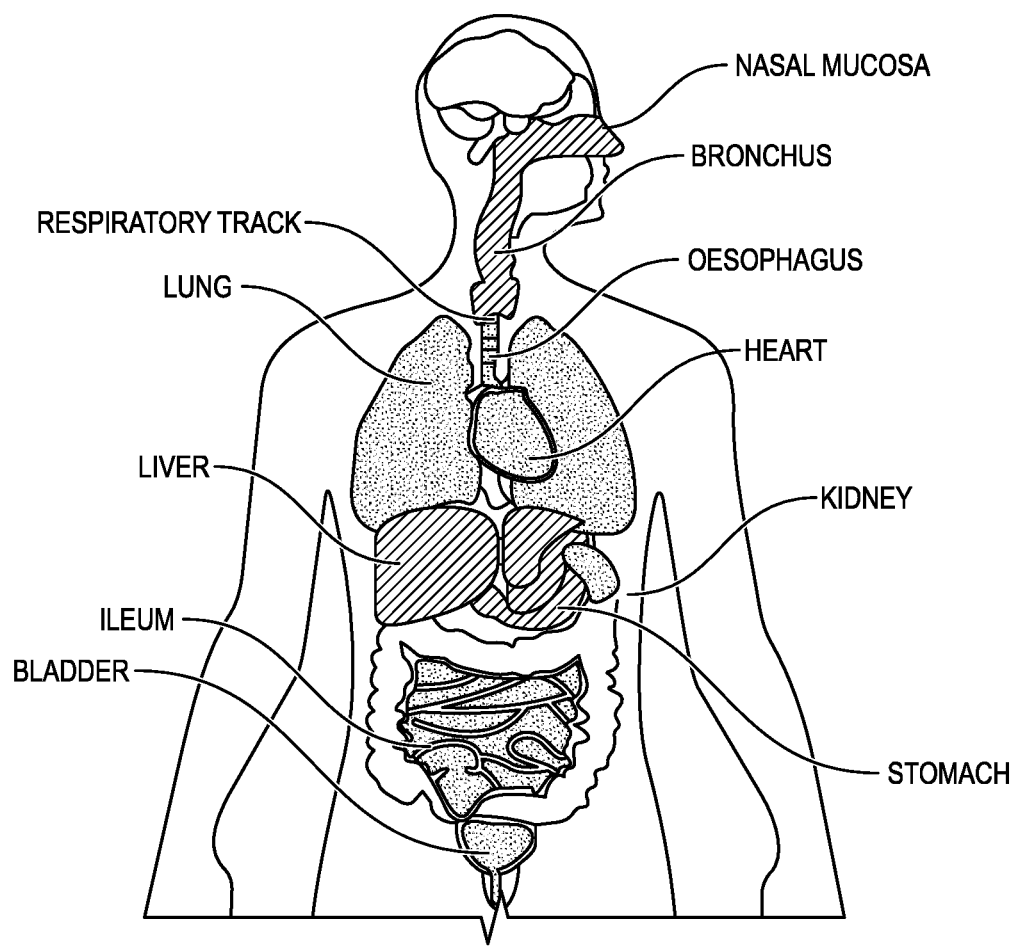
FIG. 4 is a summary of ACE2 expression in human tissues based on publicly available transciptomics and proteomics datasets.

By examining ACE2 expression pattern in different organs, tissue, and cells, we can determine areas of risk to SARS-CoV-2 virus infection via the ACE2 surface enzyme as target cells expressing ACE2 permit coronavirus entry, multiplication, spread, and pathogenesis. FIG. 4 presents a map of ACE2 expression over different cell types of different organs to predict the risk for SARS-CoV-2 virus infection and injury. In addition to the known distribution of ACE2 in the lungs and kidneys, FIG. 4 indicates that there are significant levels of ACE2 in the heart with the highest levels of expression being found in the small intestines, especially the ileum.

Based upon stringently-validated immunohistochemical analysis and high-throughput mRNA sequencing from several datasets, it has been shown that ACE2 expression is mainly localized to microvilli of the intestinal tract as well as renal proximal tubules, gallbladder epithelium, testicular Sertoli cells and Leydig cells, glandular cells of seminal vesicle, and cardiomyocytes. The expression in several other previously reported locations, including alveolar type II (AT2) cells, could not be confirmed. Furthermore, ACE2 expression was absent in the AT2 lung carcinoma cell line A549, often used as a model for viral replication studies.

Through the use of two independent, well-characterized antibodies for immunohistochemical analysis of ACE2 and stringent validation criteria and comparison of the protein expression profiles with multiple transcriptomics datasets, reliable expression could only be confirmed in microvilli of the intestinal tract and renal proximal tubules, in gallbladder epithelium, testicular Sertoli cells and Leydig cells, a subset of glandular cells in seminal vesicle and in cardiomyocytes, with no detectable expression in lung or respiratory epithelia.

Figure 5:
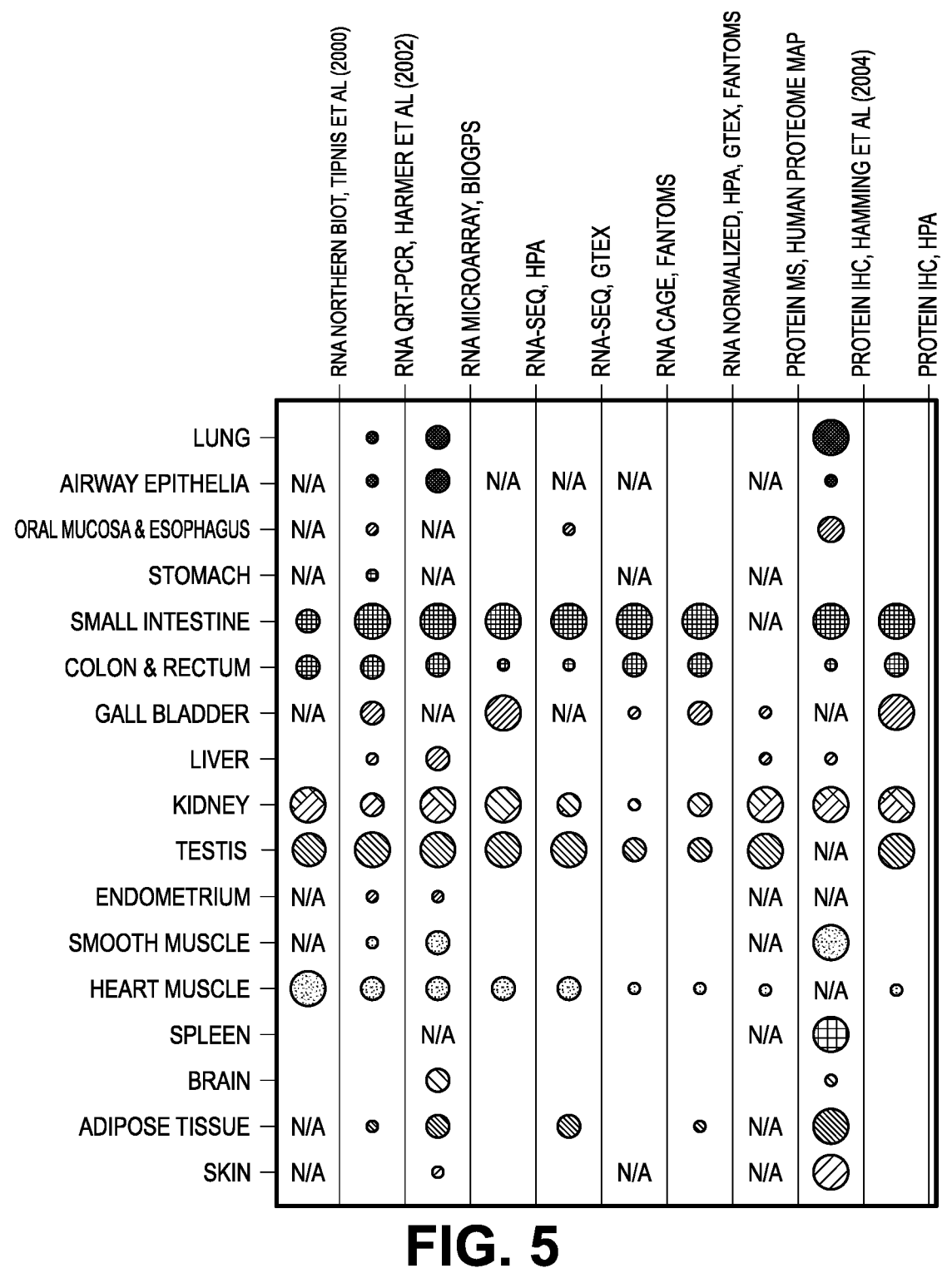

FIG. 5 presents a summary of ACE2 expression in human tissues based on publicly available transcriptomics and proteomics datasets. As shown three different sizes of circles, large, medium, and small, represent high, medium, or low expression levels, respectively. The crosshatch in each circle represents an organ system. A consistent expression in the intestinal tract, gallbladder, kidney, testis, and heart muscle is observed across all datasets. Note that the broadest reported expression profile includes lung, oral mucosa, esophagus, spleen, adipose tissue, smooth muscle, brain, and skin. N/A indicates that no data is available.

All studied datasets confirm a consistent high expression in the intestinal tract, gallbladder, and kidney. In addition to respiratory symptoms, the closely related SARS-CoV that caused the SARS outbreak was shown to also cause diarrhea, impaired liver function, and elevation of non-cardiac creatine kinase, suggesting tropism of the virus to other organs well in line with the tissues showing the highest expression levels of ACE2. Interestingly, in a recent study on pediatric COVID-19 individuals, 8 out of 10 cases showed rectal swabs positive for SARS-CoV-2 virus, suggesting that the gastrointestinal tract may shed virus and that fecal-oral transmission may be a possible route for infection.

Figure 6:
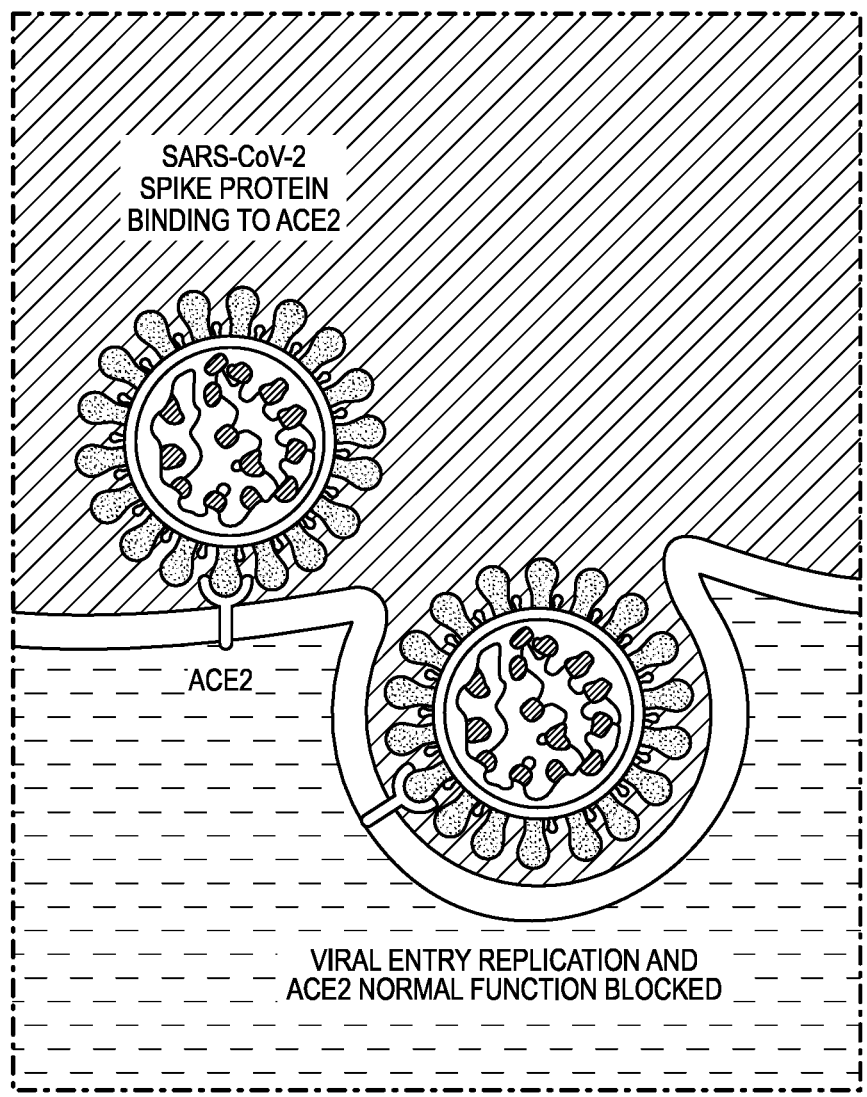
FIG. 6 is an illustration of SARS-CoV-2 spike protein binding to ACE2, viral entry, replication, and blocking of normal ACE2 function.

The intracellular entry by SARS-CoV-2 and SARS-CoV, appears to be governed by the spike protein (S Protein). This protein binds via a receptor-binding region to the extracellular domain of ACE2 with high affinity of 15 nM. Cleavage of the S protein along dibasic arginine sites by the host protease TMPRSS2 to generate the S1 and S2 subunits is a critical step for S2-induced membrane fusion and viral internalization by endocytosis with ACE2 in the pulmonary epithelium. FIG. 6 is an illustration of SARS-CoV-2 S protein binding to ACE2, viral entry, replication, and blocking of normal ACE2 function.

Figure 7:
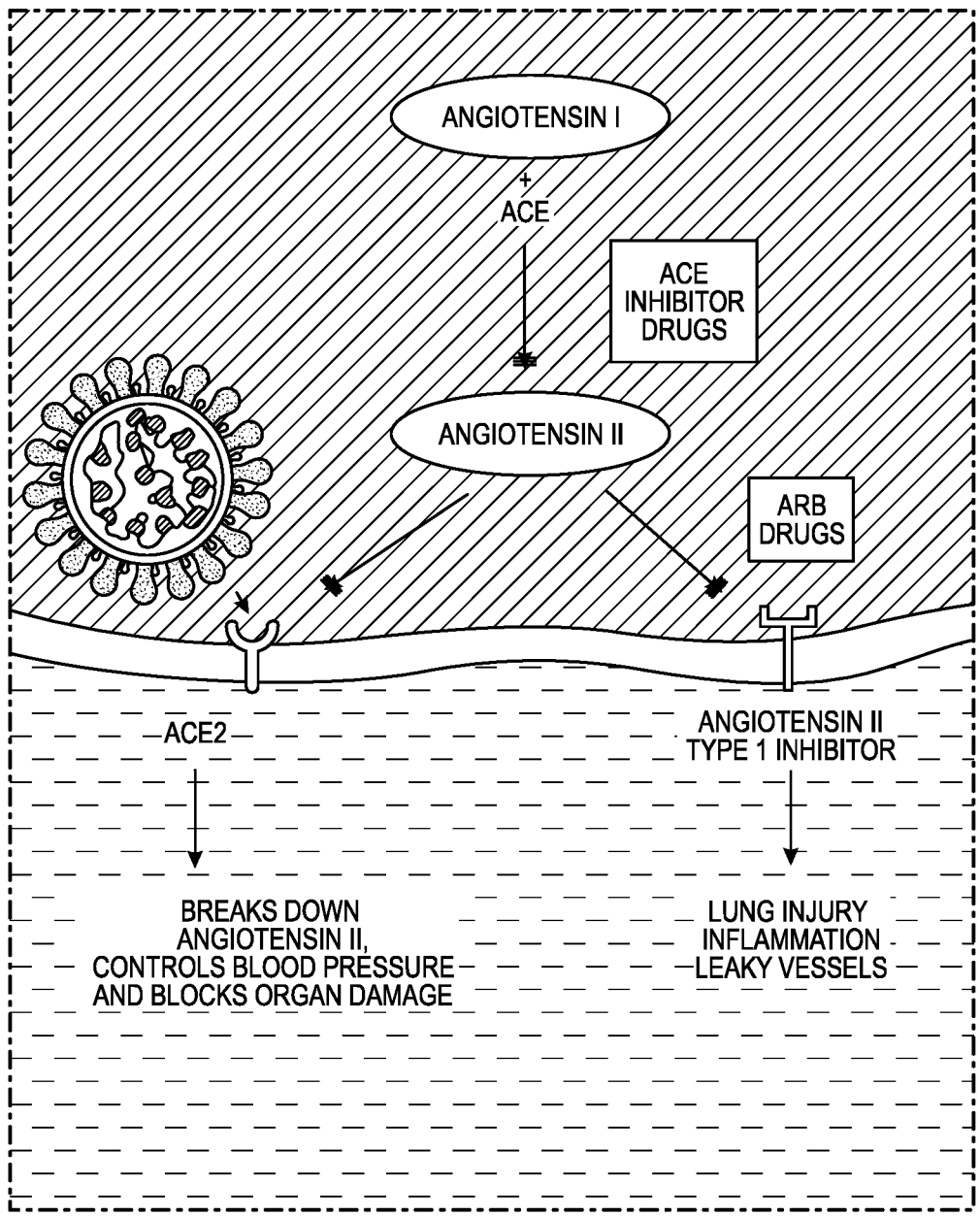
FIG. 7 is an illustration of the conversion of Angiotensin I into Angiotensin II along with ACE and ACE2 functionality.

The ACE enzyme converts angiotensin I into angiotensin II. The main role of ACE2 is to break down angiotensin II into molecules that counteract angiotensin II's harmful effects; but if the virus occupies the ACE2 'receptor' on the surface of cells, then its role is blunted. Drugs called ACE inhibitors inhibit the formation of angiotensin II, which would otherwise interact with the angiotensin type 1 receptor to produce tissue damage and inflammation. Drugs called Angiotensin II receptor blockers (ARBs) block angiotensin II from interacting with its receptor. FIG. 7 depicts the conversion of angiotensin I into angiotensin II along with ACE and ACE2 functionality.

In the association between angiotensin converting enzyme 2 (ACE2) and SARS-CoV-2, ACE2 has been shown to be a co-receptor for viral entry for SARS-CoV-2 with increasing evidence that it has a protracted role in the pathogenesis of COVID-19. ACE2 has a broad expression pattern in the human body with strong expression as noted earlier in the gastrointestinal system, heart, and kidney with more recent data identifying expression of ACE2 in type II alveolar cells in the lungs. The concern that Angiotensin-converting enzyme inhibitors (ACEIs) and Angiotensin II receptor blockers (ARBs) affect the severity and mortality of COVID-19 is 2-fold. When the SARS-CoV-2 virus enters the target cell, a surface unit of the S glycoprotein binds to a cellular receptor. Upon entry, cellular proteases cleave the S protein which leads to fusion of the viral and cellular membranes. SARS-CoV has previously been shown to enter the cell via the ACE2 receptor, primed by the cellular serine protease TMPRSS2, and recent studies suggest that also SARS-CoV-2 employs ACE2 and TMPRSS2 for host cell entry.

Figure 8:
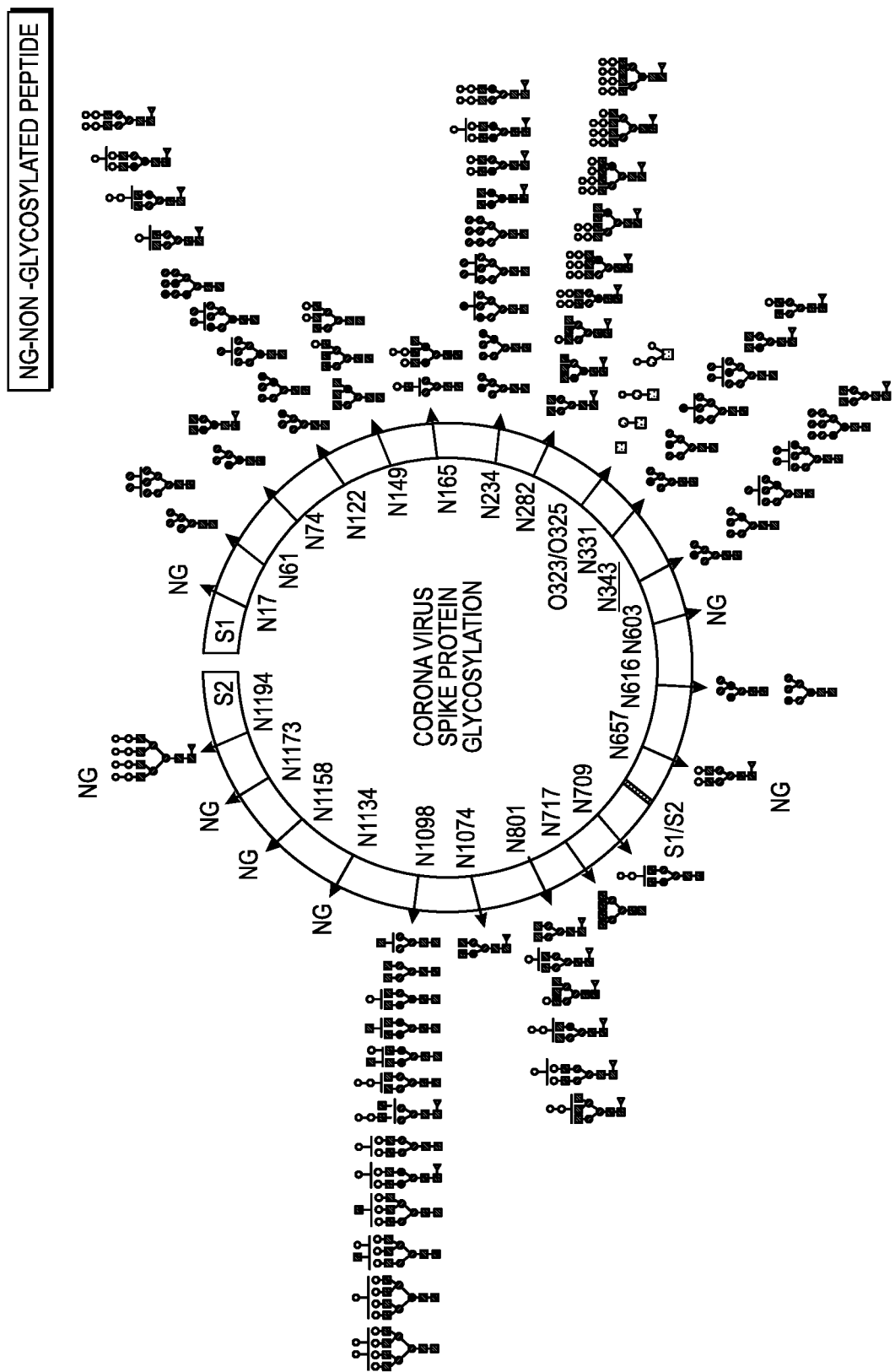
FIG. 8 is an illustration of the glycosylation profile on coronavirus SARS-CoV-2.

The S proteins of SARS-CoV-2 are heavily glycosylated. This S protein, which facilitates viral attachment, entry and membrane fusion, plays a critical role in the elicitation of the host immune response. Viral glycosylation is a mechanism viruses and other obligate parasites use to camouflage their presence and hinder immune response by the body. These glycans of the S protein have been shown to protect a large portion of the S protein from immune recognition, with the exception of the ACE2 binding region. The glycan coated S protein is considered a trimeric class I fusion protein that is composed of two functional subunits responsible for receptor binding, (S1subunit) and membrane fusion (S2 subunit), together possessing 22 potential N-glycosylation sites. This form of glycan binding to a protein through the nitrogen region of amino acids such as asparagine, is common to many viruses and occurs early during the synthesis of the viral proteins. Alternatively, post-translational modifications in the endoplasmic reticulum can also lead to O-glycosylation, for example, attachment of the carbohydrate through the oxygen of an amino acid. Various studies have produced slightly differing results with respect to the level of glycosylation on the S protein. One study utilizing high-resolution LC-MS/MS found 17 N-glycosylation sites occupied out of 22 potential sites along with two O-glycosylation sites bearing core-1 type O-glycans. Some N-glycosylation sites were partially glycosylated along with a high level of mannose and complex glycosylation along with O-glycans on the receptor binding domain of the S1 subunit of the S protein. In another study, all 22 sites are occupied most of the time while another study found glycans at all 22 sites. FIG. 8 illustrates the glycosylation profile on SARS-CoV-2.

It has further been demonstrated that the most accessible portion of the S protein is at the level of the ACE2 binding domain. To date, there do not appear to be any mutations to the N-linked glycosylation sites in SARS-CoV-2, especially compared to other viruses, such as in the HIV-1 envelope. This stable configuration of the glycosylated sites makes the S protein a target for blockage or destruction.

Site-specific mass spectrometric examination of the glycan structure in vitro on a recombinant SARS-CoV-2 S immunogen employed enzymatic degradation of the S protein to examine the glycan subunits located on each portion of the S protein. The site-specific glycosylation suggests that the glycan shield of SARS-CoV-2 S protein is consistent with other coronaviruses and similarly exhibits numerous vulnerabilities throughout the glycan shield. Trace levels of O-linked glycosylation at T323/5325 with over 99% of these sites unmodified suggesting that O-linked glycosylation of this region is minimal when the structure is native-like. The predominance of N-glycosylation represents an attack sites for unmasking of the S protein.

Gastro-Intestinal Infectivity

The disease COVID-19 has been characterized as a novel acute respiratory syndrome caused by SARS CoV-2 virus, which is a highly transmissible infectious disease. The S protein of the SARs-CoV-2 virus is responsible for the infectivity with the S1 subunit responsible for the attachment of the virus and the S2 subunit responsible for the fusion of the viral and the human membranes. The area of entry of the virus and subsequent attachment is the ACE2 receptor, with a high affinity for binding attachment. Both anti-viral treatments and vaccines being developed appear, in many cases, to target the S protein to essentially try and neutralize it, thus, preventing binding to or a targeting the ACE2 entry receptor.

The primary route of infectivity of the SARS-CoV-2 virus is believed to be through the respiratory tract. The GI tract is also a major location for ACE2 receptors. The major expression of the ACE2 receptors in the GI tract allows the gut acts as a major portal of entry and potentially gestation of the SARS-CoV-2 virus in humans. By way of example, in the case of a mother and infant both of whom were affected with SARS-CoV-2, both the neonate (<28 days) and her mother expressed viral loads in the stool, with the viral loads remaining extremely high in the both well past symptom amelioration. It was further noted that the stool samples could be positive for SARS-CoV-2 irrespective of the presence of gastrointestinal symptoms could remain positive for a least a month. Further, the SARS-CoV-2 virus was present early in the stools prior to the onset of symptoms.

Digestive symptoms occur in patients with SARS-CoV-2 infection. In April of 2020, the results of a descriptive cross-sectional multi-center study of 204 patients who presented in three hospitals in China between January and February of 2020 became available. Of the 204 patients, 103 reported digestive symptoms including diarrhea and vomiting. As the severity of the disease increased, the digestive symptoms became more pronounced. Patients with digestive symptoms had a significantly longer time from the onset to admission than patients without digestive symptoms (9.0 days vs. 7.3 days). Patients with digestive symptoms had higher mean liver enzyme levels, lower monocyte count, longer prothrombin time, and received more antimicrobial treatments than those without digestive symptoms.

While the current thinking about SARS-CoV-2 infection is that the primary site of infectivity is the lungs, and that the virus is inhaled into the body, there exists emerging evidence that the virus could enter through a fecal oral route, and or that viral shedding could become a source of re-infection in the general population.

Figure 9:
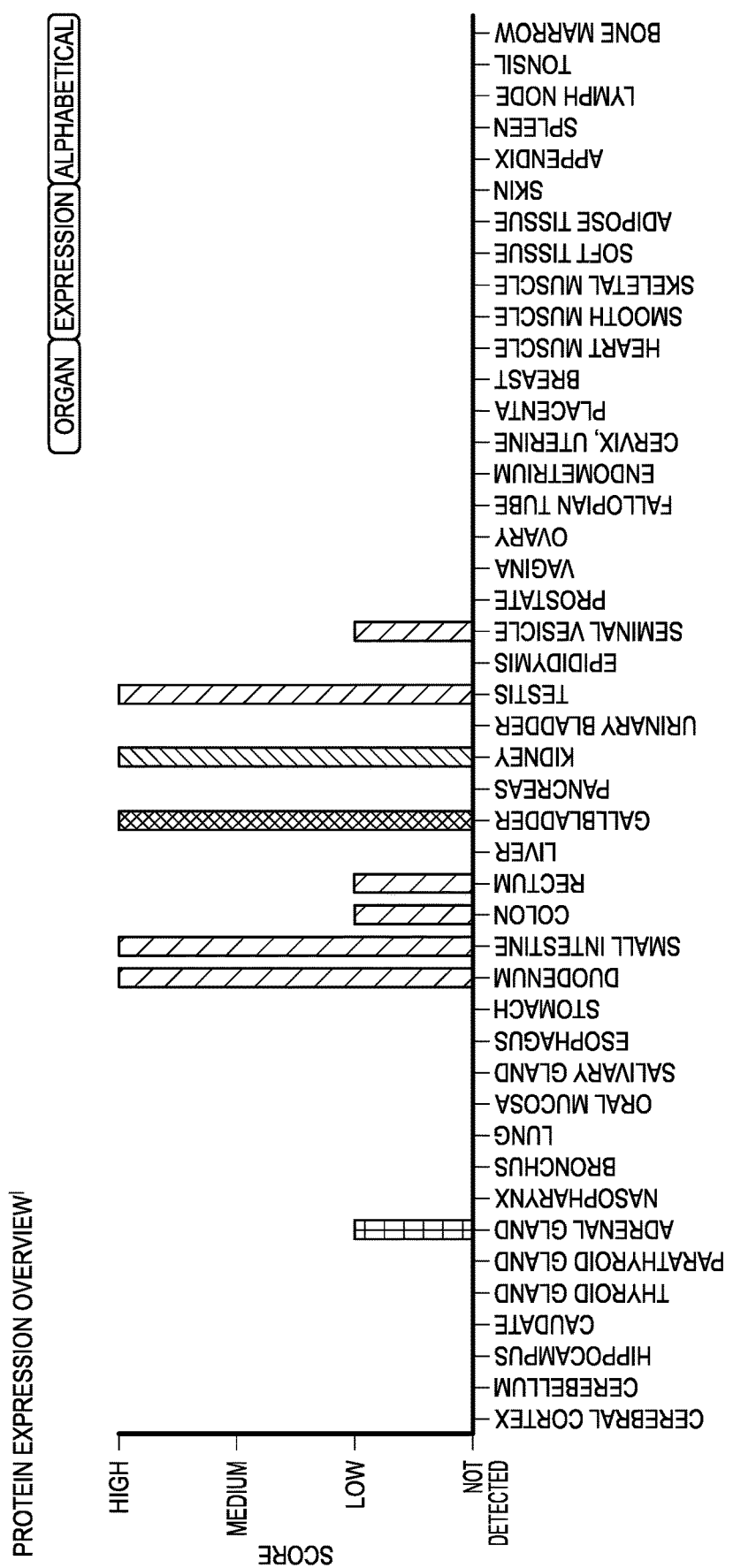
FIG. 9 is a graph of the RNA tissues specificity for the ACE2 receptor, as outlined in the tissue atlas portion of the Human Protein Atlas.
Figure 10:
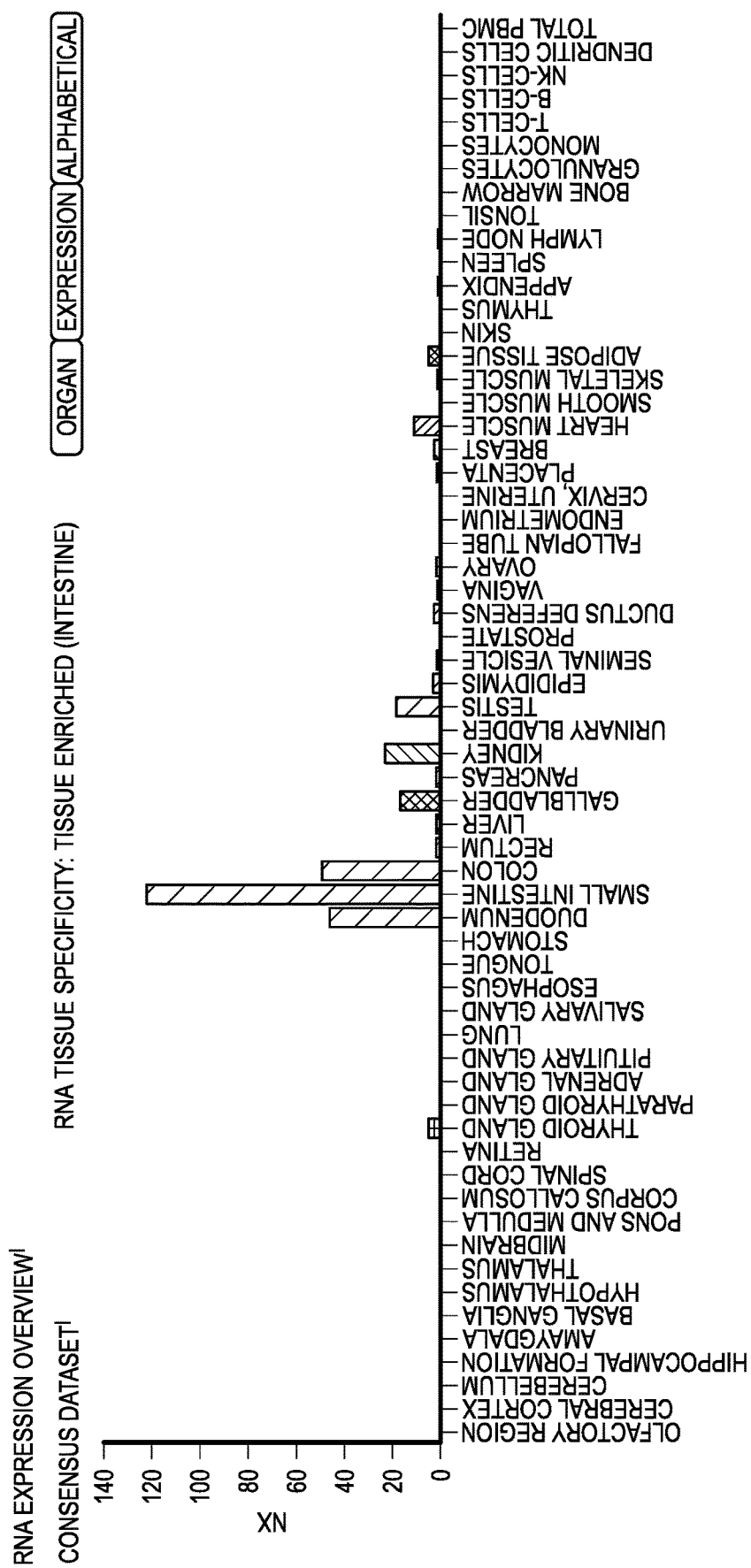
FIG. 10 is a graph of the RNA expression overview for ACE2 receptor, as outlined in the tissue atlas portion of the Human Protein Atlas, Consensus Data Set.
Figure 12:
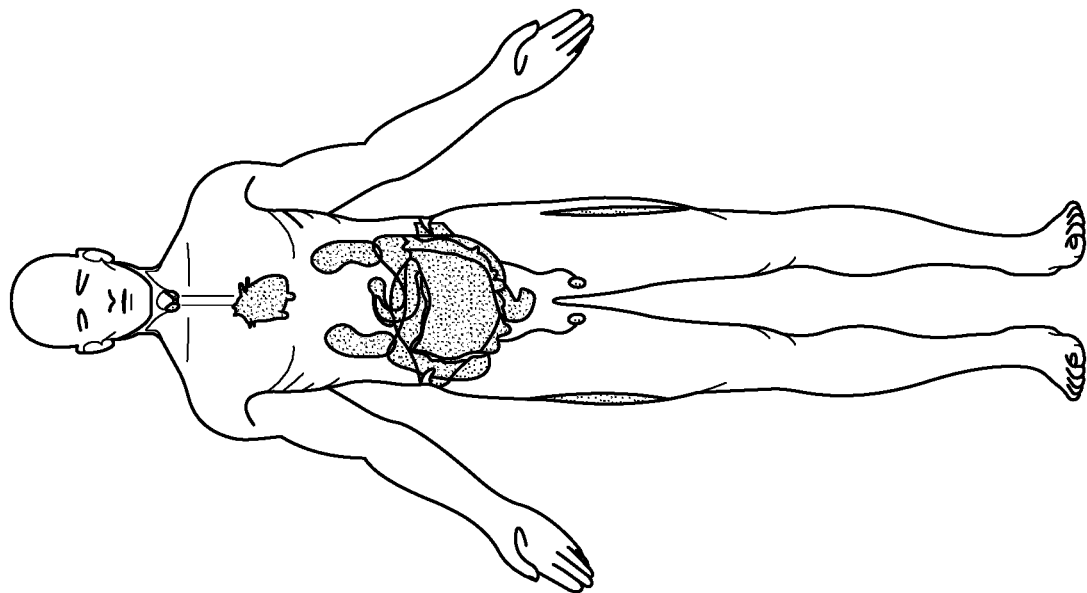
FIG. 12 is an illustration of ACE2 RNA and protein expression summary in the male anatomy.
Figure 11:
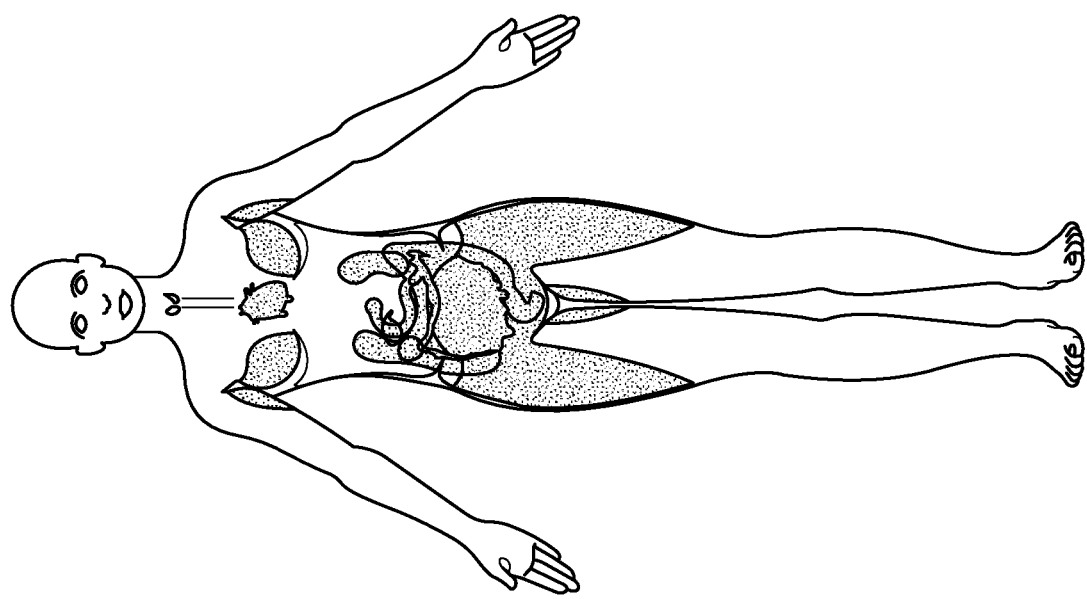
FIG. 11 is an illustration of ACE2 RNA and protein expression summary in the female anatomy.

RNA tissue specificity for the ACE2 receptor is outlined in the tissue atlas portion of the Human Protein Atlas. FIG. 9 is a graph of the RNA tissues specificity for the ACE2 receptor, as outlined in the tissue atlas portion of the Human Protein Atlas and FIG. 10 is a graph of the RNA expression overview for ACE2 receptor, as outlined in the tissue atlas portion of the Human Protein Atlas, Consensus Data Set. FIG. 11 is an illustration of ACE2 RNA and protein expression summary in the female anatomy while FIG. 12 is an illustration of ACE2 RNA and protein expression summary in the male anatomy.

Vaccines and Anti-Viral Treatments

The need to target coronaviruses (e.g., SARS-CoV-2) prior to infectivity would be optimal, thereby keeping infectivity rates lower and targeting the early stage of the disease. Vaccines are the most common form of mass control of infectious viral disease. There are, however, at least three major impediments to vaccine development for coronaviruses (e.g., SARS-CoV-2). First, the S protein is a promising immunogen but being able to optimize the design by targeting a yet to be identified portion of the of the S protein. Second, earlier work with the development of SARS and MERS vaccine raised concerns about the exacerbation of lung disease depending upon the dose administered. Third, the course of and duration of natural immunity is not yet understood. Inferring the course and duration of natural immunity from SARS and MERS disease is an uncertain proposition.

Enzymatic Anti-Viral Treatment

The present application is directed to enzyme compositions and methods for treating coronaviruses. In some cases, treatment is of subjects diagnosed with a coronavirus infection. In other cases, treatment is prophylactic of, for example, essential workers who are at higher risk for infection.

One aspect of enzymatic anti-viral treatment provided herein relates to compositions that comprise one or more enzymes that target the S protein (e.g., the S1 subunit) of a coronavirus (e.g., SARS-CoV-2), thereby rendering the virus inactive and reducing or eliminating the possibility of infectivity. Enzymatic unmasking of viral surface glycans renders the S protein vulnerable to enzymatic protease degradation, also reducing or elimination the possibility of infectivity. Delivery of one or more enzymes that target the S protein (e.g., the S1 subunit) renders the virus inactive and reduces viral loading, thereby aiding in alleviating the symptoms of a coronavirus infection (e.g., COVID-19) and aiding in patient recovery. Prophylactically, delivery of one or more enzymes that target the S protein (e.g., the S1 subunit) to a subject prevents that subject from being infected.

One composition described herein comprises uncoated enzymes. Another composition described herein comprises coated enzymes. Coated and uncoated enzymes are able to overcome the challenges associated with highly targeted immunological or pharmacological functional interference of the S protein by attacking at both the level of the S protein itself as well as the glycan mask covering a large part of the S protein.

In one embodiment, a composition to be administered to an infected subject for treatment or prophylaxis contains a coated enzymatic core, where the core has high levels of proteases, as well as amylases and lipases, and which core provides for attack of the S protein by several proteases as well as attack of the glycoprotein mask by the amylases, individually or jointly reducing the infectivity of a coronavirus (e.g., SARS-CoV-2).

Utilizing the proteases and amylases to attack vulnerable portions of the S protein will significantly impede or eliminate the proper functioning of the S protein, thereby reducing or neutralizing the ability of the virus to infect human cells. Proteases can attack multiple sites of on the S protein.

It should be noted that the embodiments described herein are not limited to SARS-CoV-2 and any resultant infection resulting in COVID-19 but are also applicable to other coronaviruses described herein. In one non-limiting aspect, provided herein is an oral preparation (e.g., a pharmaceutical composition) comprising coated or uncoated enzymes which is specifically formulated to allow passage through the oropharynx with stomach targeted delivery to the early portion of the small intestines, where there is a high prevalence of ACE2 receptors. In another aspect, provided herein is a parenteral preparation comprising coated or uncoated enzymes. In another aspect, provided herein is a nasal preparation comprising coated or uncoated enzymes. In another aspect, provided herein is a nasal preparation comprising coated or uncoated enzymes. In another aspect, provided herein is a preparation for percutaneous endoscopic gastrostomy (PEG), esophagogastroduodenoscopy (EGD), or gastrostomy (G-tube) insertion comprising coated or uncoated enzymes. In another aspect, provided herein is a suppository comprising coated or uncoated enzymes.

Figure 13:
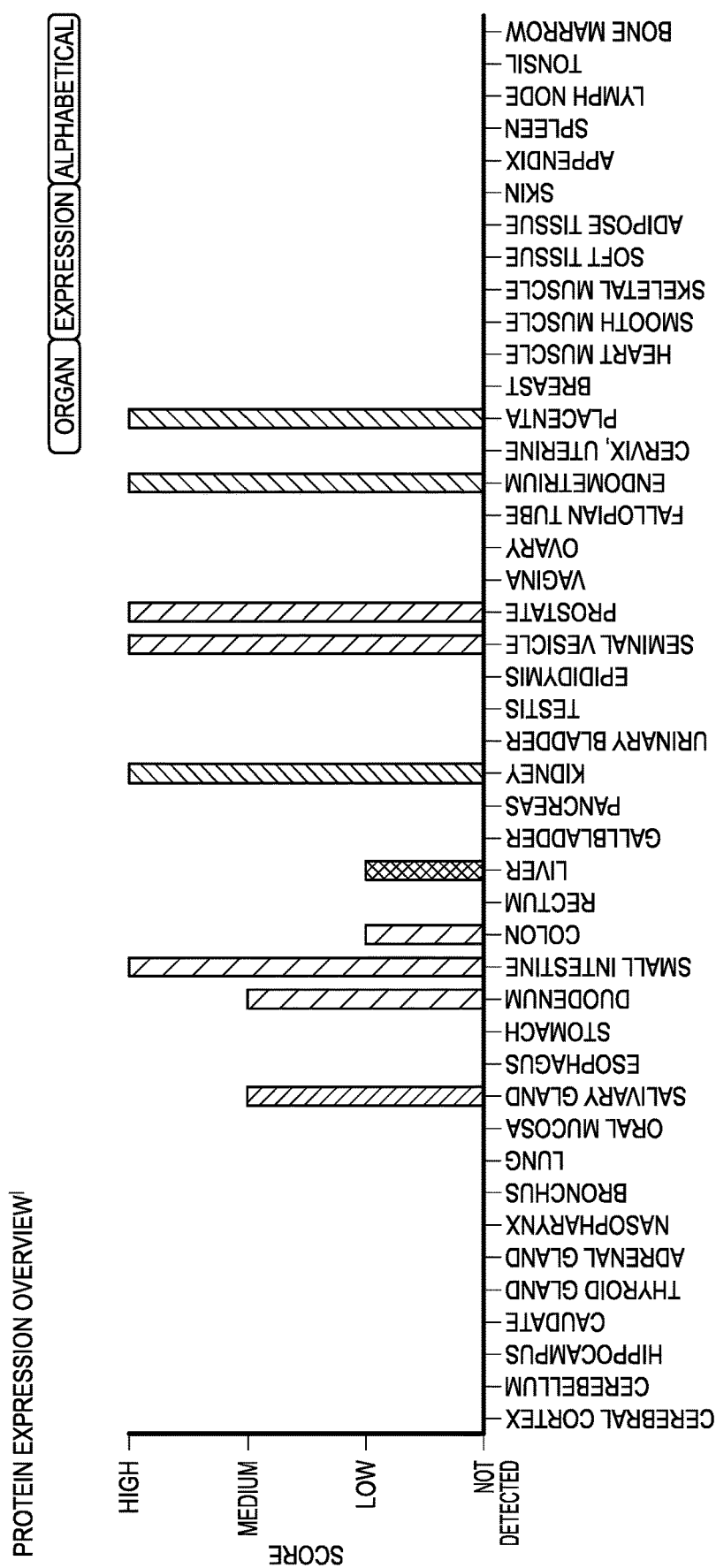
FIG. 13 depicts the protein expression of Dipeptidyl Peptidase 4 (DDP4) as given by the Human Protein Atlas Consensus Data Set.
Figure 14:
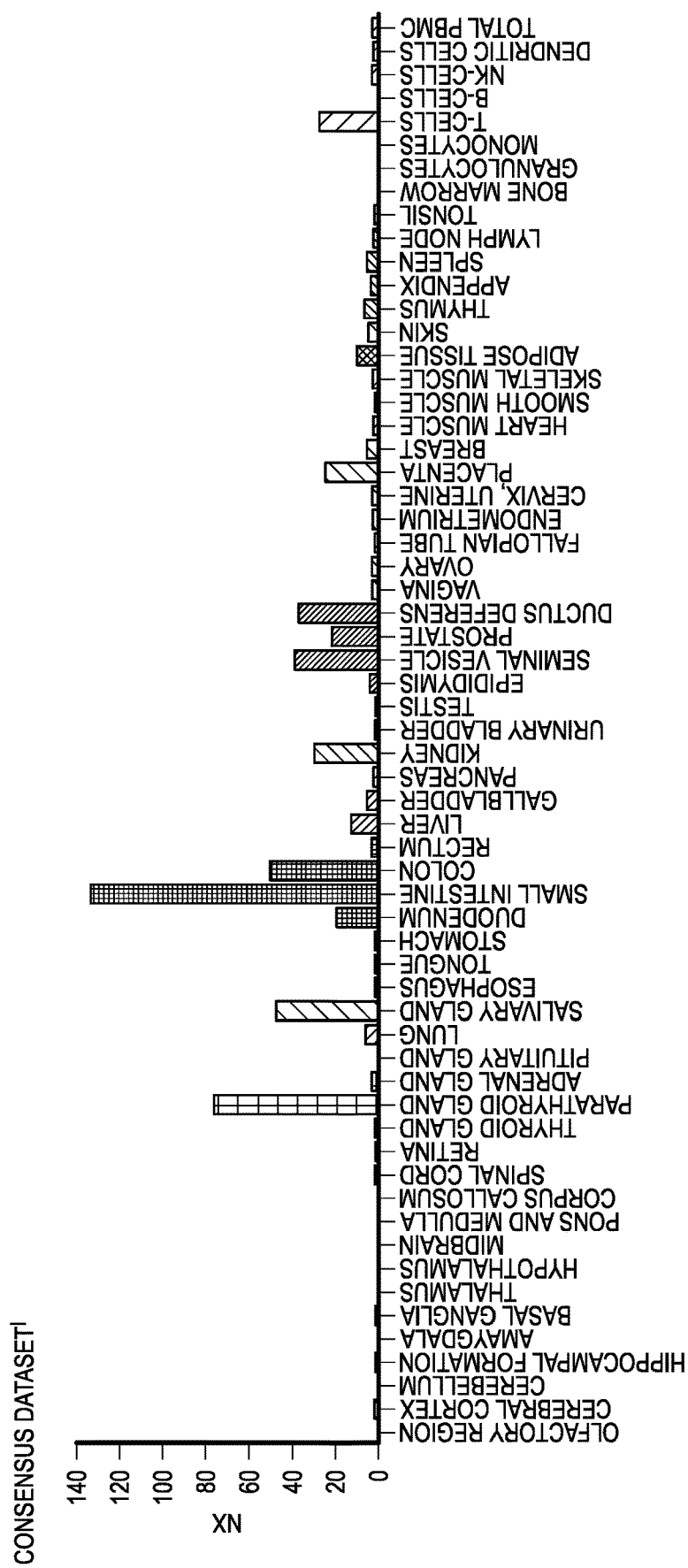
FIG. 14 depicts the protein expression of DPP4 dipeptidyl peptidase 4 concentration in the small intestine, colon, duodenum, liver, and kidneys.
Figure 15:
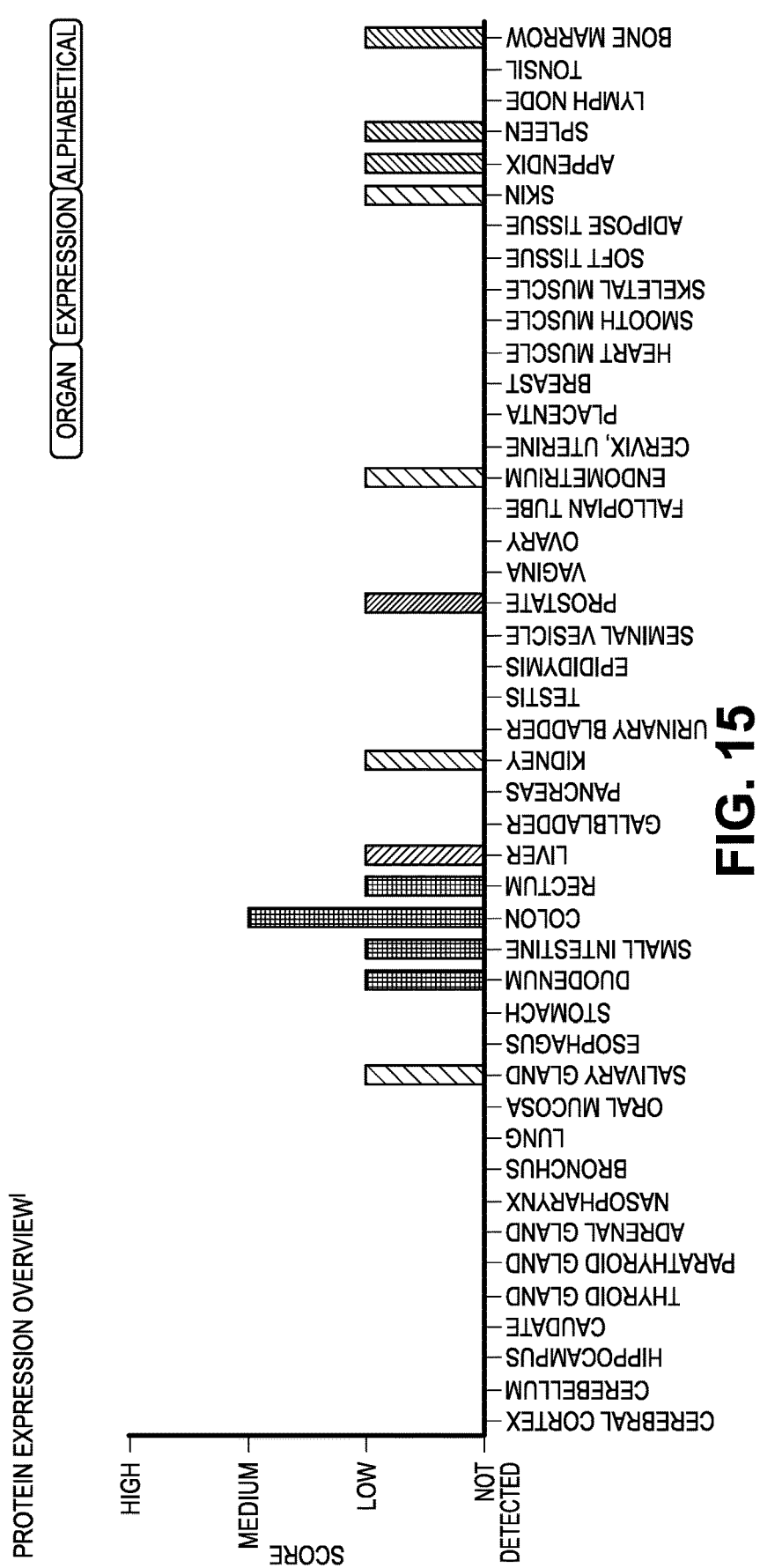
FIG. 15 depicts the protein expression of CEACAM1 as given by the Human Protein Atlas Consensus Data Set.
Figure 16:
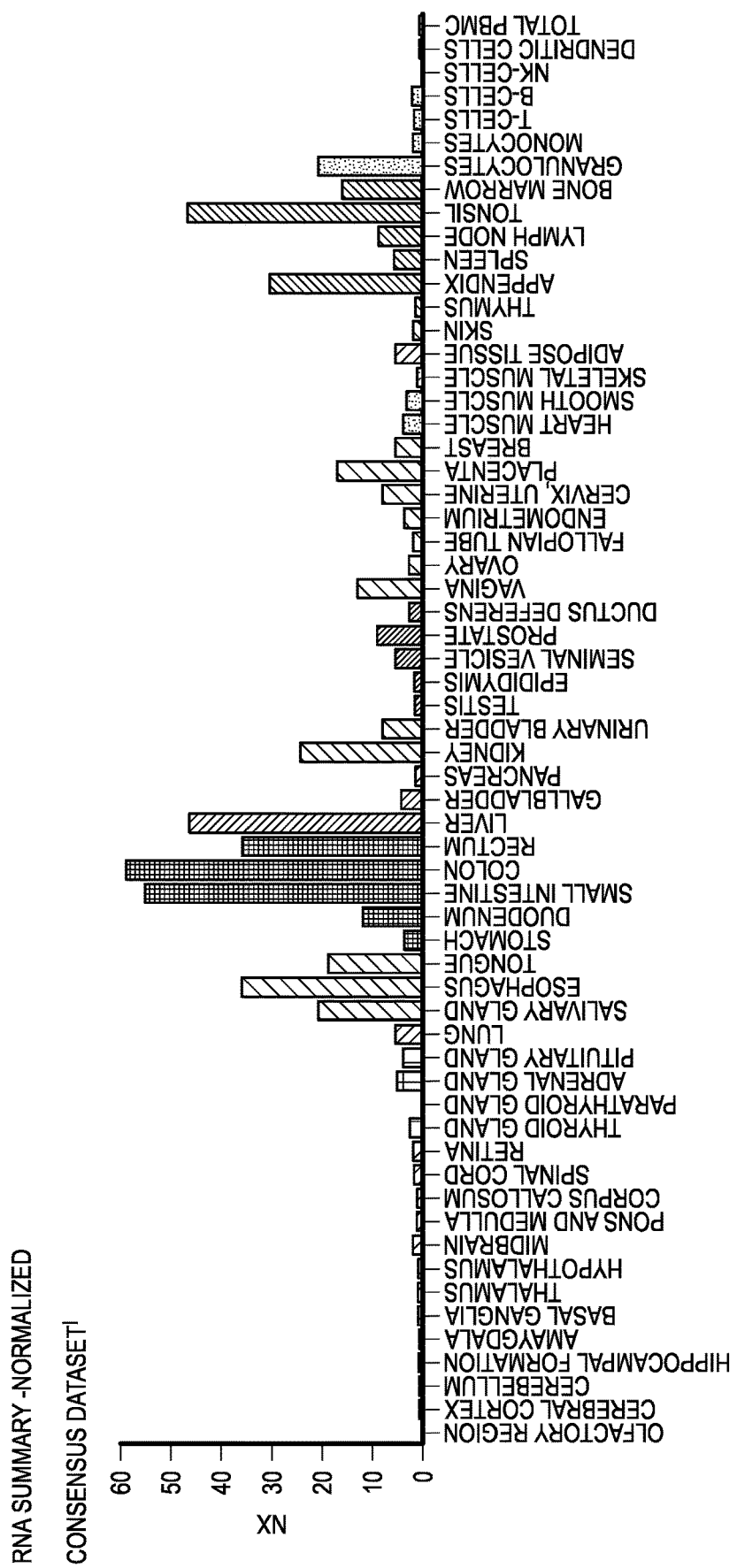
FIG. 16 depicts the RNA expression of CEACAM1 as given by the Human Protein Atlas Consensus Data Set.

As previously discussed, the viral attachment or entry point for various coronaviruses includes ACE2, along with APN, mCEACAM, and/or DPP4. FIG. 13 depicts the protein expression of DDP4 as given by the Human Protein Atlas Consensus Data Set. Note the concentration of DDP4 expression in the small intestine, colon, and duodenum. In addition, there are high degrees of expression in the liver and kidneys, which are sites of tissue damage in subjects infected with a coronavirus (e.g., SARS-CoV-2). FIG. 14, also from the Human Protein Atlas, shows a similar concentration of DPP4 dipeptidyl peptidase 4 concentration in the small intestine, colon, and duodenum, along with liver, and kidneys. FIG. 15 depicts the protein expression of CEACAM1 as given by the Human Protein Atlas Consensus Data Set. Note the similar concentration of CEACAM1 expression in the small intestine, colon, and duodenum. In addition, there are high degrees of expression in the rectum, liver, kidneys, and prostate, which are sites of tissue damage in subjects infected with a coronavirus (e.g., SARS-CoV-2). FIG. 16 depicts the RNA expression of CEACAM1 as given by the Human Protein Atlas Consensus Data Set. Note the similar concentration of CEACAM1 Expression in the small intestine, colon, and duodenum. In addition, there are high degrees of expression in the rectum, liver, kidneys, and prostate.

Figure 17:
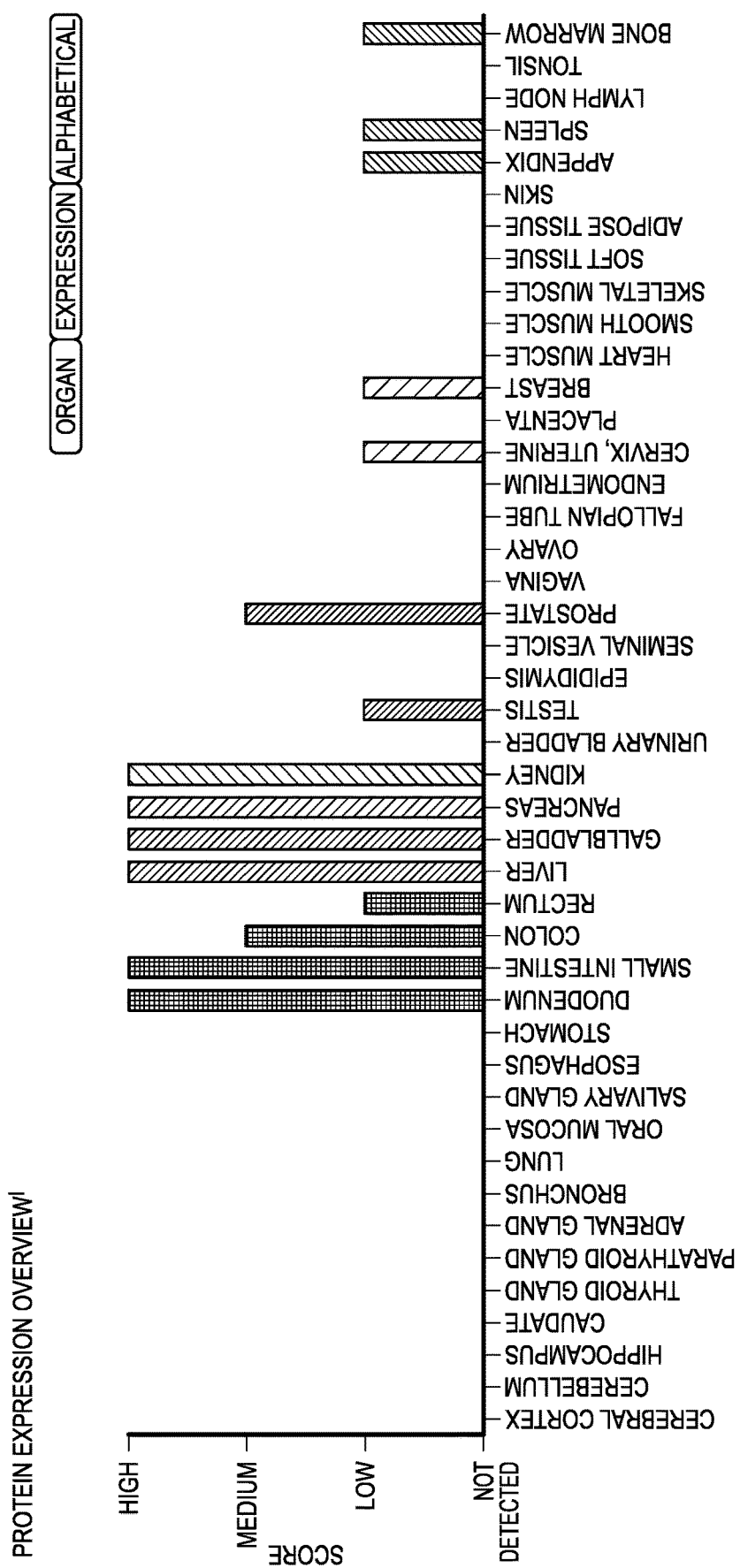
FIG. 17 depicts the protein expression of APN as given by the Human Protein Atlas Consensus Data Set.
Figure 18:
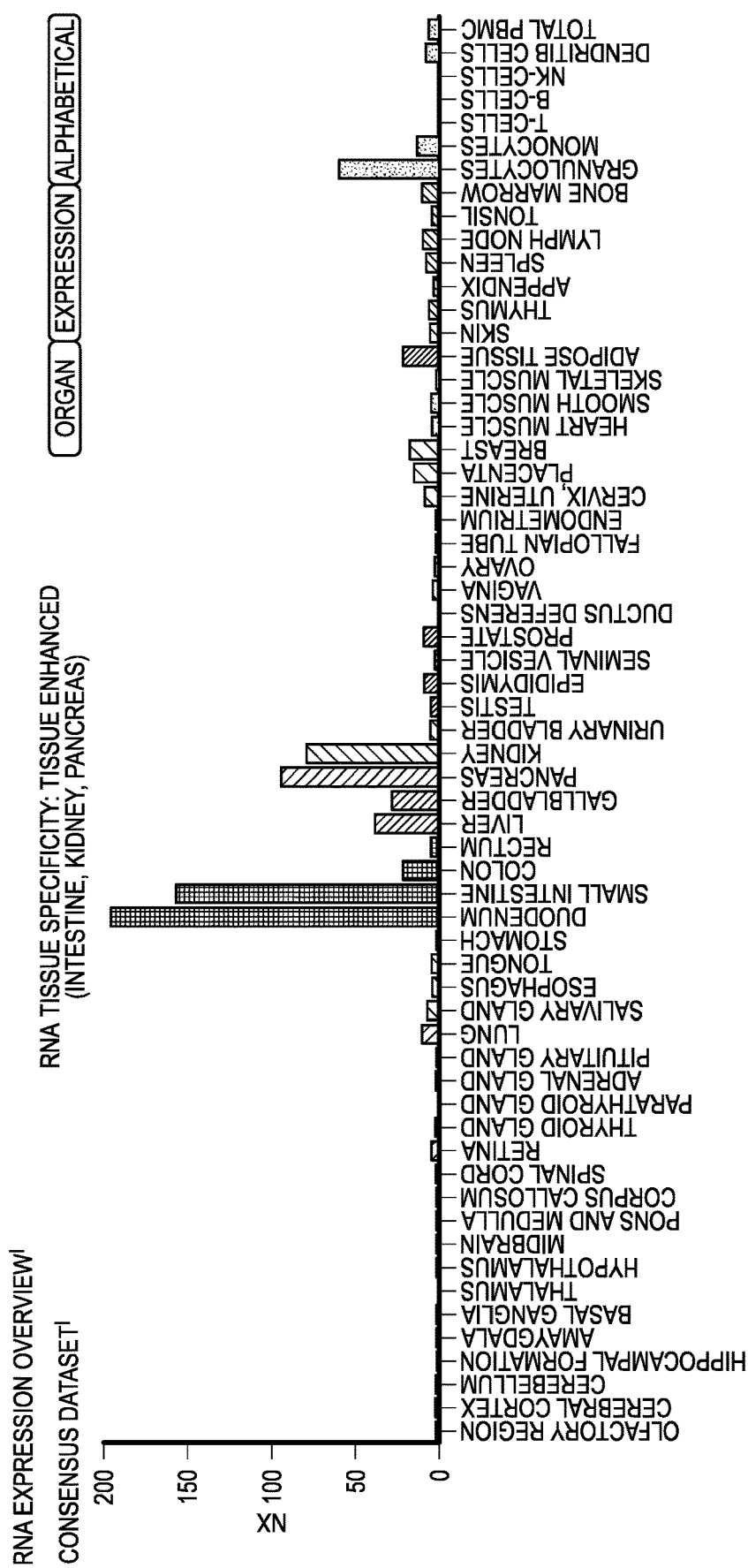
FIG. 18 depicts the RNA expression of APN as given by the Human Protein Atlas Consensus Data Set.

APN is also known as Membrane Alanyl Aminopeptidase and as Alanyl Aminopeptidase (AAP). Aminopeptidase N(APN) is an enzyme that in humans is encoded by the ANPEP gene. FIG. 17 depicts the protein expression of APN as given by the Human Protein Atlas Consensus Data Set. Note the similar concentration of APN Expression in the duodenum, small intestine, colon, and rectum. In addition, there are high degrees of expression in the liver, kidneys, gall bladder, pancreas, and prostate, which are sites of tissue damage in subjects infected with a coronavirus (e.g., SARS-CoV-2). FIG. 18 depicts the RNA expression of APN as given by the Human Protein Atlas Consensus Data Set. Note the similar concentration of APN expression in the duodenum, small intestine, colon, and rectum. In addition, there are high degrees of expression in the liver, kidneys, gall bladder, pancreas, and prostate, which are sites of tissue damage in subjects infected with a coronavirus (e.g., SARS-CoV-2).

In one embodiment, an encapsulated or coated enzymatic core that contains high levels of one or more protease(s), one or more lipase(s), one or more amylase(s), or a combination thereof provides for attack of the S protein by the one or more protease(s), as well as attack of the glycoprotein mask by the one or more amylase(s), individually or jointly affect the infectivity of a coronavirus (e.g., SARS-CoV-2).

In one embodiment, coated or uncoated digestive enzymes and their derivatives are utilized to reduce the transmission rate of a coronavirus including, but not limited to, infections from SARS-CoV-2.

In another embodiment, coated or uncoated digestive enzymes and their derivatives may be utilized as a pre- and or post-exposure prophylaxis against, and the treatment of, coronavirus infections including, but not limited to, a Coronavirus HCoV-229E, a Human Coronavirus HCoV-NL63, a Transmissible Gastroenteritis Virus (TGEV), a Porcine Epidemic Diarrhea Virus (PEDV), a Feline Infectious Peritonitis Virus (FIPV), a Canine Coronavirus (CCoV), a Murine Hepatitis Virus (MHV), a Bovine Coronavirus (BCoV), a Severe Acute Respiratory Syndrome Coronavirus (SARS-CoV-2), a SARS-CoV-1 (SARS1), a Middle East Respiratory Syndrome Coronavirus (MERS-CoV), or a combination thereof.

In one embodiment, coated or uncoated digestive enzymes are utilized to alleviate the symptoms of a coronavirus infection (e.g., a SARS-CoV-2 infection). A method of treating a coronavirus infection comprises administering to a subject one or more digestive enzyme(s) (either naturally-derived, recombinantly-derived, or their derivatives) in an amount effective to reduce the symptoms of a coronavirus infection (e.g., reduce symptoms of COVID-19). Administration can be via any suitable route including, but not limited to, oral, nasal, parenteral, percutaneous endoscopic gastrostomy (PEG), intravenous, esophagogastroduodenoscopy (EGD), gastrostomy (G-tube) insertion, rectal, etc.

Provided herein is a method for treating a subject exhibiting one or more symptoms of coronavirus infection (e.g., COVID-19) in a subject in need thereof, comprising administering to the subject a therapeutically effective amount of a composition comprising coated or uncoated digestive enzymes. In one embodiment, the one or more symptoms of the coronavirus infection include, but are not limited to, one or more of fever, chills, cough, sore throat, fatigue, malaise, headache, muscle pain, body aches, shortness of breath, dyspnea, loss of taste, loss of smell, gastrointestinal symptoms (including, but not limited to nausea, vomiting, and diarrhea), or a combination thereof. In one embodiment, the one or more symptoms of COVID-19 include, but are not limited to, one or more of fever, chills, cough, sore throat, fatigue, malaise, headache, muscle pain, body aches, shortness of breath, dyspnea, loss of taste, loss of smell, gastrointestinal symptoms (including, but not limited to nausea, vomiting, and diarrhea), or a combination thereof.

Provided herein is a method for diagnosing and treating a subject that is asymptomatic for a coronavirus, comprising diagnosing the subject with a coronavirus infection and then treating the subject by administering a therapeutically effective amount of a composition comprising coated or uncoated digestive enzymes, wherein the diagnosis of the coronavirus infection is by standard reverse transcription polymerase chain reaction (RT-PCR) assay, an antibody test, an equivalent test, or other medically accepted techniques.

Provided herein is a method for diagnosing and treating a subject that is asymptomatic for COVID-19, comprising diagnosing the subject with a SARS-CoV-2 infection and then treating the subject by administering a therapeutically effective amount of a composition comprising coated or uncoated digestive enzymes, wherein the diagnosis of a SARS-CoV-2 infection/COVID-19 is by standard reverse transcription polymerase chain reaction (RT-PCR) assay, an antibody test, an equivalent test, or other medically accepted techniques.

Essential employees and first responders are at heightened risk of being infected with a coronavirus. Provided herein is a method for prophylaxis of subject who has been exposed to a coronavirus but is asymptomatic of a coronavirus and has not been diagnosed with a coronavirus Infection, comprising administering a therapeutically effective amount of a composition comprising coated or uncoated digestive enzymes to the subject.

Provided herein is a method for prophylaxis of subject who has been exposed to SARS-CoV-2 but is asymptomatic of COVID-19 and has not been diagnosed with SARS-CoV-2 infection, comprising administering a therapeutically effective amount of a composition comprising coated or uncoated digestive enzymes to the subject.

Also provided herein is a method for treating a subject with COVID-19, wherein the baseline severity of the COVID-19 is one of asymptomatic COVID-19, mild COVID-19, moderate COVID-19, severe COVID-19, or critical COVID-19.

Provided herein is a method for treating a subject having COVID-19, wherein the baseline severity of the infection is by diagnosis of one or more clinical signs suggestive of mild COVID-19 comprising one or more of fever, chills, cough, sore throat, fatigue, malaise, headache, muscle pain, body aches; however without dyspnea or shortness of breath and no signs of moderate, severe, or critical COVID-19, and positive testing by Standard Reverse Transcription Polymerase Chain Reaction (RT-PCR) assay, an antibody test, an equivalent test, or other medically accepted techniques.

Provided herein is a method for treating a subject with COVID-19, wherein the baseline severity of the infection is by diagnosis of one or more clinical signs suggestive of Moderate COVID-19 comprising one or more of: fever, chills, cough, sore throat, fatigue, malaise, headache, muscle pain, body aches, dyspnea, loss of taste, loss of smell, and gastrointestinal symptoms including, but not limited to nausea, vomiting, and diarrhea. shortness of breath with exertion, respiratory rate≥20 breaths per minute, saturation of oxygen (SpO2)>93% on room air at sea level, heart rate≥90 beats per minute, and no signs of severe or critical COVID-19 along with a positive testing by standard reverse transcription polymerase chain reaction (RT-PCR) assay, an antibody test, an equivalent test, or other medically accepted techniques.

Provided herein is a method for treating a subject with COVID-19, wherein the baseline severity of the infection is by diagnosis of one or more clinical signs suggestive of severe COVID-19 comprising one or more of: fever, chills, cough, sore throat, fatigue, malaise, headache, muscle pain, body aches, dyspnea, loss of taste, loss of smell, and gastrointestinal symptoms including, but not limited to, nausea, vomiting, and diarrhea shortness of breath at rest, respiratory distress, respiratory rate≥30 per minute, heart rate≥125 per minute, SpO2<93% on room air at sea level or PaO2/FiO2<300, along with no signs of critical COVID-19 along with a positive testing by Standard Reverse Transcription Polymerase Chain Reaction (RT-PCR) assay, an antibody test, an equivalent test, or other medically accepted techniques.

Provided herein is a method for treating a subject with COVID-19, wherein the baseline severity of the infection is by diagnosis of one or more clinical signs suggestive of critical COVID-19 comprising one or more of: fever, chills, cough, sore throat, fatigue, malaise, headache, muscle pain, body aches, dyspnea, loss of taste, loss of smell, and gastrointestinal symptoms including, but not limited to nausea, vomiting, and diarrhea, clinical diagnosis of respiratory failure, respiratory failure requiring endotracheal intubation, mechanical ventilation, oxygen delivered by high flow nasal cannula, non-invasive positive pressure ventilation, extracorporeal membrane or other life-support machine, shock, shock defined by systolic blood pressure<90 mm Hg or diastolic blood pressure<60 mm Hg or requiring vasopressors), multi-organ dysfunction/failure, Standard Reverse Transcription Polymerase Chain Reaction (RT-PCR) assay, an antibody test, an equivalent test, or other medically accepted techniques.

In another embodiment, one or more symptoms of coronavirus infection (e.g., COVID-19), are selected from a group comprising fever, fever, chills, cough, sore throat, fatigue, malaise, headache, muscle pain, body aches, dyspnea, loss of taste, loss of smell, gastrointestinal symptoms including, but not limited to nausea, vomiting, and diarrhea), shortness of breath with exertion, respiratory rate≥20 breaths per minute, saturation of oxygen (SpO2)>93% on room air at sea level, heart rate≥90 beats per minute, shortness of breath at rest, respiratory distress, respiratory rate≥30 per minute, heart rate≥125 per minute, SpO2≤93% on room air at sea level or PaO2/FiO2<300, clinical diagnosis of respiratory failure, respiratory failure requiring endotracheal intubation, mechanical ventilation, oxygen delivered by high flow nasal cannula, non-invasive positive pressure ventilation, extracorporeal membrane or other life-support machine, shock, shock defined by systolic blood pressure<90 mm Hg or diastolic blood pressure<60 mm Hg or requiring vasopressors), multi-organ dysfunction/failure, or a combination thereof.

Provided herein are compositions of digestive enzymes which are useful in the prevention (prophylaxis) or treatment of one or more symptoms of a coronavirus infection (e.g., symptoms of COVID-19). Digestive enzymes generally comprise one or more protease(s), one or more amylase(s), one or more lipase(s), or a combination thereof, and, optionally, other proteins (e.g., those secreted in a mammal) that affect the digestive process either directly or indirectly.

Treatment of coronaviruses (e.g., SARS-CoV-2) encompasses stasis of one or more symptoms (e.g., they do not worsen), as well as reduction (partial or complete) of one or more symptoms. In one embodiment, one or more symptoms caused by such coronaviruses are reduced in severity or duration by about 2%, about 5%, about 10%, about 15%, about 20%, about 25%, about 30%, about 35%, about 40%, about 45%, about 50%, about 55%, about 60%, about 65%, about 70%, about 75%, about 80%, about 90%, about 95%, or about 100% following treatment compared to a subject that did not receive treatment, or compared to a subject that received a placebo. In another embodiment, one or more symptoms of infections caused by such coronaviruses are reduced in severity or duration by about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 90-fold, about 95-fold, about 100-fold, or more, following treatment compared to a subject that did not receive treatment, or compared to a subject that received a placebo. In yet another embodiment, the duration of one or more symptoms may be reduced in severity and/or duration following administration of a composition described herein. That is, one or more symptoms may persist for less than 6 months, 5 months, 4 months, 3 months, 2 months, 1 month, 3 weeks, 2 weeks, or 1 week.

One or more digestive enzyme(s) may be utilized for targeted delivery against a specific coronavirus by targeting delivery to one or more coronavirus receptors including, but not limited to ACE2, mCEACAM, DDP4, APN, N-acetyl-9-O-acetylneuraminic acid, or a combination thereof. One or more digestive enzyme(s) may be coated for targeted delivery against a specific coronavirus by targeting delivery to one or more coronavirus receptors including, but not limited to ACE2, mCEACAM, DDP4, APN, N-acetyl-9-O-acetylneuraminic acid, or a combination thereof.

A targeted delivery system may be utilized to deliver one or more digestive enzyme(s) as a prophylaxis against infection from SARS-CoV-2 to the GI tract or mucosa including, but not limited to, one or more of the stomach, duodenum, small intestine, colon, and/or rectum. In another embodiment, a targeted delivery system may be utilized to nasally deliver one or more digestive enzyme(s) as treatment prophylaxis against infection with SARS-CoV-2 infection. In one embodiment, a targeted delivery system is utilized to deliver one or more digestive enzyme(s) as a prophylaxis against infection from SARS-CoV-2 to one or more ACE2 receptors.

In another embodiment, a targeted delivery system may be utilized to deliver one or more digestive enzyme(s) as treatment for COVID-19 or SARS-CoV-2 infection to the GI tract or mucosa including, but not limited to, one or more of the stomach, duodenum, small intestine, colon, and/or rectum. In another embodiment, a targeted delivery system may be utilized to nasally deliver one or more digestive enzyme (s) as treatment for SARS-CoV-2 infection. In another embodiment, a targeted delivery system is utilized to deliver one or more digestive enzyme(s) as treatment for COVID-19 or SARS-CoV-2 infection to one or more ACE2 receptors.

In another embodiment, a targeted delivery system is utilized to deliver one or more digestive enzyme(s) to the GI tract or mucosa as treatment for one or more of an asymptomatic, mild, moderate, severe, or critical COVID-19 including, but not limited to one or more of the stomach, duodenum, small intestine, colon, and/or rectum. In another embodiment, a targeted delivery system is utilized to nasally deliver one or more digestive enzyme(s) to a subject as treatment for one or more of an asymptomatic, mild, moderate, severe, or critical COVID-19. In another embodiment, a targeted delivery system is utilized to deliver one or more digestive enzyme(s) as treatment for one or more of an asymptomatic, mild, moderate, severe, or critical COVID-19 caused by a SARS-CoV-2 infection, to one or more ACE2 receptors.

In one embodiment, a targeted delivery system is utilized to deliver one or more digestive enzyme(s) as a prophylaxis against infection from Severe Acute Respiratory Syndrome Coronavirus (SARS-CoV) or Human Coronavirus NL63 (HCoV-NL63) infection to the GI tract including, but not limited to one or more of the stomach, duodenum, small intestine, colon, and/or rectum. In another embodiment, a targeted delivery system is utilized to deliver one or more digestive enzyme(s) as a prophylaxis against infection from SARS-CoV or HCoV-NL63, to one or more ACE2 receptors.

In another embodiment, a targeted delivery system is utilized to deliver one or more digestive enzyme(s) as treatment for SARS-CoV or HCoV-NL63 infection to the GI tract or mucosa including, but not limited to, one or more of the stomach, duodenum, small intestine, colon, and/or rectum. In another embodiment, a targeted delivery system is utilized to deliver one or more digestive enzyme(s) as treatment for SARS-CoV or HCoV-NL63 to one or more ACE2 receptors.

In another embodiment, a targeted delivery system is utilized to deliver one or more digestive enzyme(s) as treatment for one or more of an asymptomatic, mild, moderate, severe, or critical SARS-CoV or HCoV-NL63 infection to the GI tract including, but not limited to one or more of the stomach, duodenum, small intestine, colon, and/or rectum. In another embodiment, a targeted delivery system is utilized to deliver one or more digestive enzyme(s) as treatment for one or more of an asymptomatic, mild, moderate, severe, or critical SARS-CoV or HCoV-NL63 to one or more ACE2 receptors.

In one embodiment, a targeted delivery system is utilized to deliver one or more digestive enzyme(s) as a prophylaxis against infection from Human Coronavirus 229E (HCoV-229E), Transmissible Gastroenteritis Virus (TGEV), Porcine Epidemic Diarrhea Virus (PEDV), Feline Infectious Peritonitis Virus (FIPV), or Canine Coronavirus (CCoV) to the GI tract or mucosa including, but not limited to, one or more of the stomach, duodenum, small intestine, colon, and/or rectum. In another embodiment, a targeted delivery system is utilized to deliver one or more digestive enzyme(s) as a prophylaxis against infection from HCoV-229E, TGEV, PEDV, FIPV, or CCoV, to one or more APN receptors.

In another embodiment, a targeted delivery system is utilized to deliver one or more digestive enzyme(s) as treatment for HCoV-229E, TGEV, PEDV, FIPV, or CCoV infection to the GI tract including, but not limited to one or more of the stomach, duodenum, small intestine, colon, and/or rectum. In another embodiment, a targeted delivery system is utilized to deliver one or more digestive enzyme(s) as treatment for HCoV-229E, TGEV, PEDV, FIPV, or CCoV infection to one or more APN Receptors.

In another embodiment, a targeted delivery system is utilized to deliver one or more digestive enzyme(s) as treatment for one or more of an asymptomatic, mild, moderate, severe, or critical HCoV-229E, TGEV, PEDV, FIPV, or CCoV infection to the GI tract or mucosa including, but not limited to one or more of the stomach, duodenum, small intestine, colon, and/or rectum. In another embodiment, a targeted delivery system is utilized to deliver one or more digestive enzyme(s) as treatment for one or more of an asymptomatic, mild, moderate, severe, or critical HCoV-229E, TGEV, PEDV, FIPV, or CCoV infection to one or more APN Receptors.

In one embodiment, a targeted delivery system is utilized to deliver one or more digestive enzyme(s) as a prophylaxis against infection from Murine Hepatitis Virus (MHV) to the GI tract including, but not limited to one or more of the stomach, duodenum, small intestine, colon, and/or rectum. In another one embodiment, a targeted delivery system is utilized to deliver one or more digestive enzyme(s) as a prophylaxis against infection from the MI-1V to one or more mCEACAM also known as CEACAM1 Receptors.

In another embodiment, a targeted delivery system is utilized to deliver one or more digestive enzyme(s) as treatment for MI-1V infection to the GI tract or mucosa including, but not limited to one or more of the stomach, duodenum, small intestine, colon, and/or rectum. In another embodiment, a targeted delivery system is utilized to deliver one or more digestive enzyme(s) as treatment for MI-1V infection to one or more mCEACAM, also known as CEACAM1 Receptors.

In another embodiment, a targeted delivery system is utilized to deliver one or more digestive enzyme(s) as treatment for one or more of an asymptomatic, mild, moderate, severe, or critical MHV infection to the GI tract or mucosa including, but not limited to one or more of the stomach, duodenum, small intestine, colon, and/or rectum. In another embodiment, a targeted delivery system is utilized to deliver one or more digestive enzyme(s) as treatment for one or more of an asymptomatic, mild, moderate, severe, or critical MI-1V infection to one or more mCEACAM, also known as CEACAM1 Receptors.

In one embodiment, a targeted delivery system is utilized to deliver one or more digestive enzyme(s) as a prophylaxis against infection from MERS to the GI tract or mucosa including, but not limited to one or more of the stomach, duodenum, small intestine, colon, and/or rectum. In another embodiment, a targeted delivery system is utilized to deliver one or more digestive enzyme(s) as a prophylaxis against infection from the Middle East Respiratory Syndrome Coronavirus (MERS) infection to one or more DDP4 Receptors.

In another embodiment a targeted delivery system is utilized to deliver one or more digestive enzyme(s) as treatment for MERS infection to the GI tract or mucosa including, but not limited to one or more of the stomach, duodenum, small intestine, colon, and/or rectum. In another embodiment, a targeted delivery system is utilized to deliver one or more digestive enzyme(s) as treatment for MERS to one or more DDP4 Receptors.

In another embodiment, a targeted delivery system is utilized to deliver one or more digestive enzyme(s) as treatment for one or more of an asymptomatic, mild, moderate, severe, or critical MERS infection to the GI tract or mucosa including, but not limited to one or more of the stomach, duodenum, small intestine, colon, and/or rectum. In another embodiment, a targeted delivery system is utilized to deliver one or more digestive enzyme(s) as treatment for one or more of an asymptomatic, mild, moderate, severe, or critical MERS infection to one or more DDP4 Receptors.

In one embodiment, a targeted delivery system is utilized to deliver one or more digestive enzyme(s) as a prophylaxis against infection from Bovine Coronavirus (BCoV) to the GI tract or mucosa including, but not limited to, one or more of the stomach, duodenum, small intestine, colon, and/or rectum. In another embodiment, a targeted delivery system is utilized to deliver one or more digestive enzyme(s) as a prophylaxis against infection from the BCoV to one or more N-acetyl-9-O-acetylneuraminic Acid Receptors.

In another embodiment, a targeted delivery system is utilized to deliver one or more digestive enzyme(s) as treatment for BCoV infection to the GI tract including, but not limited to, to one or more of the stomach, duodenum, small intestine, colon, and/or rectum. In another embodiment a targeted delivery system is utilized to deliver one or more digestive enzyme(s) as treatment for BCoV infection, wherein the targeted delivery system comprises one or more digestive enzyme(s) that cleave one or more N-acetyl-9-O-acetylneuraminic acid receptors.

In another embodiment, a targeted delivery system is utilized to deliver one or more digestive enzyme(s) as treatment for one or more of an asymptomatic, mild, moderate, severe, or critical BCoV infection to the GI tract including, but not limited to one or more of to one or more of the stomach, duodenum, small intestine, colon, and/or rectum. In another embodiment a targeted delivery system is utilized to deliver one or more digestive enzyme(s) as treatment for one or more of an asymptomatic, mild, moderate, severe, or critical BCoV infection to one or more of to one or more N-acetyl-9-O-acetylneuraminic acid receptors.

The diagnostic criteria described above may be used to assess whether administration of a composition described herein reduces the severity and/or duration of one or more symptoms of a coronavirus infection.

In another embodiment, the pharmaceutical composition comprising digestive enzymes in a pH buffered solution of saline solution is administered 1, 2, 3, 4, 5 6, 7, 8, 9, or 10 times or more a day to act as a prophylaxis against a coronavirus infection or a treatment of coronaviruses.

In one embodiment the pharmaceutical composition comprising digestive enzymes in a pH buffered saline solution is administered as a prophylaxis against infection from SARS-CoV-2.

In another embodiment, the pharmaceutical composition comprising digestive enzymes in a solution pH buffered saline solution is administered as treatment for COVID-19.

In another embodiment, the digestive enzymes in the nasal spray, nasal drops, or nasal wash comprise porcine digestive enzymes. In yet another embodiment, the porcine enzymes comprise one or more protease(s), one or more amylase(s), one or more lipase(s), or a combination thereof. In yet another embodiment, the porcine enzymes comprise one or more protease(s), one or more amylase(s), and one or more lipase(s).

In another embodiment, the digestive enzymes in the pharmaceutical composition comprises porcine digestive enzymes within a solution of approximately 1%, 2%, 3%, 4%, 5%, 6%, 7%, 8%, 9%, 10%, 11%, 12%,13%,14%, or 15% or more by weight. In yet another embodiment, the pharmaceutical composition comprises porcine digestive enzymes having an activity of approximately 20,000 or more U.S.P. Units protease, 15,000 or more U.S.P. Units amylase, 4,000 or more U.S.P. Units lipase in a 10 ml pH buffered saline solution Optionally, a solution of collagen or similarly enzymatically digestible target protein in a pH-buffered saline solution is administered with approximately 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes or more for a duration of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes or more after administering the pharmaceutical composition comprising the digestive enzymes to neutralize the effect of the digestive enzymes.

Digestive Enzymes

Compositions provided herein may include not only one or more digestive enzyme(s), but optionally, also one or more pharmaceutically acceptable carriers, excipients, buffers, fillers, binders, stabilizers, surfactants, diluents, extracts, lubricants, fillers, flavorings, preservatives, colorants, diluents, anti-microbials, disintegrants, and coating agents, such as for example, vegetable oil, crystalline oils, taste maskers, sweeteners, etc. In one embodiment, digestive enzymes are provided as a pharmaceutical composition.

In one embodiment, a composition may contain one or more protease(s), one or more amylase(s), one or more lipase(s), or a combination thereof. A composition may contain one or more protease(s). A composition may contain one or more amylase(s). A pharmaceutical composition may contain one or more lipase(s). A composition may contain one or more protease(s) and one or more amylase(s). A composition may contain one or more protease(s) and one or more lipase(s). A composition may contain one or more amylase(s) and one or more lipase(s). A composition may contain one or more protease(s), one or more amylase(s), and one or more lipase(s).

The one or more protease(s) can comprise, for example, papain, bromelain, chymotrypsin, trypsin, Carboxypeptidase B, serine proteases (e.g., Kallikrein), or a combination thereof. In one instance, the one or more protease(s) comprise chymotrypsin. In one instance, the one or more protease(s) comprise trypsin. In one instance, the one or more protease(s) comprise chymotrypsin and trypsin. Other enzymes that may be utilized in the pharmaceutical compositions described herein include, but are not limited to, an elastase, a sucrase, a maltase, a cellulase, a hydrolase, a colipase, a Phospholipase A2, a Cholesterol Esterase, or a combination thereof. Digestive enzymes may also be provided, in some instances, as pancreatin, pancrealipase, or derived therefrom. Pancreatin may be, for example, a crystalline pancreatin.

The one or more digestive enzyme(s) can be, independently, derived from an animal source, a microbial source, a plant source, are recombinantly-prepared, or are synthetically-prepared. In some embodiments, the animal source is a pig, e.g., a pig pancreas, or avian, e.g., "bird" proventriculus or small intestine. The digestive enzymes can be any combination of digestive enzymes of a type produced by the pancreas, including, but not limited to digestive enzymes from a pancreatic source or other source. The scope of the disclosure is not limited to pancreatic enzymes of porcine origin but can be of animal origin, microbial origin, plant origin, as well as those that are recombinantly-derived or synthetically-derived. In one embodiment, the digestive enzyme is derived from mammalian sources such as porcine-derived digestive enzymes. In another embodiment, the digestive enzyme includes one or more enzymes, and is plant-derived, synthetically-derived, or recombinantly-produced in microbial cells, yeast cells, or mammalian cells, or includes a mixture of enzymes from one or more source(s). For example, digestive enzymes may include one or more enzyme(s) from one or more source(s) mixed together. This includes, for example, the addition of single digestive enzymes to digestive enzymes derived from pancreatic sources in order to provide appropriate levels of specific enzymes that provide more effective treatment for a selected disease or condition. One exemplary source of pancreatin digestive enzymes can be obtained, for example, from Scientific Protein Laboratories. In one non-limiting embodiment provided herein utilizes one or more of the following enzymes: trypsin, chymotrypsin, elastase, kallikrein, carboxypeptidase b, alpha-amylase, lipase, colipase, phospholipase A2, cholesterol, esterase, or a combination thereof. In one embodiment the digestive enzymes are pancreatic digestive enzymes. In one embodiment, the animal enzyme is derived from a mammal. In one embodiment the mammal is a pig. In one embodiment, digestive enzymes are derived from a mammalian pancreas. In one embodiment the pancreas is a pig pancreas or avian, e.g., "bird" proventriculus or small intestine. In yet another embodiment, digestive enzymes as well as other proteins (e.g., those secreted in a mammal) that affect the digestive process either directly or indirectly may be included in a composition.

In any of such targeted delivery systems described above, the one or more digestive enzyme(s) can comprise one or more protease(s), one or more lipase(s), one or more amylase(s), or a combination thereof. For example, the one or more digestive enzyme(s) can comprise one or more protease(s); the digestive enzymes can comprise one or more lipase(s); the digestive enzymes can comprise one or more amylase(s); the digestive enzymes can comprise one or more protease(s) and one or more lipase(s); the digestive enzymes can comprise one or more protease(s) and one or more amylase(s); the digestive enzymes can comprise one or more lipase(s) and one or more amylase(s); or the digestive enzymes can comprise one or more protease(s), one or more lipase(s), and one or more amylase(s). In one non-limiting embodiment, the digestive enzymes in the targeted delivery system are provided as pancreatin.

In another embodiment, the digestive enzymes in the targeted delivery system are uncoated and, optionally, may be formulated with one or more carriers, excipients, buffers, fillers, binders, stabilizers, surfactants, diluents, extracts, lubricants, fillers, flavorings, preservatives, colorants, diluents, and coating agents, such as vegetable oil, crystalline oils, taste maskers, sweeteners, etc.

In one embodiment, a total amount of protease in a composition ranges from about 5,000 to about 1,500,000 U.S.P. Units/dose. In another embodiment, a total amount of amylase in a composition ranges from about 1,000 to about 15,000,000 U.S.P. Units/dose. In another embodiment, a total amount of lipase in a composition ranges from about 1,500 to about 282,000 U.S.P. Units/dose.

Provided herein is a composition comprising digestive enzymes for use in the methods described herein, wherein the digestive enzymes comprise about 23,000 U.S.P. Units/dose of lipase, about 144,000 U.S.P. Units/dose of amylase and about 140,000 U.S.P. Units/dose of protease. Provided herein is a composition comprising digestive enzymes for use in the methods described herein, wherein the digestive enzymes comprise about 23,040 U.S.P. Units/dose of lipase, about 144,000 U.S.P. Units/dose of amylase and about 140,400 U.S.P. Units/dose of protease. Provided herein is a composition comprising digestive enzymes for use in the methods described herein, wherein the digestive enzymes comprise about 16,800 U.S.P. Units/dose of lipase, about 70,000 U.S.P. Units/dose of protease, and about 70,000 U.S.P. Units/dose of amylase. Provided herein is a composition comprising digestive enzymes for use in the methods described herein, wherein the digestive enzymes comprise about 16,800 U.S.P. Units/dose of lipase, about 110,000 U.S.P. Units/dose of protease, and about 70,000 U.S.P. Units/dose of amylase. In one embodiment, a composition comprises about 8,400 U.S.P. Units/dose lipase, 35,000 U.S.P. Units/dose protease, and about 35,000 U.S.P. Units/dose amylase. In one embodiment, a composition comprises about 8,400 U.S.P. Units/dose lipase, 35,000 U.S.P. Units/dose protease, and about 35,000 U.S.P. Units/dose amylase. In one embodiment, a composition comprises about 16,800 U.S.P. Units/dose lipase, about 70,000 U.S.P. Units/dose protease, and about 70,000 U.S.P. Units/dose amylase. In one embodiment, a composition comprises about 33,600 U.S.P. Units/dose lipase, about 140,000 U.S.P. Units/dose protease, and about 140,000 U.S.P. Units/dose amylase. In one embodiment, a composition comprises about 50,400 U.S.P. Units/dose lipase, about 210,000 U.S.P. Units/dose protease, and about 210,000 U.S.P. Units/dose amylase. In one embodiment, a composition comprises about 67,200 U.S.P. Units/dose lipase, about 280,000 U.S.P. Units/dose protease, and about 280,000 U.S.P. Units/dose amylase. In one embodiment, a composition comprises about 84,000 U.S.P. Units/dose lipase, about 350,000 U.S.P. Units/dose protease, and about 350,000 U.S.P. Units/dose amylase. In one embodiment, a composition comprises about 100,800 U.S.P. Units/dose lipase, about 420,000 U.S.P. Units/dose protease, and about 420,000 U.S.P. Units/dose amylase. In one embodiment, a composition comprises about 117,600 U.S.P. Units/dose lipase, about 490,000 U.S.P. Units/dose protease, and about 490,000 U.S.P. Units/dose amylase. In one embodiment, a composition comprises about 134,400 U.S.P. Units/dose lipase, about 560,000 U.S.P. Units/dose protease, and about 560,000 U.S.P. Units/dose amylase. In one embodiment, a composition comprises about 151,200 U.S.P. Units/dose lipase, about 630,000 U.S.P. Units/dose protease, and about 630,000 U.S.P. Units/dose amylase. In one embodiment, a composition comprises about 168,000 U.S.P. Units/dose lipase, about 700,000 U.S.P. Units/dose protease, and about 700,000 U.S.P. Units/dose amylase. In one embodiment, a composition comprises about 184,800 U.S.P. Units/dose lipase, about 770,000 U.S.P. Units/dose protease, and about 770,000 U.S.P. Units/dose amylase. In one embodiment, a composition comprises about 201,600 U.S.P. Units/dose lipase, about 840,000 U.S.P. Units/dose protease, and about 840,000 U.S.P. Units/dose amylase. In one embodiment, a composition comprises about 218,400 U.S.P. Units/dose lipase, about 910,000 U.S.P. Units/dose protease, and about 910,000 U.S.P. Units/dose amylase. In one embodiment, a composition comprises about 235,200 U.S.P. Units/dose lipase, about 980,000 U.S.P. Units/dose protease, and about 980,000 U.S.P. Units/dose amylase. In one embodiment, a composition comprises about 252,000 U.S.P. Units/dose lipase, about 1,050,000 U.S.P. Units/dose protease, and about 1,050,000 U.S.P. Units/dose amylase.

Any of the compositions may be optionally supplemented with additional protease. In one embodiment, a composition may be supplemented with about 20,000 U.S.P. Units/dose; about 40,000 U.S.P. Units/dose; about 60,000 U.S.P. Units/dose; about 80,000 U.S.P. Units/dose; about 100,000 U.S.P. Units/dose; about 120,000 U.S.P. Units/dose; about 140,000 U.S.P. Units/dose; or about 160,000 U.S.P. Units/dose protease.

In some embodiments, the digestive enzyme composition comprises a protease, a lipase, and an amylase where the activities are: protease in an amount of from about 10,000 to about 1,500,000 United States Pharmacopeia (U.S.P.) units/dose including about any of 10,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 1,050,000, 1,100,000, 1,150,000, 1,200,00, 1,250,000, 1,300,000, 1,350,000, 1,400,000, 1,450,000, and 1,500,000 per dose, along with all values in-between, and where the ratio of protease to lipase is such that the amount of lipase is never more than 0.188 times the amount of protease and where the ratio of protease activity to amylase activity is between 1:0.1 and 1:10.

In some embodiments, the digestive enzyme composition comprises a protease and a lipase, where the activities are: protease in an amount of from about 10,000 to about 1,500,000 U.S.P. Units/dose including about any of 10,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 1,050,000, 1,100,000, 1,150,000, 1,200,00, 1,250,000, 1,300,000, 1,350,000, 1,400,000, 1,450,000, and 1,500,000 per dose, along with all values in-between, and where the ratio of protease to lipase is such that the amount of lipase is never more than 0.188 times the amount of protease.

In some embodiments, the digestive enzyme composition comprises a protease and an amylase where the activities are: protease in an amount of from about 10,000 to about 1,500,000 U.S.P. Units/dose including about any of 10,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 1,050,000, 1,100,000, 1,150,000, 1,200,00, 1,250,000, 1,300,000, 1,350,000, 1,400,000, 1,450,000, and 1,500,000 per dose, along with all values in-between, and where the ratio of protease activity to amylase activity is between 1:0.1 and 1:10.

In some embodiments, the digestive enzyme composition comprises a protease where the activity is: protease in an amount of from about 10,000 to about 1,500,000 U.S.P. Units/dose including about 10,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 1,050,000, 1,100,000, 1,150,000, 1,200,00, 1,250,000, 1,300,000, 1,350,000, 1,400,000, 1,450,000, and 1,500,000 per dose, along with all values in-between.

In some embodiments, the digestive enzyme composition comprises a protease, a lipase, and an amylase where the activities are: protease in an amount of from about 10,000 to about 1,500,000 U.S.P. Units/dose including about any of 10,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 1,050,000, 1,100,000, 1,150,000, 1,200,00, 1,250,000, 1,300,000, 1,350,000, 1,400,000, 1,450,000, and 1,500,000 per dose, along with all values in-between; lipase from about 1,880 to about 282,000 U.S.P. Units/dose including about any of 1,880, 10,000, 50,000, 100,000, 150,000, 200,000, 250,000, 282,000, per dose, along with all values in-between; amylase in amount of from about 1,000 to about 15,000,000 U.S.P. Units/dose, including about any of 1,000, 10,000, 100,000, 500,000, 1,000,000, 2,000,000, 3,000,000, 4,000,000, 5,000,000, 6,000,000, 7,000,000, 8,000,000, 9,000,000, 10,000,000, 11,000,000, 12,000,000, 13,000,000, 14,000,000, and 15,000,000 U.S.P. Units, per dose, along with all values in-between.

In some embodiments, the digestive enzyme composition is comprised of protease and lipase, where the activities are: protease from about 10,000 to about 1,500,000 U.S.P. Units/dose including about any of 10,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 1,050,000, 1,100,000, 1,150,000, 1,200,00, 1,250,000, 1,300,000, 1,350,000, 1,400,000, 1,450,000, and 1,500,000 per dose, along with all values in-between; and lipase from about 1,880 to about 282,000 U.S.P. Units/dose including about any of 1,880, 10,000, 50,000, 100,000, 150,000, 200,000, 250,000, and 282,000, per dose, along with all values in-between.

In some embodiments, the digestive enzyme composition comprises a protease and an amylase where the activities are: protease in an amount of from about 10,000 to about 1,500,000 U.S.P. Units/dose including about any of 10,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 1,050,000, 1,100,000, 1,150,000, 1,200,00, 1,250,000, 1,300,000, 1,350,000, 1,400,000, 1,450,000, and 1,500,000 per dose, along with all values in-between; amylase in an amount of from about 1,000 to about 15,000,000 U.S.P. Units/dose, including about any of 1,000, 10,000, 100,000, 500,000, 1,000,000, 2,000,000, 3,000,000, 4,000,000, 5,000,000, 6,000,000, 7,000,000, 8,000,000, 9,000,000, 10,000,000, 11,000,000, 12,000,000, 13,000,000, 14,000,000, and 15,000,000 U.S.P. Units/dose, per dose, along with all values in-between.

In some embodiments, the digestive enzyme composition comprises a protease, where the activity is: protease in an amount of from about 10,000 to about 1,500,000 U.S.P, units including about any of 10,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 1,050,000, 1,100,000, 1,150,000, 1,200,00, 1,250,000, 1,300,000, 1,350,000, 1,400,000, 1,450,000, and 1,500,000 per dose, along with all values in-between.

In some embodiments, the digestive enzyme composition comprises at least one amylase, a mixture of proteases comprising chymotrypsin and trypsin, and at least one lipase. The pharmaceutical composition can, optionally, further include papain (e.g., from papaya) or bromelain. In some embodiments, the coated pharmaceutical composition comprises per dose: amylase in amount of from about 1,000 to about 15,000,000 U.S.P. Units/dose, including about any of 1,000, 10,000, 100,000, 500,000, 1,000,000, 2,000,000, 3,000,000, 4,000,000, 5,000,000, 6,000,000, 7,000,000, 8,000,000, 9,000,000, 10,000,000, 11,000,000, 12,000,000, 13,000,000, 14,000,000, or 15,000,000 U.S.P. Units/dose, along with all values in-between; protease in an amount of from about 10,000 to about 1,500,000 U.S.P. Units/dose including about any of 10,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 1,050,000, 1,100,000, 1,150,000, 000, 1,200,00, 1,250,000, 1,300,000, 1,350,000, 1,400,000, 1,450,000, and 1,500,000 per dose, along with all values in-between, lipase in amount of from about 1,880 to about 282,000 U.S.P. Units/dose including about any of 1,880, 10,000, 50,000, 100,000, 150,000, 200,000, 250,000, and 282,000 per dose, along with all values in-between.

A pharmaceutical composition may contain an amount of protease of from about 1,000 to about 15,000,000 U.S.P. Units/dose. For example, a pharmaceutical composition may contain an amount of protease from about 5,000; about 7,500; about 10,000; about 15,000; about 20,000; about 25,000; about 30,000; about 35,000; about 40,000; about 50,000; about 55,000; about 65,000; about 70,000; about 75,000; about 90,000; about 95,000; about 100,000; about 110,000; about 115,000; about 130,000; about 140,000; about 140,400; about 150,000; about 155,000; about 160,000; about 170,000; about 175,000; about 180,000; about 190,000; about 195,000; about 200,000; about 210,000; about 220,000; about 230,000; about 240,000; about 250,000; about 280,000; about 290,000; about 300,000; about 310,000; about 320,000; about 330,000; about 340,000; about 350,000; about 360,000; about 370,000; about 380,000; about 390,000; about 400,000; about 410,000; about 420,000; about 430,000; about 440,000; about 450,000; about 465,000; about 470,000; about 480,000; about 490,000; about 500,000; about 510,000; about 520,000; about 530,000; about 540,000; about 550,000; about 560,000; about 570,000; about 580,000; about 590,000; about 600, 000; about 610,000; about 620,000; about 630,000; about 640,000; about 650,000; about 660,000; about 670,000; about 680,000; about 690,000; about 700,000; about 710,000; about 720,000; about 730,000; about 740,000; about 750,000; about 760,000; about 770,000; about 780,000; about 790,000; about 800,000; about 810,000; about 820,000; about 830,000; about 840,000; about 850,000; about 860,000; about 870,000; about 880,000; about 890,000; about 900,000; about 910,000; about 920,000; about 930,000; about 940,000; about 950,000; about 960,000; about 970,000; about 980,000; about 990,000; about 1,000,000; about 1,010,000; about 1,020,000; about 1,020,000; about 1,030,000; about 1,040,000; about 1,050,000; about 1,060,000; about 1,070,000; about 1,080,000; about 1,090,000; about 1,100,000; about 1,100,000; about 1,120,000; about 1,130,000; about 1,140,000; about 1,150,000; about 1,170,000; about 1,190,000; about 1,200,000; about 1,210,000; about 1,250,000; about 1,300,000; about 1,350,000; about 1,400,000; about 1,450,000; or about 1,500,000 U.S.P. Units/dose, or any integer in-between.

A pharmaceutical composition may contain an amount of amylase of from about 1,000 to about 15,000,000; from about 5,000 to about 1,000,000; from about 15,000 to about 750,000; from about 50,000 to about 500,000; from about 75,000 to about 250,000; from about 95,000 to about 200,000; or from about 100,000 to about 150,000 U.S.P. Units/dose. For example, a pharmaceutical composition may contain an amount of amylase including, but not limited to, about 1,000; about 3,000; about 5,000; about 7,500; about 10,000; about 15,000; about 20,000; about 25,000; about 30,000; about 35,000; about 40,000; about 50,000; about 65,000; about 70,000; about 75,000; about 100,000; about 140,000; about 144,000; about 210,000; about 280,000; about 350,000; about 420,000; about 490,000; about 500,000; about 560,000; about 630,000; about 700,000; about 770,000; about 840,000; about 910,000; about 980,000; about 1,000,000; about 1,050,000; about 2,000,000; about 3,000,000; about 4,000,000; about 5,000,000; about 6,000,000; about 7,000,000; about 8,000,000; about 9,000,000; about 10,000,000; about 11,000,000; about 12,000,000; about 13,000,000; about 14,000,000; or about 15,000,000 U.S.P. Units/dose, or any integer in-between.

A pharmaceutical composition may contain an amount of lipase of from about 1,500 to about 282,000; from about 5,000 to about 200,000; from about 5,000 to about 150,000; from about 75,000 to about 100,000; from about 10,000 to about 75,000; from about 15,000 to about 50,000; or from about 20,000 to about 40,000 U.S.P. Units/dose. For example, a pharmaceutical composition may contain an amount of lipase including, but not limited to, about 1,500; about 1,880; about 2,000; about 3,000; about 5,000; about 7,500; about 8,400; about 10,000; about 15,000; about 16,800; about 20,000; about 23,000; about 23,040; about 25,000; about 30,000; about 33,600; about 40,000; about 50,000; about 50,400; about 65,000; about 67,200; about 75,000; about 84,000; about 100,000; about 100,800; about 117,600; about 125,000; about 134,400; about 150,000; about 151,200; about 168,000; about 184,800; about 200,000; about 201,600; about 218,400; about 235,200; about 250,000; about 252,000; or about 282,000 U.S.P. Units/dose, or any integer in-between.

In one instance, a pharmaceutical composition comprises a protease, a lipase, and an amylase where the activity of the protease is from about 5,000 to about 1,500,000 U.S.P. Units/dose, or from about 10,000 to about 1,500,000 U.S.P. Units/dose including, but not limited to, about 5,000; about 7,500; about 10,000; about 15,000; about 20,000; about 25,000; about 30,000; about 35,000; about 40,000; about 50,000; about 55,000; about 65,000; about 70,000; about 75,000; about 90,000; about 95,000; about 100,000; about 110,000; about 115,000; about 130,000; about 140,000; about 140,400; about 150,000; about 155,000; about 160,000; about 170,000; about 175,000; about 180,000; about 190,000; about 195,000; about 200,000; about 210,000; about 220,000; about 230,000; about 240,000; about 250,000; about 280,000; about 290,000; about 300,000; about 310,000; about 320,000; about 330,000; about 340,000; about 350,000; about 360,000; about 370,000; about 380,000; about 390,000; about 400,000; about 410,000; about 420,000; about 430,000; about 440,000; about 450,000; about 465,000; about 470,000; about 480,000; about 490,000; about 500,000; about 510,000; about 520,000; about 530,000; about 540,000; about 550,000; about 560,000; about 570,000; about 580,000; about 590,000; about 600,000; about 610,000; about 620,000; about 630,000; about 640,000; about 650,000; about 660,000; about 670,000; about 680,000; about 690,000; about 700,000; about 710,000; about 720,000; about 730,000; about 740,000; about 750,000; about 760,000; about 770,000; about 780,000; about 790,000; about 800,000; about 810,000; about 820,000; about 830,000; about 840,000; about 850,000; about 860,000; about 870,000; about 880,000; about 890,000; about 900,000; about 910,000; about 920,000; about 930,000; about 940,000; about 950,000; about 960,000; about 970,000; about 980,000; about 990,000; about 1,000,000; about 1,010,000; about 1,020,000; about 1,020,000; about 1,030,000; about 1,040,000; about 1,050,000; about 1,060,000; about 1,070,000; about 1,080,000; about 1,090,000; about 1,100,000; about 1,100,000; about 1,120,000; about 1,130,000; about 1,140,000; about 1,150,000; about 1,170,000; about 1,190,000; about 1,200,000; about 1,210,000; about 1,250,000; about 1,300,000; about 1,350,000; about 1,400,000; about 1,450,000; or about 1,500,000 U.S.P. Units/dose, or any integer in-between, and where the ratio of protease to lipase is such that the amount of lipase is never more than 0.188 times the amount of protease; and further wherein the ratio of protease activity to amylase activity is between 1:0.1 and 1:10.

In some embodiments, the digestive enzyme composition comprises at least one protease and at least one lipase, wherein the ratio of total protease to total lipase in U.S.P. Units ranges from about 5.371:1 to about 20:1 including 5.371:1, 6:1, 7:1, 8:1, 9:1, 10:1, 11:1, 12:1, 13:1, 14:1, 15:1, 16:1, 17:1, 18:1, 19:1 and 20:1, along with all values in-between. In some embodiments, the ratio of protease to lipase in U.S.P. Units ranges from about 5.371:1 to about 10:1 including 5.371:1, 6:1, 7:1, 8:1, 9:1, and 10:1, along with all values in-between.

In yet another embodiment, the digestive enzyme composition comprises at least one protease and at least one lipase, wherein the ratio of total protease to total lipase in U.S.P. Units ranges from about 5.371:1 to about 20:1 including about 1:1, 2:1, 3:1, 4:1, 5:1 (e.g., 5.371:1), 6:1, 7:1, 8:1, 9:1, 10:1, 11:1, 12:1, 13:1, 14:1, 15:1, 16:1, 17:1, 18:1, 19:1, and 20:1, along with all values in-between. In another embodiment, the digestive enzyme composition comprises at least one protease and at least one lipase, wherein the ratio of total protease to total lipase in U.S.P. Units ranges from about 1:1 to about 20:1. In yet another embodiment, the ratio of protease to lipase in U.S.P. Units ranges from about 4:1 to about 10:1. In one embodiment, the ratio of proteases to lipases in U.S.P. Units ranges from about 5:1 (e.g., 5.371:1) to about 10:1 including 5:1 (e.g., 5.371:1), 6:1, 7:1, 8:1, 9:1, and 10:1, or any integer in-between.

In one embodiment, the digestive enzyme composition comprises at least one protease and at least one amylase, wherein the ratio of total protease to total amylase in in U.S.P. Units ranges from about 1:0.1 to about 1:10 including 1:0.1, 1:0.25, 1:0.5, 1:0.75, 1:1, 1:1.25, 1:1.5, 1:1.75:1:2, 1:1.25, 1:1.5, 1:1.75, 1:1.2, 1:1.25, 1:1.5, 1:1.75, 1:1.2, 1:1.25, 1:1.5, 1:1.75, 1:1.2:1:1.5, 1:2, 1:3, 1:4, 1:5, 1:6, 1:7, 1:8, 1.9 and 1:10, along any integer in-between.

In another embodiment, the digestive enzyme composition comprises at least one protease and at least one amylase, wherein the ratio of total protease to total amylase in U.S.P. Units ranges from about 1:6 to about 1:0.14 including any integer in-between. In another embodiment, the ratio of protease to amylase in U.S.P. Units ranges from about 1:7 to about 1:0.125 including any integer in-between.

In another embodiment, the digestive enzyme composition comprises a protease, a lipase, and an amylase where the activities are: protease in an amount of from about 5,000 to about 1,500,000 U.S.P. Units/dose, or from about 10,000 to about 1,500,000 U.S.P. Units/dose, including about 5,000, about 7,500, about 10,000, about 15,000, about 20,000, about 25,000, about 30,000, about 35,000, about 40,000, about 50,000, about 55,000, about 65,000, about 70,000, about 75,000, about 90,000, about 95,000, about 100,000, about 110,000, about 115,000, about 130,000, about 140,000, about 140,400, about 150,000, about 155,000, about 160,000, about 170,000, about 175,000, about 180,000, about 190,000, about 195,000, about 200,000, about 210,000, about 220,000, about 230,000, about 240,000, about 250,000, about 280,000, about 290,000, about 300,000, about 310,000, about 320,000, about 330,000, about 340,000, about 350,000, about 360,000, about 370,000, about 380,000, about 390,000, about 400,000, about 410,000, about 420,000, about 430,000, about 440,000, about 450,000, about 465,000, about 470,000, about 480,000, about 490,000, about 500,000, about 510,000, about 520,000, about 530,000, about 540,000, about 550,000, about 560,000, about 570,000, about 580,000, about 590,000, about 600,000, about 610,000, about 620,000, about 630,000, about 640,000, about 650,000, about 660,000, about 670,000, about 680,000, about 690,000, about 700,000, about 710,000, about 720,000, about 730,000, about 740,000, about 750,000, about 760,000, about 770,000, about 780,000, about 790,000, about 800,000, about 810,000, about 820,000, about 830,000, about 840,000, about 850,000, about 860,000, about 870,000, about 880,000, about 890,000, about 900,000, about 910,000, about 920,000, about 930,000, about 940,000, about 950,000, about 960,000, about 970,000, about 980,000, about 990,000, about 1,000,000, about 1,010,000, about 1,020,000, about 1,020,000, about 1,030,000, about 1,040,000, about 1,050,000, about 1,060,000, about 1,070,000, about 1,080,000, about 1,090,000, about 1,100,000, about 1,100,000, about 1,120,000, about 1,130,000, about 1,140,000, about 1,150,000, about 1,170,000, about 1,190,000, about 1,200,000, about 1,210,000, about 1,250,000, about 1,300,000, about 1,350,000, about 1,400,000, about 1,450,000, about 1,500,000 U.S.P. Units/dose, or any integer in-between, and where the ratio of protease to lipase is such that the amount of lipase is never more than 0.188 times the amount of protease and where the ratio of protease activity to amylase activity is from about 1:0.1 and about 1:10.

In yet another embodiment, the digestive enzyme composition comprises at least one protease wherein the activity of protease is from about 5,000, about 7,500, about 10,000, about 15,000, about 20,000, about 25,000, about 30,000, about 35,000, about 40,000, about 50,000, about 55,000, about 65,000, about 70,000, about 75,000, about 90,000, about 95,000, about 100,000, about 110,000, about 115,000, about 130,000, about 140,000, about 140,400, about 150,000, about 155,000, about 160,000, about 170,000, about 175,000, about 180,000, about 190,000, about 195,000, about 200,000, about 210,000, about 220,000, about 230,000, about 240,000, about 250,000, about 280,000, about 290,000, about 300,000, about 310,000, about 320,000, about 330,000, about 340,000, about 350,000, about 360,000, about 370,000, about 380,000, about 390,000, about 400,000, about 410,000, about 420,000, about 430,000, about 440,000, about 450,000, about 465,000, about 470,000, about 480,000, about 490,000, about 500,000, about 510,000, about 520,000, about 530,000, about 540,000, about 550,000, about 560,000, about 570,000, about 580,000, about 590,000, about 600,000, about 610,000, about 620,000, about 630,000, about 640,000, about 650,000, about 660,000, about 670,000, about 680,000, about 690,000, about 700,000, about 710,000, about 720,000, about 730,000, about 740,000, about 750,000, about 760,000, about 770,000, about 780,000, about 790,000, about 800,000, about 810,000, about 820,000, about 830,000, about 840,000, about 850,000, about 860,000, about 870,000, about 880,000, about 890,000, about 900,000, about 910,000, about 920,000, about 930,000, about 940,000, about 950,000, about 960,000, about 970,000, about 980,000, about 990,000, about 1,000,000, about 1,010,000, about 1,020,000, about 1,020,000, about 1,030,000, about 1,040,000, about 1,050,000, about 1,060,000, about 1,070,000, about 1,080,000, about 1,090,000, about 1,100,000, about 1,100,000, about 1,120,000, about 1,130,000, about 1,140,000, about 1,150,000, about 1,170,000, about 1,190,000, about 1,200,000, about 1,210,000, about 1,250,000, about 1,300,000, about 1,350,000, about 1,400,000, about 1,450,000, about 1,500,000 U.S.P. Units/dose or any integer in-between.

In yet another embodiment, the digestive enzyme composition comprises one or more coated or uncoated protease(s), wherein the activity of protease is from about 10,000 to about 1,500,000, from about 25,000 to about 1,000,000, from about 50,000 to about 750,000, from about 75,000 to about 500,000, from about 85,000 to about 250,000, from about 95,000 to about 200,000, or from about 110,000 to about 150,000 U.S.P. Units/dose. Compositions may contain an amount of protease including, but not limited to, about 5,000, about 7,500, about 10,000, about 15,000, about 20,000, about 25,000, about 30,000, about 35,000, about 40,000, about 50,000, about 55,000, about 65,000, about 70,000, about 75,000, about 90,000, about 95,000, about 100,000, about 110,000, about 115,000, about 130,000, about 140,000, about 140,400, about 150,000, about 155,000, about 160,000, about 170,000, about 175,000, about 180,000, about 190,000, about 195,000, about 200,000, about 210,000, about 220,000, about 230,000, about 240,000, about 250,000, about 280,000, about 290,000, about 300,000, about 310,000, about 320,000, about 330,000, about 340,000, about 350,000, about 360,000, about 370,000, about 380,000, about 390,000, about 400,000, about 410,000, about 420,000, about 430,000, about 440,000, about 450,000, about 465,000, about 470,000, about 480,000, about 490,000, about 500,000, about 510,000, about 520,000, about 530,000, about 540,000, about 550,000, about 560,000, about 570,000, about 580,000, about 590,000, about 600,000, about 610,000, about 620,000, about 630,000, about 640,000, about 650,000, about 660,000, about 670,000, about 680,000, about 690,000, about 700,000, about 710,000, about 720,000, about 730,000, about 740,000, about 750,000, about 760,000, about 770,000, about 780,000, about 790,000, about 800,000, about 810,000, about 820,000, about 830,000, about 840,000, about 850,000, about 860,000, about 870,000, about 880,000, about 890,000, about 900,000, about 910,000, about 920,000, about 930,000, about 940,000, about 950,000, about 960,000, about 970,000, about 980,000, about 990,000, about 1,000,000, about 1,010,000, about 1,020,000, about 1,020,000, about 1,030,000, about 1,040,000, about 1,050,000, about 1,060,000, about 1,070,000, about 1,080,000, about 1,090,000, about 1,100,000, about 1,100,000, about 1,120,000, about 1,130,000, about 1,140,000, about 1,150,000, about 1,170,000, about 1,190,000, about 1,200,000, about 1,210,000, about 1,250,000, about 1,300,000, about 1,350,000, about 1,400,000, about 1,450,000, or about 1,500,000, U.S.P. Units/dose, or any integer in-between. An added benefit is that this formulation will be useful in very young infants who are not able to tolerate lipase activity.

A dose of a pharmaceutical composition can comprise from about 100 mg to about 1500 mg, from 500 mg to about 1200 mg, from about 800 mg to about 1000 mg, or from about 850 mg to about 950 mg of digestive enzymes by weight. In one instance, a dose of a pharmaceutical composition can comprise from about 100 mg to about 1500 mg of digestive enzymes by weight. In another instance, a dose of a pharmaceutical composition can comprise from 500 mg to about 1200 mg of digestive enzymes by weight. In another instance, a dose of a pharmaceutical composition can comprise from about 800 mg to about 1000 mg of digestive enzymes by weight. In another instance, a dose of a pharmaceutical composition can comprise from about 850 mg to about 950 mg of digestive enzymes by weight.

A dose of a pharmaceutical composition can comprise about 100, about 150, about 200, about 250, about 300, about 350, about 400, about 450, about 500, about 550, about 600, 650, about 700, about 750, about 800, about 850, about 900, about 950, about 1000, about 1050, about 1100, about 1150, about 1200, about 1250, about 1300, about 1350, about 1400, about 1450, or about 1500 mg of digestive enzymes by weight. In one instance, a dose of a pharmaceutical composition can comprise about 800, about 810, about 820, about 830, about 840, about 850, about 860, about 870, about 880, about 890, about 900, about 910, about 920, about 930, about 940, about 950, about 960, about 970, about 980, about 990, or about 1000 mg of digestive enzymes by weight. In one non-limiting instance, a dose of a pharmaceutical composition comprises about 850 mg of digestive enzymes by weight. In another non-limiting instance, a dose of a pharmaceutical composition comprises about 860 mg of digestive enzymes by weight. In another non-limiting instance, a dose of a pharmaceutical composition comprises about 870 mg of digestive enzymes by weight. In another non-limiting instance, a dose of a pharmaceutical composition comprises about 880 mg of digestive enzymes by weight. In another non-limiting instance, a dose of a pharmaceutical composition comprises about 890 mg of digestive enzymes by weight. In another non-limiting instance, a dose of a pharmaceutical composition comprises about 900 mg of digestive enzymes by weight. In another non-limiting instance, a dose of a pharmaceutical composition comprises about 910 mg of digestive enzymes by weight. In another non-limiting instance, a dose of a pharmaceutical composition comprises about 920 mg of digestive enzymes by weight. In another non-limiting instance, a dose of a pharmaceutical composition comprises about 930 mg of digestive enzymes by weight. In another non-limiting instance, a dose of a pharmaceutical composition comprises about 940 mg of digestive enzymes by weight. In another non-limiting instance, a dose of a pharmaceutical composition comprises about 950 mg of digestive enzymes by weight.

A dose of a pharmaceutical composition can comprise a protease activity of not less than (NTL) about 100, about 105, about 110, about 115, about 120, about 125, about 130, about 135, about 140, about 145, about 150, about 155, about 156, about 160, about 165, about 170, about 175, about 180, about 185, about 190, about 195, or about 200 U.S.P. units/mg. In one non-limiting instance, a dose of a pharmaceutical composition can comprise a protease activity of not less than about 100 U.S.P. units/mg. In another non-limiting instance, a dose of a pharmaceutical composition can comprise a protease activity of not less than about 105 U.S.P. units/mg. In another non-limiting instance, a dose of a pharmaceutical composition can comprise a protease activity of not less than about 110 U.S.P. units/mg. In another non-limiting instance, a dose of a pharmaceutical composition can comprise a protease activity of not less than about 115 U.S.P. units/mg. In another non-limiting instance, a dose of a pharmaceutical composition can comprise a protease activity of not less than about 120 U.S.P. units/mg. In another non-limiting instance, a dose of a pharmaceutical composition can comprise a protease activity of not less than about 125 U.S.P. units/mg. In another non-limiting instance, a dose of a pharmaceutical composition can comprise a protease activity of not less than about 130 U.S.P. units/mg. In another non-limiting instance, a dose of a pharmaceutical composition can comprise a protease activity of not less than about 135 U.S.P. units/mg. In another non-limiting instance, a dose of a pharmaceutical composition can comprise a protease activity of not less than about 140 U.S.P. units/mg. In another non-limiting instance, a dose of a pharmaceutical composition can comprise a protease activity of not less than about 145 U.S.P. units/mg. In another non-limiting instance, a dose of a pharmaceutical composition can comprise a protease activity of not less than about 150 U.S.P. units/mg. In another non-limiting instance, a dose of a pharmaceutical composition can comprise a protease activity of not less than about 155 U.S.P. units/mg. In another non-limiting instance, a dose of a pharmaceutical composition can comprise a protease activity of not less than about 156 U.S.P. units/mg. In another non-limiting instance, a dose of a pharmaceutical composition can comprise a protease activity of not less than about 160 U.S.P. units/mg. In another non-limiting instance, a dose of a pharmaceutical composition can comprise a protease activity of not less than about 165 U.S.P. units/mg. In another non-limiting instance, a dose of a pharmaceutical composition can comprise a protease activity of not less than about 170 U.S.P. units/mg. In another non-limiting instance, a dose of a pharmaceutical composition can comprise a protease activity of not less than about 175 U.S.P. units/mg. In another non-limiting instance, a dose of a pharmaceutical composition can comprise a protease activity of not less than about 180 U.S.P. units/mg. In another non-limiting instance, a dose of a pharmaceutical composition can comprise a protease activity of not less than about 185 U.S.P. units/mg. In another non-limiting instance, a dose of a pharmaceutical composition can comprise a protease activity of not less than about 190 U.S.P. units/mg. In another non-limiting instance, a dose of a pharmaceutical composition can comprise a protease activity of not less than about 195 U.S.P. units/mg.

In another non-limiting instance, a dose of a pharmaceutical composition can comprise a protease activity of not less than about 200 U.S.P. units/mg.

Exemplary compositions comprising an effective amount of digestive enzymes may be administered to a subject via any conventional route including, but not limited to, oral, parenteral, intramuscular, intravenous, transmucosal, transdermal, nasal, rectal (e.g., suppository), percutaneous endoscopic gastrostomy (PEG), esophagogastroduodenoscopy (EGD), gastrostomy (G-tube) insertion, or any other appropriate delivery method. Further, the oral administration can be in the form of solutions, slurries, suspensions, sprays, washes, rinses, pellets, capsules, caplets, beadlets, sprinkles, tablets, softgels, sachets, pouches, or other. Nasal administration can be, for example, a nasal spray, a nasal drop, or a nasal rinse.

Compositions (preparations) comprising digestive enzymes may be manufactured using any appropriate technology including, but not limited to, enteric coating, polymer coating, lipid coating, lipid blend coating, lipid encapsulation, direct compression, dry granulation, wet granulation, and any combination thereof. The one or more digestive enzyme(s) may be utilized with one or more existing, emergent, or future coating technologies. A variety of physical and chemical methods are then used to combine the drug with the coating material such as coacervation, emulsions, meltable dispersion, spray drying, pan coating and fluidized bed granulations. In this manner, coatings and digestive enzymes or other active pharmaceutical ingredients can be combined to control the kinetics, duration, time, control of peak concentration, pharmacokinetics, dose, and location of drug release in the body.

A composition may be an oral dosage formulation such as, for example, a suspension, solution, a slurry, pill, tablet (mini-tab, etc.), capsule (e.g., microcapsule, mini-capsule, time-released capsule, etc.), sprinkle, or any combination thereof. One or more of the compositions described herein may be administered to a subject.

In one embodiment, the digestive enzymes and the amount of each digestive enzyme present in such compositions may be empirically determined by a physician based upon the patient to be treated. A physician can readily determine and prescribe the effective amount of the composition required. For example, the physician could start doses of the compounds employed in the composition at levels lower than that required in order to achieve the desired therapeutic effect and gradually increase the dosage until the desired effect is achieved. Alternatively, a dose can remain constant.

Coatings

The nature of the human digestive tract creates challenges for the delivery of digestive enzymes to subjects. Multiple temperature and pH changes over the course of the digestive tract make specific delivery a challenge but a necessity. For instance, pH as low as 1 is encountered in the stomach, but rapidly increases to a more basic pH of 5-6 in the proximal small intestine. For example, generally the pH in the stomach is approximately 1.2, the pH in the duodenum is about 5.0 to 6.0; the pH in the jejunum is about 6.8, and the pH is about 7.2 in the proximal ileum and about 7.5 in the distal ileum. The low pH in the stomach that changes rapidly to a more basic pH of 5-6 in the proximal small intestines calls for a specific delivery method depending upon where the enzyme is to be delivered.

In one example, the release of digestive enzymes is timed to release specific percentages of enzymes in specific portions of the gastrointestinal tract by use of coating technologies. Administration of the digestive enzymes described herein via any available route increases a concentration of the digestive enzymes in the subject such that they are available to, for example, cleave one or more spike protein(s) of a coronavirus.

A coating can, in some instances, provide a significant barrier to moisture, heat, humidity and exposure to light by allowing for a physical barrier as well as one that prevents and or reduces hydrolysis. Coated enzyme preparations undergo less hydrolysis as a result of protection from moisture in the environment by the lipid coating. As a result, digestive enzymes are provided which can tolerate storage conditions (e.g., moisture, heat, oxygen, etc.) for long periods of time thus enabling extended shelf life. The coating protects the digestive enzymes from an environment and can provide, in some instances, emulsification in a solvent without detracting from the abrasion resistance of the coating. The coated digestive enzyme preparations, therefore, reduce overfilling of the digestive enzyme dosage and enhance delivery of more accurate doses of the digestive enzymes.

In some instances, coating may be used to obtain release of digestive enzymes from a pharmaceutical composition or formulation at selected transit times or in selected locations of the gastrointestinal tract of humans. In one aspect, this disclosure relates to controlled-release enzyme preparations administered to a subject with a coronavirus infection (e.g., COVID-19). In another aspect of the present invention, one or more coating(s) are utilized to target delivery to the small intestines.

Some embodiments utilize stable enzyme preparations protected against the environment to reduce, for example, degradation and/or denaturation of the enzymes. This permits delivery of more accurate doses of the digestive enzymes to subjects needing treatment. The coating can also, in some aspects, provide emulsification when the enzyme preparations are contacted with appropriate solvents, while also surprisingly providing for controlled-release of the enzyme in the GI system. The emulsification properties of the coating in a solvent allows for controlled-release of the digestive enzymes at, for example, in selected locations in the GI tract or in the mucosa of a subject.

A pharmaceutical composition described herein, in one instance, comprises coated particles that contain (a) a core and (b) a coating. In some embodiments, a coated enzyme preparation is in the form of coated particles, which coated particles comprise: (a) a core comprising digestive enzymes present in the coated particles in an amount of from about 5% to 95% by weight and (b) a coating. In one aspect, this disclosure relates to an enzyme delivery system comprising a coated enzyme preparation in the form of coated particles, which coated particles comprise: (a) a core comprising digestive enzymes present in the coated particles in an amount of from about 50% to about 95% by weight; and (b) a coating. In yet another aspect, this disclosure relates to an enzyme delivery system comprising a coated enzyme preparation having coated particles, which coated particles comprise: (a) a core comprising digestive enzymes present in the coated particles in an amount of from about 70% to about 90% by weight; and (b) a coating. In yet another aspect, this disclosure relates to an enzyme delivery system comprising a coated enzyme preparation having coated particles, which coated particles comprise: (a) a core comprising digestive enzymes present in the coated particles an amount of from about 75% to about 85% by weight; and (b) a coating. The coated particles may be non-aerosolizable.

The core comprises one or more digestive enzyme(s) (e.g., proteases, lipases, amylases, or a combination thereof). Any suitable coating for use in the pharmaceutical compositions described herein includes, but is not limited to, a lipid, a mixture of lipids, a lipid blend, or a polymer enteric coating as described in more detail below. In one non-limiting aspect, coatings in pharmaceutical compositions create a barrier to degradation and denaturation and allow more accurate levels of active enzymes to reach the treated subjects.

A pharmaceutical composition described herein, in one instance, comprises coated particles that contain (a) a core and (b) a lipid coating. In some embodiments, a coated enzyme preparation is in the form of coated particles, which coated particles comprise: (a) a core comprising digestive enzymes (e.g., protease, amylase, and lipase) present in the coated particles in an amount of from about 5% to 95% by weight and (b) a lipid coating. In one aspect, this disclosure relates to an enzyme delivery system comprising a coated enzyme preparation in the form of coated particles, which coated particles comprise: (a) a core comprising digestive enzymes (e.g., protease, amylase, and lipase) present in the coated particles in an amount of from about 50% to about 95% by weight; and (b) a lipid coating. In yet another aspect, this disclosure relates to an enzyme delivery system comprising a coated enzyme preparation having coated particles, which coated particles comprise: (a) a core comprising digestive enzymes (e.g., protease, amylase, and lipase) present in the coated particles in an amount of from about 70% to about 90% by weight; and (b) a lipid coating. In yet another aspect, this disclosure relates to an enzyme delivery system comprising a coated enzyme preparation having coated particles, which coated particles comprise: (a) a core comprising digestive enzymes (e.g., protease, amylase, and lipase) present in the coated particles an amount of from about 75% to about 85% by weight; and (b) a lipid coating. The coated particles may be non-aerosolizable.

A pharmaceutical composition described herein, in one instance, comprises coated particles that contain (a) a core and (b) a lipid coating, wherein the lipid comprises a monoglyceride, a diglyceride, a triglyceride, or a combination thereof. In some embodiments, a coated enzyme preparation is in the form of coated particles, which coated particles comprise: (a) a core comprising digestive enzymes (e.g., protease, amylase, and lipase) present in the coated particles in an amount of from about 5% to 95% by weight and (b) a lipid coating, wherein the lipid comprises a monoglyceride, a diglyceride, a triglyceride, or a combination thereof. In one aspect, this disclosure relates to an enzyme delivery system comprising a coated enzyme preparation in the form of coated particles, which coated particles comprise: (a) a core comprising digestive enzymes (e.g., protease, amylase, and lipase) present in the coated particles in an amount of from about 50% to about 95% by weight; and (b) a lipid coating, wherein the lipid comprises a monoglyceride, a diglyceride, a triglyceride, or a combination thereof. In yet another aspect, this disclosure relates to an enzyme delivery system comprising a coated enzyme preparation having coated particles, which coated particles comprise: (a) a core comprising digestive enzymes (e.g., protease, amylase, and lipase) present in the coated particles in an amount of from about 70% to about 90% by weight; and (b) a lipid coating, wherein the lipid comprises a monoglyceride, a diglyceride, a triglyceride, or a combination thereof. In yet another aspect, this disclosure relates to an enzyme delivery system comprising a coated enzyme preparation having coated particles, which coated particles comprise: (a) a core comprising digestive enzymes (e.g., protease, amylase, and lipase) present in the coated particles an amount of from about 75% to about 85% by weight; and (b) a lipid coating, wherein the lipid comprises a monoglyceride, a diglyceride, a triglyceride, or a combination thereof. The coated particles may be non-aerosolizable.

A pharmaceutical composition described herein, in one instance, comprises coated particles that contain (a) a core and (b) a coating comprising a hydrogenated soy oil. In some embodiments, a coated enzyme preparation is in the form of coated particles, which coated particles comprise: (a) a core comprising digestive enzymes (e.g., protease, amylase, and lipase) present in the coated particles in an amount of from about 5% to 95% by weight and (b) a coating comprising a hydrogenated soy oil. In one aspect, this disclosure relates to an enzyme delivery system comprising a coated enzyme preparation in the form of coated particles, which coated particles comprise: (a) a core comprising digestive enzymes (e.g., protease, amylase, and lipase) present in the coated particles in an amount of from about 50% to about 95% by weight; and (b) a coating comprising a hydrogenated soy oil. In yet another aspect, this disclosure relates to an enzyme delivery system comprising a coated enzyme preparation having coated particles, which coated particles comprise: (a) a core comprising digestive enzymes (e.g., protease, amylase, and lipase) present in the coated particles in an amount of from about 70% to about 90% by weight; and (b) a coating comprising a hydrogenated soy oil. In yet another aspect, this disclosure relates to an enzyme delivery system comprising a coated enzyme preparation having coated particles, which coated particles comprise: (a) a core comprising digestive enzymes (e.g., protease, amylase, and lipase) present in the coated particles an amount of from about 75% to about 85% by weight; and (b) a coating comprising a hydrogenated soy oil. The coated particles may be non-aerosolizable.

A pharmaceutical composition described herein, in one instance, comprises coated particles that contain (a) a core and (b) a coating comprising a mixture of lipids. In some embodiments, a coated enzyme preparation is in the form of coated particles, which coated particles comprise: (a) a core comprising digestive enzymes (e.g., protease, amylase, and lipase) present in the coated particles in an amount of from about 5% to 95% by weight and (b) a coating comprising a mixture of lipids. In one aspect, this disclosure relates to an enzyme delivery system comprising a coated enzyme preparation in the form of coated particles, which coated particles comprise: (a) a core comprising digestive enzymes (e.g., protease, amylase, and lipase) present in the coated particles in an amount of from about 50% to about 95% by weight; and (b) a coating comprising a mixture of lipids. In yet another aspect, this disclosure relates to an enzyme delivery system comprising a coated enzyme preparation having coated particles, which coated particles comprise: (a) a core comprising digestive enzymes (e.g., protease, amylase, and lipase) present in the coated particles in an amount of from about 70% to about 90% by weight; and (b) a coating comprising a mixture of lipids. In yet another aspect, this disclosure relates to an enzyme delivery system comprising a coated enzyme preparation having coated particles, which coated particles comprise: (a) a core comprising digestive enzymes (e.g., protease, amylase, and lipase) present in the coated particles an amount of from about 75% to about 85% by weight; and (b) a coating comprising a mixture of lipids. The coated particles may be non-aerosolizable.

A pharmaceutical composition described herein, in one instance, comprises coated particles that contain (a) a core and (b) a coating comprising a lipid blend. In some embodiments, a coated enzyme preparation is in the form of coated particles, which coated particles comprise: (a) a core comprising digestive enzymes (e.g., protease, amylase, and lipase) present in the coated particles in an amount of from about 5% to 95% by weight and (b) a coating comprising a lipid blend. In one aspect, this disclosure relates to an enzyme delivery system comprising a coated enzyme preparation in the form of coated particles, which coated particles comprise: (a) a core comprising digestive enzymes (e.g., protease, amylase, and lipase) present in the coated particles in an amount of from about 50% to about 95% by weight; and (b) a coating comprising a lipid blend. In yet another aspect, this disclosure relates to an enzyme delivery system comprising a coated enzyme preparation having coated particles, which coated particles comprise: (a) a core comprising digestive enzymes (e.g., protease, amylase, and lipase) present in the coated particles in an amount of from about 70% to about 90% by weight; and (b) a coating comprising a lipid blend. In yet another aspect, this disclosure relates to an enzyme delivery system comprising a coated enzyme preparation having coated particles, which coated particles comprise: (a) a core comprising digestive enzymes (e.g., protease, amylase, and lipase) present in the coated particles an amount of from about 75% to about 85% by weight; and (b) a coating comprising a lipid blend. The coated particles may be non-aerosolizable.

A pharmaceutical composition described herein, in one instance, comprises coated particles that contain (a) a core and (b) a polymer enteric coating. In some embodiments, a coated enzyme preparation is in the form of coated particles, which coated particles comprise: (a) a core comprising digestive enzymes (e.g., protease, amylase, and lipase) present in the coated particles in an amount of from about 5% to 95% by weight and (b) a polymer enteric coating. In one aspect, this disclosure relates to an enzyme delivery system comprising a coated enzyme preparation in the form of coated particles, which coated particles comprise: (a) a core comprising digestive enzymes (e.g., protease, amylase, and lipase) present in the coated particles in an amount of from about 50% to about 95% by weight; and (b) a polymer enteric coating. In yet another aspect, this disclosure relates to an enzyme delivery system comprising a coated enzyme preparation having coated particles, which coated particles comprise: (a) a core comprising digestive enzymes (e.g., protease, amylase, and lipase) present in the coated particles in an amount of from about 70% to about 90% by weight; and (b) a polymer enteric coating. In yet another aspect, this disclosure relates to an enzyme delivery system comprising a coated enzyme preparation having coated particles, which coated particles comprise: (a) a core comprising digestive enzymes (e.g., protease, amylase, and lipase) present in the coated particles an amount of from about 75% to about 85% by weight; and (b) a polymer enteric coating.

Pharmaceutical compositions (preparations) comprising uncoated or coated digestive enzymes may be manufactured using any appropriate technology including, but not limited to, polymer enteric coating, lipid encapsulation, lipid coating, wax coating, direct compression, dry granulation, wet granulation, and any combination thereof. In one embodiment, one or more digestive enzyme(s) are utilized with one or more existing, emergent, or future coating technologies. Coating technology selection is based upon one or more desired parameters including, but not limited to, desired release kinetics, duration, control of peak concentration, pharmacokinetics, and dose.

The property of physical and chemical methods may be used to combine the digestive enzymes with a coating material such as coacervation, emulsions, meltable dispersion, spray drying, pan coating, and fluidized bed granulations. In this manner, coatings and digestive enzymes can be combined to control the kinetics, time and location of enzyme release in the body. In one non-limiting instance, about 80% of the digestive enzymes are released by about 30 minutes after the coated digestive enzyme particles reach the small intestine.

As described herein, suitable digestive enzymes and optional suitable coatings may be used in the compositions and methods of this invention. The choice of suitable digestive enzymes and of suitable coatings, including choice of the type or the amounts of digestive enzymes and/or coating, are guided by the specific digestive enzyme needs of the subject, and the selected diseases to be treated.

Delivery of digestive enzymes can also be challenging due to the rapid degradation and denaturing of enzymes at ambient room temperature, as well as the enhanced degradation and denaturing that can occur with high temperature, pressure, humidity and/or exposure to light. Moisture and heat together can quickly destabilize enzymes, reducing their effectiveness, and shortening shelf life, leading to inaccurate dosing. Denaturization or destabilization of the digestive enzymes can reduce their effectiveness by reducing the dose of active enzymes to less than the amount needed for effective treatment. Alternatively, attempting to compensate for the denaturization or destabilization by increasing the dose to ensure an effective level of active enzyme, could risk an overdose or overfilling a capsule or other dosage form.

Coatings can be used to help mitigate these factors. In one embodiment, coating of a digestive enzyme preparation is used to obtain release at selected transit times or in selected locations of the gastrointestinal tract of humans. In one aspect, this relates to controlled-release enzyme preparations administered to a subject with a coronavirus infection (e.g., COVID-19). In another aspect, one or more coatings are utilized to target delivery to the small intestines.

In addition, a coating can provide controlled-release of digestive enzymes in some instances. For example, the emulsification properties of a coating in a solvent allows for controlled-release of the enzyme in the gastrointestinal system, such as the region of the GI tract where the digestive enzymes are to be utilized after administration. The coating protects the enzyme from the environment and provides emulsification in a solvent (e.g., a biological fluid) without detracting from the abrasion resistance of the coating. For example, the release of the protease from a pharmaceutical composition may occur in the proximal small intestine, and the coating has a dissolution profile between 30-90 minutes with 80% or greater release. Lower levels of release are still beneficial and may be utilized in some embodiments. The dissolution profile may also be about 30, 35, 40, 45, 50, 55, 60, 65, 70, 75, 80, 85, or 90 minutes. Dissolution profiles may be obtained using methods and conditions known to those in the art. For example, dissolution profiles can be determined at various pHs, including pHs 1, 2, 3, 4, 5, 6, 7, 8, 9 and 10.

"Encapsulate" as used herein means that the coating completely surrounds the digestive enzyme. In the manufacture of pharmaceutical compositions, encapsulation refers to a range of techniques used to enclose medicines in a relatively stable shell known as a capsule, allowing them to, for example, be taken orally or be used as suppositories.

Lipid Coatings

Lipid coating or encapsulation may reduce aerosolization of digestive enzymes, which may be caustic to a subject if inhaled. For example, lipid encapsulation reduces aerosolization and the potential for caustic burn, aspiration, and/or aspiration pneumonias in subjects to be treated and administrators of the pharmaceutical composition, thereby reducing the potential for illness in already immunocompromised patients with a coronavirus infection, thereby leading to safer administration.

"Lipids", as used herein, refers to lipids which contain at least one hydrophilic group and at least one hydrophobic group, and have a structure capable of forming a hydrophilic and hydrophobic interface. These chemical and/or physical properties, mentioned above, of a lipid permit emulsification. Examples of interfaces include, for example, micelles and bilayers. The hydrophilic group can be a polar group and can be charged or uncharged.

Digestive enzymes obtained from a pig can possess a significant odor and/or taste similar to cured or smoked pork. This taste and smell can be strong and offensive to some subjects, such as children. In one embodiment, the addition of a lipid coating significantly masks odor and taste of digestive enzymes enzyme, which allows for the tolerance of taste as the lipid coating is odorless and tasteless. The coated digestive enzyme compositions described herein may have improved taste and odor compared to non-coated digestive enzymes.

The lipid may be any lipid, lipid mixture, or blend of lipid of lipid with emulsifiers which emulsifies when exposed to a solvent and has a melting point which allows the lipid to be a solid at typical storage temperatures and/or additives. In some embodiments, the lipid consists essentially of or comprises one or more monoglycerides, diglycerides or triglycerides, or other components including, for example, emulsifiers found in hydrogenated vegetable oils. In another embodiment the lipid is a non-polar lipid. Examples of lipids include, but are not limited to, monoglycerides, diglycerides, triglycerides, fatty acids, esters of fatty acids, phospholipids, salts thereof, and combinations thereof. In one non-limiting instance, the lipid coating comprises monoglycerides, diglycerides, triglycerides, or a combination thereof. In another non-limiting instance, the lipid coating comprises monoglycerides, diglycerides, or triglycerides. In another non-limiting instance, the lipid coating comprises a combination of monoglycerides and diglycerides. In another non-limiting instance, the lipid coating comprises a combination of diglycerides and triglycerides. In another non-limiting instance, the lipid coating comprises a combination of monoglycerides, diglycerides, and triglycerides.

In another embodiment with respect to coated particles which contain a core and a coating, the enzymatic core containing a protease, a lipase, and an amylase, is coated by an inert lipid that allows for safe delivery of the enzymatic core through the oropharynx and into the stomach where it is quickly and efficiently released in the stomach and duodenum. The enzymatic core thereby destroys the coronavirus (e.g., SARS-CoV-2) virus early in the GI tract before major sites of ACE2 expression are reached in the late portion of the gut. For nasal, rectal, parenteral, percutaneous endoscopic gastrostomy (PEG), esophagogastroduodenoscopy (EGD), gastrostomy (G-tube) insertion, intravenous, etc., types administration, digestive enzymes are absorbed into the body and made available to cleave spike proteins on circulating coronaviruses.

The lipid can be a vegetable-derived lipid or an animal-derived lipid. As used herein, animal lipids and/or vegetable lipids include, but are not limited to, fats and oils originating from plant sources, animal sources and/or tissues, and/or synthetically produced based on the structures of fats and oils originating from plant or animal sources. Lipid material may be refined, extracted or purified by known chemical or mechanical processes. Certain fatty acids present in lipids, termed essential fatty acids, must be present in the mammalian diet. The lipid may, in some embodiments, comprise a Type I US Pharmacopeia (U.S.P.) National Formulary vegetable oil. The lipid can be derived from animal origins or vegetable origins, such as, for example, palm kernel oil, soybean oil, cottonseed oil, canola oil, or poultry fat, including hydrogenated type I vegetable oils. In some embodiments, the lipid is hydrogenated. The lipid can also be saturated or partially saturated.

The rate of release of the digestive enzyme from a pharmaceutical composition upon exposure to a solvent (e.g., stomach acid) may be controlled by coating digestive enzymes with a lipid to form coated particles that comprise a core (which contains the digestive enzymes), and a coating which contains the lipid. Alternatively, the rate of release of the digestive enzyme from a pharmaceutical composition upon exposure to a solvent (e.g., stomach acid) may be controlled by (i) blending a lipid with an amount of one or more additives to obtain a lipid blend; and (ii) coating digestive enzymes with the lipid blend to form coated particles that comprise a core (which contains the digestive enzymes), and a coating which contains the lipid blend. In one instance, the coating comprises a lipid blend where the lipid and additive are not the same, and the rate of release of the digestive enzymes from the coated particles upon exposure to a solvent is decreased as the amount of additive is increased. In the alternative, the rate of release of the digestive enzymes from the coated particles upon exposure to a solvent is increased as the amount of additive is increased.

The lipid coating surprisingly does not appear to be reduced or destroyed by hydrochloric acid (HCl) present in the stomach, thereby protecting the digestive enzymes from degradation following administration until the digestive enzymes reach their target region in the proximal GI tract. Further, a lipid coating may reduce the exposure of the digestive enzymes to attack by water, thereby reducing hydrolysis, and further protecting the digestive enzymes from degradation. In addition, the inventors have found that a coating containing only lipid can be used to coat digestive enzymes that only contain one or more lipase(s).

Because, in some embodiments, a lipid coating does not require the digestive enzymes to be treated with solvents, extenders and excipients to facilitate flow or improve stability, a lipid coating described herein includes a "clean" preparation of GRAS (generally regarded as safe) substances to be administered. The reduction in the use of solvents, extenders, excipients and other additives permitted by the methods described herein reduces the exposure of the individuals taking the digestive enzymes to potential allergens, thereby producing a hypoallergenic enzyme preparation that further enhances its potential uses in the treatment of individuals who might otherwise develop an allergic response to treatment. Administration of the coated digestive enzyme compositions described herein can thus reduce exposure to potentially toxic substances and will also reduce the possibility of allergy formation. Accordingly, in some embodiments, the pharmaceutical composition is hypoallergenic.

The lipid may be, in some instances, a "food grade lipid". Examples of food grade lipids include, but are not limited to, a sorbitan monostearates, sorbitan tristearates, and calcium stearoyl lactylates. Other examples of food grade fatty acid esters which are lipids include acetic acid esters of mono- and diglycerides, citric acid esters of mono- and di-glycerides, lactic acid esters of mono- and di-glycerides, polyglycerol esters of fatty acids, propylene glycol esters of fatty acids, and diacetyl tartaric acid esters of mono- and diglycerides.

The lipid may also be, in some instances, a "pharmaceutical grade lipid". Pharmaceutical grade lipids include, but are not limited to, highly purified lipid from which all protein antigens have been removed. Such lipids are beneficial in that they do not induce allergic responses and do not include cis or trans fatty acids. One non-limiting example of a pharmaceutical grade lipid comprises a soybean oil that is fully hydrogenated. One non-limiting example of a pharmaceutical grade lipid consists of a soybean oil that is fully hydrogenated.

In some instances, a lipid coating will produce non-agglomerating, non-aerosolizing coated digestive enzyme particles.

The inclusion of one or more additives with a lipid can be used to control emulsification or dissolution of the coating and release of the digestive enzymes. For example, a triglyceride, can be blended with a monoglycerides to control emulsification or dissolution of the coating and thus control (e.g., decrease) the rate of release of the digestive enzymes from the coated particles. As a further example, a diglyceride and a triglyceride can be blended with a monoglyceride to control the rate of release of the digestive enzymes. Hydrogenated vegetable oils may contain emulsifying agents, such as soy lecithin or other components.

Properties including mechanical strength, melting point, and hydrophobicity can be considered when choosing a suitable lipid coating for the digestive enzymes. Lipids having lower melting points or more polar, hydrophilic properties are generally less suitable for the coating because they may result in a product that would cake under accelerated storage stability conditions. Coated digestive enzyme particles made using, for example, hydrogenated soy oil (e.g., partially or fully hydrogenated), which demonstrated good pouring and no caking.

In some embodiments a coated digestive enzyme preparation comprises coated particles, where the coated particles comprise (a) a core containing digestive enzymes; and (b) a coating comprising one or more lipids; where the digestive enzymes are present in the coated particles in an amount of from about 5% to about 95% by weight, including, but not limited to, about 5%, 10%, 15%, 20%, 25%, 30%, 35%, 40%, 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, and 95% by weight, along with all values/integers in-between. In some embodiments a coated digestive enzyme preparation comprises coated particles, where the coated particles comprise (a) a core containing digestive enzymes; and (b) a coating comprising a lipid blend; where the digestive enzymes are present in the coated particles in an amount of from about 5% to about 95% by weight, including, but not limited to, about 5%, 10%, 15%, 20%, 25%, 30%, 35%, 40%, 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, and 95% by weight, along with all values/integers in-between. In one embodiment, the coating continuously coats the core. In another embodiment, the lipid or the lipid blend releases the digestive enzymes upon exposure to physiological conditions.

In some embodiments, a coated enzyme preparation having particles which comprise: (a) a core comprising digestive enzymes present in an amount of from about 5% to 95% by weight of the particles, including 5%, 10%, 15%, 20%, 25%, 30%, 35%, 40%, 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 90%, and 95% by weight along with all values/integers in-between; and (b) a generally uniform coating to provide for controlled-release of the digestive enzymes, the coating comprising a crystallizable lipid. Some coated digestive enzyme preparations which comprise a coating of a crystallizable lipid and a digestive enzyme core have favorable release and activity profiles and permit site time specific and/or location specific targeted release along the GI tract.

The methods of this disclosure can be used to produce coated digestive enzyme preparations comprising digestive enzymes coated with a crystallizable lipid alone, or with a lipid blend to achieve a controlled rate of enzyme release, with increased release of the digestive enzyme upon exposure of the coated preparation to a suitable solvent. Coated digestive enzyme preparations having a coating comprising one or more monoglycerides exhibit increased release of the digestive enzyme upon exposure of the coated composite to a solvent, such as water, while protecting against release in 0.1 N HCl.

In some embodiments, the compositions according to this disclosure produce enzyme preparations, including coated enzyme preparations, characterized, for example, by controlled rates of release, reduction in aerosolization and safer administration, ability to be administered by a sprinkle/sachet delivery method, improved flow characteristics, enhanced shelf life and storage capacity, and other properties described herein. In other aspects, the coated enzyme preparation has improved pour properties which facilitate manufacturing and packaging processes, for example packaging in pouches and sachet.

In some aspects, coated digestive enzyme preparations are prepared to obtain specific delivery times or specific regions within the GI tract. In some embodiments, the crystallizable lipid composition comprises, consists essentially of, or consists of, a hydrogenated soybean oil, but may be any suitable crystallizable lipid or lipid blend. Lipid coating or encapsulation reduces aerosolization of the digestive enzymes that may be caustic to a subject if inhaled through the lungs or the nose. In another embodiment, delivery of digestive enzymes with improved safety of administration can be achieved by reducing the amount of aerosolization of the enzyme. The lipid coating or encapsulation reduces aerosolization and the potential for caustic burn, aspiration, and/or aspiration pneumonias in subjects and administrators of the enzyme preparation, thereby reducing the potential for illness in already compromised patients such as those with a coronavirus infection (e.g., COVID-19), thereby leading to safer administration.

In one instance, the method relates to preparation of coated digestive enzyme particles that have enhanced flow properties and which are useful in the treatment of subjects with a coronavirus infection, the method comprising: a) blending a lipid with one or more additives to obtain a lipid blend; and b) coating screened digestive enzyme with the lipid blend to form the coated digestive enzyme particles containing a core which contains the digestive enzymes and a coating which contains the lipid blend.

Waxes

Waxes may be utilized for coating digestive enzymes. In one embodiment an unreactive wax is utilized. The wax can be paraffin wax; a petroleum wax; a mineral wax such as ozokerite, ceresin, or montan wax; a vegetable wax such as, for example, carnauba wax, bayberry wax or flax wax; an animal wax such as, for example, spermaceti; or an insect wax such as beeswax. Additionally, the wax material can be an ester of a fatty acid having 12 to 31 carbon atoms and a fatty alcohol having 12 to 31 carbon atoms, the ester having from a carbon atom content of from 24 to 62, or a mixture thereof. Examples of waxes include, but are not limited to, myricyl palmitate, cetyl palmitate, myricyl cerotate, cetyl myristate, ceryl palmitate, ceryl certate, myricyl melissate, stearyl palmitate, stearyl myristate, and lauryl laurate. Digestive enzyme pharmaceutical compositions made using, for example, hydrogenated castor wax or carnauba wax may demonstrate good pouring and no caking.

Polymer Enteric Coatings

In another aspect, digestive enzymes may be coated with a polymeric coating. The same principles of controlled dissolution still apply but access to a variety of materials expands options for control of both the location and rate of release. In one embodiment, one or more hydrophobic or hydrophilic polymers are used separately or in combination. Polymer enteric coatings for use in a composition described herein include, but are not limited to, cellulose acetate phthalate (CAP), cellulose acetate trimellitate (CAT), hydroxyl propyl methyl cellulose phthalate (HPMCP), hydroxyl propyl methyl cellulose acetate succinate (HPMCAS), ethyl cellulose (EC), polyvinyl acetate phthalate (PVAP), a methacrylic acid copolymer, a shellac (esters of aleurtic acid), Zein, ethylcellulose, gelatins, polyvinyl alcohol, styrene maleic anhydride, or a combination thereof. It should be noted that certain coatings which utilize cellulose (e.g., HPMC/HPEC, EUDRAGIT®, etc.) may be hydrophilic and, as such, absorb moisture which degrades the activity of digestive enzymes (e.g., pancreatin, etc.) utilized in various embodiments described herein.

In some embodiments, a pharmaceutical dosage form comprises a population of extended-release beads, wherein said extended-release beads comprise: an active-containing core particle comprising digestive enzymes as the active agent; and an extended-release coating comprising a water-insoluble polymer membrane surrounding said core, wherein said water-insoluble polymer membrane comprises a polymer selected from the group consisting of ethers of cellulose, esters of cellulose, cellulose acetate, ethyl cellulose, polyvinyl acetate, neutral copolymers based on ethyl acrylate and methyl methacrylate, copolymers of acrylic and methacrylic acid esters with quaternary ammonium groups, pH-insensitive ammonio methacrylic acid copolymers, and mixtures thereof; wherein the total amount of digestive enzymes in the pharmaceutical dosage form contain from about 15,000 U.S.P. Units protease to about 1.5 million U.S.P. Units protease per dose and where the ratio of protease to lipase is such that the amount of lipase is never more than 0.188 times the amount of protease and where the ratio of protease activity to amylase activity is between 1:0.1 and 1:10.

In some embodiments, an extended-release coating further comprises a water-soluble polymer selected from the group consisting of methylcellulose, hydroxypropylcellulose, hydroxypropyl methylcellulose, polyethylene glycol, polyvinylpyrrolidone, and mixtures thereof.

Cellulose Acetate Phthalate (CAP)

Cellulose acetate phthalate, also known as cellacefate is a synthetic enteric coating polymer. Because the degree of substitution can lead to changes in CAP properties, specifications for CAP composition have been established to ensure more uniform performance from batch to batch. According to United State Pharmacopoeia (U.S.P.) specifications, CAP should contain from about 21.5% to about 26.0% w/w acetyl content and from about 30.0% to about 36.0% w/w phthalyl groups on the cellulose backbone as calculated on an anhydrous basis. CAP exhibits rapid dissolution at a pH>6 and is relatively permeable to moisture and gastric juices. Due to its high moisture permeability, CAP is susceptible to hydrolytic decomposition. Phthalic and acetic acid molecules may hydrolyze during storage and significantly compromise the degree of enteric protection that the film coating provides. The addition of a plasticizing agent can improve the water-resistance of CAP films. CAP is compatible with most water-soluble and insoluble plasticizers with diethyl phthalate (DEP), tributyl citrate (TBC), triethyl citrate (TEC), tributyrin, and triacetin being the most commonly used, typically, in the range of from about 25% to about 35% by weight of dry polymer. CAP is commercially available as a white powder from, for example, Eastman Chemical Co. A 30% solids latex dispersion version of CAP (AQUACOAT® CPD) is available for aqueous enteric coating of tablets, beads, and both hard and soft gelatin capsules.

Cellulose Acetate Trimellitate (CAT)

Chemically cellulose acetate trimellitate (CAT) bears a strong resemblance to CAP. It is formed by the same synthesis process as CAP with trimellitic anhydride as the substituent group in place of phthalic anhydride. Typical values for timellityl and acetyl substitution are 29.0% and 22.4%, respectively. Trimellitic anhydride contains an additional free carboxyl group over that of phthalic anhydride, and hence CAT contains a greater concentration of acidic groups for a given degree of substitution than CAP rendering it more soluble in aqueous media. Also, the pKa of CAT is between 4.1 and 4.3 which is slightly lower than CAP. With a relatively low pKa value and greater functional group concentration, CAT is the most soluble enteric cellulose derivative with the onset of dissolution occurring at pH 4.7-5.0. This useful property makes CAT ideal for targeted drug release to the proximal regions of the small intestine. CAT is commercially available as a white powder from Eastman Chemical Co. To obtain the best enteric coating results from aqueous processing, ammoniacal solutions of CAT in water are recommended. Plasticizer considerations for CAT are identical to that of CAP.

Hydroxyl Propyl Methyl Cellulose Phthalate (HPMCP)

HPMCP is a white to slightly off-white, free-flowing flakes or granular powder with a slightly acidic odor and a barely detectable taste. It is a derivative of hydroxypropyl methylcellulose that is produced by the transesterification of hydroxypropyl methylcellulose with phthalic acid and is a cellulose derivative for enteric coating. HPMCP has been admitted in the European and Japanese pharmacopoeias and included in the USP/NF under the name hypromellose phthalate. Depending on the degree of phthalyl substitution, HPMCP is soluble in aqueous media in a pH range of from about 5.0 to about 5.5. HPMCP is characteristically insoluble in gastric fluids but swellable and rapidly soluble in the upper intestine. It may be plasticized with diethylphthalate, acetylated monoglyceride or triacetin. Mechanically, HPMCP is a more flexible polymer and on a weight basis and will not require as much plasticizer as CAP or CAT. Solvent mixtures can be effectively prepared for commercial spray-drying by using proper spray-drying optimization.

Hydroxyl Propyl Methyl Cellulose Acetate Succinate (HPMCAS)

HPMCAS, also known as hypromellose acetate succinate, is a white to off-white powder or granules derived from HPMC by the esterification of free hydroxyl groups on the polymer backbone with acetic anhydride and succinic anhydride. It is commercially available in three grades (L, M & H), which correspond to pH-dependent release profiles of low pH (5.0), medium (5.5), and high (6.5) pH. HPMCAS is soluble in neutral pH according to ionization of free carboxyl groups on the polymer backbone.

Polyvinyl Acetate Phthalate (PVAP)

Polyvinyl acetate phthalate is a free-flowing white to off-white powder with a slight odor of acetic acid. The onset of aqueous dissolution of PVAP begins at a pH of about 5.0, allowing for enteric release as well as targeted drug release in the proximal small intestine. Although structurally similar to CAP (containing the dicarboxylic phthalic acid in a partially esterified form), PVAP is relatively more stable to hydrolysis than CAP due to its lower moisture permeability. It is compatible with plasticizers such as, for example, glyceryl triacetate, Triethyl citrate (TEC), acetyl triethylcitrate, Diethyl phthalate (DEP), and polyethylene glycol (PEG) 400. PVAP (SURETERIC®) is commercially available from COLORCON® as a complete preformulated coating system consisting of a powder blend of PVAP, plasticizers, and other functional ingredients intended for reconstitution in water for rapid coating dispersion production.

Methacrylic Acid Copolymers

Methacrylic acid copolymers (EUDRAGIT®) are widely used for enteric coating applications as they contain free carboxylic acid groups that are ionized whenever the pH of the environment exceeds 5.5. Several different types of EUDRAGIT® polymers with enteric release capabilities are commercially available in a wide range of different physical forms (aqueous dispersion, organic solution, granules and powders): Methacrylic acid methylmethacrylate copolymers (EUDRAGIT® L and S), and methacrylic acid ethyl acrylate copolymer (EUDRAGIT® L30D) are coating polymers for enteric formulations which allow targeting of specific areas of the intestine.

Shellac

Edible Shellac may be employed as a glazing agent on a pharmaceutical composition that comprises a pill. Because of its acidic properties (resisting stomach acids), shellac-coated pills may be used for a timed enteric or colonic release. Shellac provides an excellent barrier against water vapor penetration.

Zein

Zein is a class of prolamine protein found in maize (corn) that is usually manufactured as a powder from corn gluten meal. Pure zein is clear, odorless, tasteless, hard, water-insoluble, and edible. Zein's properties make it usable in pharmaceutical compositions and may be used as a coating the digestive enzymes described herein. It is classified as Generally Recognized as Safe (GRAS) by the U.S. Food and Drug Administration. For use as a pharmaceutical coating, zein is all natural and requires less testing per the U.S.P. monographs.

Ethylcellulose

Ethyl cellulose (ethylcellulose) is a derivative of cellulose in which some of the hydroxyl groups on the repeating glucose units are converted into ethyl ether groups and which may be used as a thin-film coating material for coating a pharmaceutical composition described herein. Food grade ethyl cellulose is a non-toxic film and thickener which is not water soluble.

Optional Components of Coatings

Coatings are often utilized with a variety of excipients including, but not limited to, one or more plasticizers, colorants (e.g., dyes), solvents, flavors (e.g., sweeteners), surfactants, disintegrants, lubricants, preservatives, anti-microbials, or a combination thereof.

Plasticizers are relatively low molecular weight materials which may be added to film-coating formulations to modify the physical properties of polymers. Some film-coating polymers are amorphous, and as such, exhibit a reasonably well-defined glass transition temperature, Tg (a fundamental characteristic of polymers that has an effect on polymer properties that can also influence film formation, especially when using aqueous polymer dispersions). Common effects of plasticizers on the properties of thin film coatings include: reducing tensile strength, reducing elastic modulus, altering film adhesion (including increasing under optimal use conditions), increasing the viscosity of coating liquid (effect is greater as plasticizer molecular weight is increased), altering film permeability (depends of physiochemical; properties of plasticizer), and/or reducing the glass transition temperature Tg of film (magnitude of effect influenced by compatibility with polymer). Non-limiting examples of plasticizers commonly used in film coating processes include: a. Polyols, such as glycerol (glycerin), polyethylene glycols (PEG 200-6000 grades) and propylene glycol; b. Organic esters, such as Diethyl phthalate (DEP), Dibutyl phthalate (DBP), Dibutyl sebacate (DBS), Triethyl citrate (TEC), Acetyltriethyl citrate (ATEC), Acetyltributyl citrate (ATBC), Tributyl citrate (TBC), and Triacetin (glyceryl triacetate; TA); c. Oils/glycerides, such as fractionated coconut oil, castor oil, and distilled acetylated monoglycerides (AMG); or d. a combination thereof. In some embodiments, an extended-release coating further comprises a plasticizer selected from the group consisting of triacetin, tributyl citrate, triethyl citrate, acetyl tri-n-butyl citrate, diethyl phthalate, dibutyl sebacate, polyethylene glycol, polypropylene glycol, castor oil, acetylated mono- and diglycerides, and mixtures thereof.

Colorants are included in many film-coating formulations to: a. improve product appearance and/or enable product identification; b. modify the gas permeability of a film; c. decrease the risk of counterfeiting the product; d. protect the active ingredient against light by optimizing the opacifying properties of pigments; or e. a combination thereof.

Either water-soluble colorants (known as dyes) or water-insoluble colorants (known as pigments) may be utilized. Water-insoluble colorants may be utilized in film-coating formulations based on exhibition of: a. better light stability; b. better opacity and covering power; c. optimizing moisture barrier properties of the applied film coatings; and/or d. do not suffer from the disadvantageous phenomenon of mottling (caused by solute migration) that can be observed with water-soluble colorants. The effects of colorants on thin films include, but again are not limited to: reducing tensile strength (effect may be minimized by effective pigment dispersion in film); increasing the elastic modulus; slightly increasing the viscosity of the coating liquid, reducing film permeability (unless critical pigment volume concentration CPCV is exceeded); and increasing hiding power (effect is dependent upon refractive index and light absorption characteristics of pigment). Colorants typically utilized in thin film coatings include, but are not limited to Water-soluble dyes (e.g., FD&C Yellow #5, FD&C Blue #2, etc.); FD&C Lakes such as FD&C Yellow #5 Lake, FD&C Blue #2 Lake, etc.); D&C Lakes (e.g., D&C Yellow #10 Lake, D&C Red #30 lake, etc.), Inorganic Pigments (e.g., Titanium Dioxide, Iron Oxides, etc.); and Natural Colorants (e.g., Riboflavin, Beta-carotene, Carmine lake, etc.), or a combination thereof.

Solvents may be used to dissolve or disperse coating materials and convey them to the surface of the tablet core. Common solvents used in film coating include, but are not limited to Water, Ketones such as Acetone; Alcohols such as Methanol, Ethanol, and Isopropanol; Esters such as Ethyl acetate and Ethyl lactate; and Chlorinated Hydrocarbons such as Methylene Chloride, 1:1:1: Trichloroethane, and Chloroform.

While polymers, plasticizers, colorants, and solvents constitute the major ingredients in film-coating formulations, other materials might be used occasionally in low concentrations for specific formulations. Flavors and sweeteners may be added to mask unpleasant odor of the digestive enzymes or to make them more, palatable. Surfactants or dissolution enhancers such as polyoxyethylene sorbitan derivatives may be added to i. emulsify water-insoluble plasticizers; ii. improve substrate wettability and enhance spreadability of the film during application; iii. stabilize suspensions; or iv. a combination thereof.

Additionally, some film coatings may also contain preservative/antimicrobials (e.g., carbamates, alkylisothiazolinone, benzothiazoles, etc.), adhesion enhancers (such as polydextrose, maltodextrin, and lactose), antifoaming agents (e.g., dimethylpolysiloxane), antioxidants (e.g., oximes, phenols, etc.), pore-forming agents (e.g., sucrose or sodium chloride with ethylcellulose-coated salicylic acid tablets) and waxes. In rare instances, the film coat itself may contain active drug substance. When used, all ingredients used in film-coating formulations will comply with relevant regulatory and pharmacopoeial requirements.

Suitable disintegrants include, for example, sodium starch glycolate, other starches such as pregelatinized starch, and celluloses. Suitable lubricants may be provided such as, for example, magnesium stearate, calcium stearate, talc, stearic acid, etc.

Other Coatings

The embodiments described herein are not limited to the aforementioned coatings. By way of example, other hydrophobic polymers that can be used as coatings include, but are not limited to, various forms of acrylics, amides/imides, olefins, styrenes, vinyl acetates/vinyl esters, or a combination thereof. Any existing, emergent, or yet to be developed coating which meets the appropriate safety and applicable regulatory requirements while delivering the active ingredients to the appropriate place in the gastrointestinal tract may be utilized.

API Carrier Suspensions

Utilization of nano-crystal API carrier suspensions utilizing compounds such as Hydroxypropyl cellulose (HPC), hydroxypropyl methylcellulose (HPMC), lecithin, and docusate sodium to create nanoparticles and other dispersions for improved solubility and interaction with target molecules. Nanocrystals are small particles of the API combined with an excipient "carrier" for dispersion. Typically, particles are from about 0.1 nm to about 1 nm (e.g., about 0.5 nm) in size. These are created using dissolution of the fine API particles in a carrier and subsequent utilization of precipitation and emulsification or the use of high-pressure homogenization, sonication and micro-fluidization.

Carriers used for dispersion include, but are not limited to, HPMC, HPC, and decussate sodium. Docusate sodium (bis(2-ethylhexyl) sulfosuccinate), also commonly called dioctyl sulfosuccinate (DOSS) is a long chain carbon polymer with the formula $C_{20}H_{37}NaO_7S$. Lecithin refers to a group of animal-derived fat like substances. Chemically, they are composed of mixtures of glycerophospholipids, phosphatidylcholine, phosphatidylethanolamine, phosphatidylinositol, and phosphatidylserine.

Matrices

A pharmaceutical composition may be prepared in which an excipient provides a matrix to capture and protect the digestive enzymes before delivery. Pharmaceutical compositions may be prepared whereby the subject who takes the composition has a reduction in the number of capsules/tablets per dosage; e.g., the preparation is stabilized and may contain a therapeutically effective amount of a protease, an amylase, and/or a lipase. Compositions may include, for example, a stabilizing matrix consisting essentially of a solidified microcrystalline cellulose which captures and protects therapeutically effective amounts of digestive enzyme particles within the stabilizing matrix. This can be done, for example, through the use of what is known in the art as PROSOLV® technology.

PROSOLV® is a combination of excipients which allow for optimized flow, compaction and product uniformity. This technology allows for uniformity in this combination, as well as manufacturing a very small tablet which would be amenable for children. With PROSOLV® technology, the ingredients are not just blended, but are co-processed, which assures that equal particles are uniformly distributed, and these results are easily reproducible. This allows for stability and superb product quality.

Whether utilizing the PROSOLV® method or other methodology, the one or more digestive enzyme(s) will be formulated and manufactured such that the particles will be uniformly distributed and there will be no overage with respect to the amount of enzyme found in the preparation. Said new drug formulation can be found in, but is not limited to, formulations which include digestive enzymes with and without the utilization of the PROSOLV® technology.

Digestive enzymes may be combined with one of the patented PROSOLV® technologies, e.g.: PROSOLV® SMCC 50 or PROSOLV® SMCC 90, or other PROSOLV® technologies. When employing the PROSOLV® method, the silicified microcrystalline cellulose (SMCC) used in a pharmaceutical composition described herein may be any commercially available combination of microcrystalline cellulose granulated with colloidal silicon dioxide. The SMCC generally will be as described in Sherwood et al., Pharm. Tech., October 1998, 78-88 and U.S. Pat. No. 5,585,115, which are incorporated herein by reference with respect to PROSOLV® technology. SMCC can be obtained commercially from Edward Mendell Company, Inc., a subsidiary of Penwest Ltd., under the name PROSOLV® SMCC. There are different grades of SMCC available, with particle size being the differentiating property among the grades. For example, PROSOLV® SMCC 90 has a median particle size, by sieve analysis, in the region of 90 micrometers. PROSOLV® SMCC 50 has a median particle size, by sieve analysis, in the region of from about 40 to about 50 micrometers.

Pharmaceutical Compositions

The compositions described herein can be administered either alone or in combination with one or more of a conventional pharmaceutical carrier, buffer, stabilizer, surfactant, filler, binder, sweetener, or the like. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject compounds from the administration site to a portion of the body. Each carrier is acceptable in the sense of being compatible with the other ingredients of the formulation and not injurious to a subject to whom it is administered. Nor should an acceptable carrier alter the specific activity of the subject compounds.

Acceptable carriers are physiologically acceptable to the administered patient and retain the therapeutic properties of the compounds with/in which it is administered. Acceptable carriers and their formulations are and generally described in, for example, Remington' pharmaceutical Sciences (18th Edition, ed. A. Gennaro, Mack Publishing Co., Easton, Pa. 1990). Two exemplary carriers are water and physiological saline.

Other acceptable carriers, excipients, or stabilizers are those that are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; and/or non-ionic surfactants such as TWEEN®, PLURONICS®, or polyethylene glycol (PEG).

Such other ingredients and the amounts to be used are within the knowledge of one in the art and are known in the pharmaceutical arts.

Optionally, a digestive enzyme composition is prepared without the use of extenders colorants, dyes, flow enhancers and other additives to reduce the potential for allergens and other sensitivity reactions.

Compositions comprising an effective amount of the digestive enzymes may be formulated for administration to a subject, or may be administered to a subject, via any conventional route including but not limited to oral, parenteral, intramuscular, intravenous, transmucosal, transdermal, nasal, rectal (e.g., via suppository), percutaneous endoscopic gastrostomy (PEG), esophagogastroduodenoscopy (EGD), gastrostomy (G-tube) insertion, or other method. Oral administration can be in the form of solution, suspension, slurry, pellet, capsule, caplet, beadlet, sprinkle, tablet, softgel, or other. Alternatively, the pharmaceutical compositions can also be prepared for parenteral use. Such compositions typically take the form of sterile isotonic solutions of the digestive enzymes according to standard pharmaceutical practice.

The term "unit dose" when used in reference to a pharmaceutical composition refers to physically discrete units suitable as unitary dosage for humans, each unit containing a predetermined quantity of active material calculated to produce the desired therapeutic effect of reduction of one or more symptoms associated with COVID-19 or reducing infectivity of a coronavirus (e.g., in the mucosa or gut) in a prophylactic manner.

Determining a dosage regimen of the compound is well within the purview of those in the art. By way of example, the dose levels may range from about 100 milligrams to about 10 grams as determined by weight of a subject. Further activity of the digestive enzymes may range from 100 units of activity to 1,500,000 units of activity per dose for amylases, lipases and proteases, respectively.

Different dosage forms have different benefits. Tablets and capsules are the most common dosage forms for oral administration due to ease of manufacture, packaging and administration. Different forms of tablets have been primarily devised to meet the needs of select populations while maintaining the integrity of the active pharmaceutical ingredient. Some populations, notably infants and young children, cannot swallow tablets or capsules, or find it difficult to do so. In these instances, a tablet that dissolves under the tongue, in the mouth, or in a specified liquid, or one that could be harmlessly chewed would be beneficial. Tablets may also be micro-coated and placed in a capsule for administration. A tablet is a mixture of active substances and excipients, usually in powder form, pressed or compacted into a solid. The excipients include binders, glidants (flow aids) and lubricants to ensure efficient tableting; disintegrants to ensure that the tablet breaks up in the digestive tract; sweeteners or flavors to mask the taste of bad-tasting active ingredients; and pigments to make uncoated tablets visually attractive. A coating (sugar, enteric or film) may be applied to hide the taste of the tablet's components, to make the tablet smoother and easier to swallow, and/or to make it more resistant to the environment, extending its shelf life. Tablets, in some instances, may be buffered (by potassium metaphosphate, potassium phosphate, monobasic sodium acetate, etc.) to combat change in pH.

Tablets may be delayed-release, sustained-release, extended-release, controlled-delivery, long-acting, orally-disintegrating or melts, among others, often denoting the pharmacokinetic profile of the active agent. A capsule-shaped tablet is a caplet. Some tablets may be taken sublingually or allowed to dissolve in the mouth. The principle behind sublingual administration is simple. When a chemical comes in contact with the mucous membrane beneath the tongue, or buccal mucosa, it diffuses through it. Because the connective tissue beneath the epithelium contains a profusion of capillaries, the substance then diffuses into them and enters the venous circulation. Troches are medicated lozenges designed to dissolve in the mouth. Soluble tablets dissolve on contact with the tongue. A dose of a composition described herein may be formulated for oral administered in an amount of, for example, about ½ tablet, about 1 tablet, about 1.5 tablets, about 2 tablets, about 2.5 tablets, about 3 tablets, about 3.5 tablets, or about 4 tablets.

In one non-limiting embodiment, a direct compression method may be used for the manufacture of a pharmaceutical tablet preparation including the steps of: (a) forming an active blend by blending an intimate admixture of silicified microcrystalline cellulose and a therapeutic agent comprising one or more digestive enzyme(s); (b) forming a color blend by blending an intimate admixture of one or more pharmaceutically acceptable dyes and silicified microcrystalline cellulose, if color is necessary; (c) combining the active blend, the color blend, and a disintegrant into a pre-blend; (d) adding a lubricant to the pre-blend to form a final blend; and (e) compressing the final blend to form a pharmaceutical tablet preparation or a mixture of time released microtabs or a time-released tablet.

Capsules that could be opened and their contents sprinkled over a small amount of food or in a liquid would also be beneficial. Any improvement that eases the administration of a necessary medication or lessens the antagonism associated with said administration, without compromising the effectiveness of the active pharmaceutical ingredient, is worthwhile.

In the manufacture of pharmaceuticals, encapsulation refers to a range of techniques used to enclose medicines in a relatively stable shell known as a capsule, allowing them to, for example, be taken orally or be used as suppositories. The two main types of capsules are hard-shelled capsules, which are normally used for dry, powdered ingredients, and soft-shelled capsules, primarily used for oils and for active ingredients that are dissolved or suspended in oil. Both of these classes of capsule are made both from gelatin and from plant-based gelling substances like carrageenans and modified forms of starch and cellulose, and the latter form is usually seamless. Capsules are made in two parts by dipping metal rods in molten gelatin solution. The capsules are supplied as closed units to the pharmaceutical manufacturer. Before use, the two halves are separated, the capsule is filled with powder (either by placing a compressed slug of powder into one half of the capsule, or by filling one half of the capsule with loose powder) and the other half of the capsule is pressed on. The advantage of inserting a slug of compressed powder is that control of weight variation is better, but the machinery involved is more complex.

Sprinkle capsules are a dosage form consisting of small beads or granules of an active drug contained in a capsule that can be readily administered by simply opening up the capsule and distributing the contents over something to be swallowed.

In one embodiment, a coated digestive enzyme preparation or an uncoated digestive enzyme preparation is housed in a sachet which allows for particular types of administration including, but not limited to, administration in food, drink, or direct administration into the oral cavity or directly into the GI system through a NG-tube, G-tube or other GI entrances. The use of a sachet delivery of enzymes has heretofore not been utilized in the enzyme preparations presently marketed. In one embodiment, the sachet represents a single unit dosage or multiple doses for a day. The sachet of a trilaminar pouch allows the enzyme or enzyme/ lipid powder to remain stable and allows for ease of administration.

In addition, the encapsulation also provides controlled-release of the digestive enzyme. In one embodiment, the emulsification properties of the coating in a solvent allows for controlled-release of the enzyme in the gastrointestinal (GI) system, preferably the region of the GI tract where the digestive enzymes are to be utilized.

Other types of solid dosage forms such as thin strips, lollipops or gum bring a novel concept to the administration of medications. Aside from the obvious ease of administration from the viewpoint of the caregiver, there may be an added benefit. The administration of medication is oftentimes a private issue and the ability of a caregiver to provide a dose of medication in a seemingly matter-of-fact form may preserve that perception and instill in the user a mindset that views the administration as pleasant rather than monotonous or negative.

Liquid dosage forms also provide benefits of administration to infants and young children or anyone with compromised swallowing capability. Syrups, solutions and suspensions are easily swallowed. Unpleasant tastes can be masked by flavoring. An oral spray allows for the quick administration of a pre-measured dose of medication and supplies multiple metered doses in one handy device. With no need to aid swallowing (such as a glass of water, etc.) and the convenience of not having to rifle through a bottle of tablets, administration is simplified. A dose of a pharmaceutical composition described herein may be formulated for oral administered in an amount of, for example, about 3 teaspoons, about 2.75 teaspoons, about 2.5 teaspoons, about 2.25 teaspoons, about 2 teaspoons, about 1.75 teaspoons, about 1.5 teaspoons, about 1.25 teaspoons, about 1 teaspoon, about ½ teaspoon, about ¼ teaspoon, or about ⅛ teaspoon.

A slurry may be made when a dissolvable tablet containing a gelling agent is added to a liquid.

A suspension is a heterogeneous fluid containing solid particles that are sufficiently large for sedimentation. Usually they must be larger than 1 micrometer. The internal phase (solid) is dispersed throughout the external phase (fluid) through mechanical agitation, with the use of certain excipients or suspending agents. Unlike colloids, suspensions will eventually settle. An example of a suspension would be sand in water. The suspended particles are visible under a microscope and will settle over time if left undisturbed. This distinguishes a suspension from a colloid in which the suspended particles are smaller and do not settle. Colloids and suspensions are different from a solution, in which the dissolved substance (solute) does not exist as a solid and solvent and solute are homogeneously mixed. Oftentimes, powders of active ingredients may be packaged such that the addition of a diluent dissolves the powder and holds it in a liquid suspension.

When used as a pharmaceutical preparation, elixirs contain an active ingredient that is dissolved in a solution that contains some percentage (usually 40-60%) of ethyl alcohol and is designed to be taken orally.

Syrups are oftentimes employed as a base for medicinal purposes and consist of a concentrated or saturated solution of refined sugar in distilled water.

A suspension of liquid droplets or fine solid particles in a gas is called an aerosol. This can take the form of an oral spray, an oral rinse, a nasal spray, a nasal drop, etc.

A gum may be devised whereby an active ingredient is incorporated into a vegetative resinous substance (e.g. acacia) and released via the actual mechanical effect of chewing or the action of saliva on the gum itself.

A thinstrip is an active pharmaceutical product coated by a lipid layer designed to dissolve in the mouth over a brief period of time. The same technology could be used to produce a medicated lollipop for transmucosal delivery.

In pharmaceutical terms, a granule is a small particle gathered into a larger, permanent aggregate in which the original particles can still be identified.

Methods of preparing dosage forms are known, or will be apparent, to in this art; for example, Remington: The Science and Practice of Pharmacy, 21st Ed. (Lippincott Williams & Wilkins. 2005). Appropriate dosages will depend on the patient (age, weight, overall health, etc.), the severity of the condition, the type of formulation and other factors known to those having ordinary skill in the art. It is to be noted that concentrations and dosage values can vary with the severity of the condition. It is to be further understood that for any particular patient, specific dosage regimens should be adjusted over time according to the individual need and the professional judgment of the person administering or supervising the administration of the compositions.

Representative dosages for each of the combination formulations is presented below by drug, disease, and appropriate age category. In addition, dosages are provided for those who are renally or hepatically impaired. It should be noted that the use of these compositions in pregnancy may have risks as identified by the FDA Pregnancy Category Guidelines. Specifically, omeprazole and omeprazole/sodium bicarbonate, as well as bismuth subsalicylate are designated as Pregnancy Category C. All others listed below are designated Pregnancy Category B.

A pharmaceutical composition described herein may be prepared using a direct compression method, a dry granulation method, or by wet granulation. Preferably, the digestive enzyme preparation may be prepared using a direct compression process. This preferred process consists of two main steps: blending and compression. The blending step is composed of an active blend, color blend, pre-blend, and final blend (lubrication). A formulation may include a number of other ingredients for optimal characteristics of the pharmaceutical composition.

The rate of release of digestive enzymes can also be controlled by the addition of one or more additives. For example, when a pharmaceutical composition is exposed to a solvent, the solvent interacts with the coating and results in emulsification of the coating and release of the digestive enzymes.

In one embodiment, packaging of a pharmaceutical composition comprises single dose sachet-housed sprinkle preparations that allow for ease of delivery and accurate dosing of the digestive enzymes by allowing a specific amount of digestive enzymes to be delivered in each dosing. Allowing for specific unit dosing of digestive enzymes which maintains the enzyme activity within specific stability parameters is an enhancement over other sprinkle formulations, which are housed in a multi-unit dosing form that allows for air, moisture and heat to depredate and denature the enzyme preparation. In one embodiment, a powder or sachet is housed in a trilaminar pouch of which one layer is foil, or similar barrier to keep out moisture and to protect the enzyme preparation from adverse environmental factors.

A pharmaceutical composition can be administered to a subject one (1) or more times a day, such as for example, 1, 2, 3, 4, 5, 6, 7, 8, 9, or 10 times per day. In one instance, a composition can be administered orally 1, 2, or 3 times a day. Alternatively, a pharmaceutical composition can be administered to a subject, for example, 1, 2, 3, 4, 5, 6, 7, 8, 9, or 10 times per week. Alternatively, a pharmaceutical composition can be administered to a subject, for example, 1, 2, 3, 4, 5, 6, 7, 8, 9, or 10 times per month. In some instances, a subject is administered 1, 2, 3, 4, 5, 6, 7, 8, 9, or 10 doses at each treatment time. Administration can be with or without food.

Representative Coated Compositions

In one aspect, a pharmaceutical composition comprises coated particles comprising (i) a core that comprises digestive enzymes, wherein the digestive enzymes comprise a protease, an amylase, a lipase, or a combination thereof; and (ii) a polymer coating. In some instances, the polymer coating comprises a polymer enteric coating.

In one aspect, a pharmaceutical composition comprises coated particles comprising (i) a core that comprises digestive enzymes, wherein the digestive enzymes comprise a protease, an amylase, a lipase, or a combination thereof; and (ii) an enteric coating.

In one aspect, a pharmaceutical composition comprises coated particles comprising (i) a core that comprises digestive enzymes, wherein the digestive enzymes comprise a protease, an amylase, a lipase, or a combination thereof; and (ii) a polymer coating. In some instances, the polymer coating comprises a polymer enteric coating.

In one aspect, a pharmaceutical composition comprises coated particles comprising (i) a core that comprises digestive enzymes, wherein the digestive enzymes comprise a protease, an amylase, a lipase, or a combination thereof; and (ii) a lipid coating.

The minimum amount of digestive enzymes present in the coated particles is about 5% active enzymes by weight. The maximum amount of digestive enzymes present in the coated particles is about 99% by weight, and in other embodiments at most about 90%, 85%, 80%, 75% or 70% of the coated enzyme preparation. In other embodiments, the amount of digestive enzymes present in the composite is about 5%, 6%, 7%, 8%, 9%, 10%, 15%, 20%, 25%, 35%, 40%, 45%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 92.5%, 95%, or 99% by weight or anywhere in between. In other embodiments, the amount of digestive enzymes present in the composite is about 70%, 71%, 72%, 73%, 74%, 75%, 76%, 77%, 78%, 79%, 80%, 81%, 82%, 83%, 84%, 85%, 86%, 87%, 88%, 89%, or 90% by weight or anywhere in between. In other embodiments, the amount of digestive enzymes present in the composite is about 75%, 76%, 77%, 78%, 79%, 80%, 81%, 82%, 83%, 84%, or 85% by weight or anywhere in between. At least about or at most about a % of enzyme may include equal to or about that % of enzyme.

In some embodiments, a pharmaceutical composition comprises a coated particles which comprise: (a) a core comprising digestive enzymes present in an amount of from about 5% to about 95% by weight of the coated particles, including 5%, 6%, 7%, 8%, 9%, 10%, 15%, 20%, 25%, 30%, 35%, 40%, 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 92.5%, 95%%, or 99% by weight along with all values in-between; and (b) a coating, the coating comprising a crystallizable lipid. In some embodiments, a pharmaceutical composition comprises a coated particles which comprise: (a) a core comprising digestive enzymes present in an amount of from about 70% to about 90% by weight of the coated particles, including 70%, 71%, 72%, 73%, 74%, 75%, 76%, 77%, 78%, 79%, 80%, 81%, 82%, 83%, 84%, 85%, 86%, 87%, 88%, 89%, or 90% by weight along with all values in-between; and (b) a coating, the coating comprising a crystallizable lipid. In some embodiments, a pharmaceutical composition comprises a coated particles which comprise: (a) a core comprising digestive enzymes present in an amount of from about 75% to about 85% by weight of the coated particles, including 75%, 76%, 77%, 78%, 79%, 80%, 81%, 82%, 83%, 84%, or 85% by weight along with all values in-between; and (b) a coating, the coating comprising a crystallizable lipid. In some embodiments, the coated enzyme preparation particles of the enzyme delivery system are non-aerosolizable. In some instances, the coating is generally uniform and provides for controlled-release of the digestive enzymes when administered to a subject.

In some embodiments a pharmaceutical dosage comprising a population of extended-release beads, wherein said extended-release beads comprise: an active-containing core particle comprising digestive enzymes as the active agent; and an extended-release coating comprising a water-insoluble polymer membrane surrounding said core, wherein said water-insoluble polymer membrane comprises a polymer selected from the group consisting of ethers of cellulose, esters of cellulose, cellulose acetate, ethyl cellulose, polyvinyl acetate, neutral copolymers based on ethyl acrylate and methyl methacrylate, copolymers of acrylic and methacrylic acid esters with quaternary ammonium groups, pH-insensitive ammonio methacrylic acid copolymers, and mixtures thereof; wherein the total amount of pancreatin in the pharmaceutical dosage form contains from about 15,000 U.S.P. Units protease to about 1.5 million U.S.P. Units protease per dose and where the ratio of protease to lipase in U.S.P. Units is such that the amount of lipase in the composition is never more than 0.188 times the amount of protease, and where the ratio of protease activity to amylase activity in U.S.P. Units is between 1:0.1 and 1:10.

In some embodiments the extended-release coating further comprises a water-soluble polymer selected from the group consisting of methylcellulose, hydroxypropylcellulose, hydroxypropyl methylcellulose, polyethylene glycol, polyvinylpyrrolidone and mixtures thereof.

In some embodiments the extended-release coating further comprises a plasticizer selected from the group consisting of triacetin, tributyl citrate, triethyl citrate, acetyl tri-n-butyl citrate, diethyl phthalate, dibutyl sebacate, polyethylene glycol, polypropylene glycol, castor oil, acetylated mono- and di-glycerides, and mixtures thereof.

In some embodiments, the pharmaceutical compositions are characterized, for example, by controlled rates of release, reduction in aerosolization and safer administration, ability to be administered by a sprinkle/sachet delivery method, improved flow characteristics, enhanced shelf life and storage capacity, and other properties described herein. In other aspects, the coated enzyme preparation has improved pour properties which facilitate manufacturing and packaging processes, for example packaging in pouches and sachet.

Some coated digestive enzyme preparations which comprise a coating of a crystallizable lipid and a digestive enzyme core have favorable release and activity profiles and permit site time specific and/or location specific targeted release along the GI tract. In some aspects, the coated digestive enzyme preparations are prepared to obtain specific delivery times or specific regions within the human GI tract. In some embodiments, the crystallizable lipid composition is hydrogenated soybean oil, but may be any suitable crystallizable lipid or lipid blend. Additionally, the coating of the coated digestive enzyme preparations may be tailored for optimal targeted release of the enzyme(s) to achieve maximal combined efficacy of the digestive enzymes when used in conjunction with acid reducer(s).

Some embodiments utilize stable enzyme preparations protected against the environment to reduce, for example, degradation and/or denaturation of the enzymes. This permits delivery of more accurate doses of the enzyme preparation to treated subjects. The coating can also, in some aspects, provide emulsification when the enzyme preparations are contacted with appropriate solvents, while also surprisingly providing for controlled-release of the enzyme in the GI system. The emulsification properties of the coating in a solvent allows for controlled-release of the enzyme, preferably at selected locations in the GI tract, where enzyme utilization provides the most effective prophylaxis or treatment.

In one embodiment, the digestive enzyme used present as consisting of particles having various sizes. In another embodiment, the particles of digestive enzyme are screened to obtain particles of a suitable size for encapsulation by removing particles that are too fine or too large. For example, the particles may be sieved to obtain particles of a suitable size or more uniform size range for encapsulation.

Compositions contemplated herein include, but are not limited to, solutions, suspensions, suppositories, pellets, capsules, caplets, beadlets, sprinkles, tablets, softgels, sachets, pouches, etc.

The minimum amount of digestive enzymes present in the coated particles is at least about 5% by weight. In one embodiment, the minimum amount of digestive enzymes present in the coated particles is at least about 30%, about 35%, about 40%, or about 50% by weight. The maximum amount of digestive enzymes present in the coated particles is about 99% by weight. For example, the amount of digestive enzymes present in the coated particles is at most 99%, about 98%, about 95%, about 90%, about 87.5%, about 85%, about 82.5%, about 80%, about 77.5%, about 75%, about 72.5%, or about 70% by weight.

In one instance, the amount of digestive enzymes present in the coated particles is about 5%, 10%, 15%, 20%, 25%, 35%, 40%, 45%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 92.5%, or 95% by weight, or any integer in-between. "At least about" or "at most about" a percentage (%) of enzyme may include equal to or about that % of enzyme.

The coating can be present in coated digestive enzyme particles in an amount of from about 1% to about 50%, from about 1% to about 30%, or about 20%. The coating can be present in coated digestive enzyme particles in an amount of about 1%, about 2%, about 3%, about 4%, about 5%, about 6%, about 7%, about 8%, about 9%, about 10%, about 11%, about 12%, about 13%, about 14%, about 15%, about 16%, about 16.5%, about 17%, about 17.5%, about 18%, about 18.5%, about 19%, about 19.5%, about 20%, about 20.5%, about 21%, about 21.5%, about 22%, about 22.5%, about 23%, about 23.5%, about 24%, about 24.5%, about 25%, about 25.5%, about 26%, about 26.5%, about 27%, about 27.5%, about 28%, about 28.5%, about 29%, about 29.5%, about 30%, about 30.5%, about 31%, about 31.5%, about 32%, about 32.5%, about 33%, about 33.5%, about 34%, about 34.5%, about 35%, about 35.5%, about 36%, about 36.5%, about 37%, about 37.5%, about 38%, about 38.5%, about 39%, about 39.5%, about 40%, about 40.5%, about 41%, about 41.5%, about 42%, about 42.5%, about 43%, about 43.5%, about 44%, about 44.5%, about 45%, about 45.5%, about 46%, about 46.5%, about 47%, about 47.5%, about 48%, about 48.5%, about 49%, about 49.5%, or about 50%, by weight. In some instances, the coating can be present in coated digestive enzyme particles in an amount of from about 10% to about 30% by weight. In some instances, the coating can be present in coated digestive enzyme particles in an amount of from about 15% to about 25% by weight. In some instances, the coating can be present in coated digestive enzyme particles in an amount of about 20% by weight.

In another embodiment enzyme preparations are utilized with lipid coating of enzymes. The method of making the preparations comprises providing a crystallizable lipid, and coating size-specific digestive enzyme particles as described herein with a lipid. The digestive enzymes may be present in the coated particles in an amount of from about 5% to about 95% by weight, including, but not limited to, about 5%, 10%, 15%, 20%, 25%, 30%, 35%, 40%, 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 92.5%, or 95% along with all values in-between. The digestive enzymes may be present in the coated particles in an amount of from about 70% to about 90% by weight. The digestive enzymes may be present in the coated particles in an amount of from about 72.5% to about 87.5% by weight. The digestive enzymes may be present in the coated particles in an amount of from about 75% to about 85% by weight. The digestive enzymes may be present in the coated particles in an amount of from about 77.5% to about 82.5% by weight. The digestive enzymes may be present in the coated particles in an amount of about 80%.

In another example, the coatings and digestive enzymes are concentrically nested to allow timed release of enzymes in more than one portion of the gastrointestinal tract to prophylaxis or treat an infection or the symptoms thereof treat the symptoms thereof for one or more coronavirus(es).

The digestive enzymes can be used in cores of coated particles where about 90% of the coated particles are from about #40 to about #140 USSS mesh in size, or from about 105 to about 425 μm in size (diameter). Alternatively, the digestive enzyme particles used in cores of coated particles where about 75% of the particles are from about #40 to about #80 USSS mesh, or from about 180 to about 425 μm in size (diameter). Particles from about #40 to about #140 USSS mesh in size pass through #40 USSS mesh but do not pass through #140 USSS mesh. The coated digestive enzymes, in one embodiment, may comprise less than about 35%, 30%, 25%, 20%, 15%, or 10% of coated particles which can be sieved through #100 USSS mesh (150 μm). In some embodiments, the term "non-aerosolizable" refers to a digestive enzyme preparation where less than about 20% of the coated particles can be sieved through #100 USSS mesh (150 μm). In some embodiments, the term "non-aerosolizable" refers to a digestive enzyme preparation where less than about 15% of the coated particles can be sieved through #100 USSS mesh (150 μm). The digestive enzyme preparation can be an encapsulated digestive enzyme composite where the digestive enzyme particles can contain one, two, three, four, five, six, seven, eight, nine, ten, or more digestive enzymes.

Coated particles may be sieved to obtain coated particles of a suitable size or more uniform size range. The coated particles may be sieved through #40 USSS mesh and through USSS #140 USSS mesh. Coated particles that pass through the #40 USSS mesh but are retained by the #140 USSS mesh are of an appropriate size range. In some instances, the particles may also be screened to obtain particles of a suitable size for encapsulation by removing particles that are too fine or too large. For example, the coated particles may be sieved to obtain coated particles of a suitable size or more uniform size range for encapsulation. As a further example, the coated particles may be sieved through #40 USSS mesh and through USSS #140 USSS mesh. Coated particles that pass through the #40 USSS mesh but are retained by the #140 USSS mesh are of an appropriate size range for coating or encapsulation. Particles may also be screened by sieving through USSS #140, #120, #100, #80, #70, #60, #50, #45, or #40 USSS mesh, or any combination thereof.

Non-limiting examples of compositions that contain digestive enzymes have been discussed above. Other exemplary compositions are provided herein below. Each of the compositions described herein may be formulated with any combination of the described excipients.

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. a polymer coating.

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. an enteric coating.

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. a coating that comprises a Cellulose acetate phthalate (CAP).

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. a coating that comprises a cellulose acetate trimellitate (CAT).

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. a coating that comprises a hydroxyl propyl methyl cellulose phthalate (HPMCP).

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. a coating that comprises a hydroxyl propyl methyl cellulose acetate succinate (HPMCAS).

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. a coating that comprises a polyvinyl acetate phthalate (PVAP).

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. a coating that comprises a methacrylic acid copolymer.

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. a coating that comprises a shellac (Esters of Aleurtic Acid).

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. a coating that comprises a Zein.

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. a coating that comprises an ethylcellulose (EC).

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. a coating that comprises a lipid.

A pharmaceutical composition can comprise a. a core that comprises from about 10,000 to about 1,500,000 U.S.P. Units protease, from about 1,500 to about 282,000 U.S.P.

Units lipase, and from about 1,000 to about 15,000,000 U.S.P. Units amylase; and b. a coating that comprises a food grade lipid.

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. a coating that comprises a sorbitan monostearate, a sorbitan tristearate, or a calcium stearoyl lactylate.

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. a coating that comprises a pharmaceutical grade lipid.

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. a coating that comprises a fully-hydrogenated soybean oil.

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. a coating that comprises one or more monoglycerides, one or more diglycerides, one or more triglycerides, fatty acids, esters of fatty acids, phospholipids, or a combination thereof.

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. a coating that comprises one or more monoglycerides, one or more diglycerides, one or more triglycerides, fatty acids, esters of fatty acids, phospholipids, or a combination thereof.

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and a coating that comprises a soy lipid.

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. a coating that comprises a hydrogenated soy lipid.

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. a coating that comprises the esters of fatty acids, wherein the esters of fatty acids are selected from the group consisting of acetic acid esters of mono- and diglycerides, citric acid esters of mono- and diglycerides, lactic acid esters of mono- and diglycerides, polyglycerol esters of fatty acids, propylene glycol esters of fatty acids, and diacetyl tartaric acid esters of mono- and diglycerides.

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. a coating that comprises a hydrogenated castor wax or a hydrogenated carnauba wax.

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. a coating that comprises an animal lipid or a vegetable lipid.

A pharmaceutical composition can comprise a. a core that comprises from about 10,000 to about 1,500,000 U.S.P. Units protease, from about 1,500 to about 282,000 U.S.P. Units lipase, and from about 1,000 to about 15,000,000 U.S.P. Units amylase; and b. a coating selected from the group consisting of a palm kernel oil, a soybean oil, a cottonseed oil, a canola oil, and a poultry fat.

A composition as described herein can comprise a. a core that comprises about 8,400 U.S.P. Units lipase, 35,000 U.S.P. Units protease, about 35,000 U.S.P. Units amylase, and b. a polymer coating. A composition as described herein can comprise a. a core that comprises about 134,400 U.S.P. Units lipase, about 560,000 U.S.P. Units protease, and about 560,000 U.S.P. Units amylase, and b. a polymer coating. A composition as described herein can comprise a. a core that comprises about 252,000 U.S.P. Units lipase, about 1,050,000 U.S.P. Units protease, and about 1,050,000 U.S.P. Units amylase, and b. a polymer coating.

A composition as described herein can comprise a. a core that comprises about 8,400 U.S.P. Units lipase, 35,000 U.S.P. Units protease, about 35,000 U.S.P. Units amylase, and b. an enteric coating. A composition as described herein can comprise a. a core that comprises about 134,400 U.S.P. Units lipase, about 560,000 U.S.P. Units protease, and about 560,000 U.S.P. Units amylase, and b. an enteric coating. A composition as described herein can comprise a. a core that comprises about 252,000 U.S.P. Units lipase, about 1,050,000 U.S.P. Units protease, and about 1,050,000 U.S.P. Units amylase, and b. an enteric coating.

A composition as described herein can comprise a. a core that comprises about 8,400 U.S.P. Units lipase, 35,000 U.S.P. Units protease, about 35,000 U.S.P. Units amylase, and b. a lipid coating. A composition as described herein comprises a. a core that comprises about 134,400 U.S.P. Units lipase, about 560,000 U.S.P. Units protease, and about 560,000 U.S.P. Units amylase, and b. a lipid coating. A composition as described herein that comprises a. a core can comprise about 252,000 U.S.P. Units lipase, about 1,050,000 U.S.P. Units protease, and about 1,050,000 U.S.P. Units amylase, and b. a lipid coating.

A composition as described herein can comprise a. a core that comprises about 8,400 U.S.P. Units lipase, 35,000 U.S.P. Units protease, about 35,000 U.S.P. Units amylase and b. a fully-hydrogenated soybean oil. A composition as described herein can comprise a. a core that comprises about 134,400 U.S.P. Units lipase, about 560,00 U.S.P. Units protease, and about 560,000 U.S.P. Units amylase, and b. a fully-hydrogenated soybean oil. A composition as described herein can comprise a. a core that comprises about 252,000 U.S.P. Units lipase, about 1,050,000 U.S.P. Units protease, and about 1,050,000 U.S.P. Units amylase, and b. a fully-hydrogenated soybean oil.

For explanation purposes only, in one non-limiting example, a subject is administered 8 capsules twice a day, wherein each capsule comprises digestive enzymes having about 560,000 U.S.P. Units protease and about 560,000 U.S.P. Units amylase. In an additional nonlimiting example, a subject is administered 10 capsules coated with an enteric coating stabile at a pH below about 7.2 to target delivery to the proximal ileum, wherein each capsule comprises about 252,000 U.S.P. Units lipase, about 1,050,000 U.S.P. Units protease, and about 1,050,000 U.S.P. Units amylase. In an additional nonlimiting example, a subject is administered 4 capsules four times a day, wherein the capsules have a dissolution time of approximately 90 minutes and comprise about 8,400 U.S.P. Units lipase, 35,000 U.S.P. Units protease, and about 35,000 U.S.P. Units amylase.

In one embodiment, a lipid-microencapsulated porcine pancreatic enzyme concentrate with high protease and low lipase levels is utilized for prophylaxis against infection from SARS-CoV-2. The non-pH dependent microencapsulation, applied by fluidized bed coating comprises pharmaceutical-grade fully hydrogenated soy oil (approximately 20% by weight) with a dissolution profile of approximately 85% in 60 minutes or less, allows the delivery of the digestive enzymes from a pharmaceutical composition in the duodenum. Drug delivery is sprinkles housed in a sachet that are sprinkled over food. Non-limiting exemplary dosing for subjects of various ages and exposure levels are given in Table 2.

In one embodiment, infant subjects with a weight greater than 4 Kg and less than three years old receive 2 doses per day, where each dose comprises about 90,000 U.S.P. Units protease, about 18,000 U.S.P. Units lipase, and about 108,000 U.S.P. Units of amylase delivered as lipid-microencapsulated porcine pancreatic enzyme concentrate sprinkles as a prophylaxis against SARS-CoV-2 infection. Each dose is approximately 450 mg of lipid-microencapsulated porcine pancreatic enzyme packaged in a tri-foil laminate sachet and given orally by sprinkling over food.

In one embodiment, child subjects three years of age and older receive 3 doses a day, where each dose comprises about 180,000 U.S.P. Units protease, about 36,000 U.S.P. Units lipase, and about 216,000 U.S.P. Units of amylase delivered as lipid-microencapsulated porcine pancreatic enzyme concentrate sprinkles as a prophylaxis against SARS-CoV-2 infection. Each dose is approximately 900 mg of lipid-microencapsulated porcine pancreatic enzyme packaged in a tri-foil laminate sachet and given orally by sprinkling over food.

In one embodiment, teen subjects receive 3 doses a day, where each dose comprises about 360,000 U.S.P. Units protease, about 72,000 U.S.P. Units lipase, and about 432,000 U.S.P. Units of amylase delivered as lipid-microencapsulated porcine pancreatic enzyme concentrate sprinkles as a prophylaxis against SARS-CoV-2 infection. Each dose is approximately 1,800 mg of lipid-microencapsulated porcine pancreatic enzyme packaged in a tri-foil laminate sachet and given orally by sprinkling over food.

In one embodiment, adults receive 3 doses a day, where each dose comprises about 720,000 U.S.P. Units protease, about 144,000 U.S.P. Units lipase, and about 864,000 U.S.P. Units of Amylase delivered as lipid-microencapsulated porcine pancreatic enzyme concentrate sprinkles as a prophylaxis against SARS-CoV-2 infection. Each dose is approximately 3,600 mg of lipid-microencapsulated porcine pancreatic enzyme packaged in a tri-foil laminate sachet and given orally by sprinkling over food.

In one embodiment, elderly subjects receive 3 doses a day, where each dose comprises about 360,000 U.S.P. Units protease, about 72,000 U.S.P. Units lipase, and about 432,000 U.S.P. Units of Amylase delivered as lipid-microencapsulated porcine pancreatic enzyme concentrate sprinkles as a prophylaxis against SARS-CoV-2 infection. Each dose is approximately 1,800 mg of lipid-microencapsulated porcine pancreatic enzyme packaged in a tri-foil laminate sachet and given orally by sprinkling over food.

In one embodiment, a lipid-microencapsulated porcine pancreatic enzyme concentrate with high protease and low lipase levels is utilized for treatment of COVID-19. The non-pH dependent microencapsulation allows the delivery of protease from a pharmaceutical composition in the early portion of the duodenum. Drug delivery is sprinkles housed in a sachet that are sprinkled over food. Dosing for subjects of various ages and exposure levels are given in Tables 3A and 3B.

In one embodiment, infant subjects with a weight greater than 4 Kg and less than three years old receive 2 doses per day, where each dose comprises about 90,000 U.S.P. Units protease, about 18,000 U.S.P. Units lipase, and about 108,000 U.S.P. Units amylase delivered as lipid-microencapsulated or lipid-coated digestive enzyme (e.g., porcine pancreatic digestive enzymes) concentrate sprinkles as treatment for COVID-19. Each dose is approximately 450 mg of lipid-microencapsulated or lipid-coated digestive enzymes (e.g., porcine pancreatic digestive enzymes) packaged in a tri-foil laminate sachet and given orally by sprinkling over food.

In one embodiment, child subjects three years of age and older receive 3 doses a day, where each dose comprises about 180,000 U.S.P. Units protease, about 36,000 U.S.P. Units lipase, and about 216,000 U.S.P. Units amylase delivered as lipid-microencapsulated or lipid-coated digestive enzyme (e.g., porcine pancreatic digestive enzymes) concentrate sprinkles as treatment for COVID-19. Each dose is approximately 900 mg of lipid-microencapsulated or lipid-coated digestive enzymes (e.g., porcine pancreatic digestive enzymes) packaged in a tri-foil laminate sachet and given orally by sprinkling over food.

In one embodiment, teen subjects receive 3 doses a day, where each dose comprises about 360,000 U.S.P. Units protease, about 72,000 U.S.P. Units lipase, and about 432,000 U.S.P. Units amylase delivered as lipid-microencapsulated or lipid-coated digestive enzyme (e.g., porcine pancreatic digestive enzymes) concentrate sprinkles as treatment for COVID-19. Each dose is approximately 1,800 mg of lipid-microencapsulated or lipid-coated digestive enzymes (e.g., porcine pancreatic digestive enzymes) packaged in a tri-foil laminate sachet and given orally by sprinkling over food.

In one embodiment, adults receive 3 doses a day, where each dose comprises about 720,000 U.S.P. Units protease, about 144,000 U.S.P. Units lipase, and about 864,000 U.S.P. Units amylase delivered as lipid-microencapsulated or lipid-coated digestive enzyme (e.g., porcine pancreatic digestive enzymes) concentrate sprinkles as treatment for COVID-19. Each dose is approximately 3,600 mg of lipid-microencapsulated or lipid-coated digestive enzymes (e.g., porcine pancreatic digestive enzymes) packaged in a tri-foil laminate sachet and given orally by sprinkling over food.

In one embodiment, elderly subjects receive 3 doses a day, where each dose comprises about 360,000 U.S.P. Units protease, about 72,000 U.S.P. Units lipase, and about 432,000 U.S.P. Units amylase delivered as lipid-microencapsulated or lipid-coated digestive enzyme (e.g., porcine pancreatic digestive enzymes) concentrate sprinkles as treatment for COVID-19. Each dose is approximately 1,800 mg of lipid-microencapsulated or lipid-coated digestive enzymes (e.g., porcine pancreatic digestive enzymes) packaged in a tri-foil laminate sachet and given orally by sprinkling over food.

In one embodiment, the dosing for prophylaxis by baseline exposure utilizing lipid-microencapsulated or lipid-coated digestive enzyme (e.g., porcine pancreatic digestive enzymes) concentrate (CoGen-2) is shown below in Table 2:

TABLE 2

| | Prophylaxis Baseline Exposure | | |
|---|---|---|---|
| | Subject Asymptomatic and has No SARS-CoV-2 Infection No SARS-CoV-2 Exposure | Subject Asymptomatic and has No SARS-CoV-2 Infection Likely SARS-CoV-2 Exposure | Subject Asymptomatic and has No SARS-CoV-2 Infection SARS-CoV-2 Definite Exposure |
| Infant (weight 4 kg or greater) | 2 doses per day. Each dose containing 90,000 U.S.P. Units protease, 18,000 U.S.P. Units lipase and 108,000 U.S.P. Units amylase. | 2 doses per day. Each dose containing 90,000 U.S.P. Units protease, 18,000 U.S.P. Units lipase and 108,000 U.S.P. Units amylase. | 2 doses per day. Each dose containing 90,000 U.S.P. Units protease, 18,000 U.S.P. Units lipase and 108,000 U.S.P. Units amylase. |
| Child (age 3 or greater) | 3 doses per day. Each dose containing 180,000 U.S.P. Units protease, 36,000 U.S.P. Units lipase and 216,000 U.S.P. Units amylase | 3 doses per day. Each dose containing 180,000 U.S.P. Units protease, 36,000 U.S.P. Units lipase and 216,000 U.S.P. Units amylase | 3 doses per day. Each dose containing 180,000 U.S.P. Units protease, 36,000 U.S.P. Units lipase and 216,000 U.S.P. Units amylase |
| Teen | 3 doses per day. Each dose containing 360,000 U.S.P. Uni Protease, 72,000 U.S.P. Units lipase and 432,000 U.S.P. Units amylase | 3 doses per day. Each dose containing 360,000 U.S.P. Units protease, 72,000 U.S.P. Units lipase and 432,000 U.S.P. Units amylase | 3 doses per day. Each dose containing 360,000 U.S.P. Units protease, 72,000 U.S.P. Units lipase and 432,000 U.S.P. Units amylase |
| Adult | 3 doses per day. Each dose containing 720,000 U.S.P. Units protease, 144,000 U.S.P. Units lipase and 864,000 U.S.P. Units amylase | 3 doses per day. Each dose containing 720,000 U.S.P. Units protease, 144,000 U.S.P. Units lipase and 864,000 Units Amylase | 3 doses per day. Each dose containing 720,000 U.S.P. Units protease, 144,000 U.S.P. Units lipase and 864,000 U.S.P. Units amylase |
| Elderly | 3 doses per day. Each dose containing 360,000 U.S.P. Units protease, 72,000 U.S.P. Units lipase and 432,000 U.S.P. Unit Amylase | 3 doses per day. Each dose containing 360,000 U.S.P. Units protease, 72,000 U.S.P. Units lipase and 432,000 U.S.P. Units amylase | 3 doses per day. Each dose containing 360,000 U.S.P. Units protease, 72,000 U.S.P. Units lipase and 432,000 U.S.P. Units amylase |

In another embodiment, the dosing for treatment of SARS-CoV-2 Infection (COVID-19) by severity utilizing lipid-microencapsulated porcine pancreatic enzyme concentrate (CoGen-2) is shown below in Tables 3A and 3B:

TABLE 3A

| | Treatment Baseline Severity | | |
|---|---|---|---|
| | Subject Asymptomatic Positive for COVID-19 | Subject has Mild COVID-19 | Subject has Moderate COVID-19 |
| Infant (weight 4 kg or greater) | 2 doses per day Each dose containing 90,000 U.S.P. Units protease, 18,000 U.S.P. Units lipase and 108,000 U.S.P. Units amylase. | 2 doses per day. Each dose containing 90,000 U.S.P. Units protease, 18,000 U.S.P. Unit Lipase and 108,000 U.S.P. Units amylase. | 2 doses per day. Each dose containing 90,000 U.S.P. Units protease, 18,000 U.S.P. Units lipase and 108,000 U.S.P. Units amylase. |
| Child (age 3 or greater) | 3 doses per day. Each dose containing 180,000 U.S.P. Units protease, 36,000 U.S.P. Units lipase and 216,000 U.S.P. Units amylase | 3 doses per day. Each dose containing 180,000 U.S.P. Units protease, 36,000 U.S.P. Units lipase and 216,000 U.S.P. Units amylase | 3 doses per day. Each dose containing 180,000 U.S.P. Units protease, 36,000 U.S.P. Units lipase and 216,000 U.S.P. Units amylase |
| Teen | 3 doses per day. Each dose containing 360,000 U.S.P. Units protease, 72,000 U.S.P. Units lipase and 432,000 U.S.P. Units amylase | 3 doses per day. Each dose containing 360,000 U.S.P. Units protease, 72,000 U.S.P. Units lipase and 432,000 U.S.P. Units amylase | 3 doses per day. Each dose containing 360,000 U.S.P. Units protease, 72,000 U.S.P. Units lipase and 432,000 U.S.P. Units amylase |

TABLE 3A-continued

| | Treatment Baseline Severity | | |
|---|---|---|---|
| | Subject Asymptomatic Positive for COVID-19 | Subject has Mild COVID-19 | Subject has Moderate COVID-19 |
| Adult | 3 doses per day. Each dose containing 720,000 U.S.P. Units protease, 144,000 U.S.P. Units lipase and 864,000 U.S.P. Units amylase | 3 doses per day. Each dose containing 720,000 U.S.P. Units protease, 144,000 U.S.P. Units lipase and 864,000 U.S.P. Units amylase | 3 doses per day. Each dose containing 720,000 U.S.P. Units protease, 144,000 U.S.P. Units lipase and 864,000 U.S.P. Units amylase |
| Elderly | 3 doses per day. Each dose containing 360,000 U.S.P. Units protease, 72,000 U.S.P. Units lipase and 432,000 U.S.P. Units amylase | 3 doses per day. Each dose containing 360,000 U.S.P. Units protease, 72,000 U.S.P. Units lipase and 432,000 U.S.P. Units amylase | 3 doses per day. Each dose containing 360,000 U.S.P. Units protease, 72,000 U.S.P. Units lipase and 432,000 U.S.P. Units amylase |

TABLE 3B

| | Treatment Baseline Severity | |
|---|---|---|
| | Subject has Severe COVID-19 | Subject has Critical COVID-19 |
| Infant (weight 4 kg or greater) | 2 doses per day. Each dose containing 90,000 U.S.P. Units protease, 18,000 U.S.P. Units lipase and 108,000 U.S.P. Units amylase. | 2 doses per day. Each dose containing 90,000 U.S.P. Units protease, 18,000 U.S.P. Units lipase and 108,000 U.S.P. Units amylase. |
| Child (age 3 or greater) | 3 doses per day. Each dose containing 180,000 U.S.P. Units protease, 36,000 U.S.P. Units lipase and 216,000 U.S.P. Units amylase | 3 doses per day. Each dose containing 180,000 U.S.P. Units protease, 36,000 U.S.P. Units lipase and 216,000 U.S.P. Units amylase |
| Teen | 3 doses per day. Each dose containing 360,000 U.S.P. Units protease, 72,000 U.S.P. Units lipase and 432,000 U.S.P. Units amylase | 3 doses per day. Each dose containing 360,000 U.S.P. Units protease, 72,000 U.S.P. Units lipase and 432,000 U.S.P. Units amylase |
| Adult | 3 doses per day. Each dose containing 720,000 U.S.P. Units protease, 144,000 U.S.P. Units lipase and 864,000 U.S.P. Units amylase | 3 doses per day. Each dose containing 720,000 U.S.P. Units protease, 144,000 U.S.P. Units lipase and 864,000 U.S.P. Units amylase |
| Elderly | 3 doses per day. Each dose containing 360,000 U.S.P. Units protease, 72,000 U.S.P. Units lipase and 432,000 U.S.P. Units amylase | 3 doses per day. Each dose containing 360,000 U.S.P. Units protease, 72,000 U.S.P. Units lipase and U.S.P. 432,000 Units Amylase |

SARS-CoV-2 Prophylaxis—Dosing Examples

An eight-month-old infant female subject weighing about 7.9 kg is asymptomatic for COVID-19 with definite SARS-CoV-2 exposure, but not diagnosed SARS-CoV-2 infection. As a prophylaxis against SARS-CoV-2 infection, the infant subject is orally administered 2 doses/day of lipid-microencapsulated or lipid-coated digestive enzyme (e.g., porcine pancreatic digestive enzymes) concentrate; each dose containing of about 90,000 U.S.P. Units (U) protease, about 18,000 U.S.P. U lipase, and about 108,000 U.S.P. U amylase. The non-pH dependent microencapsulation or coating applied by fluidized bed coating comprises pharmaceutical-grade, fully hydrogenated soy oil (approximately 20% by weight) with a dissolution profile of approximately 85% in 60 minutes or less. The drug delivery is sprinkles housed in a sachet that are sprinkled over food. The dosing is for about 6 weeks assuming no additional or ongoing SARS-CoV-2 exposure and no SARS-CoV-2 infection.

A five-year-old male subject is asymptomatic for COVID-19 with a likelihood of SARS-CoV-2 exposure and no diagnosed SARS-CoV-2 infection. As a prophylaxis against SARS-CoV-2 infection, the subject is orally administered 3 doses/day of lipid-microencapsulated or lipid-coated digestive enzyme (e.g., porcine pancreatic digestive enzymes) concentrate; each dose contains about 180,000 U.S.P. U protease, about 36,000 U.S.P. U lipase, and about 216,000 U.S.P. U amylase. The non-pH microencapsulation or coating, applied by fluidized bed coating, comprises pharmaceutical-grade, fully hydrogenated soy oil (approximately 20% by weight) with a dissolution profile of approximately 85% in 60 minutes or less. The drug delivery is sprinkles housed in a sachet that are sprinkled over food. The dosing is for about 8 weeks assuming no additional or ongoing SARS-CoV-2 exposure and no SARS-CoV-2 infection.

A fourteen-year-old female subject is asymptomatic for COVID-19 with no SARS-CoV-2 exposure and no diagnosed SARS-CoV-2 infection. As a prophylaxis against SARS-CoV-2 infection, the subject is orally administered 3 doses/day of lipid-microencapsulated or lipid-coated digestive enzyme (e.g., porcine pancreatic digestive enzymes) concentrate; each dose containing about 360,000 U.S.P. U protease, about 72,000 U.S.P. U lipase, and about 432,000 U.S.P. U amylase. The non-pH dependent microencapsulation or coating, applied by fluidized bed coating, comprises pharmaceutical-grade, fully hydrogenated soy oil (approximately 20% by weight) with a dissolution profile of approximately 85% in 60 minutes or less. The drug delivery is sprinkles housed in a sachet that are sprinkled over food. The dosing is for about 16 weeks during the course of the COVID-19 pandemic, assuming no SARS-CoV-2 infection.

A thirty-five-year-old adult male subject is asymptomatic for COVID-19 with definite SARS-CoV-2 exposure and no diagnosed SARS-CoV-2 infection. As a prophylaxis against symptomatic COVID-19, the subject is orally administered 3 doses/day of lipid-microencapsulated or lipid-coated digestive enzyme (e.g., porcine pancreatic digestive enzymes) concentrate; each dose containing about 720,000 U.S.P. U protease, about 144,000 U.S.P. U lipase, and about 863,000 U.S.P. U amylase. The non-pH dependent microencapsulation or coating, applied by fluidized bed coating, comprises pharmaceutical-grade, fully hydrogenated soy oil (approximately 20% by weight) with a dissolution profile of approximately 85% in 60 minutes or less. The drug delivery is sprinkles housed in a sachet that are sprinkled over food. The dosing is for about 8 weeks assuming no additional or ongoing SARS-CoV-2 exposure or SARS-CoV-2 infection.

A seventy-five-year-old elderly female subject is asymptomatic for COVID-19 with definite SARS-CoV-2 exposure and no diagnosed SARS-CoV-2 infection. As a prophylaxis against SARS-CoV-2 infection, the subject is orally administered 3 doses/day of lipid-microencapsulated or lipid-coated digestive enzyme (e.g., porcine pancreatic digestive enzymes) concentrate; each dose containing about 360,000 U.S.P. U protease, about 72,000 U.S.P. U lipase, and about 432,000 U.S.P. U amylase. The non-pH dependent microencapsulation or coating, applied by fluidized bed coating, comprises pharmaceutical-grade fully hydrogenated soy oil (approximately 20% by weight) with a dissolution profile of approximately 85% in 60 minutes or less. The drug delivery is sprinkles housed in a sachet that are sprinkled over food. The dosing is for about 8 weeks assuming no additional or ongoing SARS-CoV-2 exposure and no SARS-CoV-2 infection.

COVID-19 Treatment—Dosing Examples

It will be understood that the following dosing examples are representative and non-limiting.

A ten-month-old infant male subject weighing approximately 9.2 kg is asymptomatic for COVID-19 but does have a SARS-CoV-2 infection. As a treatment for the SARS-CoV-2 infection, the infant subject is orally administered 2 doses/day of lipid-microencapsulated or lipid-coated digestive enzyme (e.g., porcine pancreatic digestive enzymes) concentrate; each dose containing of about 90,000 U.S.P. Units (U) protease, 18,000 U.S.P. U lipase, and 108,000 U.S.P. U amylase. The non-pH dependent microencapsulation or coating (e.g., applied by fluidized bed coating) comprises pharmaceutical-grade, fully hydrogenated soy oil (approximately 20% by weight) with a dissolution profile of approximately 85% in 60 minutes or less. The drug delivery is sprinkles housed in a sachet that are sprinkled over food. The dosing is for about 8 weeks or until the subject is no longer infected with SARS-CoV-2.

An eight-year-old female subject has a mild COVID-19 caused by a SARS-CoV-2 infection and exhibits symptoms of fever, chills, cough, along with gastrointestinal symptoms of nausea and diarrhea. As a treatment for mild COVID-19, the subject is orally administered 3 doses/day of lipid-microencapsulated or lipid-coated digestive enzyme (e.g., porcine pancreatic digestive enzymes) concentrate; each dose contains about 180,000 U.S.P. Units (U) protease, about 36,000 U.S.P. U lipase, and about 216,000 U.S.P. U amylase. The non-pH dependent microencapsulation or coating comprises pharmaceutical-grade, fully hydrogenated soy oil (approximately 20% by weight) with a dissolution profile of approximately 85% in 60 minutes or less. The drug delivery is sprinkles housed in a sachet that are sprinkled over food. The dosing is for about 8 weeks or until the subject no longer has a symptoms of COVID-19 or a SARS-CoV-2 infection.

A sixteen-year-old male has a moderate COVID-19 caused by a SARS-CoV-2 infection and exhibits the symptoms of fever, chills, cough along with shortness of breath with exertion. As a treatment for the moderate COVID-19, the subject is orally administered 3 doses/day of lipid-microencapsulated or lipid-coated digestive enzyme (e.g., porcine pancreatic digestive enzymes) concentrate; each dose containing about 360,000 U.S.P. U protease, about 72,000 U.S.P. U lipase, and about 432,000 U.S.P. U amylase. The non-pH dependent microencapsulation or coating comprises pharmaceutical-grade, fully hydrogenated soy oil (approximately 20% by weight) with a dissolution profile of approximately 85% in 60 minutes or less. The drug delivery is sprinkles housed in a sachet that are sprinkled over food. The dosing is for about 12 weeks or until the subject no longer has symptoms of COVID-19 or a SARS-CoV-2 infection.

A forty-year-old female subject has a severe COVID-19 caused by a SARS-CoV-2 infection and exhibits the symptoms of fever, chills, cough along with dyspnea loss of taste, loss of smell and shortness of breath at rest, respiratory distress, and a respiratory rate$\geq$30 per minute. As a treatment for severe COVID-19, the subject is orally administered 3 doses/day of lipid-microencapsulated or lipid-coated digestive enzyme (e.g., porcine pancreatic digestive enzymes) concentrate, each dose containing about 720,000 U.S.P. U protease, about 144,000 U.S.P. U lipase, and about 863,000 U.S.P. U amylase. The non-pH dependent microencapsulation or coating comprises pharmaceutical-grade fully hydrogenated soy oil (approximately 20% by weight) with a dissolution profile of approximately 85% in 60 minutes or less. The drug delivery is sprinkles housed in a sachet that are sprinkled over food. The dosing is for about 12 weeks or until the subject no longer has symptoms of COVID-19 or a SARS-CoV-2 infection.

An eighty-year-old male subject has a critical COVID-19 caused by a SARS-CoV-2 infection and exhibits the symptoms of fever, chills, dyspnea, along with a clinical diagnosis of respiratory failure. As a treatment for the critical SARS-CoV-2 infection, the subject is orally administered 3 doses/day of lipid-microencapsulated or lipid-coated digestive enzyme (e.g., porcine pancreatic digestive enzymes) concentrate; each dose containing about 360,000 U.S.P. U protease, about 72,000 U.S.P. U lipase, and about 432,000 U.S.P. U amylase. The non-pH dependent microencapsulation or coating comprises pharmaceutical-grade, fully hydrogenated soy oil (approximately 20% by weight) with a dissolution profile of approximately 85% in 60 minutes or less. The drug delivery is sprinkles housed in a sachet that are sprinkled over food. The dosing is for about 16 weeks or until the subject no longer has a SARS-CoV-2 infection.

Combination Therapy

It will be understood that administration of a pharmaceutical composition described herein can be supplemented by one or more additional therapies or drugs such as, for example, respiratory therapy; one or more blood thinners or anti-coagulants; statins, intubation; hydroxy chloroquine; one or more antibiotics (e.g., doxycycline, Azithromycin, etc.); one or more decongestants (e.g., MUCINEX®, SUDAFED®, etc.); one or more anti-histamines and/or glucocorticoids (e.g., ZYRTEC®, CLARITIN®, ALLEGRA®, fluticasone luroate, etc.); one or more pain relievers (e.g., acetaminophen); one or more zinc-containing medications (e.g., ZYRTEC®, etc.); Azithromycin, hydroquinolone, or a combination thereof; one or more integrase inhibitors (e.g., Bictegravir, dolutegravir (TIVICAY®), elvitegravir, raltegravir, or a combination thereof); one or more nucleoside/nucleotide reverse transcriptase inhibitors (NRTIs; e.g., abacavir (ZIAGEN®), emtricitabine (EMTRIVA®), lamivudine (EPIVIR®), tenofovir alafenamide fumarate (VEMLIDY®), tenofovir disoproxil fumarate (VIREAD®), zidovudine (Retrovir®), didanosine (VIDEX®, VIDEX EC®), stavudine (ZERIT®), or a combination thereof); a combination of NRTIs (e.g., (i) abacavir, lamivudine, and zidovudine (TRIZIVIR®); (ii) abacavir and lamivudine (EPZICOM®); (iii) emtricitabine and tenofovir alafenamide fumarate (DESCOVY®); (iv) emtricitabine and tenofovir disoproxil fumarate (TRUVADA®); (v) lamivudine and tenofovir disoproxil fumarate (CIMDUO®, TEMIXYS®); (vi) lamivudine and zidovudine (COMBIVIR®); etc.); a combination of DESCOVY® and TRUVADA®; one or more non-nucleoside reverse transcriptase inhibitors (NNRTIs; e.g., doravirine (PIFELTRO®), efavirenz (SUSTIVA®), etravirine (INTELENCE®), nevirapine (VIRAMUNE®, VIRAMUNE XR®), rilpivirine (EDURANT®), delavirdine (RESCRIPTOR®), or a combination thereof); one or more Cytochrome P4503A (CYP3A) inhibitors (e.g., cobicistat (TYBOST®), ritonavir (NORVIR®), etc.); one or more protease inhibitors (PIs; e.g., atazanavir (REYATAZ®), darunavir (PREZISTA®), fosamprenavir (LEXIVA®), lopinavir, ritonavir (NORVIR®), tipranavir (APTIVUS®), etc.); one or PIs in combination with cobicistat, ritonavir, Lopinavir, Tipranavir, Atazanavir, fosamprenavir, indinavir (CRIXIVAN®), nelfinavir (VIRACEPT®), saquinavir (INVIRASE®), or a combination thereof; Atazanavir; fosamprenavir; a combination of Atazanavir, darunavir and cobicistat; one or more fusion inhibitors (e.g., enfuvirtide (FUZEON®); one or more post-attachment inhibitors (e.g., ibalizumab-uiyk (TROGARZO®)); one or more Chemokine coreceptor antagonists (CCR5 antagonists; e.g., maraviroc (SELZENTRY®)); and one or more viral entry inhibitors (e.g., enfuvirtide (FUZEON®), ibalizumab-uiyk (TROGARZO®), maraviroc (SELZENTRY®), etc.); or a combination thereof.

Non-limiting examples of combinations include pharmaceutical compositions described herein to be administered with one or more of the following: (1) Azithromycin, hydroquinolone, or a combination thereof, (2) darunavir and cobicistat (PREZCOBIX®), (3) lopinavir and ritonavir (KALETRA®), (4) abacavir, lamivudine, and zidovudine (TRIZIVIR®), (5) abacavir and lamivudine (EPZICOM®), (6) emtricitabine and tenofovir alafenamide fumarate (DESCOVY®), (7) emtricitabine and tenofovir disoproxil fumarate (TRUVADA®), (8) lamivudine and tenofovir disoproxil fumarate (CIMDUO®, TEMIXYS®), (9) lamivudine and zidovudine (Combivir), (10), atazanavir and cobicistat (EVOTAZ®), (11) doravirine, lamivudine, and tenofovir disoproxil fumarate (DELSTRIGO®), (12) efavirenz, lamivudine, and tenofovir disoproxil fumarate (SYMFI®), (13) efavirenz, lamivudine, and tenofovir disoproxil fumarate (SYMFI LO®), (14) efavirenz, emtricitabine, and tenofovir disoproxil fumarate (ATRIPLA®), (15) emtricitabine, rilpivirine, and tenofovir alafenamide fumarate (ODEFSEY®), (16) emtricitabine, rilpivirine, and tenofovir disoproxil fumarate (COMPLERA®), (17) elvitegravir, cobicistat, emtricitabine, and tenofovir disoproxil fumarate (STRIBILD®), (18) elvitegravir, cobicistat, emtricitabine, and tenofovir alafenamide fumarate (GENVOYA®), (19) abacavir, dolutegravir, and lamivudine (TRIUMEQ®), (20) bictegravir, emtricitabine, and tenofovir alafenamide fumarate (BIKTARVY®), (21) dolutegravir and lamivudine (DOVATO®), (22) dolutegravir and rilpivirine (JULUCA®), (23) darunavir, cobicistat, emtricitabine, and tenofovir alafenamide fumarate (SYMTUZA®).

Non-limiting examples of combinations include pharmaceutical compositions described herein to be administered with one or more blood thinners. Blood thinners to be co-administered include, but are not limited to, anti-platelet, and anti-coagulation medications. Antiplatelet medications are those such as, for example, aspirin, clopidogrel (PLAVIX®); prasugrel (EFFIENT®); ticlopidine (TICLID®); ticagrelor (BRILINTA®); and combinations thereof. Anticoagulants include, but are not limited to, Warfarin (COUMADIN®, JANTOVEN®); Heparin (e.g., FRAGMIN®, INNOHEP®, and LOVENOX®); Eabigatran (PRADAXA®); Epixaban (ELIQUIS®); Non-vitamin K antagonist oral anticoagulants (NOACs) such as, for example, Rivaroxaban (XARELTO®); Factor Xa inhibitors such as, for example, Edoxaban (SAVAYSA®), Fondaparinux (ARIXTRA®); and combinations thereof.

Other non-limiting examples of combinations include pharmaceutical compositions described herein to be administered with one or more gastrointestinal modulators (e.g., an agent that reduces stomach acid in a subject). A gastrointestinal modulators of stomach acid can be utilized in combination with coated or uncoated digestive enzyme compositions are utilized to prophylaxis against or treat coronavirus infections. The combination of gastrointestinal modulators of stomach acid (also referred to as agents that reduce stomach acid) and pharmaceutical compositions enhance the controlled targeted delivery of enzymes having increased stability and enhanced administration properties.

As previously discussed, coronavirus receptors lie in various portions of the GI tract and in various organs, dependent upon the type of coronavirus. Delivery to the appropriate receptor sites may be more precise in the gut with more efficient delivery through the combination of appropriate coatings and GI modulators.

The use of gastrointestinal modulators in conjunction with one or more coatings for the digestive enzymes can provide for many different dissolution profiles to achieve optimal efficacy and delivery of the digestive enzymes. In another example of the present disclosure the amount and or types of gastrointestinal modulators are varied around a fixed enzyme coating to maximize efficacious release of digestive enzymes in the appropriate portion(s) of the gastrointestinal tract to treat the symptoms or causes of one or more diseases.

In another example, the amount and/or types of gastrointestinal modulators are fixed and the thickness of the coating is varied to maximize efficacious release of digestive enzymes in the appropriate portion(s) of the gastrointestinal tract to treat the symptoms or causes of one or more diseases.

In another example, the timing of giving one or more gastrointestinal modulators are varied and the thickness of the coating is fixed to maximize efficacious release of digestive enzymes in the appropriate portion(s) of the gastrointestinal tract to prophylaxis or treat an infection or symptoms thereof from one or more coronaviruses.

In one aspect, coated or uncoated compositions comprising one or more digestive enzyme(s) are utilized in combination with Histamine-2 receptor antagonists (H2-blockers) including, but not limited to, ranitidine (tradename ZANTAC®), nizatidine (tradename AXID®) famotidine (tradename PEPCID®), cimetidine (tradename TAGAMET®) to enhance the controlled and targeted delivery of one or more digestive enzyme(s) to patients.

In one aspect, coated or uncoated compositions comprising one or more digestive enzyme(s) are utilized in combination with Proton Pump Inhibitors (PPIs) including, but not limited to omeprazole (tradename PRILOSEC®) esomeprazole (tradename NEXIUM®) omeprazole and sodium bicarbonate (tradename ZEGERID®) lansoprazole (tradename PREVACID®) dexlansoprazole (tradename DEXILANT®) rabeprazole (tradename ACIPHEX®) pantoprazole (tradename PROTONIX®) to enhance the controlled and targeted delivery of one or more digestive enzyme(s) to patients.

In one aspect, coated or uncoated compositions comprising one or more digestive enzyme(s) are utilized in combination with Mucosal Protectants including, but not limited to, sucralfate (tradename CARAFATE®) bismuth subsalicylate (tradename PEPTO-BISMOL®) to enhance the controlled and targeted delivery of one or more digestive enzyme(s) to patients.

In one aspect, coated or uncoated compositions comprising one or more digestive enzyme(s) are utilized in combination with Pro-kinetic Agents including, but not limited to, metoclopramide (tradename Reglan) bethanecol (tradename URECHOLINE®) to enhance the controlled and targeted delivery of one or more digestive enzyme(s) to patients.

In one aspect, coated or uncoated compositions comprising one or more digestive enzyme(s) are utilized in combination with Anticholinergic Agents including, but not limited to, scopolamine (tradename TransdermScop), trihexyphenidyl (tradename Artane), benztropine (tradename COGENTIN®), dicyclomine (tradename BENTYL®), glycopyrrolate (tradename ROBINUL®), hyoscyamine (tradename LEVSIN®), or atropine to enhance the controlled and targeted delivery of one or more digestive enzyme(s) to patients.

Gastric Acid Suppression

Therapies to limit the ability of stomach acid to digest substrate do so either by limiting the amount of stomach acid or by limiting its contact with substrate. When digestive enzymes are administered orally, the digestive enzymes are exposed to highly acidic conditions in the stomach, with a pH of 1 or 2, as well as gastric proteases which denature and degrade the enzymes.

Gastric acid is a secretion produced in the stomach. It is one of the main isotonic solutions secreted, together with several enzymes and intrinsic factors. Chemically it is an acid solution with a pH of 1 to 2 in the stomach lumen, consisting mainly of hydrochloric acid (HCl) (around 0.5%, or about 5000 parts per million), and large quantities of potassium chloride (KCl) and sodium chloride (NaCl).

Gastric acid is produced by parietal cells (also called oxyntic cells) in the stomach. Its secretion is a complex and relatively energetically expensive process. Parietal cells contain an extensive secretory network (called canaliculi) from which the gastric acid is secreted into the lumen of the stomach. These cells are part of epithelial fundic glands in the gastric mucosa. The pH of gastric acid is 2 to 3 in the human stomach lumen, the acidity being maintained by the proton pump H+/K+ ATPase (also referred to as the hydrogen ion pump herein). The parietal cell releases bicarbonate into the blood stream in the process, which causes the temporary rise of pH in the blood, known as alkaline tide.

The resulting highly acidic environment in the stomach lumen causes proteins from food to lose their characteristic folded structure (or denature). This exposes the protein's peptide bonds. The chief cells of the stomach secrete enzymes for protein breakdown (inactive pepsinogen and renin). Gastric acid activates pepsinogen into pepsin—this enzyme then helps digestion by breaking the bonds linking amino acids, a process known as proteolysis.

Gastric acid secretion happens in several steps. Chloride and hydrogen ions are secreted separately from the cytoplasm of parietal cells and mixed in the canaliculi. Gastric acid is then secreted into the lumen of the oxyntic gland and gradually reaches the main stomach lumen. Chloride and sodium ions are secreted actively from the cytoplasm of the parietal cell into the lumen of the canaliculus. This creates a negative potential of −40 mV to −70 mV across the parietal cell membrane that causes potassium ions and a small number of sodium ions to diffuse from the cytoplasm into the parietal cell canaliculi.

The enzyme carbonic anhydrase catalyzes the reaction between carbon dioxide and water to form carbonic acid. This acid immediately dissociates into hydrogen and bicarbonate ions. The hydrogen ions leave the cell through H+/K+ ATPase antiporter pumps. At the same time sodium ions are actively reabsorbed. This means the majority of secreted K+ and Na+ ions return to the cytoplasm. In the canaliculus, secreted hydrogen and chloride ions mix and are secreted into the lumen of the oxyntic gland.

The highest concentration that gastric acid reaches in the stomach is 160 mM in the canaliculi. This is about 3 million times that of arterial blood, but almost exactly isotonic with other bodily fluids. The lowest pH of the secreted acid is 0.8, but the acid is diluted in the stomach lumen to a pH between 1 and 3.

There are three phases in the secretion of gastric acid: 1. the cephalic phase: 30% of the total gastric acid to be produced is stimulated by anticipation of eating and the smell or taste of food; 2. the gastric phase: 60% of the acid secreted is stimulated by the distention of the stomach with food and digestion produces proteins, which causes even more gastrin production; and 3. the intestinal phase: the remaining 10% of acid is secreted when chyme enters the small intestine, and is stimulated by small intestine distention.

Gastric acid production is regulated by both the autonomic nervous system and several hormones. The parasympathetic nervous system, via the vagus nerve, and the hormone gastrin stimulate the parietal cell to produce gastric acid, both directly acting on parietal cells and indirectly, through the stimulation of the secretion of the hormone histamine from enterochromaffin-like cells (ECL). Vasoactive intestinal peptide, cholecystokinin, and secretin all inhibit production.

The production of gastric acid in the stomach is tightly regulated by positive regulators and negative feedback mechanisms. Four types of cells are involved in this process: parietal cells, G cells, D cells and enterochromaffine-like cells. Besides this, the endings of the vagus nerve (X) and the intramural nervous plexus in the digestive tract influence the secretion significantly.

In one example, the release of digestive enzymes is timed to release specific percentages of enzymes in specific portions of the gastrointestinal tract by a combined use of gastrointestinal modulators and coating technologies.

In another example, the amount and or types of gastrointestinal modulators are varied around a fixed enzyme coating to maximize efficacious release of digestive enzymes in the appropriate portion(s) of the gastrointestinal tract to treat the symptoms or causes of coronavirus infections.

In another example, the amount and or types of gastrointestinal modulators are fixed and the thickness of the enzyme coating is varied to maximize efficacious release of digestive enzymes in the appropriate portion(s) of the gastrointestinal tract to treat the symptoms or causes of coronavirus infections.

In another example, the timing of giving one or more gastrointestinal modulator(s) are varied and the thickness of the coating is fixed to maximize efficacious release of digestive enzymes in the appropriate portion(s) of the gastrointestinal tract to prophylaxis or treat an infection or symptoms thereof from one or more coronavirus infections.

In another example, the coatings and enzymes are concentrically nested to allow timed release of enzymes in more than one portion of the gastrointestinal tract to prophylaxis or treat an infection or the symptoms thereof treat the symptoms thereof for one or more coronavirus(es).

Nerve endings in the stomach secrete two stimulatory neurotransmitters: acetylcholine and gastrin-releasing peptide. Their action is both direct on parietal cells and mediated through the secretion of gastrin from G cells and histamine from enterochromaffine-like cells. Gastrin acts on parietal cells directly and indirectly too, by stimulating the release of histamine. The release of histamine is the most important positive regulation mechanism of the secretion of gastric acid in the stomach. Its release is stimulated by gastrin and acetylcholine and inhibited by somatostatin.

Parietal cells in the stomach produce acid necessary for digestion. Histamine release stimulates these cells to do so. Specific receptors on the parietal cell membrane, designated histamine-2 receptors, react to the presence of histamine at their active sites by beginning production of acid. Hydrogen ions, the essential building blocks of stomach acid, are then pumped into the stomach. Histamine-2 receptor antagonists (H2-blockers) are a class of drugs used to decrease the amount of acid produced in the stomach by inhibiting the ability of histamine to stimulate the histamine receptor on parietal cells. The acid-suppressing effects of most H2-blockers range from 6 to 24 hours. Examples of H2-blockers include ZANTAC® (ranitidine), ARID® (nizatidine), PEPCID® (famotidine) and TAGAMET® (cimetidine).

Histamine 2-receptor blockers (H2-RBs) also come in various dosage forms. All come in a tablet form and ranitidine also comes in a soluble tablet as well as a syrup. Famotidine is available in a chewable tablet and a suspension.

Proton pump inhibitors (PPIs) are a class of drugs used to decrease the amount of acid produced in the stomach by irreversibly inhibiting the hydrogen ion pump from working. The acid-suppressing effects of most PPIs can last as long as 24 hours. Examples of PPIs include PRILOSEC® (omeprazole), NEXIUM® (esomeprazole), ZEGERID (omeprazole+sodium bicarbonate), PREVACID® (lansoprazole), DEXILANT® (dexlansoprazole), ACIPHEX® (rabeprazole), and PROTONIX® (pantoprazole).

Proton-pump inhibitors (PPIs) come in various dosage forms. Examples of PPIs that come in a tablet form are pantoprazole, rabeprazole and omeprazole. Omeprazole, esomeprazole, lansoprazole and dexlansoprazole all come in capsule form and can either be swallowed whole or opened and their contents sprinkled over select foods or in select juices as noted by their respective manufacturers. Lansoprazole is also available as a soluble tablet. Esomeprazole is available in a granule formulation. Omeprazole also comes in a combination with NaHCO in capsule and granule formulations.

Mucosal protectants provide a barrier that stomach acid must first penetrate before contacting digestive material and include sucralfate, bismuth subsalicylate, ranitidine bismuth citrate (RBC), and bismuth subgallate.

Sucralfate is a mucosal protectant that attenuates the power of stomach acid in digesting substrate by coating the GI tract and providing a barrier that acid must first penetrate before contacting digestible material. Sucralfate (CARAFATE®) is a complex metal salt of sulfated sucrose. Although the sucralfate molecule contains aluminum hydroxide, the agent has little acid-neutralizing capacity. It is an aluminum salt of sulfated sucrose that disassociates under the acidic conditions in the stomach. It is speculated that the sucrose polymerizes and binds to protein in the ulcer crater to produce a kind of protective coating that can last for up to 6 hours. When exposed to gastric acid, the aluminum hydroxide dissociates, leaving sulfate anions that can bind electrostatically where it appears to form a protective barrier that may prevent further acid-peptic attack. Because of the lack of systemic absorption, sucralfate appears to have no systemic toxicity. Similar agents include PEPTO-BISMOL® (bismuth subsalicylate), ranitidine bismuth citrate (RBC) and bismuth subgallate. Bismuth preparations have been used widely to treat diarrhea, abdominal pain, and dyspepsia for hundreds of years. Two colloidal preparations of bismuth that have been most commonly used are colloidal bismuth subcitrate and bismuth subsalicylate (e.g., PEPTO-BISMOL®). The bismuth forms complexes with mucus to form a protective barrier that may prevent further acid-peptic attack. Bismuth is largely unabsorbed and is excreted in the feces.

Pro-kinetic agents are typically used to increase lower esophageal sphincter (LES) pressure and also accelerate gastric emptying by stimulating the smooth muscles of the GI tract. Examples include PROPULSID® (cisapride), REGLAN® (metoclopramide), and URECHOLINE® (bethanecol).

The combination of gastrointestinal modulator agents in a pharmaceutical composition described herein in appropriate therapeutic dosages would be beneficial for enhancing their efficacy. Concerning agents that decrease the amount of acid present to digest substrate, more unaffected compositions comprising one or more digestive enzyme(s) (coated or otherwise) would be able to make it to its target site in the small intestine. Concerning agents that limit the amount of time acid contacts substrate, compositions comprising one or more digestive enzyme(s) (coated or otherwise) would arrive at its target site in the small intestine sooner and with less degradation.

While certain embodiments have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the methods and structures within the scope of the following claims and their equivalents be covered thereby.

Certain Definitions

All terms are intended to be understood as they would be understood by a person skilled in the art and. Unless defined otherwise, all technical and scientific terms used herein have the same meaning as commonly understood by one of ordinary skill in the art to which the disclosure pertains. Accordingly, the terminology used herein is for the purpose of describing particular embodiments only and is not intended to be limiting. Although any methods and materials similar or equivalent to those described herein can be used in the practice for testing of the present disclosure, the preferred materials and methods are described herein.

Reference in the specification to "certain instances," "some instances," "an instance," "one instance," "other instances," "some embodiments," "an embodiment," "one embodiment" or "other embodiments" means that a particular feature, structure, or characteristic described in connection with the embodiments is included in at least some instances/embodiments, but not necessarily all instances/embodiments, of the present disclosure. To facilitate an understanding of the present disclosure, a number of terms and phrases are defined below.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

The term "about" as used herein, generally refers to a range that is 1%, 2%, 5%, 10%, 15% greater than or less than (±) a stated numerical value within the context of the particular usage. For example, "about 10" would include a range from 8.5 to 11.5. As used herein, the terms "about" and "approximately," when used to modify a numeric value or numeric range, indicate that deviations of up to about 0.2%, about 0.5%, about 1%, about 2%, about 5%, about 7.5%, or about 10% (or any integer between about 1% and 10%) above or below the value or range remain within the intended meaning of the recited value or range.

As used in this specification and the appended claims, the singular forms "a," "an," and "the" include plural references unless the context clearly dictates otherwise. Thus, for example, references to "a method" include one or more methods, and/or steps of the type described herein and/or which will become apparent to those persons skilled in the art upon reading this disclosure.

Polypeptides (e.g., proteins) described herein can be isolated and/or purified from their natural environment in substantially pure or homogeneous form.

There are two types of pancreatic enzymes which have United States Pharmacopeia (U.S.P.) designations: pancreatin and pancrealipase.

"Pancreatin" is a substance containing enzymes, principally amylase, lipase, and protease, obtained from the pancreas of the hog Sus scrofa Linne var. domesticus Gray (Fam. Suidae) or of the ox Bos Taurus Linne (Fam. Bocidae). Pancreatin contains, in each mg, not less than 25 U.S.P. Units of amylase activity, not less than 2 U.S.P. Units of lipase activity, and not less than 25 U.S.P. of protease activity. Pancreatin of a higher digestive power may be labeled as a whole-number multiple of the three minimum activities or may be diluted by admixture with lactose, or with sucrose containing not more than 3.25 percent of starch, or with pancreatin of a lower digestive power. Pancreatin can be provided as a crystalline substance.

In contrast, "pancrealipase" refers to a cream-colored, amorphous powder, having a faint, characteristic meaty odor, which contains lipase in an amount of not less than 24 U.S.P. Units/mg; protease in an amount of not less than 100 U.S.P. Units/mg; and amylase in an amount of not less than 100 U.S.P. Units/mg; with not more than 5% fat and not more than 5% loss on drying.

"CREON®" is a form of pancrealipase that is sold as formulations of (i) 3,000 Units of a lipase, 9,500 Units of a protease, 15,000 Units of an amylase; (ii) 6,000 Units of a lipase, 19,000 Units of a protease, 30,000 Units of an amylase; (iii) 12,000 Units of a lipase, 38,000 Units of a protease, 60,000 Units of an amylase; (iv) 24,000 Units of a lipase, 76,000 Units of a protease, and 120,000 Units of an amylase; or (v) 36,000 Units of a lipase, 114,000 Units of a protease, and 180,000 Units of an amylase. CREON® formulations are known to be irritating to mucosa of a subject and also is known to cause the following adverse side effects: Abdominal pain, abnormal feces, cough, dizziness, flatulence, headache, weight decreased; hyperuricemia, fibrosing colonopathy (with high doses), and/or allergic reactions.

As used herein, the term "non-aerosolizable" will be used to refer to coated particles where substantially all of the coated particles are large enough to eliminate or reduce aerosolization upon pouring compared to uncoated digestive enzyme.

The phrase "pharmaceutically acceptable" refers to molecular entities and compositions that are physiologically tolerable.

An enzyme described herein can be isolated, purified, recombinant, synthetic, or a combination thereof. For example, an enzyme can be produced recombinantly or synthetically. In some instances, an enzyme can be produced recombinantly or synthetically and then isolated and/or purified.

EXAMPLES

The application may be better understood by reference to the following non-limiting examples, which are provided as exemplary embodiments of the application. The following examples are presented in order to more fully illustrate embodiments and should in no way be construed, however, as limiting the broad scope of the application.

The following experiments tested and verified the cytoprotective effects of both Pancreatic Enzyme Concentrate and Microencapsulated Pancreatic Enzyme Concentrate in various concentrations against cell death and SARS-CoV-2 infection spread.

Materials and Methods

Cell Preparation:

The cell line utilized for the infection and plaque assays is Vero E6 cells (ATCC® CRL-1586). These cells were grown from a frozen aliquot of a laboratory working cell line. Passage number is limited to no more than 50 passages from the original aliquot. Cells were grown in T150 flasks in 1× DMEM (ThermoFisher cat. no. 12500062) supplemented with 2 mM L-glutamine (Hyclone cat. no. H30034.01), non-essential amino acids (Hyclone cat. no. SH30238.01), and 10% heat inactivated Fetal Bovine Serum (FBS) (Atlas Biologicals cat. no. EF-0500-A).

On the day prior to executing the assay, Vero E6 cells were removed from T150 flasks by trypsinization (0.25% Trypsin, Corning cat. no. 25-053-Cl) and measured for count and viability by Hemocytometer in trypan blue. Cells were resuspended to $2.7 \times 10^5$ cells per mL in 1× DMEM (supplemented as indicated above) and plated at 0.15 mL per well (40,000 cells/well) in 96-well plates. The plates were then incubated for approximately 24 hours to allow cell adherence at 37° C., 5% $CO_2$.

Virus Stocks:

The virus strain used for the assay was SARS-CoV2, USA WA 01/2020, CSU V2 03/17/202 passage 3. Virus stocks were obtained from BEI Resources and amplified in Vero E6 cells to Passage 3 (P3) with a titer of $1.6 \times 10^6$ PFU/mL. Stocks were stored at −80° C. Virus infection of indicated wells were carried out with two MOI (0.001 and 0.0001). See, plate format of Table 19.

Compounds, Source, and Concentration

| | | |
|---|---|---|
| Pancreatic Enzyme Concentrate (100 g) | Lot 2226-0001 | 3 mg/ml in PBS* |
| Pancreatic Enzyme Concentrate (100 g) | Lot 2226-0003 | 3 mg/ml in PBS |
| Pancreatic Enzyme Concentrate (100 g) | Lot 2226-0004 | 3 mg/ml in PBS |
| Microencapsulated Pancreatic Enzyme Concentrate | Curemark Supplied | 3 mg/ml in PBS |

*PBS: phosphate buffered saline.

Assay Setup:

1. Stock solutions were prepared in PBS (PH 7.2), then incubated at 37° C. for 30 min, and vortexed regularly.
2. Stock solutions were centrifugated at 4° C. at 1400 rpm for 10 minutes.
3. Stock solutions were diluted (1:50, 1:200, 1:400, or 1:1000) in 1×DMEM+++ media.
4. Four 96-well plates were set up as shown in FIG. 19, Plate Map.
3. Pre-treatment: Media was aspirated from the 96 wells, 100 μL of the compound dilutions (and controls) as shown above (step 2) were added, and the plate(s) incubated at 37° C./5% $CO_2$ for 1 hour (hr).
4. After the pre-treatment, virus (MOI 0.001 and 0.0001) was added dropwise into the media, plates were sealed with aeroseal and incubated for 72 hr at 37° C./5% $CO_2$. For cytotoxicity assays, no virus was added.
5. At 72 hr, supernatants were harvested and stored at −80° C. Cytoprotection was measured using neutral red.
5a. Neutral red (NR) solution (0.33% NRS, Sigma Aldrich cat. no. N2889) maintained at room temperature was diluted 1:24 in 10% 1× DMEM warmed to 37° C. Immediately after dilution the solution was centrifuged at 4000 rpm in a tabletop centrifuge for 30 min (to remove any NR crystals).
5b. The diluted NR solution was added to the cells (150 μl/well).
5c. The plate was incubated at 37° C., 5% $CO_2$ for approximately 2 hours.
5d. NR solution was removed, and NR solubilization solution (1% glacial acetic acid in 50% ethanol) was added to each well at 150 μl/well. Plates were incubated at room temperature for 10 minutes, and solubilization solution mixed by pipetting.
5e. 130 μL from each well was transferred to a new plate.
5f. Absorbance was read on a plate reader at 540 nm. Plate background absorbance was read at 590 nm.

Plaque Assay:

Four 10-fold serial dilutions of the supernatants were carried out for each sample in 1× DMEM. 200 μL of these dilutions were dispensed onto wells in a 12-well plate. Plates were incubated at 37° C./5% $CO_2$ for 1 hour to allow virus to adsorb (plates were rocked intermittently). After an hour, wells were overlaid with 2% agarose and 2× DMEM (supplemented with 10% FBS). Plaque assays were incubated at 37° C./5% $CO_2$ for 72 hr. Cell Staining: 72 hrs. post-plaque assay, cells were stained with 1× PBS and neutral red solution (NRS) (0.33% NRS, Sigma Aldrich cat. no. N2889) at a ratio of 11.5 mL 1× PBS and 0.5 mL NRS per 12-well plate (1 ml/well). Staining was carried out overnight (about 12 hrs).

Experiment 1

Figure 20:
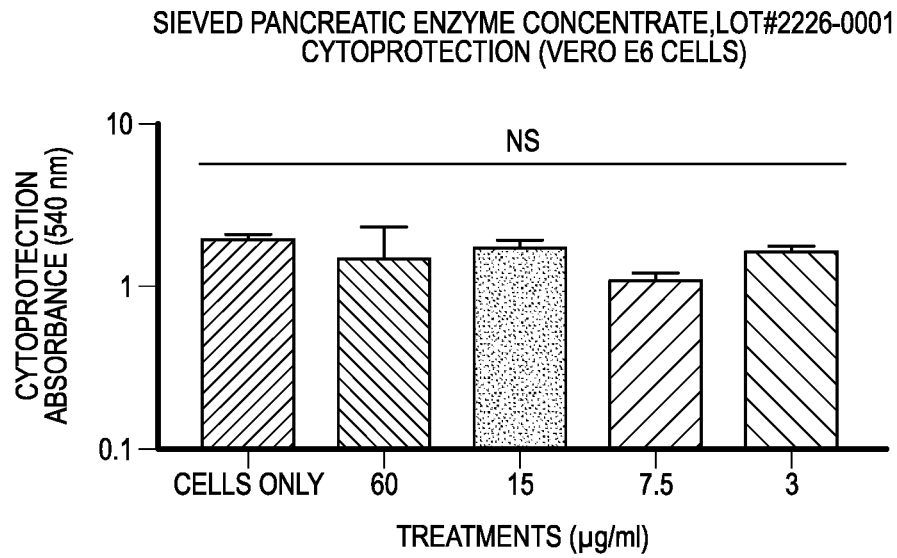
FIG. 20 presents the Cytoprotection of Vero E6 Cells against cell death after treatment with Pancreatic Enzyme Concentrate lot number 2226-0001.
Figure 21:
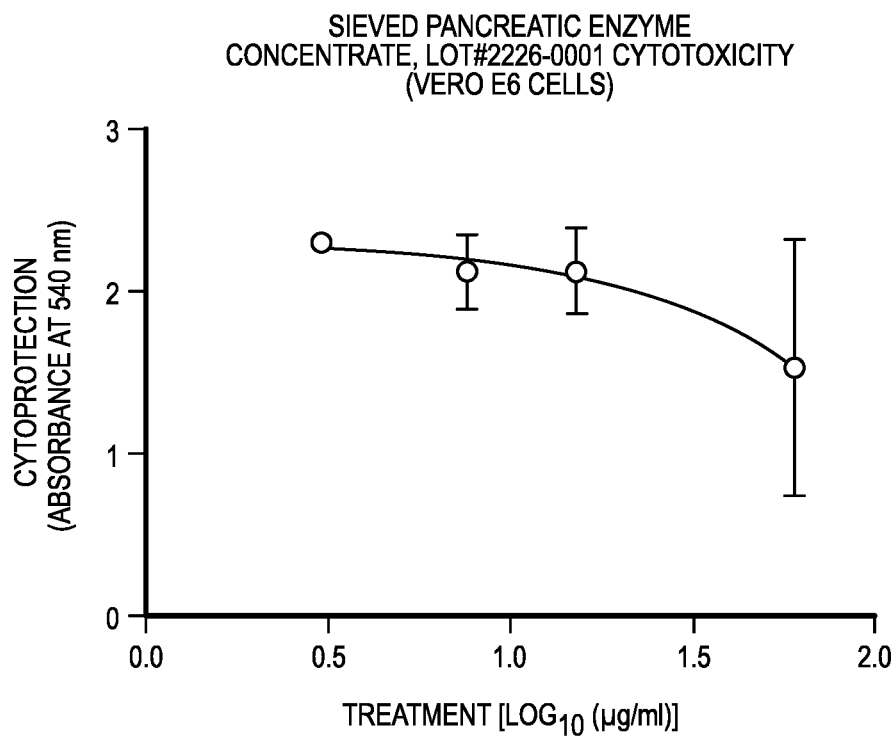
FIG. 21 demonstrate cytotoxicity of Vero E6 Cells after treatment with Pancreatic Enzyme Concentrate lot number 2226-0001.

A series of baseline tests were performed to evaluate cytotoxicity of Pancreatic Enzyme Concentrate to Vero E6 cells. FIG. 20 presents the Cytoprotection of Vero E6 Cells against cell death after treatment with Pancreatic Enzyme Concentrate in lot number 2226-0001. As shown, Vero E6 cells have cytoprotection against cell death with Pancreatic Enzyme Concentrate in concentrations of 15, 7.5 and 3.0 micrograms (μg) per milliliter as is shown by the fact that treated cells show the same viability as untreated controls (no significant difference between viability of treated and untreated cells). At a concentration of 60 μg per milliliter the treatment was slightly cytotoxic to Vero E6 cells but is still at a dosing level otherwise safe for use in humans and mammals. FIG. 21, Cytotoxicity of Vero E6 Cells after treatment with Pancreatic Enzyme Concentrate (Lot number 2226-0001), presents these same results as a function of treatment concentration. The above data are acquired using the neutral red cytoprotection assay.

Figure 22:
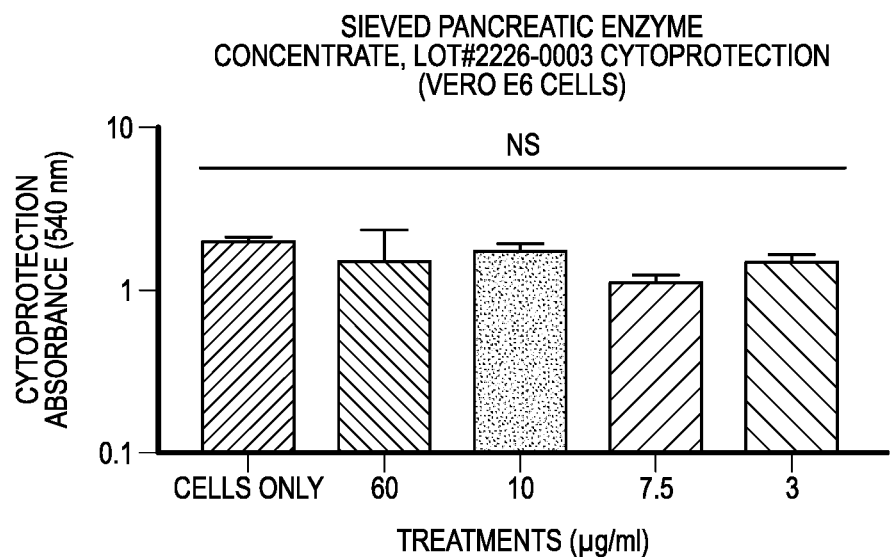
FIG. 22 demonstrate cytotoxicity of Vero E6 Cells against cell death after treatment with Pancreatic Enzyme Concentrate lot number 2226-0003.
Figure 23:
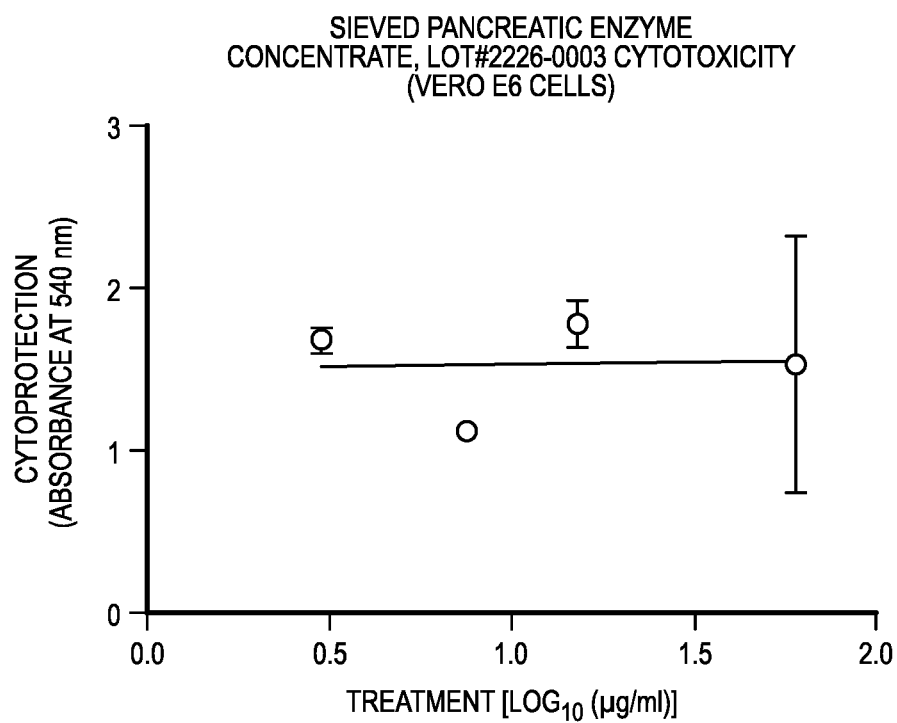
FIG. 23 demonstrate cytotoxicity of Vero E6 Cells after treatment with Pancreatic Enzyme Concentrate lot number 2226-0003.

FIG. 22 presents the Cytoprotection of Vero E6 Cells against cell death after treatment with Pancreatic Enzyme Concentrate in a second lot of pancreatin (Lot 2226-0003). As shown, Vero E6 cells have cytoprotection against cell death with Pancreatic Enzyme Concentrate in concentrations of 15, 7.5 and 3.0 μg per milliliter with a statistically non-significant difference compared with the untreated cells. At a concentration of 60 μg per milliliter the treatment did have some cytotoxicity to Vero E6 cells but is still at a dosing level otherwise safe for use in humans and mammals. FIG. 23, Cytotoxicity of Vero E6 Cells after treatment with Pancreatic Enzyme Concentrate lot number 2226-0003, presents these same results as a function of treatment concentration. The above data are acquired using the neutral red cytoprotection assay.

Figure 24:
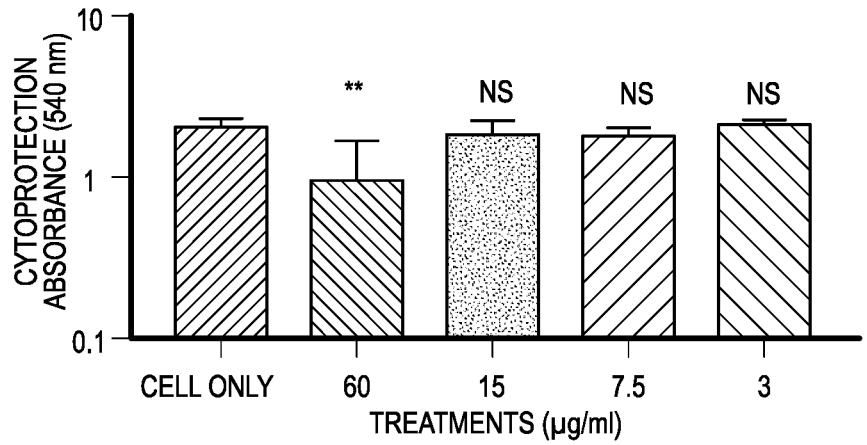
FIG. 24 demonstrate cytotoxicity of Vero E6 Cells against cell death after treatment with Pancreatic Enzyme Concentrate lot number 2226-0004.
Figure 25:
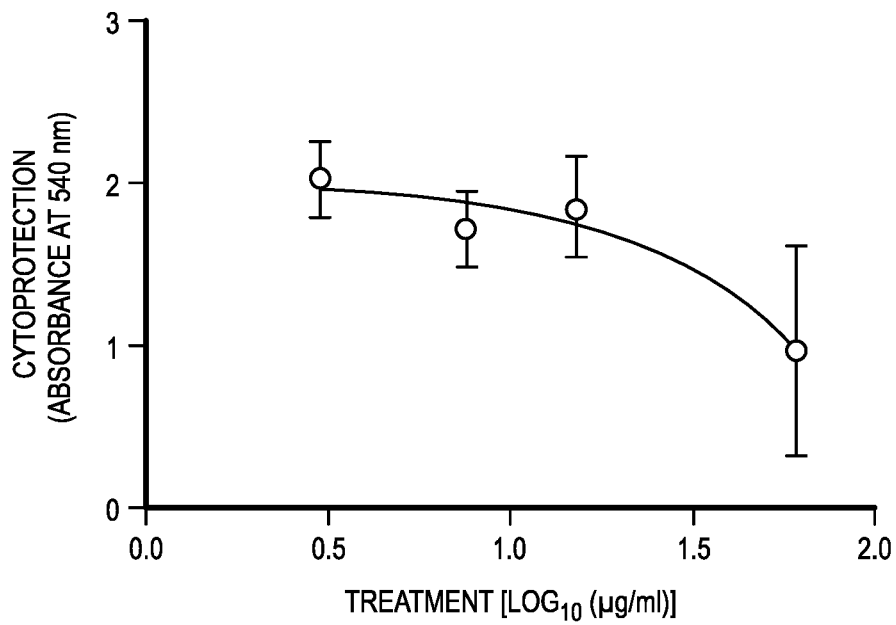
FIG. 25 demonstrate cytotoxicity of Vero E6 Cells after treatment with Pancreatic Enzyme Concentrate lot number 2226-0003.

FIG. 24 presents the Cytoprotection of Vero E6 Cells against cell death after treatment with ka third lot of Pancreatic Enzyme Concentrate (Lot 2226-0004). Once again, as shown, Vero E6 cells have cytoprotection against cell death with Pancreatic Enzyme Concentrate in concentrations of 15, 7.5 and 3.0 μg per milliliter with a statistically non-significant difference compared with the untreated cells. At a concentration of 60 μg per milliliter the treatment did have some cytotoxicity to Vero E6 cells but is still at a dosing level otherwise safe for use in humans and mammals. FIG. 25, Cytotoxicity of Vero E6 Cells after treatment with Pancreatic Enzyme Concentrate lot number 2226-0004, presents these same results as a function of treatment concentration. The above data are acquired using the neutral red cytoprotection assay.

Figure 26:
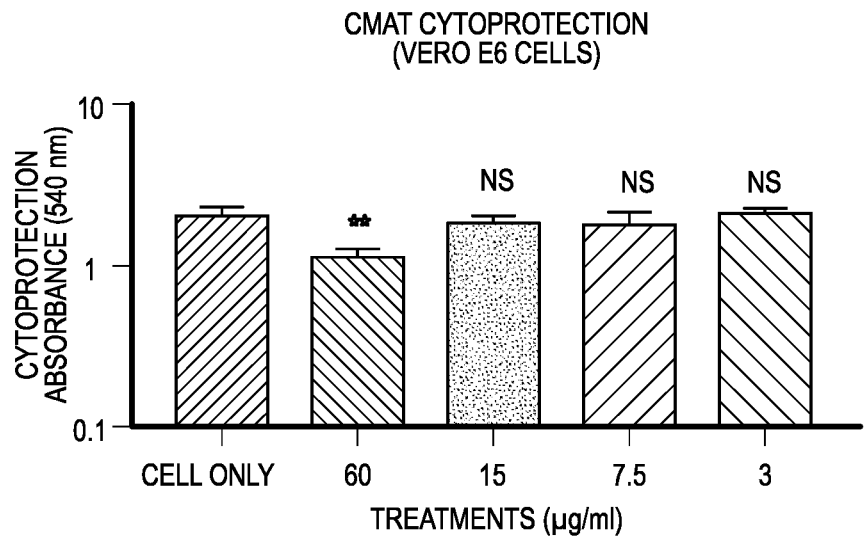
FIG. 26 demonstrate cytotoxicity of Vero E6 Cells against cell death after treatment with Microencapsulated Pancreatic Enzyme Concentrate.
Figure 27:
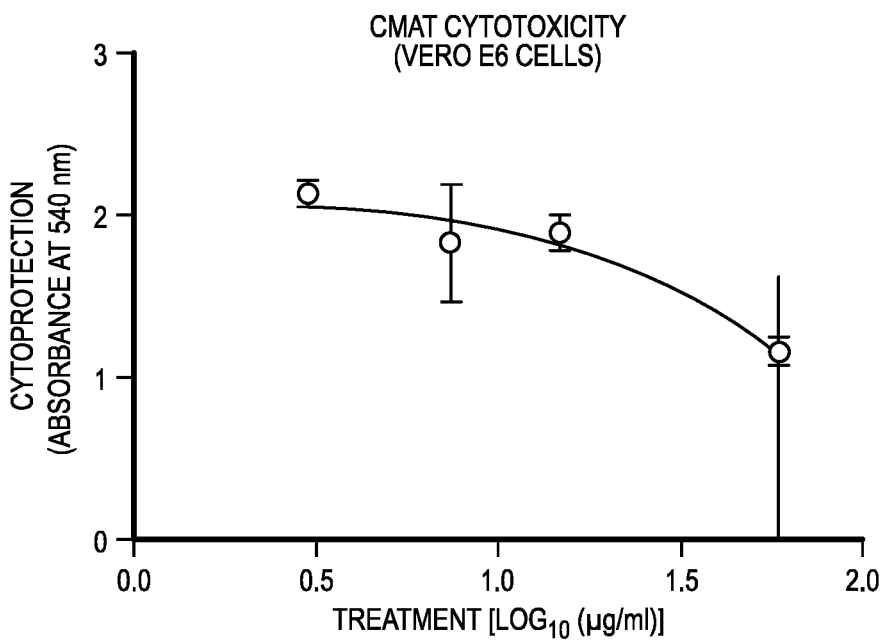
FIG. 27 demonstrate cytotoxicity of Vero E6 Cells after treatment with Microencapsulated Pancreatic Enzyme Concentrate.

FIG. 26 presents the Cytoprotection of Vero E6 Cells against cell death after treatment with Microencapsulated Pancreatic Enzyme Concentrate. As shown, Vero E6 cells have cytoprotection against cell death with Microencapsulate Pancreatic Enzyme Concentrate in concentrations of 15, 7.5 and 3.0 µg per milliliter with a statistically non-significant difference compared with the untreated cells. Microencapsulated Pancreatic Enzyme Concentrate only showed a cytotoxicity at 60 µg/mL. Data was analyzed using an unpaired t-test compared to the cells only control. **P=0.0016-0.0080.

Experiment 2

Figure 28:
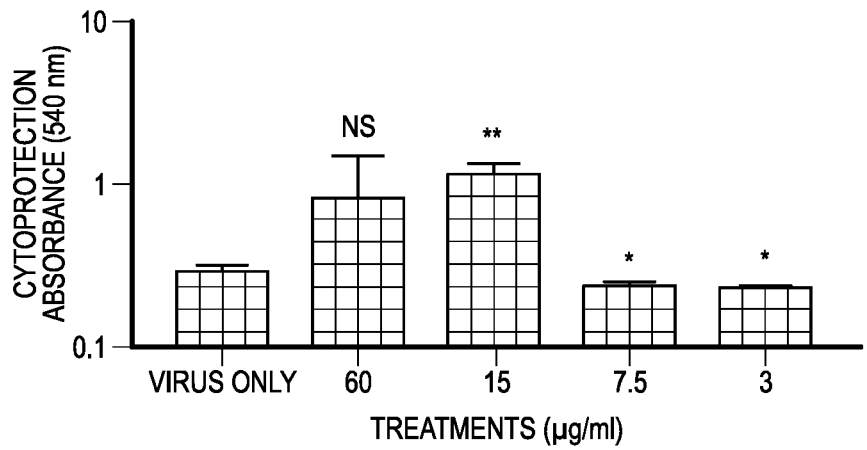
FIG. 28 demonstrate inhibition of SASRS-CoV-2 in Vero E6 Cells with Multiple of Infection (MOI)=0.001 after treatment with Pancreatic Enzyme Concentrate lot number 2226-0001.
Figure 29:
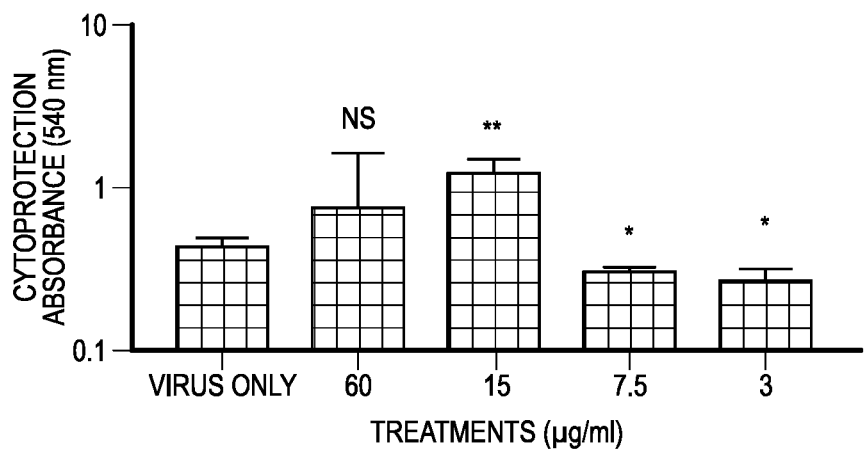
FIG. 29 demonstrate inhibition of SASRS-CoV-2 in Vero E6 Cells with Multiple of Infection (MOI)=0.001 after treatment with Pancreatic Enzyme Concentrate lot number 2226-0003.

A series of tests were performed to evaluate the Inhibition of SASRS-CoV-2 infectivity by Pancreatic Enzyme Concentrate and Microencapsulated Pancreatic Enzyme Concentrate using Vero E6 Cells with Multiples of Infection (MOI)=0.001 and MOI=0.0001. FIG. 28 presents the Inhibition of SASRS-CoV-2 in Vero E6 Cells with Multiple of Infection (MOI)=0.001 after treatment with Pancreatic Enzyme Concentrate lot number 2226-0001. Similarly FIG. 29 presents the Inhibition of SASRS-CoV-2 in Vero E6 Cells with Multiple of Infection (MOI)=0.001 after treatment of the virus with Pancreatic Enzyme Concentrate lot number 2226-0003 and FIG. 30 presents the Inhibition of SASRS-CoV-2 in Vero E6 Cells with Multiple of Infection (MOI)=0.001 after treatment of the virus with Pancreatic Enzyme Concentrate lot number 2226-0004. At a Concentration of 15 mg/ml Pancreatic Enzyme Concentrate is cytoprotective in the three tested lots above of Pancreatic Enzyme Concentrate indicating a statistically relevant reduction in virus infection (antiviral). Data were analyzed using an unpaired t test compared to the virus only control. *P=0.0287, *P=0.002-0.004, P<0.0001. The above data are acquired using the neutral red cytoprotection assay FIG. 31 presents the Inhibition of SASRS-CoV-2 in Vero E6 Cells with Multiple of Infection (MOI)=0.001 after treatment with Microencapsulated Pancreatic Enzyme Concentrate. While statistical inhibition was not shown, this is likely due to the diffusion required from the inert coating coupled with a 20% reduction by weight of active enzyme. It should be noted that significance was shown at an MOI=0.0001 (See FIG. 35**).

Figure 32:
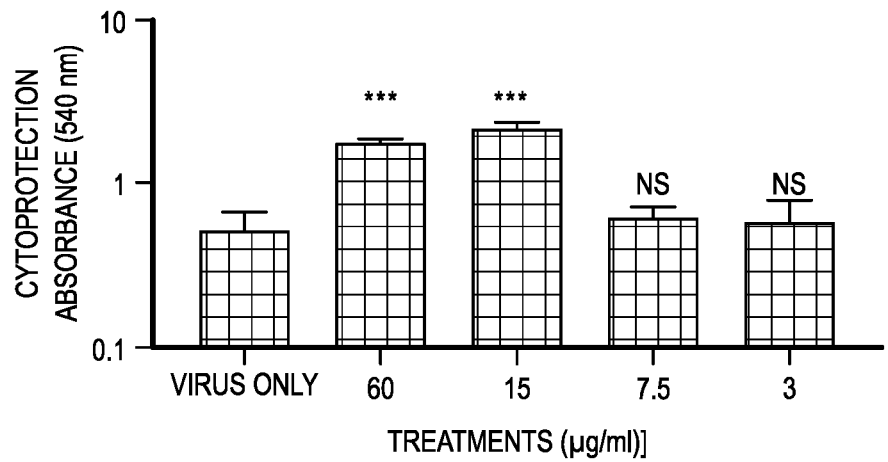
FIG. 32 demonstrate inhibition of SASRS-CoV-2 in Vero E6 Cells with Multiple of Infection (MOI)=0.0001 after treatment with Pancreatic Enzyme Concentrate lot number 2226-0001
Figure 33:
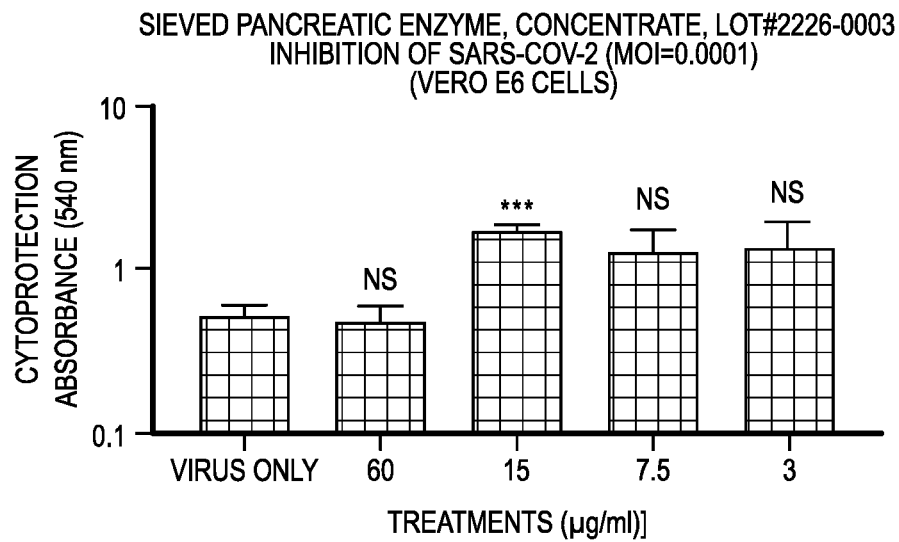
FIG. 33 demonstrate inhibition of SASRS-CoV-2 in Vero E6 Cells with Multiple of Infection (MOI)=0.0001 after treatment with Pancreatic Enzyme Concentrate lot number 2226-0003.
Figure 34:
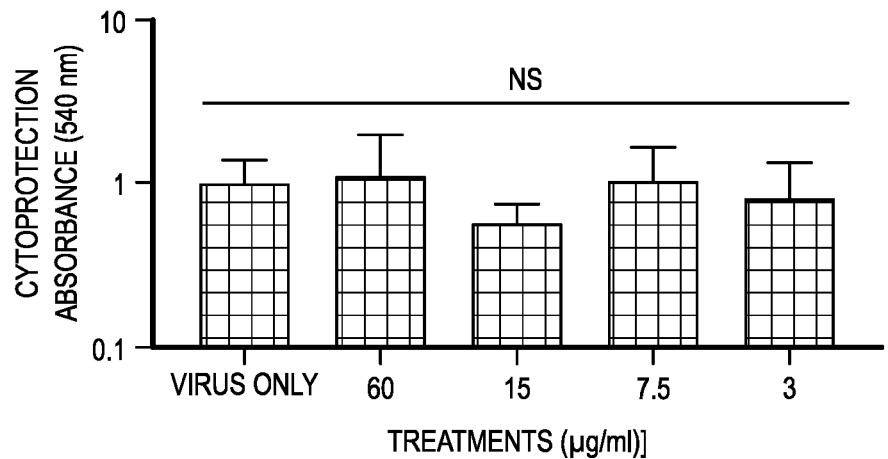
FIG. 34 demonstrate inhibition of SASRS-CoV-2 in Vero E6 Cells with Multiple of Infection (MOI)=0.0001 after treatment with Pancreatic Enzyme Concentrate lot number 2226-0004.

FIG. 32 presents the Inhibition of SASRS-CoV-2 in Vero E6 Cells with Multiple of Infection (MOI)=0.0001 after treatment with Pancreatic Enzyme Concentrate lot number 2226-0001. Similarly FIG. 33 presents the Inhibition of SASRS-CoV-2 in Vero E6 Cells with Multiple of Infection (MOI)=0.0001 after treatment of the virus with Pancreatic Enzyme Concentrate lot number 2226-0003 and FIG. 34 presents the Inhibition of SASRS-CoV-2 in Vero E6 Cells with Multiple of Infection (MOI)=0.0001 after treatment with Pancreatic Enzyme Concentrate lot number 2226-0004. At a concentration level of 15 mg/ml is cytoprotective in lots number 2226-0001 and lot 2226-0003 of Pancreatic Enzyme Concentrate indicating a statistically relevant reduction in virus infection (antiviral). Data were analyzed using an unpaired t test compared to the virus only control. *P=0.0287, *P=0.002-0.004, **P<0.0001.

Figure 35:
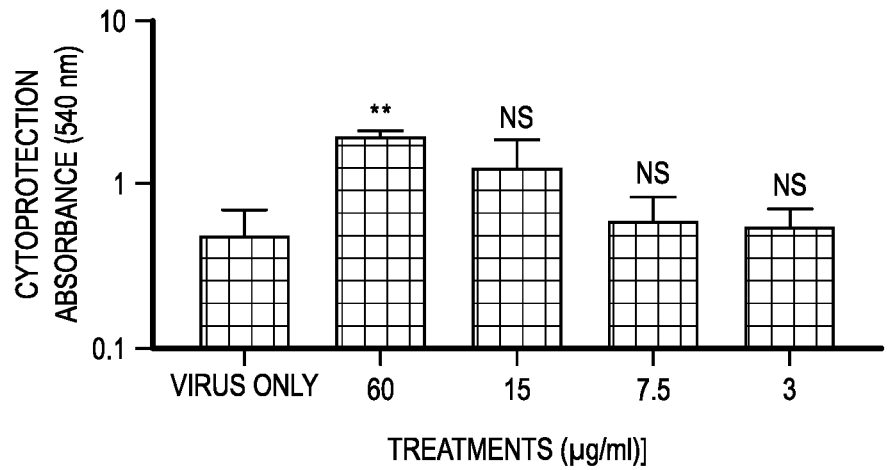
FIG. 35 demonstrate inhibition of SASRS-CoV-2 in Vero E6 Cells with Multiple of Infection (MOI)=0.0001 after treatment with Microencapsulated Pancreatic Enzyme Concentrate.

FIG. 35 presents the Inhibition of SASRS-CoV-2 in Vero E6 Cells with Multiple of Infection (MOI)=0.0001 after treatment with Microencapsulated Pancreatic Enzyme Concentrate. Statistical variance in the data, likely due to self-cytotoxicity, makes interpretation of the cytoprotection data for CMAT concentrations of 3-15 µg, it is clear there is a statistically significant cytoprotective effect in the 60 µg dose. This is confirmed in FIG. 42, which presents the Virus Titer of SASRS-CoV-2 in Vero E6 Cells with a Multiple of Infection (MOI)=0.0001 after treatment with Microencapsulated Pancreatic Enzyme Concentrate. As will be shown, there is a 1,000 times reduction in active virus at a dosing of 15 µg/mL.

Figure 36:
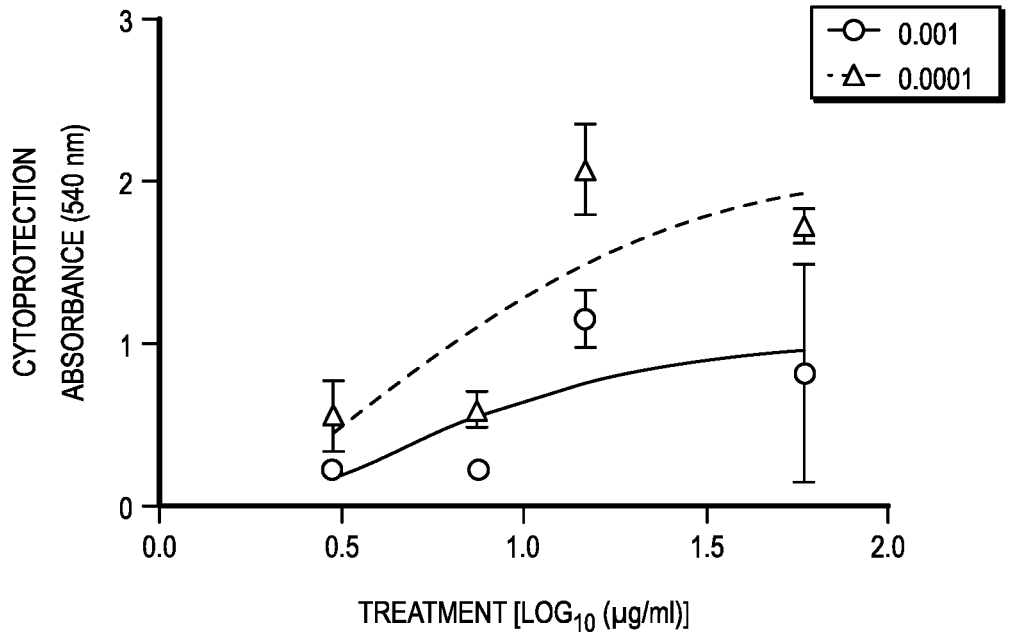
FIG. 36 demonstrate inhibition of SASRS-CoV-2 in Vero E6 Cells with Multiples of Infection (MOI)=0.0001 and MOI=0.001 after treatment with Pancreatic Enzyme Concentrate lot number 2226-0001.

FIG. 36 presents a summary of the Inhibition of SASRS-CoV-2 in Vero E6 Cells with Multiples of Infection (MOI)= 0.0001 and MOI=0.001 after treatment of the virus with Pancreatic Enzyme Concentrate lot number 2226-0001. A shown, cytoprotection and SARS-CoV-2 increases with increasing treatment concentration.

Figure 37:
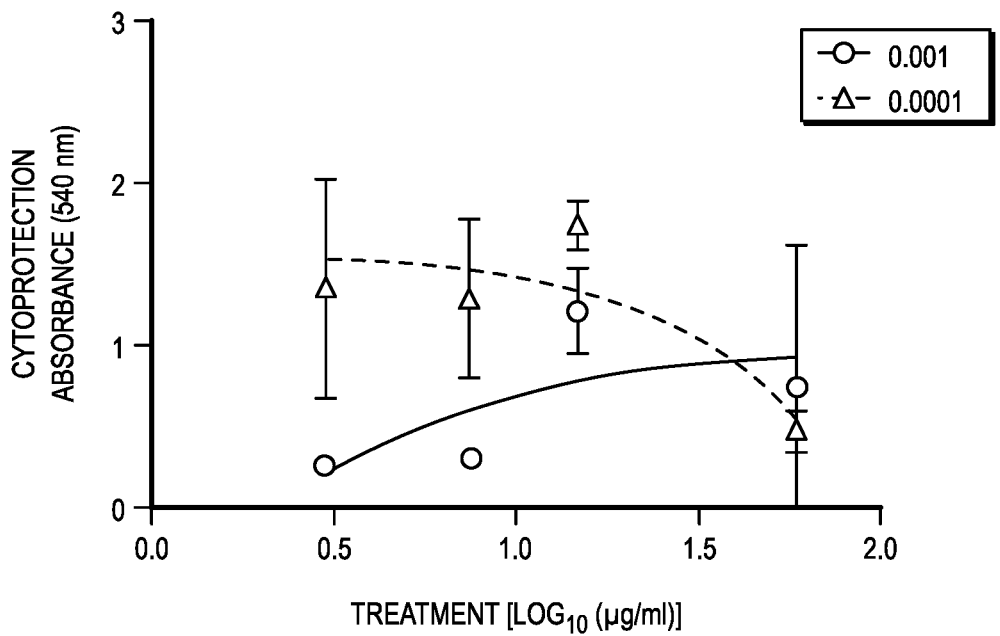
FIG. 37 demonstrate inhibition of SASRS-CoV-2 in Vero E6 Cells with Multiples of Infection (MOI)=0.0001 and MOI=0.001 after treatment with Pancreatic Enzyme Concentrate lot number 2226-0003.

FIG. 37 presents a summary of the Inhibition of SASRS-CoV-2 in Vero E6 Cells with Multiples of Infection (MOI)= 0.0001 and MOI=0.001 after treatment with Pancreatic Enzyme Concentrate lot number 2226-0003. A shown, cytoprotection and SARS-CoV-2 also increases with increasing treatment concentration until higher concentrations, where results are skewed by pancreatic Enzyme concentrate dosing inducing cytotoxicity to Vero E6 cells.

FIG. 38 presents a summary of the Inhibition of SASRS-CoV-2 in Vero E6 Cells with Multiples of Infection (MOI)= 0.0001 and MOI=0.001 after treatment with Pancreatic Enzyme Concentrate lot number 2226-0004. Once again, as shown, cytoprotection and SARS-CoV-2 increases with increasing treatment concentration.

FIG. 39 presents a summary of the Inhibition of SASRS-CoV-2 in Vero E6 Cells with Multiples of Infection (MOI)= 0.0001 and MOI=0.001 after treatment with Microencapsulated Pancreatic Enzyme Concentrate. Once again, as shown, cytoprotection and SARS-CoV-2 increases with increasing treatment concentration.

Results Summary

Figure 40:
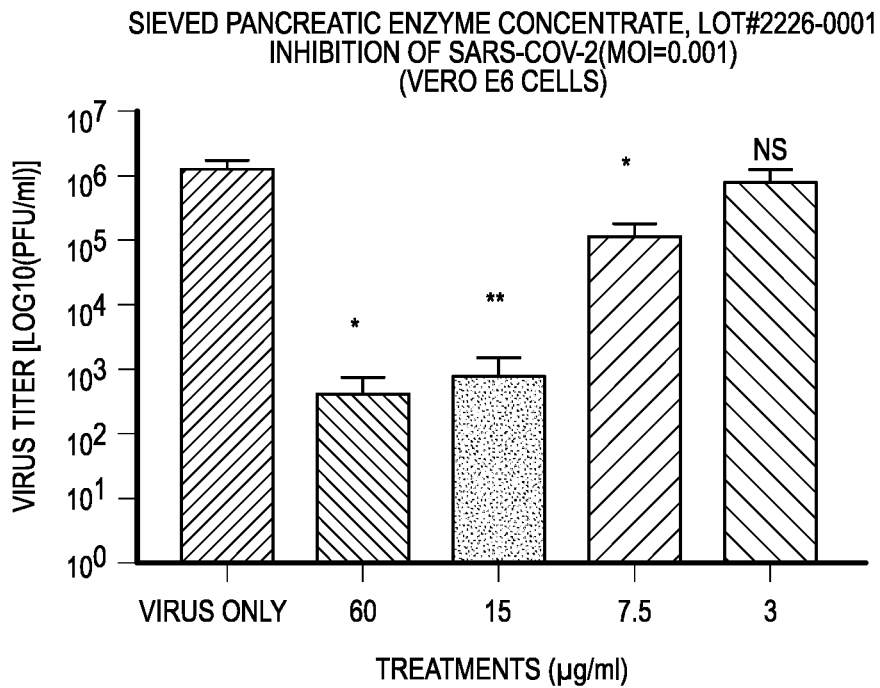
FIG. 40 provides virus titer of SASRS-CoV-2 in Vero E6 Cells with a Multiple of Infection (MOI)=0.001 after treatment with Sieved Pancreatic Enzyme Concentrate lot number 2226-0001.

Significant virus reductions were obtained at 60, 15 and 7.5 µg/mL with Pancreatic Enzyme Concentrate. FIG. 40 presents the Virus Titer of SASRS-CoV-2 in Vero E6 Cells with a Multiple of Infection (MOI)=0.001 after treatment with Pancreatic Enzyme Concentrate lot number 2226-0001. As shown, there is well over a 1000 times reduction in active virus at a dosing of 60 µg/mL as well as at a doing of 15 µg/mL.

Figure 41:
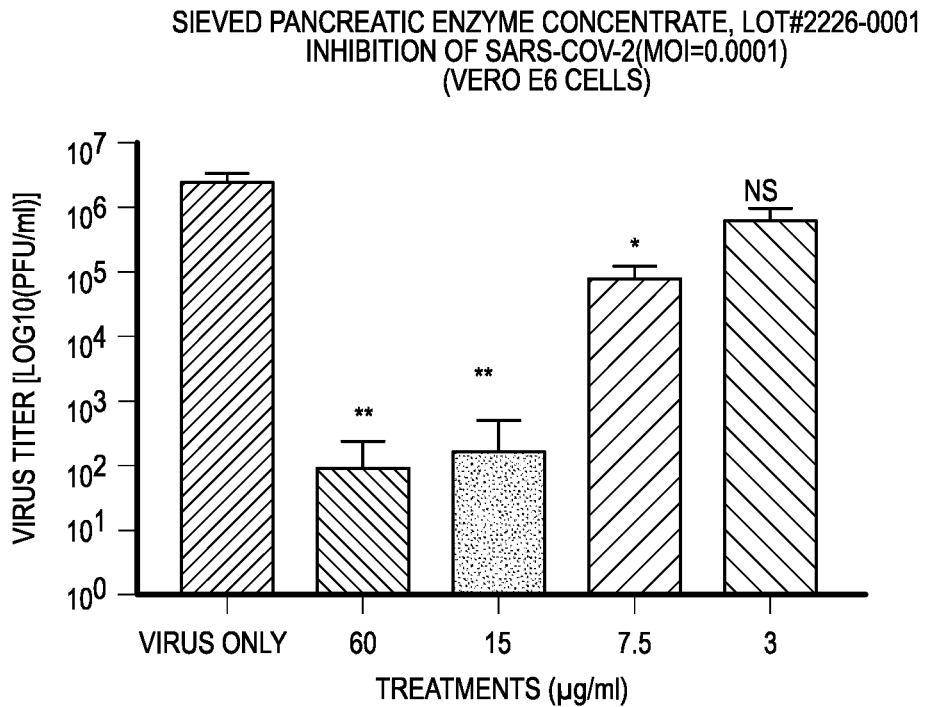
FIG. 41 provides virus titer of SASRS-CoV-2 in Vero E6 Cells with a Multiple of Infection (MOI)=0.0001 after treatment with Sieved Pancreatic Enzyme Concentrate lot number 2226-0001.

FIG. 41 presents the Virus Titer of SASRS-CoV-2 in Vero E6 Cells with a Multiple of Infection (MOI)=0.0001 after treatment with Pancreatic Enzyme Concentrate lot number 2226-0001. Once again significant virus reductions were obtained at 60, 15 and 7.5 µg/mL with Pancreatic Enzyme Concentrate. At a doing of 15 µg/mL there is over a 10,000 times reduction in active virus.

Figure 42:
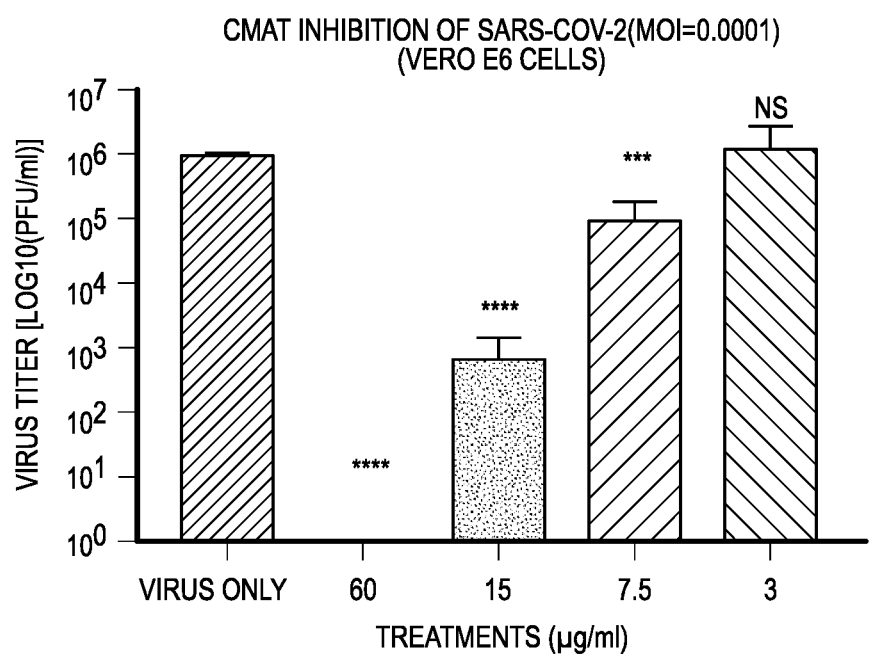
FIG. 42 provides virus titer of SASRS-CoV-2 in Vero E6 Cells with a Multiple of Infection (MOI)=0.0001 after treatment with Microencapsulated Pancreatic Enzyme Concentrate.

For Microencapsulated Pancreatic Enzyme Concentrate, concentrations 15 and 7.5 ug/ml showed significant virus reduction, while 60 mg/ml was inhibitory possibly due to cytotoxicity since this was observed in the cytoprotection/cytotoxicity assay as well. FIG. 42 presents the Virus Titer of SASRS-CoV-2 in Vero E6 Cells with a Multiple of Infection (MOI)=0.0001 after treatment with Microencapsulated Pancreatic Enzyme Concentrate. As shown, there is a 1,000 times reduction in active virus at a dosing of 15 µg/mL.

Conclusion

At a minimum, these aforecited tests demonstrate that concentrations of 7.5 and 15 ∞g/mL of Pancreatic Enzyme Concentrate and Microencapsulated Pancreatic Enzyme Concentrate inhibit the SARS-CoV-2 virus. This interpretation would be supported by the cytoprotection assay. **P=0.0045-0.0076.

While certain embodiments of the present application have been shown and described herein, it will be obvious that such embodiments are provided by way of example only. Numerous variations, changes, and substitutions may occur to those skilled in the art without departing from the embodiments; it should be understood that various alternatives to the embodiments described herein may be employed in practicing the methods described herein.

What is claimed is:

1. A method for treating a Severe Acute Respiratory Syndrome 2 (SARS-CoV-2) infection in a subject in need thereof, comprising administering to the subject a pharmaceutical composition that comprises digestive enzymes, wherein the digestive enzymes comprise a protease, a lipase, and an amylase, and wherein the digestive enzymes are provided as pancreatin.

2. The method of claim 1, wherein the digestive enzymes are coated.

3. The method of claim 2, wherein digestive enzymes comprise coated digestive enzyme particles, and wherein the coated digestive enzyme particles comprise (i) a core comprising the digestive enzymes and (ii) a coating.

4. The method of claim 3, wherein the digestive enzymes are present in the coated digestive enzyme particles in an amount of from about 5% to about 99% by weight.

5. The method of claim 2, wherein the digestive enzymes are coated with a lipid.

6. The method of claim 5, wherein the lipid comprises a pharmaceutical grade lipid or a food grade lipid.

7. The methodof claim 1, wherein the subject has COVID-19.

8. The method of claim 1, wherein the pharmaceutical composition is an oral, a nasal, a rectal, a parenteral, a percutaneous endoscopic gastrostomy (PEG), an esophagogastroduodenoscopy (EGD), or a gastrostomy (G-tube) formulation.

9. The method of claim 8, wherein the pharmaceutical composition comprises a buffer, an excipient, or a combination thereof.

10. The method of claim 1, wherein the pharmaceutical composition is a dosage formulation selected from the group consisting of a pill, a solution, a tablet, a capsule, a mini-tab, a sprinkle, and a combination thereof.

11. The method of claim 1, wherein the pharmaceutical composition comprises an oral composition.

12. The method of claim 1, wherein a total amount of protease in the pharmaceutical composition ranges from about 10,000 to about 1,500,000 United States Pharmacopeia (U.S.P.) units/dose.

13. The method of claim 1, wherein a total amount of lipase in the pharmaceutical composition ranges from about 1,500 to about 282,000 U.S.P. units/dose.

14. The method of claim 1, wherein a total amount of amylase in the pharmaceutical composition ranges from about 1,000 to about 15,000,000 U.S.P. units/dose.

15. The method of claim 1, wherein the digestive enzymes comprise at least one protease and at least one lipase, and wherein the total protease and the total lipase in the pharmaceutical composition in U.S.P. units are present in a ratio of protease to lipase of from about 1:1 to about 20:1.

16. The method of claim 15, wherein the total protease and the total lipase in the pharmaceutical composition in U.S.P. units are present in a ratio of protease to lipase of from about 4:1 to about 10:1.

17. The method of claim 1, wherein the digestive enzymes comprise at least one protease and at least one amylase, and wherein the total protease and the total amylase in the pharmaceutical composition in U.S.P. units are present in a ratio of protease to amylase of from about 1:0.1 to about 1:10.

* * * * *